United States Patent
Klasson et al.

(10) Patent No.: US 12,221,459 B2
(45) Date of Patent: Feb. 11, 2025

(54) CANCER TREATMENT WITH (2,2-BISHYDROXYMETHYL) METHYLENECYCLOPROPANE NUCLEOTIDES

(71) Applicant: MEDIVIR AB, Huddinge (SE)

(72) Inventors: Björn Klasson, Huddinge (SE); Fredrik Öberg, Huddinge (SE)

(73) Assignee: MEDIVIR AB, Huddinge (SE)

( * ) Notice: Subject to any disclaimer, the term of this patent is extended or adjusted under 35 U.S.C. 154(b) by 852 days.

(21) Appl. No.: 16/979,152

(22) PCT Filed: Mar. 8, 2019

(86) PCT No.: PCT/SE2019/050209
§ 371 (c)(1),
(2) Date: Sep. 8, 2020

(87) PCT Pub. No.: WO2019/172835
PCT Pub. Date: Sep. 12, 2019

(65) Prior Publication Data
US 2020/0399295 A1 Dec. 24, 2020

(30) Foreign Application Priority Data

Mar. 9, 2018 (SE) .................................. 1850262-5
Nov. 30, 2018 (SE) .................................. 1851495-0

(51) Int. Cl.
C07F 9/06 (2006.01)
A61P 35/02 (2006.01)

(52) U.S. Cl.
CPC ............. *C07F 9/062* (2013.01); *A61P 35/02* (2018.01)

(58) Field of Classification Search
CPC ............ C07F 9/062; A61P 35/00; A61P 35/02
See application file for complete search history.

(56) References Cited

FOREIGN PATENT DOCUMENTS

| CN | 107011383 A | 8/2017 |
|----|-------------|--------|
| CN | 107286190 A | 10/2017 |
| WO | 2018022221 A1 | 2/2018 |

OTHER PUBLICATIONS

Ambrose, Amalraj et al., "Phosphoralaninate Pronucleotides of Pyrimidine Methylenecyclopropane Analogues of Nucleosides: Synthesis and Antiviral Activity", Aug. 2006, vol. 24, No. 10-12, pp. 1763-1774.

Li, Chengwei et al., "Nucleosides, Nucleotides & Nucleic Acids", 2009, vol. 28(9), pp. 795-808.

Qin, X et al., "Synthesis, antiviral, and antitumor activity of 2-substitued purine methylenecyclopropane analogues of nucleosides" In: Bioorg. Med. Chem., Feb. 2006, vol. 14, No. 4, pp. 1247-1254.

Wang, R. et al., "Tryptophanyl Phosphoramidates as Prodrigs of Synadenol and Its E-isomer: Synthesis and Biological Activity" In: Bioorg. Med. Chem Lett. Sep. 2002, vol. 12, No. 17, pp. 2467-2470.

Williams, J. D. et al, "Synthesis and antiviral activity of certain second generation methylenecyclopropane nucleosides" In: Bioorg. Med. Chem., May 2012, vol. 20, No. 12, pp. 3710-3718.

Wu, Z. et al. "L-Valine ester of cyclopropavir: a new antiviral prodrug" In: Antivir. Chem. Chemother., Sep. 2009, vol. 20, No. 1, pp. 37-46.

Yan, Z et al., "Nucleotides and Pronucleotides of 2,2-Bis(hydroxymethyl)methylenecyclopropane Analogues of Purine Nucleosides: Synthesis and Antiviral Activity", J. Med hem, 2005, 48, 91-99.

International Search Report Issued on Feb. 5, 2019.

*Primary Examiner* — Shobha Kantamneni
(74) *Attorney, Agent, or Firm* — GORMAN IP LAW, APC; Susan W. Gorman

(57) ABSTRACT

The invention provides a compound of formula (I)

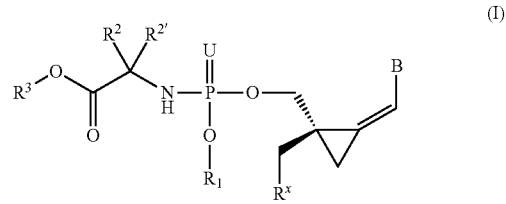

(I)

wherein
B is a nucleobase;
U is O or S;
$R^x$ is $-OC(=O)R^y$, $-OC(=O)CH(R^y)NH_2$, $-OCH_2OC(=O)R^y$;
$R^y$ is optionally substituted alkyl or alkenyl or the side chain of a natural or unnatural amino acid
$R^1$ is H, or optionally substituted phenyl, benzyl, naphthyl, pyridyl or indolyl, or
$R^x$ and $R^1$ together define a bond thus forming a cyclic phosphate;
$R^2$ and $R^{2'}$ together define the side chain of a natural or unnatural amino acid;
$R^3$ is optionally substituted alkyl, cycloalkyl, phenyl or benzyl;
and pharmaceutically acceptable salts and compositions thereof
which are useful in the treatment of cancer, especially leukemias.

26 Claims, No Drawings

CANCER TREATMENT WITH (2,2-BISHYDROXYMETHYL) METHYLENECYCLOPROPANE NUCLEOTIDES

This application is the National Phase Under 35 USC § 371 of PCT International Application No. PCT/SE2019/050209 filed on Mar. 8, 2019, which claims priority under 35 U.S.C. § 119 on Patent Application No. 1850262-5 filed in Sweden on Mar. 9, 2018, and Patent Application No. 1851495-0 filed in Sweden on Nov. 11, 2018, the entire contents of each of which are hereby incorporated by reference.

FIELD OF THE INVENTION

The present invention relates to phosphorus prodrugs of (2,2-bishydroxymethyl) methylenecyclopropane nucleoside analogues and derivatives thereof including the guanine derivative cyclopropavir (CPV), which are useful in the treatment of cancer. The invention further relates to compositions and combinations comprising these compounds, and methods for their use in the treatment of cancers, particularly leukemia.

BACKGROUND TO THE INVENTION

Methylenecyclopropane nucleoside analogues are established antiviral agents effective against various herpesviruses, e.g. cytomegalovirus (CMV) Epstein-Barr virus (EBV) and human herpes virus 6 and 8 (HHV-6 and HHV-8). One such antiviral agent is cyclopropavir, 2,2-bis-(hydroxymethyl) cyclopropylidene methyl guanine (otherwise known as CPV, filociclovir or MBX400), whose synthesis and anti-herpes activity is disclosed in WO2003/104440. CPV is administered as the nucleoside.

Mechanism of action studies have shown that CPV is initially phosphorylated by the viral protein kinase UL97 while conversion of CPV monophosphate (CPV-MP) to CPV diphosphate (CPV-DP) and CPV triphosphate (CPV-TP) can be performed by cellular kinases. CPV is thus only activated to the antivirally active species in cells infected with one of the herpes viruses. CPV completed phase I clinical trials in 2017 in the indication CMV infection.

No cancer activity has previously been disclosed for cyclopropavir or derivatives thereof neither in WO2003/104440 nor in the academic literature or elsewhere, which is understandable given that CPV is only phosphorylated in herpesvirus-infected cells, meaning that the nucleoside CPV is non-toxic to uninfected cells.

Yan et al, J Med Chem, 2005, 48, 91-99 describe attempts to broaden the antiviral spectrum of CPV, using a cyclic phosphate or triester phosphoralininate approach:

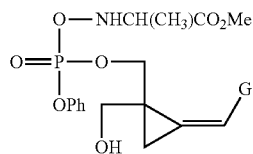

7a

However, Yan discloses that compound 7a above was more than 10-fold less potent against murine and human cytomegalovirus, than the corresponding nucleoside CPV, remembering that CMV infection is the clinical target for CPV. Compound 7a was also inactive against herpes virus 1 and 2, but was substantially equipotent with the parent nucleoside CPV against EBV, although Yan et al qualifies this by stating that the activity is assay-dependent. Clearly compound 7a is not a promising startpoint to develop novel compounds in the oncology indication, where the herpes UL97 kinase will not be present. Additionally, as demonstrated by Comparative Example 1 below, the present patent applicant has established that compounds of the class represented by compound 7a, ie triester phosphoralininates of CPV, are unstable. In solution, they decompose losing approximately a quarter of their integrity within 22 days. A similar phenomenon has been observed, but not yet quantitated, with compounds of this class in solid form.

Yan et al further discloses at page 93, right column, first complete sentence below Table 1, that there was "no evidence for the formation of the cyclic phosphate 26":

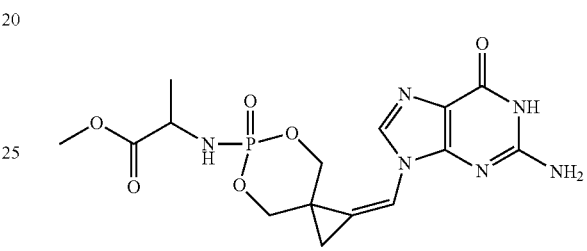

as depicted, and not otherwise synthesized or isolated, in Scheme 5 of Yan et al.

DESCRIPTION OF THE INVENTION

The present invention relates to compounds of the formula I, as defined below, pharmaceutical compositions comprising such compounds and methods of synthesizing the compounds. Thus, in one aspect, the present invention provides a compound by Formula (I):

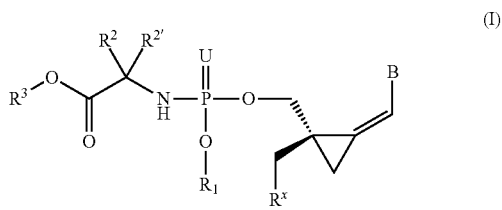

(I)

wherein:

B is a nucleobase selected from the groups (a) to (d):

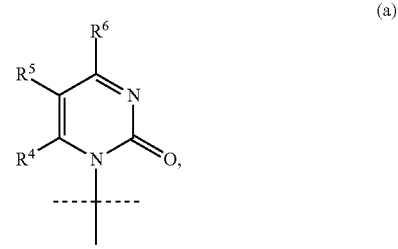

(a)

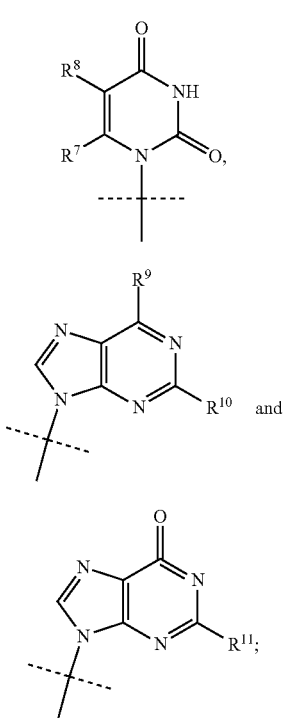

U is O or S;

R$^x$ is —OC(=O)R$^y$, —OC(=O)CH(R$^y$)NH$_2$, —OCH$_2$OC(=O)R$^y$; or

R$^x$ and R$^1$ together define a bond thus forming a cyclic phosphate;

R$^y$ is C$_1$-C$_{20}$alkyl or C$_2$-C$_{20}$alkenyl any of which is optionally substituted with one, two or three substituents each independently selected from fluoro, hydroxy and amino; or R$^y$ is the side chain of a natural amino acid, which may be in the D or L configuration;

R$^1$ is H, or a cyclic group selected from phenyl, benzyl, naphthyl, pyridyl or indolyl, each of which cyclic groups is optionally substituted with one, two or three R$^{22}$; or R$^1$ and R$^x$ together define a bond thus forming a cyclic phosphate;

each R$^{22}$ is independently selected from halo, hydroxy, C$_1$-C$_6$alkyl, C$_3$-C$_6$cycloalkyl, haloC$_1$-C$_6$alkyl, hydroxyC$_1$-C$_6$alkyl, C$_1$-C$_6$alkoxy, haloC$_1$-C$_6$alkoxy, C$_1$-C$_6$alkylcarbonyl, C$_3$-C$_6$cycloalkylcarbonyl, azido, cyano, amino, or any two R$^{22}$ groups attached to adjacent ring carbon atoms can combine to form —O—(CH$_2$)$_{1-2}$—O—, wherein C$_3$-C$_6$cycloalkyl is optionally substituted with C$_1$-C$_3$alkyl;

R$^2$ and R$^{2'}$ are each independently selected from H, C$_1$-C$_6$alkyl, C$_3$-C$_7$cycloalkyl, C$_3$-C$_7$cycloalkylC$_1$-C$_3$alkyl, phenyl, benzyl and indolyl; or R$^2$ and R$^{2'}$ together with the carbon atom to which they are attached form a C$_3$-C$_7$cycloalkylene group;

wherein each C$_1$-C$_6$alkyl is optionally substituted with halo or OR$^{12}$, and each C$_3$-C$_7$cycloalkyl, C$_3$-C$_7$cycloalkylene, phenyl and benzyl is optionally substituted with one or two groups independently selected from C$_1$-C$_3$alkyl, halo and OR$^{12}$; or one of R$^2$ and R$^{2'}$ is H, and the other is the side chain of a natural amino acid; wherein the carboxy terminus of an Asp or Glu is optionally esterified with C$_1$-C$_6$alkyl;

R$^3$ is C$_1$-C$_{10}$alkyl, C$_3$-C$_7$cycloalkyl, C$_1$-C$_3$alkylC$_3$-C$_7$cycloalkyl, phenyl or benzyl; any of which is optionally substituted with 1, 2 or 3 substituents each independently selected from halo, hydroxy, C$_1$-C$_6$alkoxy, C$_1$-C$_6$haloalkoxy and N(R$^{12}$)$_2$;

R$^4$, R$^5$, R$^7$ and R$^8$ are each independently H, C$_1$-C$_6$alkyl, C$_1$-C$_6$haloalkyl, C$_1$-C$_6$hydroxyalkyl, halo, —OR$^{12}$ or —N(R$^{12}$)$_2$;

R$^6$, R$^9$, R$^{10}$ and R$^{11}$ are each independently H, C$_1$-C$_6$alkyl, C$_2$-C$_6$alkenyl, C$_2$-C$_6$alkynyl, C$_3$-C$_7$cycloalkyl, C$_1$-C$_6$haloalkyl, C$_1$-C$_6$hydroxyalkyl, halo, OR$^{12}$, —N(R$^{12}$)$_2$, —NHC(O)OR$^{12}$, cyano, —C(O)OR$^{12}$, —C(O)N(R$^{12}$)$_2$ or —NHC(O)R$^{13}$, wherein C$_2$-C$_6$alkenyl and C$_2$-C$_6$alkynyl is optionally substituted with halo or C$_3$-C$_5$cycloalkyl;

each R$^{12}$ is independently H, C$_1$-C$_6$alkyl, haloC$_1$-C$_6$alkyl, C$_3$-C$_7$cycloalkyl or C$_1$-C$_6$alkylC$_3$-C$_7$cycloalkyl;

R$^{13}$ is R$^{12}$ or CH$_2$CH(NH$_2$)C(=O)OH;

or a pharmaceutically acceptable salt thereof, with the proviso that the compound is not

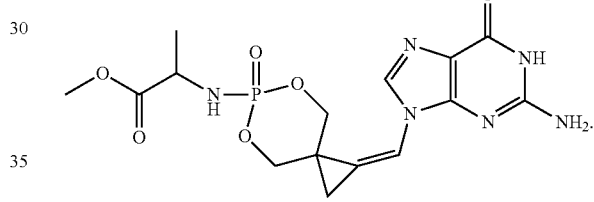

The compounds of Formula (I) may optionally be provided in the form of a pharmaceutically acceptable salt and/or solvate. In one aspect, the invention provides a compound of formula (I) in the form of a pharmaceutically acceptable salt. In another aspect, the invention provides the compound of formula (I) in the form of a pharmaceutically acceptable solvate. In another aspect, the invention provides the compound of formula (I) in its free form.

In a typical embodiment of the invention, the nucleobase B is the group (d):

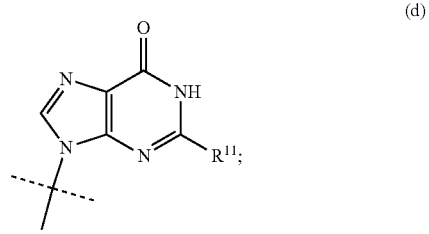

wherein

R$^{11}$ is NH$_2$ or NHCOC$_1$-C$_6$alkyl, especially guanine.

In an alternative embodiment of the invention, the nucleobase B is the group (c):

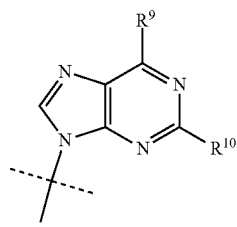

wherein R⁹ is $C_1$-$C_6$alkoxy, $C_1$-$C_6$cycloalkoxy, $C_1$-$C_6$alkylamine or $C_3$-$C_6$cycloalkylamine, and $R^{10}$ is $NH_2$ or $NHCOC_1$-$C_6$alkyl.

In an alternative embodiment of the invention, the nucleobase B is the group (c):

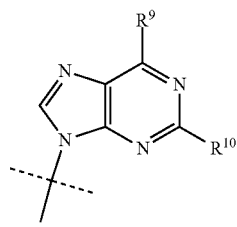

wherein $R^9$ is H and and $R^{10}$ is $NH_2$.

In an alternative embodiment of the invention, the nucleobase B is cytosine or 5-fluorocytosine within group (a):

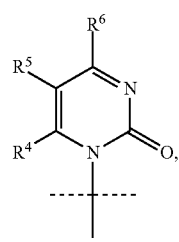

wherein: $R^4$ is H,
$R^5$ is F or H, and
$R^6$ is $NH_2$,

Certain embodiments of the invention have $R^1$ as H.

Other embodiments of the invention have $R_1$ as phenyl which is optionally substituted with one or two $R^{22}$, and each $R^{22}$ is independently selected from halo, $C_1$-$C_3$alkyl, $C_3$-$C_4$cycloalkyl, halo-$C_1$-$C_3$alkyl, $C_1$-$C_3$alkoxy, halo$C_1$-$C_3$alkoxy, $C_1$-$C_3$alkylcarbonyl, $C_3$-$C_4$cycloalkylcarbonyl, wherein $C_3$-$C_4$cycloalkyl is optionally substituted with methyl;

An embodiment of the invention has $R_1$ as phenyl, substituted in the 4-position with Br. An alternative embodiment has unsubstituted phenyl as $R_1$.

In certain embodiments, the —O—C(=O)—CR2'(R2)-NH— moiety within formula I represents an L-, or a D- or a DL-amino acid bearing any of the side chains of the natural amino acids, such as glycine, alanine, valine, leucine, isoleucine, serine, threonine, phenylalanine, tyrosine, tryptophan, asparagine or glutamine. The carboxy terminus of an Asp or Glu side chain is optionally esterified with $C_1$-$C_6$alkyl, for example with the same alkyl as $R^3$.

Certain embodiments of the invention have $R^{2'}$ as H and $R^2$ is $C_1$-$C_6$alkyl or halo$C_1$-$C_6$alkyl, such as t-butyl, n-butyl or the side chain of fluoroleucine.

In certain embodiments, the stereochemistry is as indicated in the partial formula:

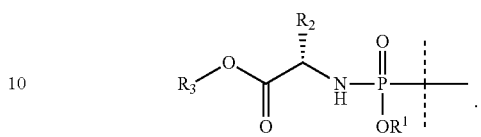

Especially, wherein $R^2$ is methyl.

An embodiment of the invention has $R^3$ as $C_1$-$C_{10}$alkyl, preferably methyl, isopropyl, 2-propylpentyl or 2-ethylbutyl.

Alternative embodiments of the invention have $R^3$ as benzyl or $C_3$-$C_7$cycloalkyl, such as cyclopentyl or cyclohexyl Certain embodiments of the invention have $R^x$ as —OC(=O)$C_1$-$C_6$alkyl, preferably wherein the $C_1$-$C_6$alkyl moiety is methyl, isopropyl, isobutyl or t-butyl.

Still further embodiments of the invention have $R^x$ as —OC(=O)$C_1$-$C_{20}$alkyl, preferably —OC(=O)$C_{17}$alkyl, such as cetoyl, stearoyl or eicosoyl.

In alternative embodiments, $R^x$ is —OC(=O)CH($R^y$)$NH_2$ wherein $R^y$ is the side chain of a natural amino acid, such as isoleucine, leucine and preferably valine, and the configuration at the chiral center to which R is attached is that of an L-amino acid.

In alternative embodiments of the invention, $R^x$ is —$OCH_2OC(=O)CH_3$ or —$OCH_2OC(=O)C(CH_3)_3$, preferably —$OCH_2OC(=O)C(CH_3)_3$.

In favoured embodiments of the invention, U is O.

Specific embodiments of the invention include:

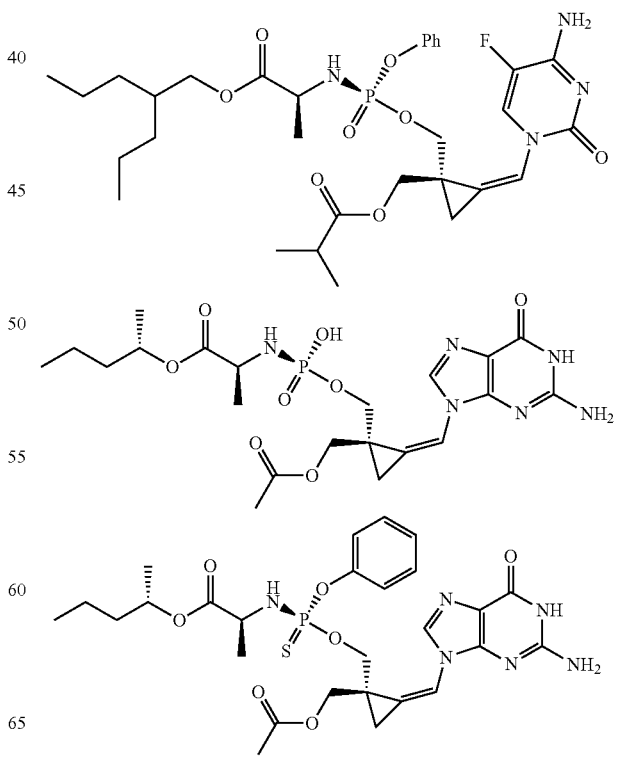

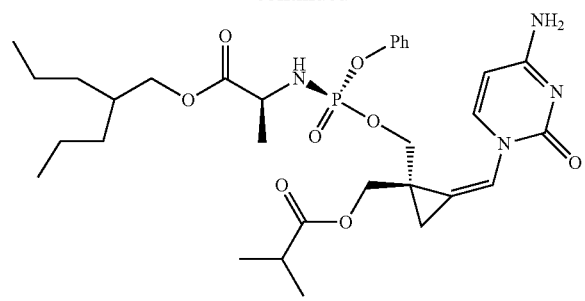
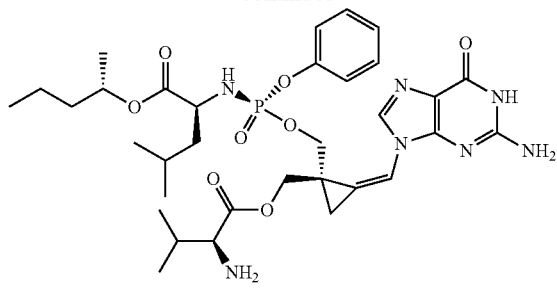
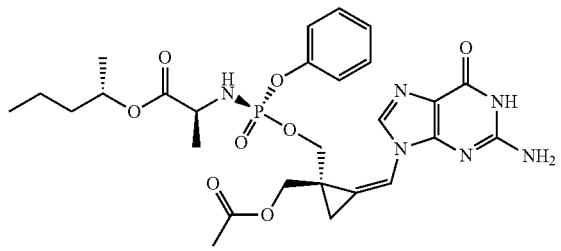
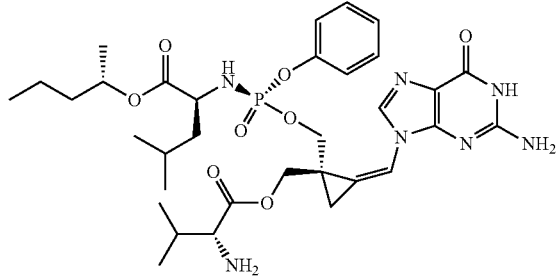
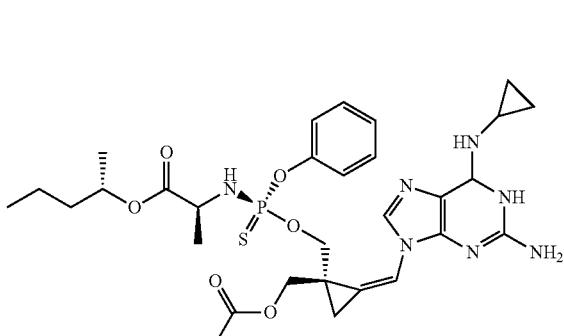
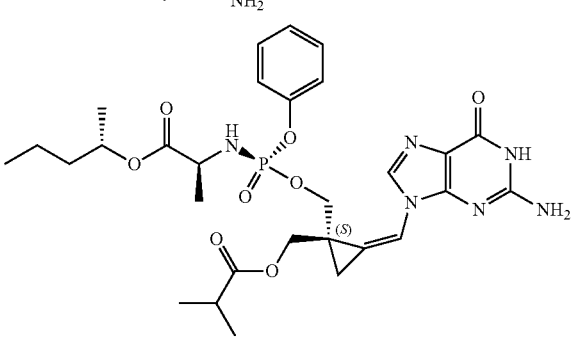
and pharmaceutically acceptable salts thereof.
Further specific embodiments of the invention include:
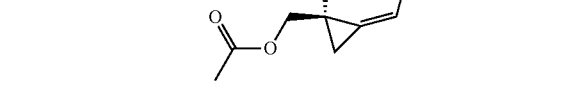
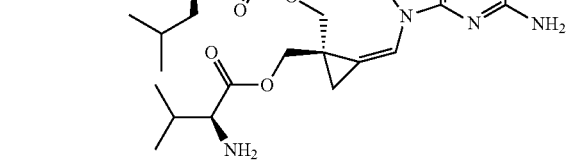
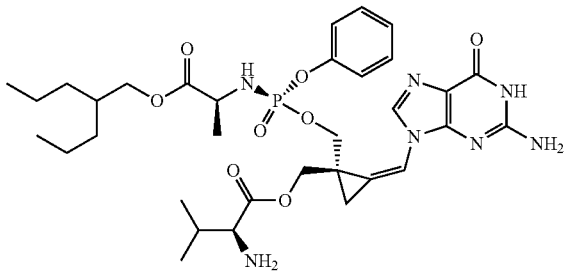
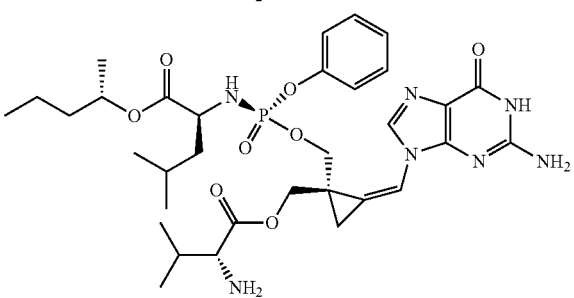
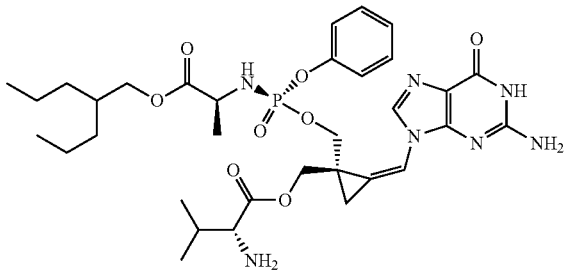
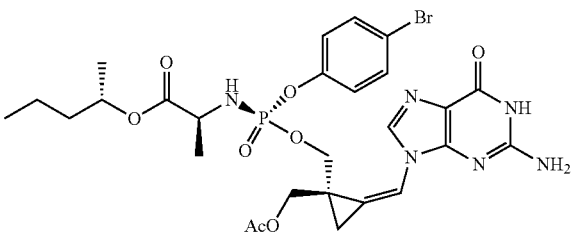

-continued
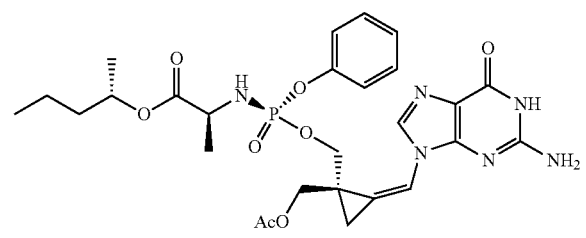
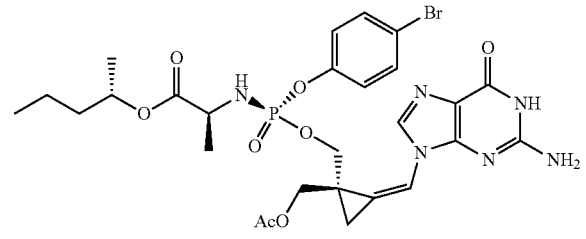
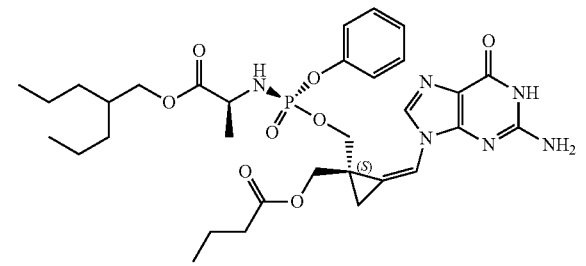
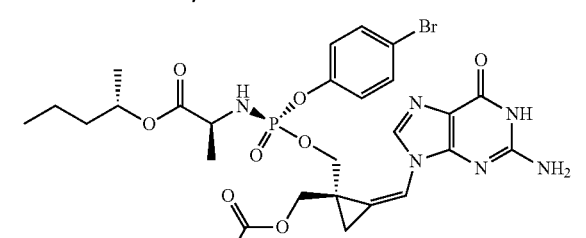
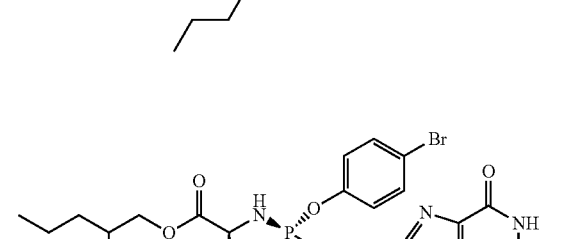
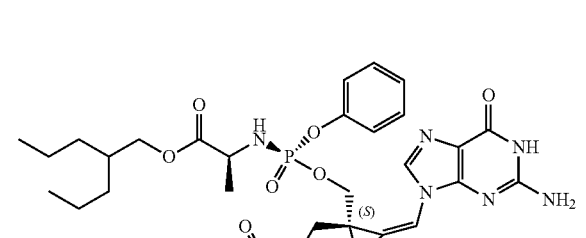
-continued
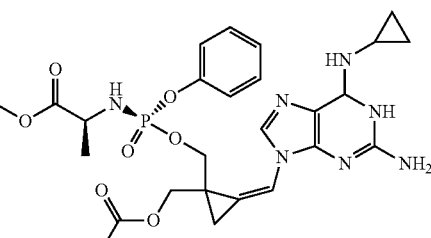
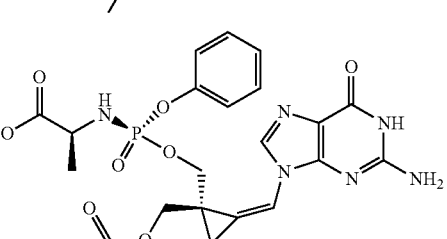
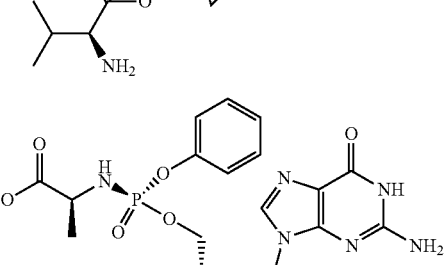
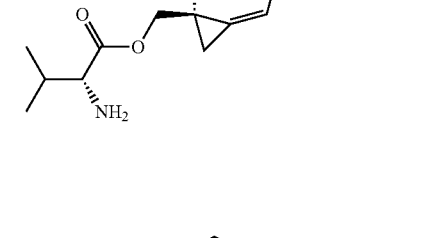
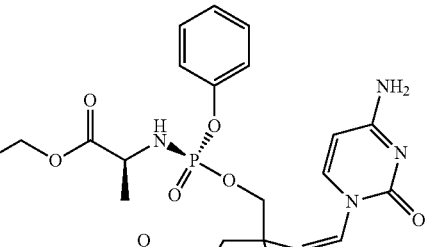
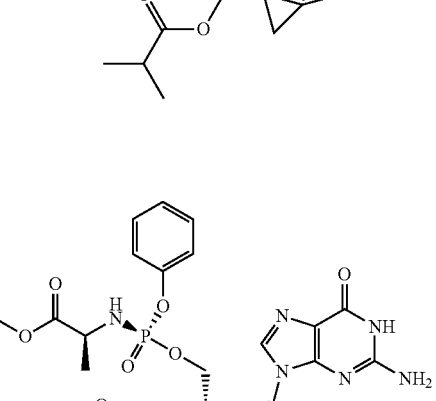

-continued
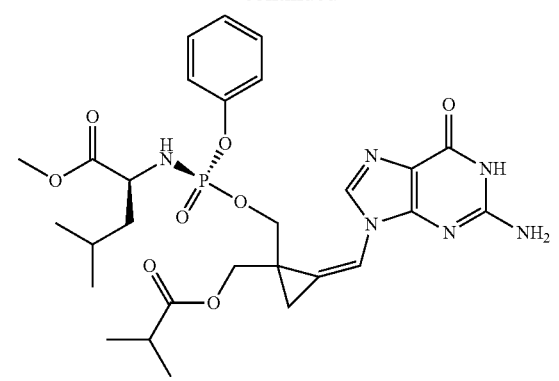
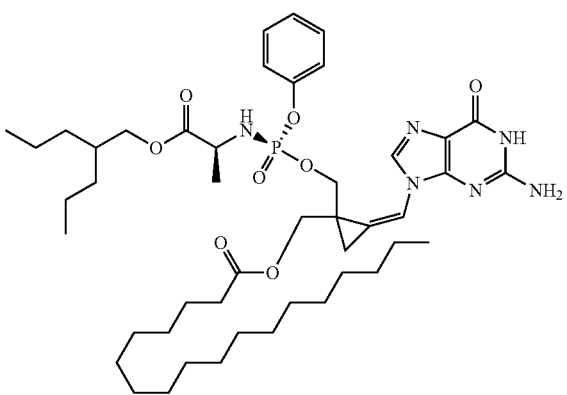
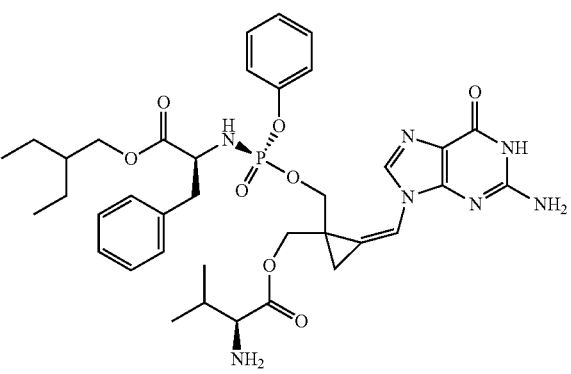
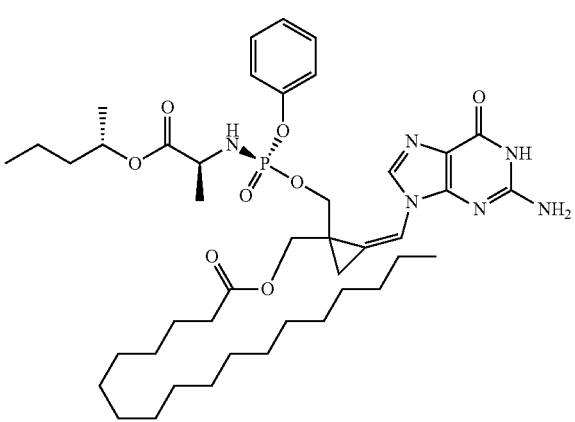
-continued
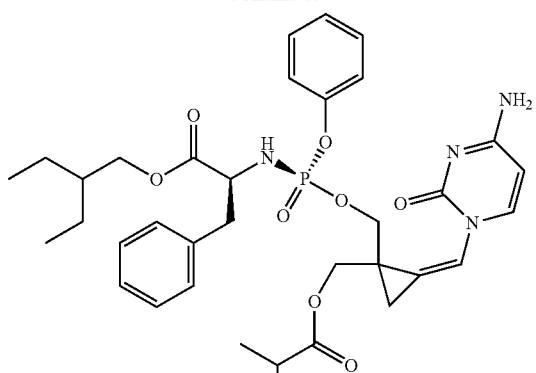
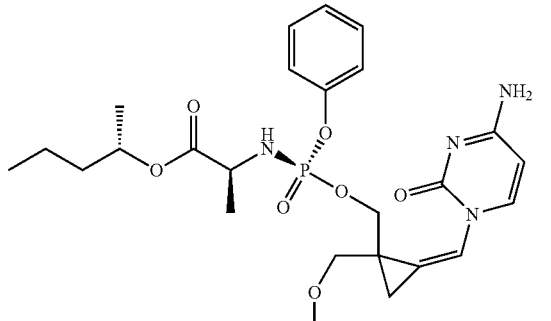
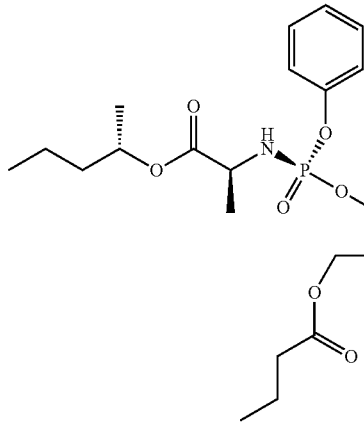
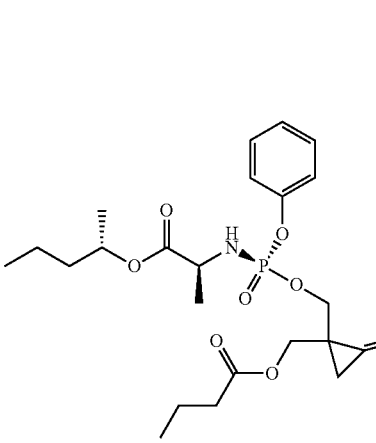

-continued
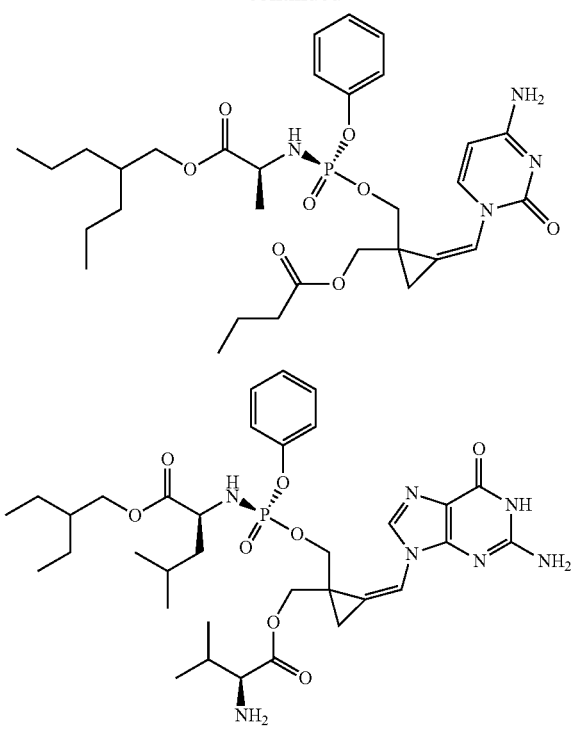
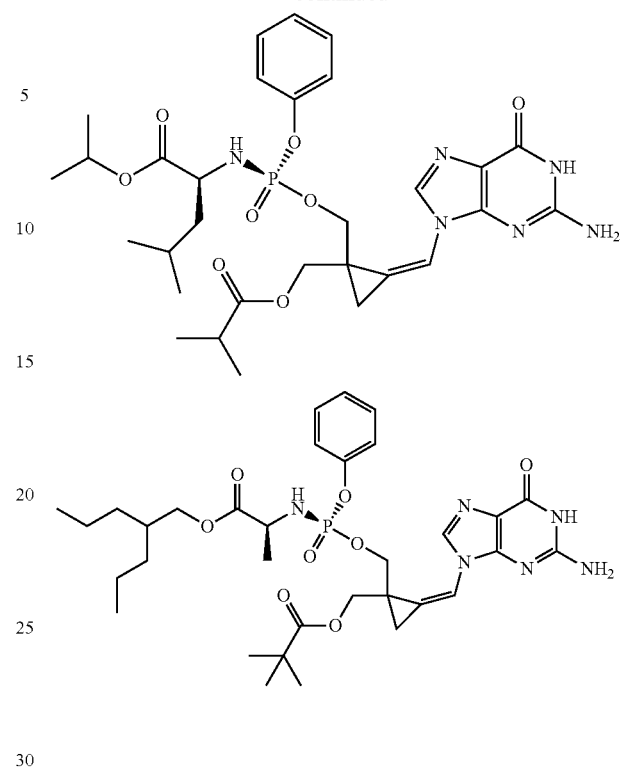
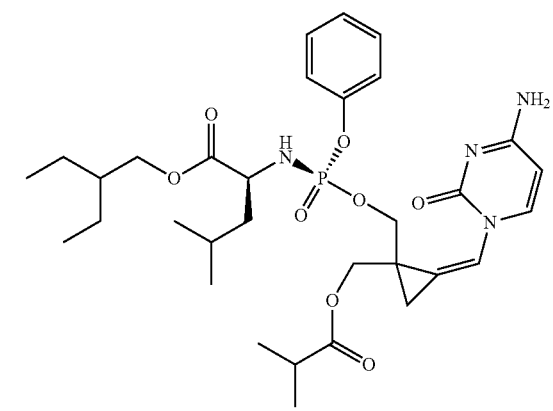
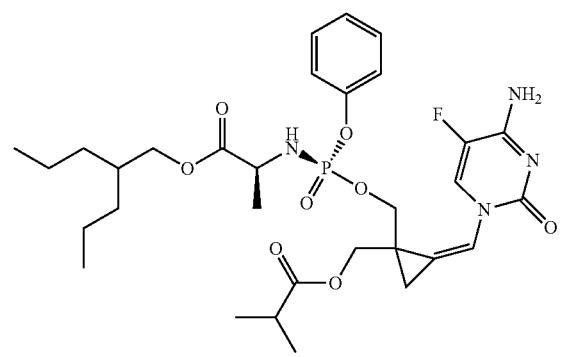
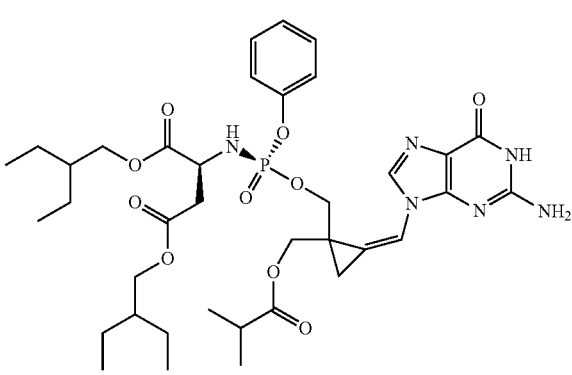

-continued

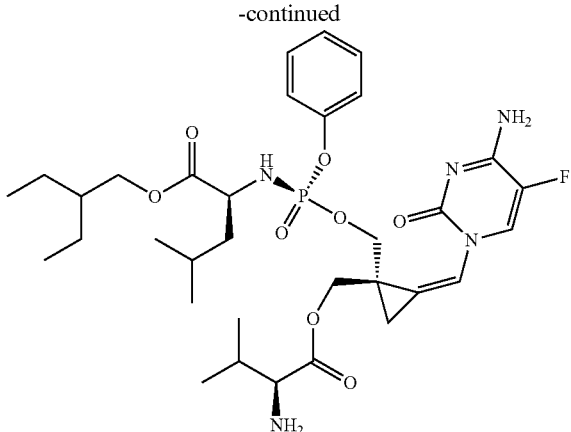

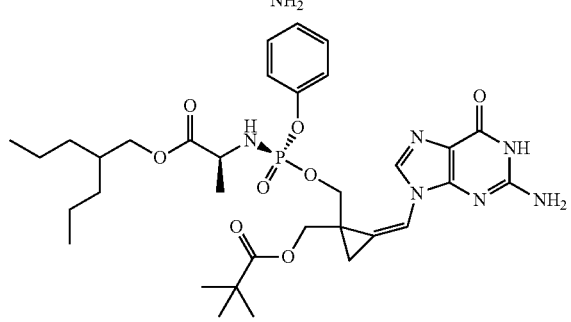

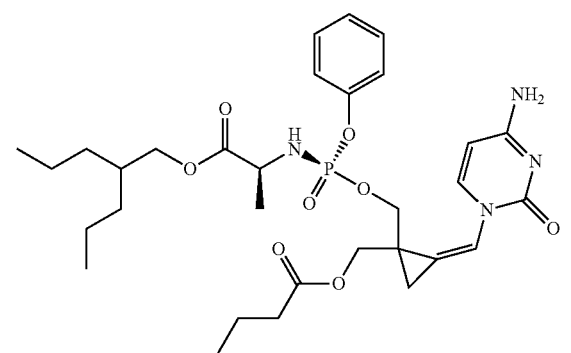 [SMILES: CCCC(=O)OCC1(CO[P@@](=O)(N[C@@H](C)C(=O)OCC(CCC)CCC)Oc2ccccc2)C/C1=C/n1ccc(N)nc1=O]

and pharmaceutically acceptable salt thereof.
A specific embodiment of the invention has the formula:

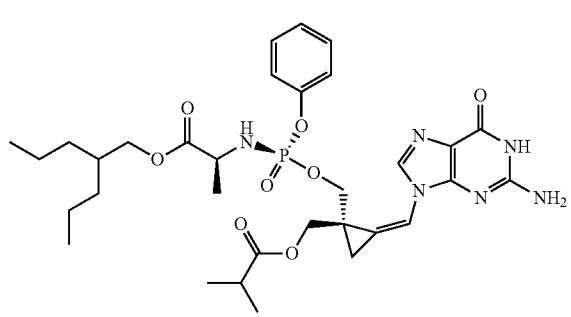 [SMILES: CCCC(CCC)COC(=O)[C@H](C)N[P@](=O)(OC[C@@]1(COC(=O)C(C)C)C/C1=C/n1cnc2c(=O)[nH]c(N)nc21)Oc1ccccc1]

and pharmaceutically acceptable salts thereof.

A specific embodiments of the invention has the formula:

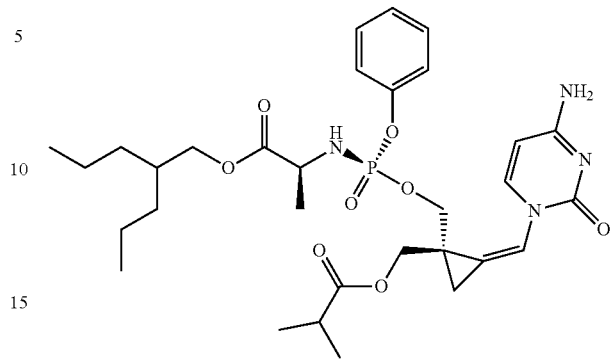

and pharmaceutically acceptable salts thereof.
A specific embodiment of the invention has the formula:

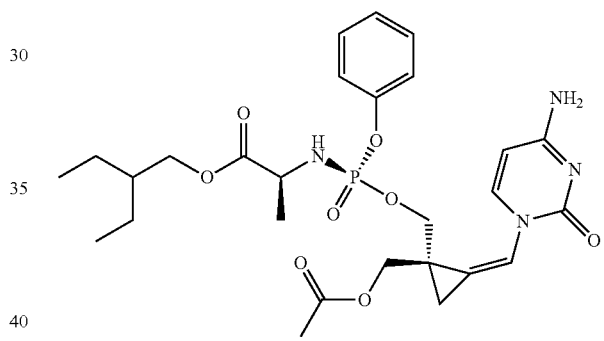

and pharmaceutically acceptable salts thereof.
A specific embodiment of the invention has the formula:

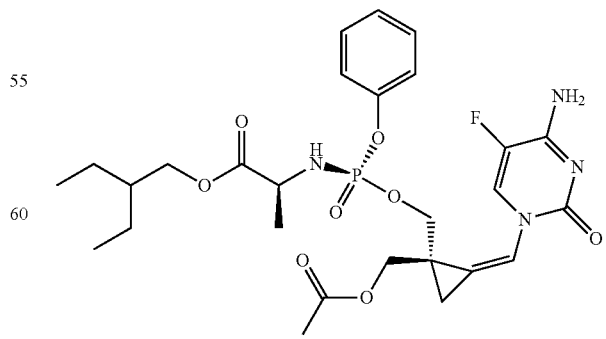

and pharmaceutically acceptable salts thereof.

A specific embodiment of the invention has the formula:

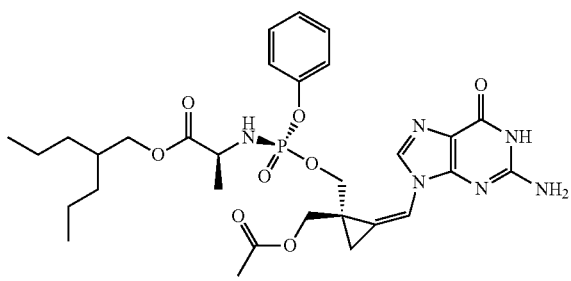 [SMILES: CCCC(CCC)COC(=O)[C@H](C)N[P@](=O)(OC[C@@]1(COC(C)=O)C/C1=C/n1cnc2c(=O)[nH]c(N)nc21)Oc1ccccc1]

and pharmaceutically acceptable salts thereof.

The compounds of the present invention show activity against cancer, especially leukemias of the lymphocytic and myelogenous types, and can be used as medicine in the treatment of warm-blooded animals, particularly humans, having such cancers. Lymphocytic cancers to which the invention may be applied include acute lymphoblastic leukemia (ALL) or chronic lymphocytic leukemia (CLL). Myelogenous leukemias to which the invention may be applied include acute myelogenous leukemia (AML), myeloblastic leukemia, and chronic myelogenous leukemia (CML), including chronic myelomonocytic. Other leukemias include hairy cell leukemia (HCL) and juvenile myelomonocytic leukemia.

Whenever used foregoing and hereinafter, the term 'compounds of Formula (I)', or 'a compound of the invention", or "a compound of the present invention" or similar terms, it is meant to include a compound of Formula (I), its pharmaceutically acceptable prodrugs, salts, solvates, quaternary amines, stereoisomers and tautomers and metal complexes.

Another aspect of the present invention provides a pharmaceutical composition comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant. Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In another aspect, the invention provides a compound of Formula (I), or a pharmaceutically acceptable salt, hydrate, solvate, prodrug, stereoisomer, or tautomer thereof, for use as a medicament, especially in the treatment of cancer such as leukemias.

In another aspect, the invention provides a compound of Formula (I), or a pharmaceutically acceptable salt, hydrate, solvate, prodrug, stereoisomer, or tautomer thereof, for use in the treatment or prevention of cancer, especially in the treatment of cancer such as leukemias.

In one aspect, the compounds of the invention are administered in therapeutically effective amounts in a combination therapy with one or more therapeutic agents (pharmaceutical combinations) or modalities, e.g. non-drug therapies. For example, synergistic effects can occur with other antiproliferative, anti-cancer, immunomodulatory or anti-inflammatory substances. Where the compounds of the invention are administered in conjunction with other therapies, dosages of the co-administered compounds will vary depending on the type of co-drug employed, on the specific drug employed, on the condition being treated and so forth.

Combination therapy according to the invention includes administration of a compound of the invention in combination with one or more other biologically active ingredient, including but not limited to, a second and different antineoplastic agent or a second agent that targets DNA repair and non-drug therapies, including but not limited to, surgery or radiation treatment. For instance, the compounds of the invention can be used in combination with other pharmaceutically active compounds, preferably compounds that are able to enhance the effect of the compounds of the invention. The compounds of the invention can be administered simultaneously or sequentially to the other drug therapy or treatment modality, e.g. as a single preparation or a separate preparation. In general, a combination therapy envisions administration of two or more drugs during a single cycle or course of therapy.

In one embodiment, the invention provides a method of enhancing the chemotherapeutic treatment of cancer in a mammal undergoing treatment with an anti-cancer agent, which method comprises co-administering to the mammal an effective amount of a compound of the invention. In certain embodiments, the anti-cancer agent is a DNA damaging agent. The DNA damaging agent can be any suitable DNA damaging agent. Non-limiting examples of suitable DNA damaging agents include DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, tenyposide, triethylenethiophosphoramide and etoposide. In a preferred embodiment, the DNA damaging agent is cisplatin. The DNA damaging agent can also be radiation or a biotherapeutic agent such as antibody.

In certain embodiments, the DNA damaging agent can be radiation, such as radiation that induces a DNA cross-linking in a cell when applied to the cell. DNA cross-linking radiation includes ionizing radiation and ultraviolet (UV) radiation. Ionizing radiation consist of subatomic particles or electromagnetic waves that are sufficiently energetic to cause ionization by detaching electrons from atoms or molecules. Ionization depends on the energy of the impinging individual particles or waves. In general, ionizing particles or photons with energies above a few electron volts can be ionizing. Non-limiting examples of ionizing particles are alpha particles, beta particles, and neutrons. The ability of photons to ionize an atom or molecule depends on its frequency. Short-wavelength radiation such as high frequency ultraviolet, x-rays, and gamma rays, is ionizing. Ionizing radiation comes from radioactive materials, x-ray tubes, and particle accelerators.

In some embodiments, administration of a compound of Formula (I) or a pharmaceutical composition comprising a compound of the present invention and a pharmaceutically acceptable carrier induces a change in the cell cycle or cell viability.

The method of the invention may additionally comprise administering to the subject a further therapeutic agent. The further therapeutic agent may preferably be:
(i) an additional immunomodulatory agent which blocks or inhibits an immune system checkpoint; and/or
(ii) an agent which directly stimulates an immune effector response, such as a cytokine or chemokine (or an agent which stimulates production of either), a tumour specific adoptively transferred T cell population, or an antibody specific for a protein expressed by a tumour cell; and/or (iii) a composition comprising a tumour antigen or immunogenic fragment thereof; and/or (iv) a chemotherapeutic agent; and/or (v) radiation.

The compound of the invention may be administered either simultaneously with, or before or after, the further therapeutic agent. The compound of the invention may be administered separately, by the same or different route of administration, or together in the same pharmaceutical composition as the further therapeutic agent.

Examples of immune system checkpoints include:

a) The interaction between Indoleamine 2,3-dioxygenase (IDO1) and its substrate;

b) The interaction between PD1 and PDL1 and/or PD1 and PDL2;

c) The interaction between CTLA4 and CD86 and/or CTLA4 and CD80;

d) The interaction between B7-H3 and/or B7-H4 and their respective ligands;

e) The interaction between HVEM and BTLA;

f) The interaction between GAL9 and TIM3;

g) The interaction between MHC class I or II and LAG3; and h) The interaction between MHC class I or II and KIR i) The interaction between OX40(CD134) and OX40L (CD252)

k) The interaction between CD40 and CD40L (CD154)

l) The interaction between 4-1BB (CD137) and ligands including 4-1BBL m) The interaction between GITR and ligands including GITRL A preferred checkpoint for the purposes of the present invention is checkpoint (b), namely the interaction between PD1 and either of its ligands PD-L1 and PD-L2. PD1 is expressed on effector T cells. Engagement with either ligand results in a signal which downregulates activation. The ligands are expressed by some tumours. PD-L1 in particular is expressed by many solid tumours, including melanoma. These tumours may therefore down regulate immune mediated anti-tumour effects through activation of the inhibitory PD-1 receptors on T cells. By blocking the interaction between PD1 and one or both of its ligands, a checkpoint of the immune response may be removed, leading to augmented anti-tumour T cell responses. Therefore, PD1 and its ligands are examples of components of an immune system checkpoint which may preferably be targeted in combination with the invention.

Another preferred checkpoint for the purposes of combining with the invention is checkpoint (c), namely the interaction between the T cell receptor CTLA-4 and its ligands, the B7 proteins (B7-1 and B7-2). CTLA-4 is ordinarily upregulated on the T cell surface following initial activation, and ligand binding results in a signal which inhibits further/continued activation. CTLA-4 competes for binding to the B7 proteins with the receptor CD28, which is also expressed on the T cell surface but which upregulates activation. Thus, by blocking the CTLA-4 interaction with the B7 proteins, but not the CD28 interaction with the B7 proteins, one of the normal check points of the immune response may be removed, leading to augmented anti-tumour T cell responses. Therefore CTLA4 and its ligands are examples of components of an immune system checkpoint which may preferably be targeted in conjunction with the invention.

Immunomodulatory Agent

An "immunomodulatory agent" is used herein to mean any agent which, when administered to a subject, blocks or inhibits the action of an immune system checkpoint, resulting in the upregulation of an immune effector response in the subject, typically a T cell effector response, which preferably comprises an anti-tumour T cell effector response.

The immunomodulatory agent used in the method of the present invention may block or inhibit any of the immune system checkpoints described above. The agent may be an antibody or any other suitable agent which results in said blocking or inhibition. The agent may thus be referred to generally as an inhibitor of a said checkpoint.

An "antibody" as used herein includes whole antibodies and any antigen binding fragment (i.e., "antigen-binding portion") or single chains thereof. An antibody may be a polyclonal antibody or a monoclonal antibody and may be produced by any suitable method. Examples of binding fragments encompassed within the term "antigen-binding portion" of an antibody include a Fab fragment, a F(ab')2 fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody.

Preferred antibodies which block or inhibit the CTLA-4 interaction with B7 proteins include ipilumumab, tremelimumab, or any of the antibodies disclosed in WO2014/207063. Other molecules include polypeptides, or soluble mutant CD86 polypeptides. Ipilumumab is most preferred.

Preferred antibodies which block or inhibit the PD1 interaction with PD-L1 include Nivolumab, Pembrolizumab, Lambrolizumab, Pidilzumab, BGB-A317 and AMP-224. Nivolumab or pembrolizumab is most preferred. Anti-PD-L1 antibodies include atezolizemab, avelumab or durvalumab, MEDI-4736 and MPDL3280A.

Preferred antibodies which block or inhibit the interaction between 4-1BB and its ligand include utomilumab.

Other suitable inhibitors include small molecule inhibitors (SMI), which are typically small organic molecules. Preferred inhibitors of IDO1 include Epacadostat (INCB24360), Indoximod, GDC-0919 (NLG919) and F001287. Other inhibitors of IDO1 include 1-methyltryptophan (1MT).

Direct Stimulation of Immune Effector Responses

As used herein, "an agent which directly stimulates an immune effector response" means any suitable agent, but typically refers to a cytokine or chemokine (or an agent which stimulates production of either), a tumour specific adoptively transferred T cell population, or an antibody specific for a protein expressed by a tumour cell.

The cytokine may be an interferon selected from IFNα, IFNβ, IFNγ and IFNλ, or an interleukin, preferably IL-2. The chemokine may be an inflammatory mediator, for example selected from CXCL9, 10, and 11, which attract T cells expressing CXCR3. The agent which stimulates production of a cytokine or chemokine may be an adjuvant suitable for administration to humans. A preferred example is Bacille Calmette-Guerin (BCG), which is typically administered intravesically (i.e. urethral catheter) for treatment of bladder cancer. A typical dosage regime of BCG for bladder cancer is once per week for six weeks, but given its long safety history it is also administered indefinitely as maintenance. BCG has been shown to stimulate immune responses to bladder cancer. BCG has also been used as an adjuvant in combination with compositions which comprise tumour antigens (i.e. with cancer vaccines), particularly for colon cancer when it is administered typically intradermally. Such uses of BCG are also envisaged in the present invention.

Administration of the compounds of the invention can be accomplished via any mode of administration of therapeutic agents. including systemic or local administration such as oral, nasal, parenteral, transdermal, subcutaneous, vaginal, buccal, rectal or topical administration modes. In one embodiment, the administering is performed orally, parentally, subcutaneously, by injection or by infusion.

Depending on the intended mode of administration, the disclosed compositions can be in solid, semi-solid or liquid dosage form, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. The compositions can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the invention and a pharmaceutically acceptable carrier, such as
- a) a diluent, e.g. purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine;
- b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also;
- c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired;
- d) a disintegrant, e.g., starches, agar, methyl cellulose, bentonite, xanthan gum, algic acid or its sodium salt, or effervescent mixtures;
- e) absorbent, colorant, flavorant and sweetener;
- f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or
- g) an agent that enhances absorption of the compound such as cyclodextrin, hydroxypropyl-cyclodextrin, PEG400, and PEG200.

Liquid, particularly injectable, compositions can, for example, be prepared by dissolution, dispersion, etc. For example, the compound of the invention is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The compounds of the invention can be also formulated as a suppository that can be prepared from fatty emulsions or suspensions using polyalkylene glycols such as propylene glycol, as the carrier.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

The compounds of the invention can also be delivered by the use of monoclonal antibodies as individual carriers to which the disclosed compounds are coupled. The compounds of the invention can also be coupled with soluble polymers as targetable drug carriers. Such polymers can include polyvinylpyrrolidone, pyran copolymer, polyhydroxypropylmethacrylamide-phenol, polyhydroxyethyl-aspanamidephenol, or polyethyleneoxidepolylysine substituted with palmitoyl residues. Furthermore, the compounds of the invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

The dosage regimen utilizing the compounds of the invention is selected in accordance with a variety of factors including type, species, age, sex and medical condition of the patient, the nature of the condition to be treated, the route of administration, the renal or hepatic function of the patient and the particular compound employed. A physician or veterinarian of ordinary skill in the art can readily determine and prescribe the effective amount of the drug required to prevent, counter or arrest the progress of the condition.

Effective dosage amounts of the compounds of the invention in compositions for in vivo or in vitro use for the indicated effects, range from about 0.5 mg to about 5000 mg of the compound, such as 0.5, 5, 20, 50, 75, 100, 150, 250, 500, 750, 1000, 1250, 2500, 3500, or 5000 mg of the compound, or, in a range of from one amount to another amount. In general however a suitable dose may be in the range of from about 0.005 to about 30 mg/kg of body weight per day, preferably in the range of 0.05 to 20 mg/kg/day. The desired dose is conveniently presented in a single dose or as divided dose administered at appropriate intervals, for example as two, three, four or more doses per day. Dependent on the need of the treatment and/or prevention, the desired dose may also be, for example, once every two days, once every three days, or even once a week.

The compound is conveniently administered in unit dosage form; for example containing 0.5 to 1500 mg, conveniently 1 to 1000 mg, most conveniently 5 to 700 mg of active ingredient per unit dosage form.

The compounds of the invention will normally be administrated via the oral, parenteral, intravenous, intramuscular, subcutaneous or other injectable ways, buccal, rectal, vaginal, transdermal and/or nasal route and/or via inhalation, in the form of pharmaceutical preparations comprising the active ingredient or a pharmaceutically acceptable salt or prodrug or solvate thereof, or a solvate of such a salt, in a pharmaceutically acceptable dosage form. Depending upon the disorder and patient to be treated and the route of administration, the compositions may be administered at varying doses.

There is also provided pharmaceutically acceptable salts of the compounds of Formula (I) of the present invention. By the term "a pharmaceutically acceptable salt" is meant a salt derived from a pharmaceutically acceptable inorganic and organic acid or base. A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quarternary ammonium ion, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R, 2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine, arginine and the like.

The present invention includes unlabelled compounds as well compounds wherein one or more of the atom(s) is/are replaced by an isotope of that atom(s), i.e. an atom having the same atomic number but an atomic mass different from the one(s) typically found in nature. Examples of isotopes that may be incorporated into the compounds of the invention, include but are not limited to isotopes of hydrogen, such as $^{2}H$ (deuterium, also denoted D) and $^{3}H$ (tritium, also denoted T), carbon, such as $^{11}C$, $^{13}C$ and $^{14}C$, nitrogen, such as $^{13}N$ and $^{15}N$, oxygen, such as $^{15}O$, $^{17}O$ and $^{18}O$, phosphorus, such as $^{31}P$ and $^{32}P$, fluorine, such as $^{18}F$, chlorine, such as $^{36}Cl$ and bromine such as $^{75}Br$, $^{76}Br$, $^{77}Br$ and $^{12}Br$. Isotopically labelled compounds include for example those wherein radioactive isotopes, such as $^{3}H$ and $^{14}C$ are present, or those wherein non-radioactive isotopes, such as $^{2}H$ and $^{13}C$ are present.

The choice of isotope included in an isotope-containing compound will depend on the specific application of that compound. For example, for drug or substrate tissue distribution assays or in metabolic studies compounds wherein a radioactive isotope such as $^{3}H$ or $^{14}C$ is incorporated, will generally be most useful. For radio-imaging applications, for example positron emission tomography (PET) a positron emitting isotope such as $^{11}C$, $^{18}F$, $^{13}N$ or $^{15}O$ will be useful. The incorporation of a heavier isotope, such as deuterium, i.e. $^{2}H$, may provide certain therapeutic advantages resulting from greater metabolic stability to a compound of the invention, which may result in, for example, an increased in vivo half-life of the compound, reduced dosage requirements or an improvement in therapeutic index.

Isotopically-labelled compounds of formula (I) or any subgroup thereof can generally be prepared by conventional techniques known to those skilled in the art or by processes analogous to those described in the Schemes and/or Examples herein by using the appropriate isotopically-labelled reagents or starting material instead of the corresponding non-isotopically-labelled reagent or starting material.

Pharmaceutically acceptable solvates include those wherein the solvent of crystallization may be isotopically substituted, e.g. $D_2O$, $d_6$-acetone, $d_6$-DMSO.

Where tautomers exist in the compounds of the invention and pharmaceutically acceptable salts, hydrates, solvates, stereoisomers and prodrugs thereof, all individual tautomeric forms and combinations thereof are meant to be within the scope of the invention as individual specific embodiments.

The presence of one or more chiral center(s) in a compound of the invention can give rise to stereoisomers. Consequently, a compound of the invention having one or more chiral center(s) may be present as a mixture of stereoisomers, in racemic or in enantiomerically enriched form, i.e. each chiral centre may have the (R)-, (S)- or (R,S)-configuration. At each chiral center the ratio of the two configurations is preferably at least 75/25, at least 80/20, at least 85/15, at least 90/10, at least 98/2 or at least 99.5/0.5. In embodiments of the invention where the compounds are enantiomers, the enantiomeric excess is at least 50%, at least 60%, at least 70%, at least 80%, at least 95% or at least 99%. Compounds of the invention having two or more chiral centers may in addition be epimers or diastereomers respectively, i.e. have different stereochemistry at one or more steric centres. Substituents at atoms with unsaturated double bonds may, if possible, be present in cis-(Z)- or trans-(E)-form. Unless the stereochemistry is clearly defined by the chemical structures, in each case the invention is to be understood to extend to all such stereoisomers, both in pure form and mixed with each other, including enantiomers, epimers, diastereomers, and mixtures including racemic mixtures thereof.

Accordingly, all isomeric forms of the compounds of the invention are meant to be within the scope of the invention, including all possible isomers, rotamers, atropisomers, tautomers, cis and trans isomers, diastereomers, optical isomers, racemates and mixtures thereof. If a compound contains a double bond, the substituent may be in the E or Z configuration.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, followed by liberation of the optically active acidic or basic compound. In particular, a basic moiety may be used to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase or by Supercritical Fluid Chromatography (SFC).

It will be appreciated that the compounds of formula (I) may have metal binding, chelating or complex forming properties and therefore may exist as metal complexes or metal chelates.

Such metalated derivatives of the compounds of formula (I) are intended to be included within the scope of the invention.

The scientific and technological terms and nomenclatures used in the foregoing and hereinafter have the same meaning as commonly understood by a person of ordinary skill in the art, in addition, the following definitions shall apply throughout the specification and the appended claims unless specifically stated otherwise.

The sign "-" is sometimes added to clarify which bond serves as a connection point. For example, RO— represents a radical wherein R is bonded to an oxygen atom and the said oxygen atom is at the connecting point for the whole radical, similarly, —C(=O)R represents an R-substituted carbonyl moiety linked to the scaffold via the C-atom.

The term '$C_m$-$C_n$alkyl' as a group or part of a group such as $C_m$-$C_n$haloalkyl, $C_m$-$C_n$alkylcarbonyl, $C_m$-$C_n$alkylamine, etc. wherein m and n are integers ≥0, and m<n, denotes a saturated straight or branched chain hydrocarbon radical having the number of carbon atoms indicated, e.g. $C_1$-$C_4$alkyl means an alkyl radical having from 1 to 4 carbon atoms and includes methyl, ethyl, n-propyl, isopropyl, t-butyl, n-butyl and isobutyl, similarly, $C_1$-$C_6$alkyl means a straight or branched alkyl radical having from 1 to 6 carbon atoms, including also all straight and branched chain isomers of pentyl and hexyl.

The term '$C_m$-$C_n$alkylene' as a group or part of a group defines a bivalent straight or branched saturated hydrocarbon chain having from m to n carbon atoms wherein m and n are integers >0, and m<n, such as, for example, methylene, ethylene, 1,3-propanediyl, 1,2-propanediyl, and the like.

The term '$C_2$-$C_n$alkenyl' as a group or part of a group denotes a straight or branched chain hydrocarbon radical having saturated carbon-carbon bonds and at least one carbon-carbon double bond, and having the number of carbon atoms indicated wherein n is an integer >2, e.g. $C_2$-$C_6$alkenyl means an alkenyl group having from 2 to 6 carbon atoms. Exemplary alkenyl groups include, but are not limited to, ethenyl (or vinyl), 1-propenyl, 2-propenyl (or allyl), isopropenyl, butenyl, and the like.

The term '$C_2$-$C_n$alkynyl' as a group or part of a group denoted s a straight or branched chain hydrocarbon radical having saturated carbon-carbon bonds and at least one carbon-carbon triple bond, and having the number of carbon atoms indicated wherein n is an integer >2, e.g. $C_2$-$C_6$alkynyl means an alkynyl group having from 2 to 6 carbon atoms. Exemplary alkynyl groups include, but are not limited to, ethynyl, propynyl, propynyl, butynyl, and the like.

The term '$C_3$-$C_n$cycloalkyl' as a group or part of a group denotes a saturated cyclic hydrocarbon radical having the number of carbon atoms indicated wherein n is an integer >4, e.g. $C_3$-$C_6$cycloalkyl means a cycloalkyl group having 3, 4, 5 or 6, carbon atoms. Exemplary cycloalkyl groups include, but are not limited to, cyclopropyl, cyclobutyl cyclopentyl, cyclohexyl and the like, especially cyclopropyl.

The term '$C_3$-$C_n$cycloalkyl$C_m$-$C_n$alkyl' denotes a $C_m$-$C_n$alkyl radical which is substituted with a $C_3$-$C_n$cycloalkyl moiety, wherein $C_3$-$C_n$cycloalkyl and $C_m$-$C_n$alkyl are as defined above for $C_3$-$C_n$cycloalkyl and $C_m$-$C_n$alkyl respectively. Exemplary $C_3$-$C_n$cycloalkyl$C_m$-$C_n$alkyl groups include, but are not limited to, $C_3$-$C_7$cycloalkyl$C_1$-$C_3$alkyl, i.e. the cycloalkyl moiety is bonded through a methyl, ethyl, n-propyl or isopropyl group.

The term '$C_m$-$C_n$alkoxy' defines a radical O—$C_m$—$C_n$alkyl wherein $C_m$—$C_n$alkyl is as defined above. Preferred $C_m$-$C_n$alkoxy groups for use in the invention are $C_1$-$C_6$alkoxy, i.e. alkoxy groups having from 1 to 6 carbon atoms. Exemplary alkoxy groups include but are not limited to methoxy, ethoxy n-propoxy isopropoxy and the like.

The term 'halo' or 'halogen' is generic to fluoro, chloro, bromo and iodo.

The term 'halo$C_m$-$C_n$alkyl' as a group or part of a group, represents a $C_m$-$C_n$alkyl wherein at least one C-atom is substituted with one or more halogen atom(s), in particular $C_1$-$C_4$alkyl substituted with one, two, three, four, five, six, or more halo atoms, such as methyl or ethyl with one or more fluoro atoms, for example difluoromethyl, trifluoromethyl, trifluoroethyl. In case more than one halogen atom is attached to an alkyl group within the definition of halo$C_m$-$C_n$alkyl, the halogen atoms may be the same or different. In many cases trifluoromethyl is preferred.

The term 'halo$C_n$-$C_m$alkoxy' represents a $C_n$-$C_m$alkoxy having the number of carbon atoms indicated, wherein at least one C-atom is substituted with one or more halogen atom(s), typically chloro or fluoro. Of particular interest is $C_1$-$C_6$haloalkoxy. In many cases trifluoromethoxy is preferred.

The term "hydroxyalkyl" means an alkyl group as defined above, where the alkyl group is substituted with one or more —OH groups. Examples of hydroxyalkyl groups include but is not limited to HO—$CH_2$—, HO—$CH_2$—$CH_2$— and $CH_3$—CH(OH)—.

The term 'oxo' or '(=O)' represents double bonded oxygen atom, i.e. forms a carbonyl moiety when attached to a carbon atom, a sulfoxide moiety when attached to a sulphur atom and a sulphonyl moiety when two of said terms are attached to the same sulphur atom. It should be noted that an atom can only be substituted with an oxo group when the valency of that atom so permits.

The term 'amino' means $NH_2$.

The term '$C_m$-$C_n$alkylamino' denotes an amino group wherein one of the hydrogen atoms is replaced by $C_m$-$C_n$alkyl wherein $C_m$-$C_n$alkyl is as defined above.

The term 'di($C_m$-$C_n$alkyl)amino' denotes an amino group wherein both hydrogen atoms are replaced by $C_m$-$C_n$alkyl wherein $C_m$-$C_n$alkyl is as defined above and the two $C_m$-$C_n$alkyl groups may be the same or different, i.e. the m and n in the ($C_m$-$C_n$alkyl)$_2$ are selected independently of each other.

The term 'alkoxyamido' denotes NHC(=O)$C_1$-$C_6$alkoxy, such as tert.butoxycarbonylamino.

The term 'aryl' as a group or part of a group as applied herein denotes an aryl moiety such as a phenyl or naphthyl or a phenyl fused to a $C_4$-$C_6$cycloalkyl (for example indanyl), or a $C_4$-$C_6$cycloalkenyl. Examples of suitable aryl groups include but are not limited to phenyl, biphenyl, naphthyl, tetrahydronaphthyl, indenyl and indanyl.

The term 'aryl$C_m$-$C_n$alkyl' denotes a $C_m$-$C_n$alkyl which is substituted with aryl, wherein aryl and $C_m$-$C_n$alkyl are as defined above. Preferred aryl$C_m$-$C_n$alkyl groups for use in the invention are aryl$C_1$-$C_3$alkyl, i.e. the aryl moiety is bonded through a methyl, ethyl, n-propyl or isopropyl group.

The term 'heterocyclyl', 'heterocyclic' or 'heterocycle' as applied herein denotes, unless otherwise specified, a saturated or partially unsaturated mono- or bicyclic ring system composed of 4-10 atoms, whereof 1, 2, 3 or 4 are heteroatoms each independently selected from S, O and N. Examples of suitable heterocyclyl groups include but are not limited to pyranyl, tetrahydropyranyl, tetrahydrothiopyranyl, thiopyranyl, furanyl, tetrahydrofuranyl, piperidinyl, piperazinyl, morpholinyl, pyrazolinyl, pyrazolidinyl, thiazolidinyl, thiadiazolyl, pyrrolinyl, pyrrolidinyl, azetidinyl, azeridinyl etc. Unless otherwise indicated the heterocyclyl group is optionally substituted with one, two or three substituents.

The term 'heterocycloxy' defines a radical a O-heterocyclyl wherein heterocyclyl is as defined above.

The term 'heterocylyl$C_m$-$C_n$alkyl' denotes a $C_m$-$C_n$alkyl which is substituted with heterocyclyl, wherein heterocyclyl and $C_m$—$C_n$alkyl are as defined above. Preferred heterocylyl$C_m$-$C_n$alkyl groups for use in the invention are heterocylyl$C_1$-$C_3$alkyl, i.e. the heterocyclyl moiety is bonded through a methyl, ethyl, n-propyl or isopropyl group.

The term "heteroaryl" as applied herein means a mono- bi- or tricyclic ring system containing one, two, three or four heteroatoms each independently selected from N, O and S, consisting of 5 to 14 ring atoms wherein at least one of the heteroatoms is part of an aromatic ring. The term "heteroaryl" is intended to include all the possible isomeric forms and all fused, bridged and spiro forms. The "heteroaryl" may be optionally substituted with one or more substituents.

Examples of suitable heteroaryl groups include but are not limited to pyridinyl, pyrimidinyl, pyridazinyl, pyrazinyl, pyrrolyl, pyrazolyl, imidazolyl, oxazolyl, isoxazolyl, thiazolyl, isothiazolyl, quinolinyl, tetrahydroquinolinyl, isoquinolinyl, tetrahydroisoquinolinyl, quinazolinyl, tetrahydroquinazolinyl, quinoxalinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidinyl, benzopyridazinyl, benzopyrazolyl, indolyl, isoindolyl indolinyl, isoindolinyl, indanyl, pyrrolopyridinyl, pyrazolopyridinyl etc. Unless otherwise indicated the heteroaryl group is optionally substituted with one, two or three substituents.

It should be noted that the radical position(s) on any moiety used in the definitions may be anywhere on such a moiety as long as it is chemically stable. Radicals used in the definitions of the variables include all possible isomers unless otherwise indicated. For instance pyridinyl includes 2-pyridinyl, 3-pyridinyl and 4-pyridinyl.

The term 'heteroaryl$C_m$-$C_n$alkyl' denotes a $C_m$-$C_n$alkyl which is substituted with heteroaryl, wherein heteroaryl and $C_m$-$C_n$alkyl are as defined above. Preferred heteroaryl$C_m$-$C_n$alkyl groups for use in the invention are heteroaryl$C_1$-$C_3$alkyl, i.e. the heteroaryl moiety is bonded through a methyl, ethyl, n-propyl or isopropyl group.

The term "optionally substituted" as used herein, means that substitution is optional, i.e. there may or may not be substitution. For instance, the expression "alkyl group optionally substituted with one or more substituents" means that the alkyl group is substituted by zero, one or more substituents.

The term "substituted" refers to a molecule wherein at least one hydrogen atom is replaced with a substituent.

When a variable occurs more than one time in any constituent, each definition is independent.

As used herein, the terms "salt" or "salts" refers to an acid addition or base addition salt of a compound. "Salts" include in particular "pharmaceutically acceptable salts". The term "pharmaceutically acceptable salts" refers to salts that retain the biological effectiveness and properties of the compounds of this invention and, which typically are not biologically or otherwise undesirable, in many cases, the compounds are capable of forming acid and/or base salts by virtue of the presence of amino and/or carboxyl groups or groups similar thereto.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH and AcOH. Solvates wherein water is the solvent molecule are typically referred to as hydrates. Hydrates include compositions containing stoichiometric amounts of water, as well as compositions containing variable amounts of water.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" refers to an amount of a substance that will elicit a biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of the invention that, when administered to a subject, is sufficient to achieve an immunomodulatory effect which at least partially alleviates, inhibits, prevents and/or ameliorates a cancerous condition.

As used herein, "chemotherapeutic agent" means any agent which has been approved for use as a chemotherapy for cancer. Examples include but are not limited to: all-trans retinoic acid, actimide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, etoposide, fludarabine, fluorouracil, gemcitabine, hydroxyurea, idarubicin, irinotecan, lenalidomide, leucovorin, mechlorethamine, melphalan, mercaptopurine, methotrexate, mitomycin, mitoxantrone, oxaliplatin, paclitaxel, pemetrexed, revlimid, temozolomide, teniposide, thioguanine, thiotepa, valrubicin, vinblastine, vincristine, vindesine and vinorelbine. a chemotherapeutic agent for use in the combinations described herein may, itself, be a combination of different chemotherapeutic agents. suitable combinations include a combination of 5-fluorouracil (5-FU), leucovorin, and oxaliplatin (may be referred to as FOLFOX), or a combination of irinotecan, 5-FU, and leucovorin (may be referred to as IFL).

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like, in certain embodiments, the subject is a primate. In yet other embodiments, the subject is a human.

As used herein, a subject is "in need of" a treatment if such subject would benefit biologically, medically or in quality of life from such treatment.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof), in another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

In addition, the singular forms "a", "an", and "the" as used in this specification and the appended claims include plural referents unless the content clearly dictates otherwise. Thus, for example, reference to "an inhibitor" includes two or more such inhibitors.

The invention also relates to methods of making the compounds of the invention. The compounds may be prepared by any of the applicable methods and techniques of organic synthesis. Many such methods and techniques are well known in the art and some of the known methods techniques are elaborated in *Compendium of Organic Synthetic Methods*, in 12 volumes (John Wiley & Sons, New York); *Advanced Organic Chemistry*, 5 ed. M. Smith & J. March (John Wiley & Sons, New York, 2001) and *Comprehensive Organic Synthesis. Selectivity. Strategy & Efficiency in Modern Organic Chemistry*, in 9 Volumes. Barry M. Trost, Editor-in-Chief (Pergamon Press, New York, 1993).

A number of exemplary methods for the preparation of the compounds of the invention are provided in the general schemes and the preparative examples below. These methods are intended to illustrate the nature of such preparations and are not intended to limit the scope of applicable methods. Alternative routes, which will be readily apparent to the ordinary skilled organic chemist, may also be used to synthesize the compounds of the invention or their intermediates.

In the course of the process described below for the preparation of compounds of Formula (I), functional groups in starting materials which are prone to participate in undesired side reactions, especially amino, amide, carboxy, hydroxy and phosphate groups, may be protected by suitable conventional protecting groups which are customarily used in the organic synthesis. Those protecting groups may already be present in the precursors and they are intended to protect the functional groups in question against undesired secondary reactions, such as acylation, etherification, esterification, alkylation, oxidation, reduction, solvolysis, etc. In certain cases the protecting groups can additionally cause the reactions to proceed selectively, for example regioselectively or stereoselectively. It is characteristic of protecting groups that they can be removed easily, i.e. without undesired secondary reactions taking place, for example by acid treatment, fluoride treatment, solvolysis, reduction, or by photolysis. The protection of functional groups by such protecting groups, the protecting groups themselves, and the reactions for their removal are described, for example, in standard works such as T. W. Greene and P. G. M. Wuts "Protective Groups in Organic Synthesis" John Wiley & Sons, Inc., New York 1999.

Abbreviations

In addition to the definitions above, the following abbreviations are used in the synthetic schemes above and the examples below. If an abbreviation used herein is not defined, it has its generally accepted meaning.

Ac Acetyl
$Ac_2O$ Acetic anhydride
AcOH Acetic acid
Bn Benzyl
Bz Benzoyl
DCM Dichloromethane
DEAD Diethyl azodicarboxylate
DIPEA Diisopropylethylamine
DMAP 4-Dimethylaminopyridine
DMF N,N-Dimethylformamide
Et Ethyl
EtOAc Ethyl acetate
$Et_3N$ Triethylamine
EtOH Ethanol
$Et_2O$ Diethyl ether
HPLC High performance liquid chromatography
i-Pr Isopropyl
LC Liquid chromatography
LCMS Liquid chromatography-mass spectrometry
Me Methyl
MeCN Acetonitrile
MeOH Methanol
MS Mass spectrometry
MTBE Methyl tert.butyl ether
NP HPLC Normal phase HPLC
on Over night
p. ether Petroleum ether
Pg Protecting group
Ph Phenyl
rt Room temperature
SOR Specific Optical Rotation
THF Tetrahydrofuran
TEA Triethylamine
TFA Trifluoroacetic acid
TFAA Trifluoroacetic anhydride
TIPS Triisopropylsilyl
TLC Thin layer chromatography
TMS Trimethylsilyl If there is any inconsistency between the chemical name of the exemplified chemical compound and corresponding structure of said example, then the chemical structure should be used for determining the chemical compound of said example.

General Synthesis of Compounds of the Invention

Compounds of the present invention and intermediates useful for the synthesis of these compounds may be prepared according to literature procedures and/or as illustrated in the general synthetic schemes and as detailed in the experimental part herein below using a variety of methods and techniques known to those skilled in the art. The general synthetic schemes and preparative examples shown and described below illustrate typical synthetic routes to the compounds of the invention. As will be readily apparent to the ordinary skilled organic chemist, other routes may alternatively be used for the preparation of the entire compounds or to various portions of the compounds. Starting materials and reagents used are available from commercial suppliers or can be prepared according to literature procedures using methods well known to those skilled in the art.

In the case any functional groups are present on any of the building blocks or intermediates that may interfere in reactions, these are suitably protected during the reaction in order to avoid undesired side reactions, and deprotected at the end of the synthesis. Appropriate protecting groups that can be used are extensively described in the literature, e.g. in Greene, "Protective Groups in Organic Chemistry", John Wiley & Sons, New York (1981).

Compounds of the invention are prepared by introduction of the desired groups to the two alcohols of the 2,2-(bishydroxymethyl)methylenecyclopropane nucleoside analogue. To enable introduction of different groups on the two primary hydroxy groups, a protecting group strategy need to be employed. A general route to compounds of formula (I) wherein $R^x$ is an ester, i.e. a group of formula —OC(=O)CR$^y$ is illustrated in Scheme 1.

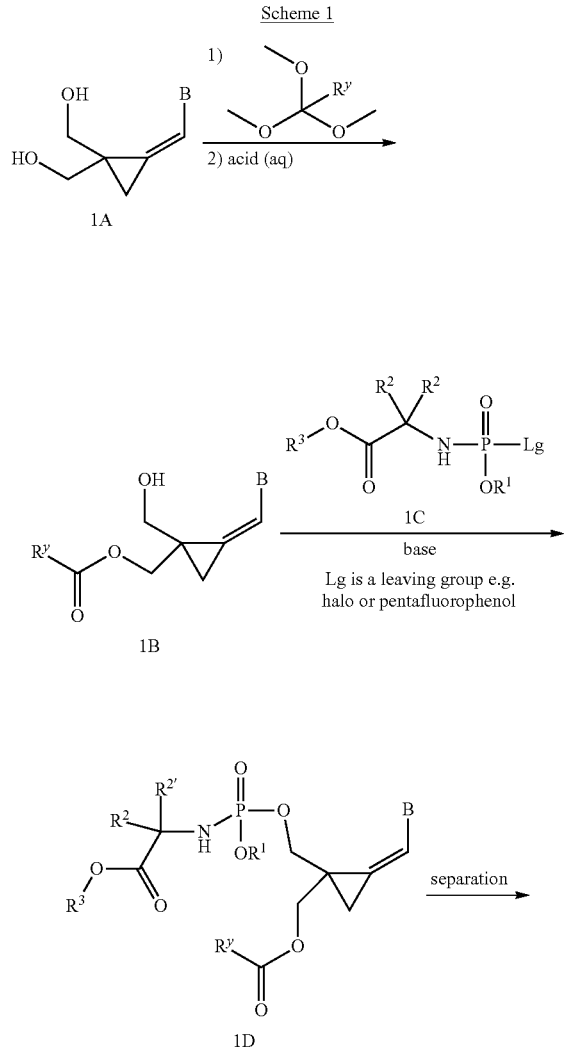

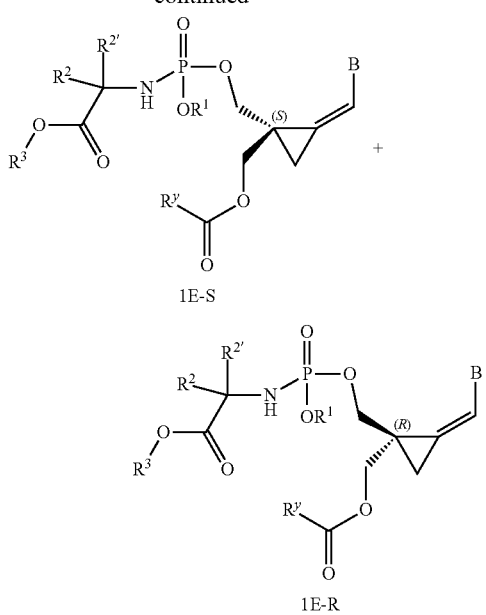

The monoacylated compound (1B) is conveniently obtained by formation of an ortho ester followed by opening of the ortho ester. Typically, the ortho ester is formed by reaction of the diol (1A) with the desired trimethyl ortho alkanoate under acidic conditions such as in the presence of an acid like p-toluene sulfonic acid or the like. The orthoester is then opened by treatment with acid in the presence of water e.g. aqueous acetic acid thus providing the desired monoacylated compound as a mixture of stereoisomers. The phosphoramidate moiety is then introduced using methodology known in the field of phosphoramidate nucleosides, e.g. by condensation of the alcohol (1B) with a suitable phosphorylating agent (1C) in the presence of a base. For example, a phosphorylating agent like the pentafluorophenol of the desired phosphoramidate can be used or a phosphorylating agent wherein the leaving group is a halogen like chloride, or an activated phenol like p-nitrophenol or a halogenated phenol such as mono-, di- or tri-chlorophenol or pentachlorophenol or the like. Suitable bases for this condensation include for instance N-methylimidazole (NMI), especially useful for the formation of p-nitrophenol phosphoramidates, or a Grignard reagent like tert. butylmagnesium chloride or the like which is especially useful for the formation of pentafluorophenol phosphoramidates. The stereoisomers of the isomeric mixture of the cyclopropne phosphoramidate derivative (1D) obtained are then separated using any suitable separation method for instance chiral HPLC or SFC thus providing the separated isomers (1E-R & 1E-S). Preferably, a chiral phosphorylating agent is used.

As will be evident to a person skilled in the art, separation of isomers may alternatively be performed prior to introduction of the phosphoramidate moiety. The compound of formula (I) wherein $R^x$ is a group of formula —OC(=O)R$^y$, is then obtained as sketched in Scheme 2.

Scheme 2

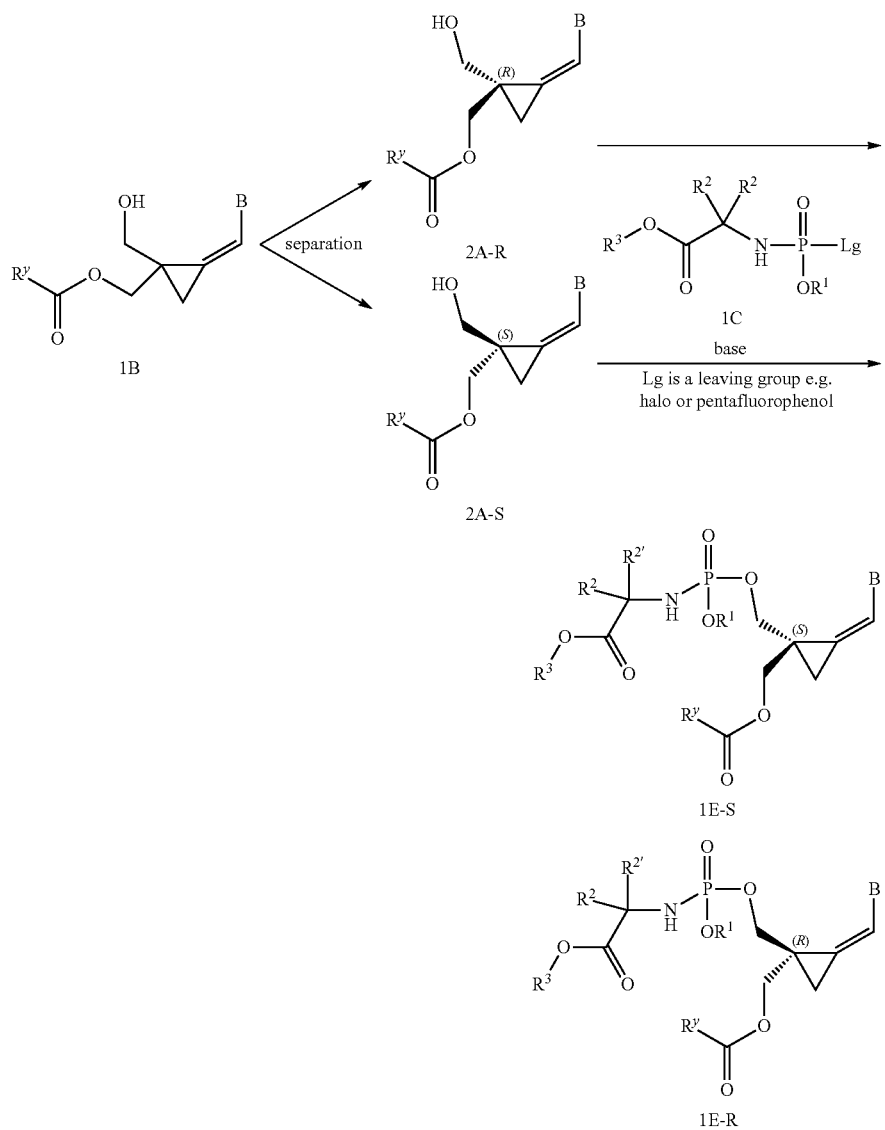

In an alternative approach to the S-isomer of the mono-acylated derivative (2A-S) wherein R is methyl, the diol (1A) is di-acetylated using standard methods well known in the art, whereafter a selective deacetylation of only one of the acetyl groups is effected by an enzymatic reaction.

Compounds of the invention wherein $R^x$ is a group of formula —OC(=O)CH($R^y$)NH$_2$ are typically prepared from an intermediate orthogonally protected cyclopropylmethylene nucleoside analogue. A typical route to such compounds is illustrated in Scheme 3.

Scheme 3

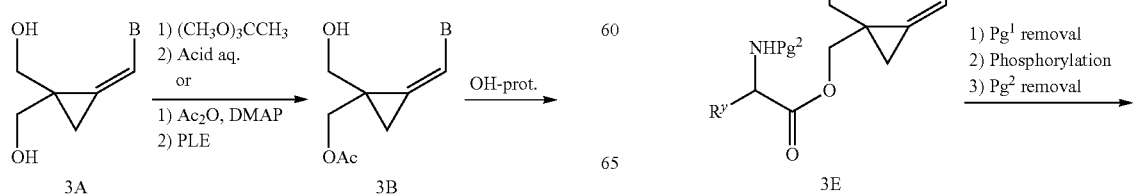

-continued

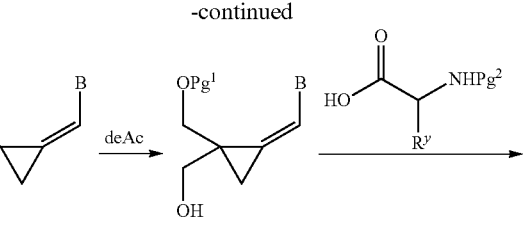

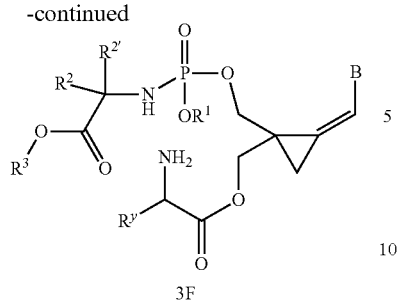

3F

The monoacetylated cyclopropylmethylene derivative (3B) is typically obtained from the diol (3A) as described above, i.e. either by reaction with trimethylorthoacetate in the presence of an acid, followed by opening of the orthoester effected by treatment with acid in aqueous conditions e.g. aqueous acetic acid, or by acetylation of both hydroxy groups followed by selective enzymatic mono-deacetylation. In the case the orthoester route is used, the stereoisomers can be separated using any suitable chiral separation method e.g. chiral HPLC or SFC, or the synthesis may continue with a mixture of isomers and the separation performed at a later stage of the synthesis. The free alcohol is then protected with a protecting group that subsequently can be removed without effecting the introduced $R^x$ group. For example, an acetal such as tetrahydropyranyl, an ether such as benzyl or derivative thereof or trityl or derivative thereof or similar can be used or a as protecting group. Removal of the acetate using standard methods, typically basic conditions such as NaOMe or $NH_3$ in MeOH or the like, followed by coupling of the amino acid effected by standard peptide coupling conditions i.e. using a peptide coupling agent like HOBt, EDAC or HATU or similar in the presence of a base, typically a tertiary amine like triethylamine, diisopropylamine or the like, provides the acylated derivative (3E). Removal of the hydroxy protecting group using the appropriate conditions according to the protecting group used, such as acidic treatment in the case of an acetal or trityl derivative, followed by phosphorylation using methodology known in the field of phosphoramidate nucleosides as outlined above followed by removal of the N-protecting group, provides the phosphoramidate (3F).

Compounds of the invention wherein $R^x$ is a group of formula —$OCH_2OC(=O)R$ are typically prepared from an orthogonally protected intermediate obtained in a manner similar to the previously described, using a protecting group that can be removed without effecting the introduced $R^x$. Useful protecting groups for this purpose will be known to a person skilled in the art. For example, mono- or dimethoxytrityl, or a p-methoxybenzyl group can be used. A general route is illustrated in Scheme 4.

Scheme 4

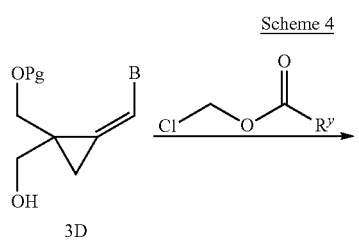

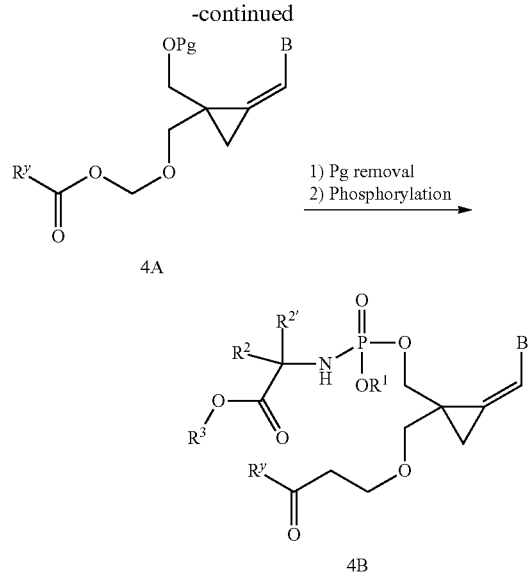

Reaction of the alcohol (3D) under elevated temperature with the chloroalkyl ester (11b) or ester in the presence of DIEA or similar provides the acetal derivative (4A). Removal of the protecting group followed by phosphorylation as previously described then provides the phosphoramidate (4B).

Phosphoramidate reagents to be used in the preparation of the compounds of the invention are extensively described in the literature. For example phosphoramidochloridates can be prepared in a two-step reaction as illustrated in Scheme 5.

Scheme 5

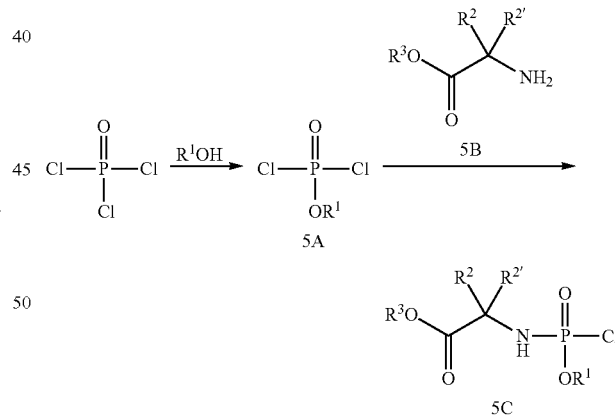

Condensation of $P(=O)Cl_3$ with a desired alcohol $R^1OH$ in an inert solvent like $Et_2O$ provides aryloxy or heteroaryloxy phosphorodichloridate (5A). Subsequent reaction with an amino acid derivative (5B) provides the phosphoramidochloridate (5C).

If desired, the obtained phosphoramidochloridate (5C) can be converted to a phosphorylating agent having an activated phenol as leaving group instead of the chloro leaving group, for instance pentaflurorophenol or p-$NO_2$-phenol as generally illustrated in Scheme 6.

Scheme 6

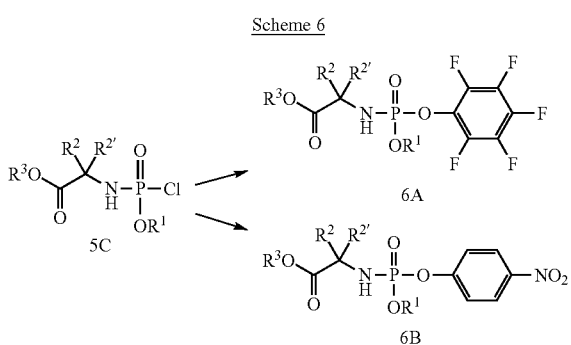

This conversion is conveniently performed by reaction of the chloro derivative (5C) with the desired activated phenol, e.g. pentafluorophenol or p-nitrophenol in the presence of a base like triethylamine or similar, thus providing phosphorylating agents (6A) and (6B).

Any mixtures of enantiomers, diastereomers, cis/trans isomers resulting from the process described above can be separated into their single components by chiral salt technique, chromatography using normal phase, reverse phase, chiral column or supercritical fluid chromatography (SFC), depending on the nature of the separation.

It should be understood that in the description and formulae shown above, the various R-groups and other variables are as defined above, except where otherwise indicated. Furthermore, for synthetic purposes, the compounds of the general Schemes are mere representative with elected radicals to illustrate the general synthetic methodology of the compounds of Formula (I), subgroups of compounds of formula (I) and intermediates to compounds of formula (I) and subgroups thereto, as defined herein.

DETAILED DESCRIPTION OF THE EMBODIMENTS

Various embodiments of the compounds invention and intermediates therefore will now be illustrated by the following examples. The Examples are just intended to further illustrate certain embodiments of the invention and are by no means intended to limit the scope of the invention.

Chemistry Examples & Intermediates

As is well known to a person skilled in the art, reactions are performed in an inert atmosphere, including but not limited to nitrogen and argon atmosphere when necessary to protect reaction components from air or moisture. Temperatures are given in degrees Celsius (° C.). Solution percentages and ratios express a volume to volume relationship, unless stated otherwise. The reactants used in the examples below may be obtained from commercial sources or prepared from commercially available starting materials as described herein or by methods known in the art.

The compounds of the invention including intermediates are prepared as described in the Examples and in the general schemes herein. It will be apparent to a skilled person that analogous synthetic routes may be used, with appropriate modifications, to prepare the compounds of the invention as described herein. The progress of the reactions described herein were followed as appropriate by e.g. LC, GC or TLC, and as the skilled person will readily realise, reaction times and temperatures may be adjusted accordingly.

Nuclear magnetic resonance (NMR) spectra were recorded on a Bruker spectrometer operating at 500 MHz for $^1$H NMR and at 126 MHz for $^{13}$C NMR using CDCl$_3$ (deuterated chloroform) or DMSO-d$_6$ (deuterated DMSO, dimethyl-d$_6$ sulfoxide) as solvent. Chemical shifts (δ) are reported in parts per million (ppm) relative to tetramethylsilane (TMS) which was used as internal reference, or to residual solvent peak. Coupling constants, J, are reported in Hertz. NMR shifts indicated were obtained using an automated process wherein residual solvent and/or impurities may be present, integrals and chemical shifts may not be completely accurate, signals may be broad with a low signal to noise ratio and may overlap with signals from residual solvents, and multiplicities may have been misinterpreted. Despite this, all spectra obtained by the automated process are supporting the structure of each of the analysed compounds.

The compound names were generated by ChemDraw Ultra software, Cambridgesoft, version 12.0.2.

Preparatory HPLC were conducted using any one of the Methods A-E

Prep HPLC Method A
  Column: Kromosil C18 (25×150)mm 10μ
  Mobile phase: 10 mM ABC in H$_2$O:MeCN (gradient)
Prep HPLC Method B:
  Column: Kromosil C18 (25×150) mm 10μ
  Mobile phase: 0.1% formic acid in H$_2$O:MeCN (gradient)
Prep HPLC Method C
  Column: X-Select C18 (19×150) mm 5μ
  Mobile phase: 10 mM ABC IN H$_2$O:MeCN (gradient)
Prep HPLC Method D
  Column: X-Select C18 (19×150) mm 5μ
  Mobile phase: 0.1% formic acid in H$_2$O:MeCN (gradient)
Prep HPLC Method E
  Column: X-Bridge C18 (30×250) mm 5μ
  Mobile phase: 0.1% formic acid in H$_2$O:MeCN (gradient)
Prep HPLC Method F
  Column: X-Bridge Amide C18 (19×250) mm 5μ
  Mobile phase: 10 mM ABC IN H$_2$O:MeCN (gradient)
Prep HPLC Method G
  Column: YMC TRIAT C18 (25×150) mm 10μ
  Mobile phase: 10 mM ABC IN H$_2$O:MeCN (gradient)
Prep HPLC Method H
  Column: YMC TRIAT C18 (25×150) mm 10μ
  Mobile phase: 0.1% formic acid in H$_2$O:MeCN (gradient)

Intermediate 1

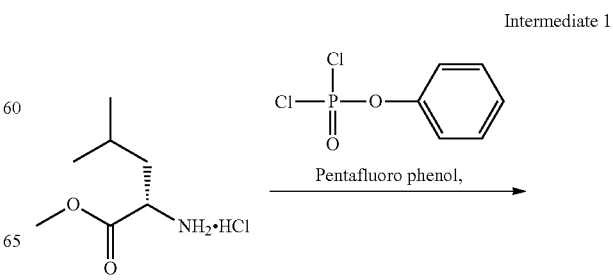

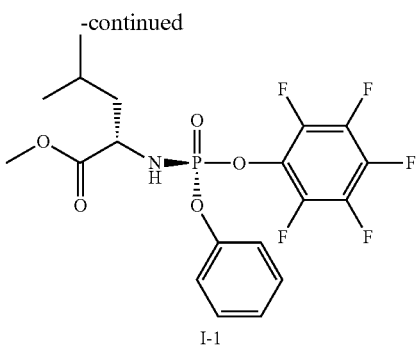

(S)-Methyl 4-methyl-2-(((S)-(perfluorophenoxy)(phenoxy)phosphoryl)amino)pentanoate (I-1)

Triethylamine (11 mL, 79 mmol) was added dropwise at −70° C. for 30 minutes under nitrogen to a stirred solution of (S)-methyl 2-amino-4-methylpentanoate hydrochloride (6.5 g, 35 mmol) in DCM (70 mL). Phenyl phosphodichloridate (5.4 ml, 36 mmol) in DCM (70 mL) was added dropwise at −70° C. over a period of 45 min, then reaction mixture was stirred at −70° C. to 0° C. for 3 h. To this mixture was added a solution of pentafluorophenol (6.3 g, 34 mmol) and triethylamine (5.5 mL, 40 mmol) in DCM (60 mL) during 45 minutes. The reaction mixture was stirred at 0° C. for 2 h, then concentrated and the residue was taken in tert-butyl methyl ether (100 mL) and insolubles were filtered off through Celite and the filtrated was concentrated under reduced pressure. The crude compound was purified by column chromatography on silica gel eluted with 15-20% EtOAc in p.ether. Pure fractions were pooled and concentrated under reduced pressure. The afforded racemic compound was dissolved in 20% EtOAc in p. ether (70 mL) and kept at refrigerator for 16 h and the thus formed crystals were filtered off which gave the title compound (3 g, 18%) as a solid. LC-MS showed 99.7% desired compound mass. MS (ES+) m/z 468.28 [M+H]$^+$.

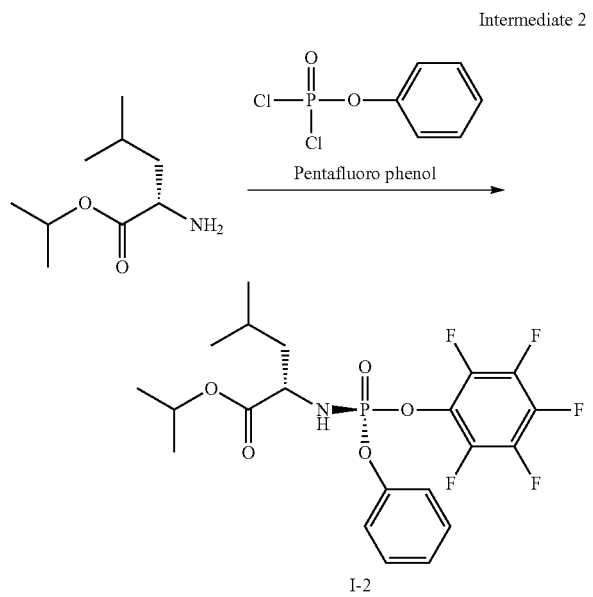

Intermediate 2

(S)-Isopropyl 4-methyl-2-(((S)-(perfluorophenoxy)(phenoxy)phosphoryl)amino)pentanoate (I-2)

To a stirred solution of (S)-isopropyl 2-amino-4-methylpentanoate (3.8 g, 18 mmol) in DCM (50 mL) at −78° C. was added Et$_3$N (5.6 mL, 40 mmol) dropwise for 10 min. Phenyl phosphorodichloridate (2.7 mL, 18 mmol) in DCM (30 mL) was added dropwise for 30 min. The reaction mixture was stirred at −78° C. for additional 30 min, then allowed to warm to 0° C. during 2 h and stirred for additionally 1 h. A solution of 2,3,4,5,6-pentafluorophenol (3.0 g, 16 mmol) and Et$_3$N (2.0 mL, 20 mmol) in DCM (20 mL) was added dropwise to the reaction mixture. The reaction mixture was stirred at rt for 2 h, then concentrated under reduced pressure. The afforded residue was dissolved in of MTBE (100 mL), insolubles were filtered off and the filtrate concentrated. The crude compound was purified by column chromatography on silica gel eluted with 10% EtOAc in p.ether. Pure fractions were pooled and concentrated under reduced pressure. The afforded racemic mixture (4.5 g, 44% undesired isomer and 55% desired isomer), was dissolved in 20% EtOAc in hexane (100 mL) and kept standing for 2 h at 0° C. The thus formed crystals were filtered off, washed with cold hexane (2×30 mL) and dried under reduced pressure which gave the title compound (2.0 g, 22%, chiral purity 98.9%). MS (ES+) m/z 496.15 [M+H]$^+$. LCMS shown 99% of desired product.

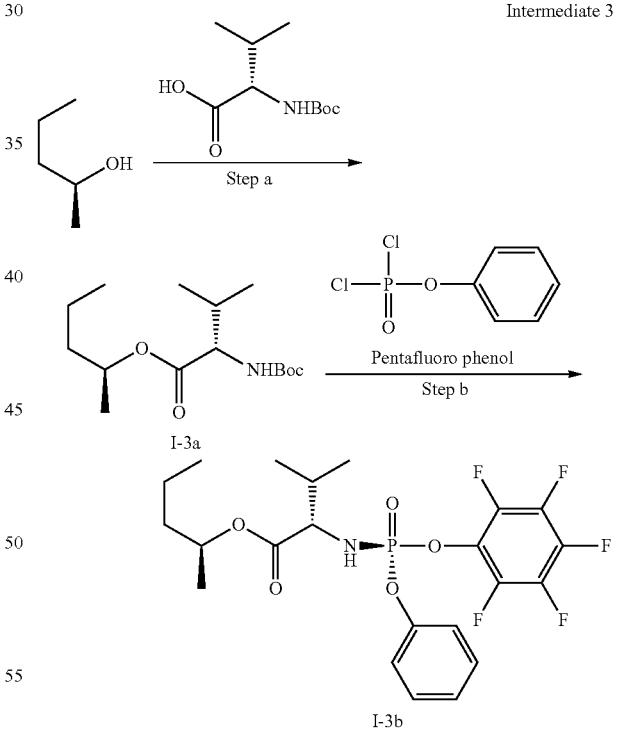

Intermediate 3

Step a) (S)—(S)-Pentan-2-yl 2-((tert-butoxycarbonyl)amino)-3-methylbutanoate (I-3a)

To a stirred solution of Boc-Val-OH (7.0 g, 32 mmol) and (S)-pentan-2-ol (3.4 ml, 31 mmol) in DCM (100 mL) was added DMAP (400 mg, 3.2 mmol), EDCI (6.8 g, 35 mmol) at rt. The solution was stirred for 16 h, then diluted with DCM (100 mL), washed with water (2×50 mL), saturated sodium bicarbonate solution (2×50 mL), 2M HCl (2×50 mL) and brine (100 mL). The organic layer was dried over anhydrous sodium sulfate and concentrated under reduced pressure. The afforded crude compound was purified by column chromatography on silica gel, eluted with 5-10% ethyl acetate in p. ether which gave the title compound (7.5 g, 80%). MS (ES+) m/z 288.29 [M+H]⁺.

Step b) (S)—(S)-Pentan-2-yl 3-methyl-2-(((S)-(perfluorophenoxy)(phenoxy)phosphoryl)amino)butanoate (I-3b)

To a stirred solution of compound I-3a (7.5 g, 26 mmol) in dry 1,4-dioxane (30 mL) was added 4.0 M HCl in dioxane (34 mL, 135 mmol) at rt. The solution was stirred for 2 h, then concentrated under reduced pressure and co-distilled with toluene (2×50 mL). The residue was dissolved in DCM (50 mL), put under nitrogen and cooled to −70° C. Et₃N (8.2 mL, 58 mmol) was added dropwise for 10 min followed by dropwise addition of a solution of phenyl phosphorodichloridate (3.8 mL, 26 mmol) in DCM (20 mL). The reaction mixture was stirred at −70° C. to 0° C. for 3 h, then a solution of pentafluoro phenol (4.8 g, 26 mmol) and Et₃N (4.0 mL, 29 mmol) in DCM (30 mL) was added dropwise. The reaction mixture was stirred at 0° C. for 2 h, then concentrated. The residue was taken in tert. butyl methyl ether (100 mL) and insolubles were filtered off. The filter was washed with tert. butyl methyl ether (2×30 mL) and the combined filtrate was concentrated under reduced pressure. The crude product was purified by column chromatography on silica gel eluted with 10% EtOAc in hexane. Pure fractions were pooled and concentrated under reduced pressure. The afforded racemic mixture was dissolved in 15% EtOAc in p. ether (150 mL) and kept in refrigerator for overnight. The thus formed crystals were filtered off, washed with p. ether (100 mL) and dried under reduced pressure which gave the title compound (3.5 g, 26%, chiral purity 98.1%). MS (ES+) m/z 510.16 [M+H]⁺.

ate (10 g, 42 mmol) in DCM (100 mL) followed by dropwise addition of a solution of phenyl phosphorodichloridate (1.4 mL, 42 mmol) in DCM (70 mL). The reaction mixture was stirred at −78° C. for 30 min, then allowed to warm to 0° C. during 2 h and was then stirred for additionally 1 h at 0° C. A solution of 2,3,4,5,6-pentafluorophenol (7 g, 38 mmol) and Et₃N (6.5 mL, 46 mmol) in DCM (80 mL) was added dropwise at 0° C. and the reaction mixture was then stirred for at rt 3 h, then concentrated to dryness under reduced pressure, The crude product was dissolved in MTBE (200 mL), insolubles were filtered off and the filtrate was concentrated to dryness under reduced pressure. The crude compound was purified by column chromatography on silica gel eluted with 10% EtOAc in hexane. Pure fractions were pooled and concentrated under reduced pressure. The afforded racemic compound was dissolved in 20% EtOAc in n-pentane (100 mL) and kept at rt for 2 h, the thus formed crystals were filtered off and washed with cold n-pentane (2×30 mL), and dried under vacuum which gave the title compound (3.1 g, 14%, chiral purity 99%). MS (ES+) m/z 524.17 [M+H]⁺.

Intermediate 5

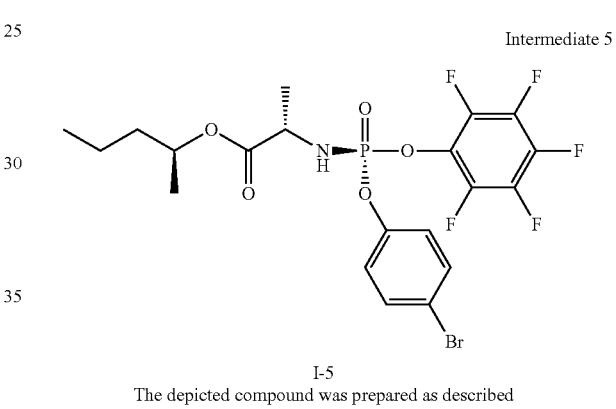

I-5
The depicted compound was prepared as described in WO2016/030335

Intermediate 4

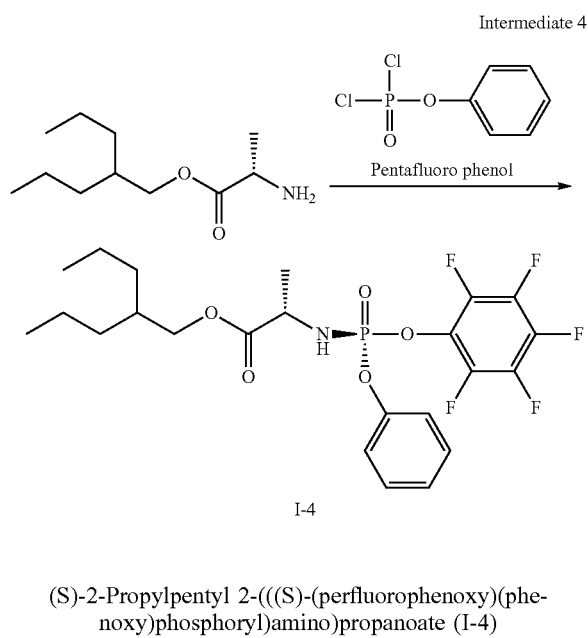

(S)-2-Propylpentyl 2-(((S)-(perfluorophenoxy)(phenoxy)phosphoryl)amino)propanoate (I-4)

Et₃N (12.3 mL, 88 mmol) was added dropwise at −78° C. to a stirred solution of (S)-2-propylpentyl 2-aminopropano- Intermediate 6

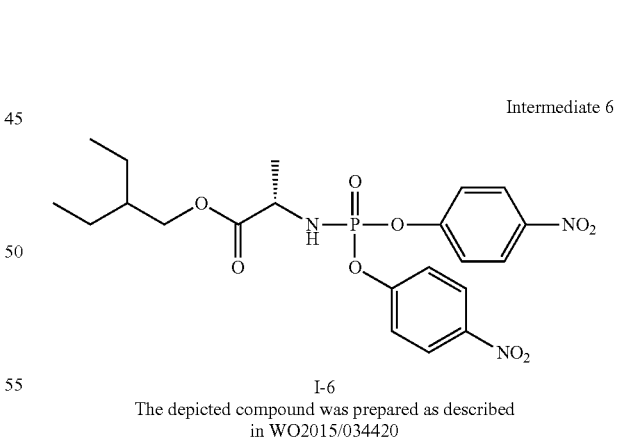

I-6
The depicted compound was prepared as described in WO2015/034420

Intermediate 7

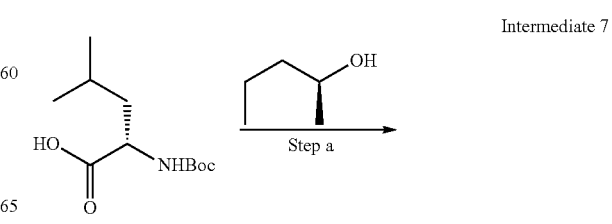

Step a

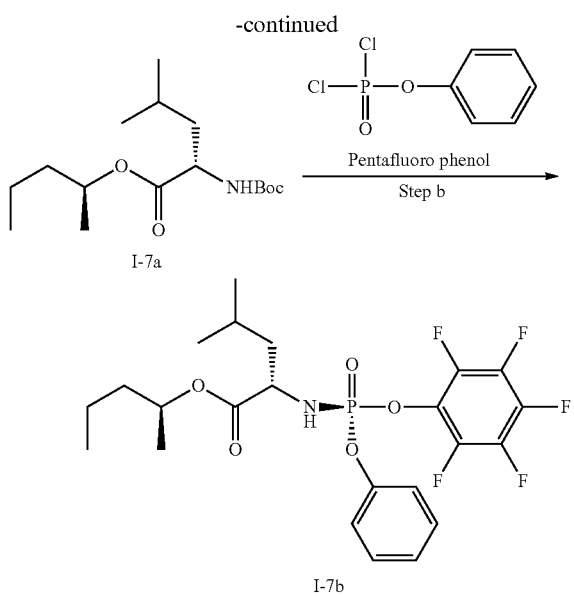
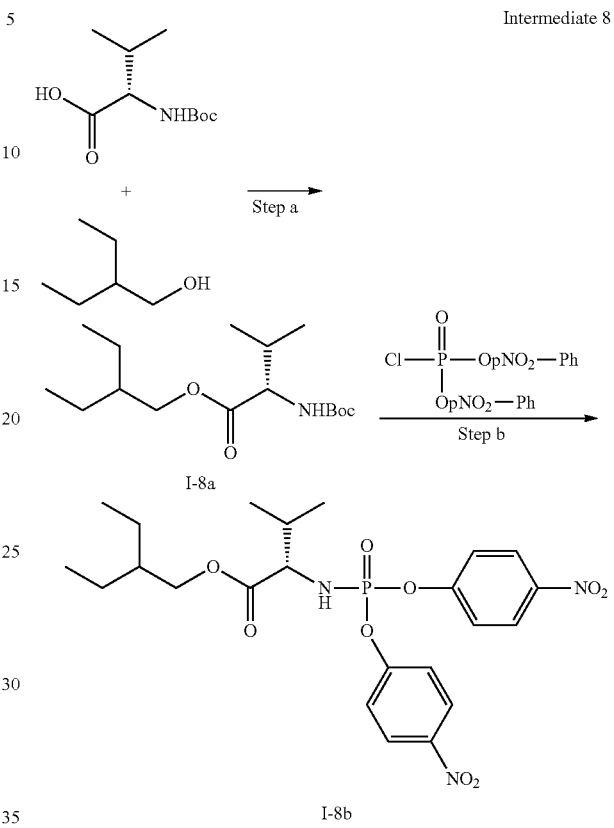

Step a) (S)—(S)-Pentan-2-yl 2-((tert-butoxycarbonyl)amino)-4-methylpentanoate (I-7a)

To a stirred solution of (tert-butoxycarbonyl)-L-leucine (5.0 g, 22 mmol) and (S)-pentan-2-ol (2.1 mL, 19 mmol) in DCM (50 mL) were added DMAP (400 mg, 3.24 mmol) and EDC-HCl (5.0 g, 26 mmol). The solution was stirred at rt for 18 h, then diluted with DCM (200 mL) and washed with water (100 mL) and brine (100 mL). The organic layer was dried over anhydrous sodium sulfate, filtered and concentrated under reduced pressure. The afforded crude compound was purified by column chromatography on silica gel eluted with a gradient of 5-10% EtOAc in p. ether, which gave the title compound (4.0 g, 61%).

Step b) (S)—(S)-Pentan-2-yl 4-methyl-2-(((S)-(perfluorophenoxy)(phenoxy) phosphoryl)amino)pentanoate (I-7b)

4 M HCl in dioxane (14 mL, 56 mmol) was added to a stirred solution of compound I-7a (4.0 g, 13 mmol) in 1,4-dioxane (40 mL). The reaction mixture was stirred at rt for 2 h, then concentrated. The residue was dissolved in DCM (50 mL), the solution was cooled to −78° C. and Et₃N (3.7 mL, 26.50 mmol) was added dropwise followed by dropwise addition of a solution of phenyl phosphorodichloridate (1.9 mL, 13 mmol) in DCM (25 mL). The reaction mixture was stirred at −78° C. for 30 min, then allowed to warm to 0° C. during 2 h and stirred for additionally 1 h at 0° C. A solution of 2,3,4,5,6-pentafluorophenol (2.1 g, 11 mmol) and Et₃N (1.9 mL, 14 mmol) in DCM (25 mL) was added dropwise at 0° C. to the reaction mixture. The mixture was stirred at rt for 5 h, then diluted with MTBE (100 mL) and stirred for 10 min. Precipitated insoluble were filtered off and the filtrate was concentrated under reduced pressure. The afforded crude compound was purified by column chromatography on silica gel eluted with 20% EtOAc in hexane. The afforded racemic mixture was dissolved in 10% EtOAc in p. ether (50 mL) and kept in refrigerator for 4 h. The thus formed crystals were filtered off, washed with p. ether (50 mL) and dried under vacuum which gave the title compound (1.5 g, 22%). MS (ES+) m/z 524.21 [M+H]⁺. Chiral HPLC showed 99.75% of the desired isomer.

Intermediate 8

Step a) (S)-2-Ethylbutyl 2-((tert-butoxycarbonyl)amino)-3-methylbutanoate (I-8a)

To a stirred solution of N-Boc-L-valine (4.68 g, 21.5 mmol) in DCM (20 mL) were added EDC-HCl (4.13 g, 21.5 mmol) and 4-dimethyl amino pyridine (0.24 g, 2.0 mmol) at 0° C. The mixture was stirred for 30 min at 0° C., then 2-ethylbutan-1-ol (2.41 mL, 19.6 mmol) was added dropwise at 0° C. The mixture was stirred for 16 h at rt, then diluted with DCM (150 mL) and washed with water (200 mL) and brine (200 mL), dried over sodium sulfate and concentrated. The crude compound was purified by column chromatography on silica gel and eluted with 10% EtOAc in hexane, which gave the title compound. (ES+) m/z 302.26 [M+H]⁺.

Step b) (S)-2-Ethylbutyl 2-((bis(4-nitrophenoxy) phosphoryl)amino)-3-methylbutanoate (I-8b)

pTSA monohydrate (1.8 g, 9.5 mmol) was added at rt to a stirred solution of I-8a (2.6 g, 8.6 mmol) in EtOAc (25 mL). The mixture was stirred at 70° C. for 4 h, then concentrated under reduced pressure, co-distilled with toluene (×2) and washed with n-pentane. The afforded residue and bis(4-nitrophenyl) phosphorochloridate (3.0 g, 8.3 mmol) were dissolved in DCM (60 mL) at 0° C., Et₃N (2.3 mL, 17 mmol) was added dropwise. The solution was stirred at rt for 16 h, then extracted with DCM (2×20 mL) and water (20 mL). The organic layer was washed with NaHCO₃ aq.

(20 mL) and brine (20 mL), dried over Na$_2$SO$_4$, filtered and concentrated which gave the title compound (2 g).

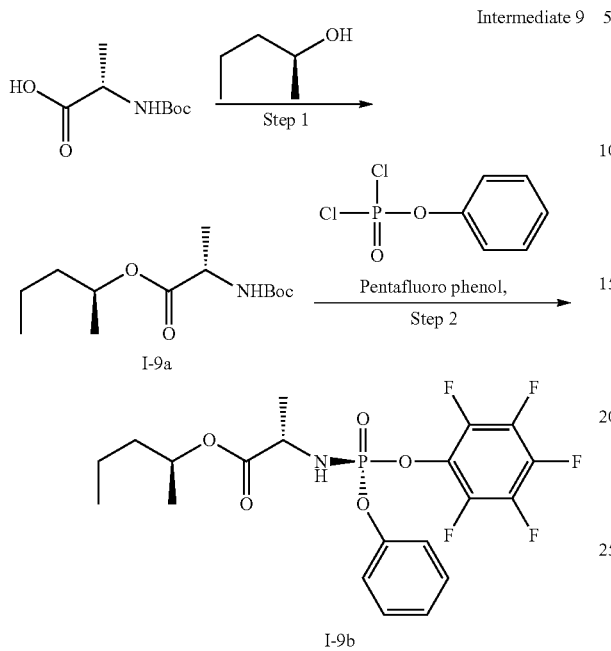

Intermediate 9

I-9a

I-9b

Step a) (S)-(S)-Pentan-2-yl 2-((tert-butoxycarbonyl)amino)propanoate (I-9a)

To a stirred solution of (tert-butoxycarbonyl)-L-alanine (4.5 g, 24 mmol) and (S)-pentan-2-ol (3.1 mL, 29 mmol) in DCM (50 mL) were added EDC-HCl (5.1 g, 26 mmol) and DMAP (0.3 g, 2 mmol) at 0° C. The reaction was stirred for 16 h at rt, then diluted with DCM (50 mL) and washed with water (2×50 mL) and brine (2×50 mL), dried over sodium sulfate, filtered and concentrated. The crude compound was purified by column chromatography on silica gel eluted with 10% EtOAc in hexane, which gave the title compound (3.5 g).

Step b) (S)-(S)-Pentan-2-yl 2-(((S)-(perfluorophenoxy)(phenoxy) phosphoryl)amino)propanoate (I-9b)

To a stirred solution of compound I-9a (3.5 g, 13.5 mmol) in 1,4-dioxane (15 mL) was added 4 M HCl in dioxane (14 mL, 57 mmol) at rt. The reaction mixture was stirred at rt for 2 h, then concentrated. The residue was dissolved in DCM (30 mL) and cooled to −78° C. Et$_3$N (3.9 mL, 28 mmol) was added dropwise followed by dropwise addition of a solution of phenyl phosphorodichloridate (2.0 mL, 13 mmol) in DCM (20 mL). The reaction mixture was stirred at −78° C. for additional 30 min, then allowed to warm to 0° C. during 2 h and stirred for additionally 1 h at 0° C. A solution of 2,3,4,5,6-pentafluorophenol (2.2 g, 12 mmol) and Et$_3$N (2.1 mL, mmol) in DCM (20 mL) was added dropwise at 0° C. to the reaction mixture. The reaction mixture was stirred at rt for 3 h. After 3 h, then concentrated under reduced pressure. The crude product was purified by column chromatography on silica gel and eluted with 10% EtOAc in hexane. The afforded solid was dissolved in 10% EtOAc in p. ether (100 mL) and kept standing at rt for 2 h. The thus formed crystals were filtered off, washed with p. ether (2×20 mL) and dried under vacuum which gave the title compound (1.3 g, 20% yield, 99.86% chiral purity). LCMS (ES+) m/z 482.11 [M+H]$^+$.

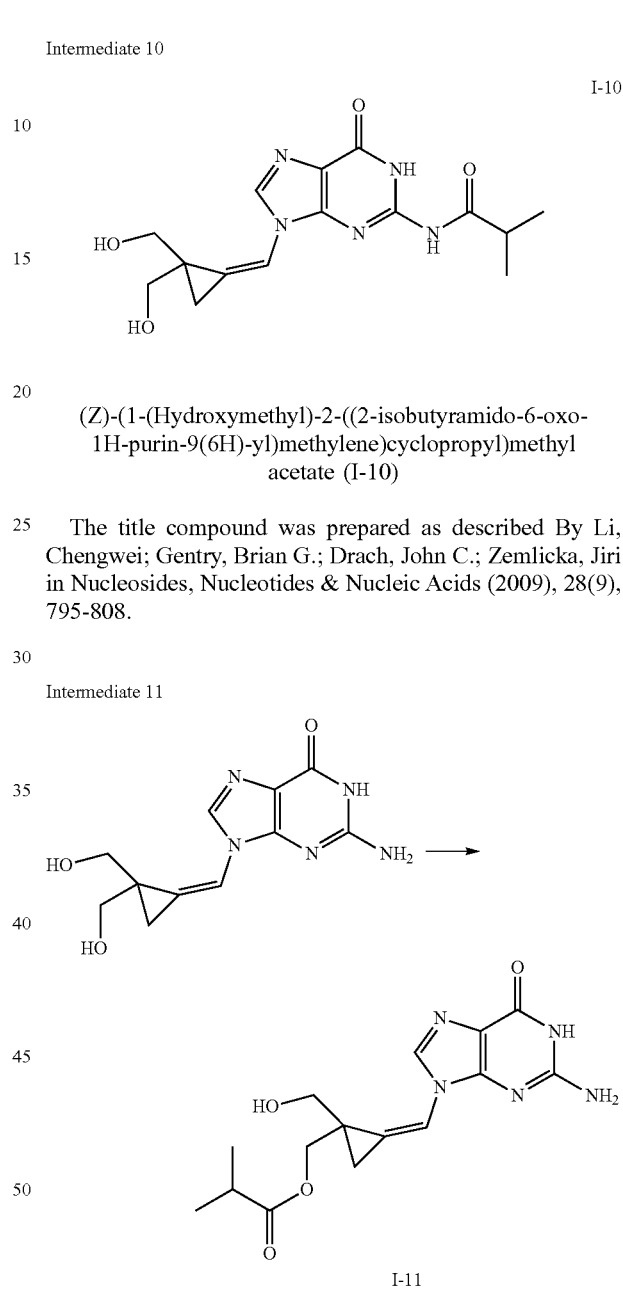

Intermediate 10

I-10

(Z)-(1-(Hydroxymethyl)-2-((2-isobutyramido-6-oxo-1H-purin-9(6H)-yl)methylene)cyclopropyl)methyl acetate (I-10)

The title compound was prepared as described By Li, Chengwei; Gentry, Brian G.; Drach, John C.; Zemlicka, Jiri in Nucleosides, Nucleotides & Nucleic Acids (2009), 28(9), 795-808.

Intermediate 11

I-11

(Z)-(2-((2-Amino-6-oxo-1H-purin-9(6H)-yl)methylene)-1-(hydroxymethyl)cyclopropyl)methyl isobutyrate (I-11)

To a stirred solution of (Z)-2-amino-9-((2,2-bis(hydroxymethyl)cyclopropylidene)methyl)-1H-purin-6(9H)-one (500 mg, 1.9 mmol) in DMF (30 mL) were added trimethyl ortho butyrate (1.2 mL, 7.6 mmol) and p-TSA (360 mg, 1.9 mmol) at rt. The reaction mixture was stirred at rt for 3 h, then concentrated. Acetic acid (80% in water, 50 mL) was added to the residue and the mixture was stirred at rt for 3 h, then concentrated. The crude compound was purified by column chromatography on silica gel eluted with 10-15% MeOH in DCM, which gave the title compound (350 mg, 5%) as a solid. LCMS (ES+) m/z 334.30 [M+H]⁺.

Intermediate 12

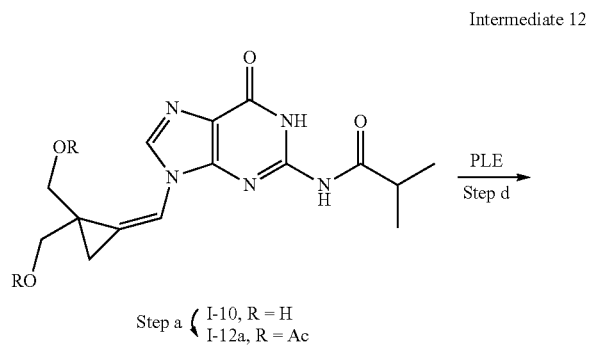

Step a) (Z)-(2-((2-Isobutyramido-6-oxo-1H-purin-9 (6H)-yl)methylene)cyclopropane-1,1-diyl)bis(methylene) diacetate (I-12a)

To a stirred solution of compound I-10 (100 mg, 0.30 mmol) in DMF (10 mL) were added DMAP (7 mg, 0.06 mmol) and acetic anhydride (0.2 mL, 2.1 mmol) at rt. The mixture was stirred for 1 h at rt then concentrated under reduced pressure. The afforded crude compound was purified by column chromatography on silica gel eluted with 5% MeOH, which gave the title compound (110 mg, 82%) as a solid. LCMS (ES+) m/z 418.41[M+H]⁺.

Step b) (R,Z)-(1-(Hydroxymethyl)-2-((2-isobutyramido-6-oxo-1H-purin-9(6H)-yl)methylene)cyclopropyl)methyl acetate (I-12b)

To a stirred solution of compound 2a (110 mg, 0.26 mmol) in DMF (15 mL) were added 0.02 M phosphate buffer (pH 7, 110 mL) and porcine liver esterase (230 mg) at rt. The reaction mixture was stirred at rt for 1 h, then concentrated under reduced pressure. The afforded crude compound was purified by column chromatography on silica gel eluted with 10% MeOH in DCM. Appropriate fractions were pooled and concentrated under reduced pressure. Chiral HPLC showed 91.7% of the desired isomer. The residue was purified by chiral SFC, which gave the title compound (40 mg, 39%) as a solid. LCMS (ES+) m/z 376.32 [M+H]⁺. The afforded compound was analyzed by LCMS, ¹H NMR, chiral HPLC & specific optical rotation (SOR). SOR of the afforded compound was found to be +26.52° (c 0.5, DMSO) which is in accordance with reported literature values for the R-isomer (+21.7, c 1.0, DMSO, *Nucleosides, Nucleotides and Nucleic Acids*, 28:795-808, 2009).

Preparative SFC Conditions:
Column/dimensions: Chiralpak IC (21×250 mm), 5μ
$CO_2$: 70.0%
Co solvent: 30.0% (100% EtOH)
Total Flow: 60.0 g/min
Back Pressure: 90.0 bar
UV: 234 nm
Stack time: 6.0 min
Load/inj.: 3.5 mg Intermediate 13

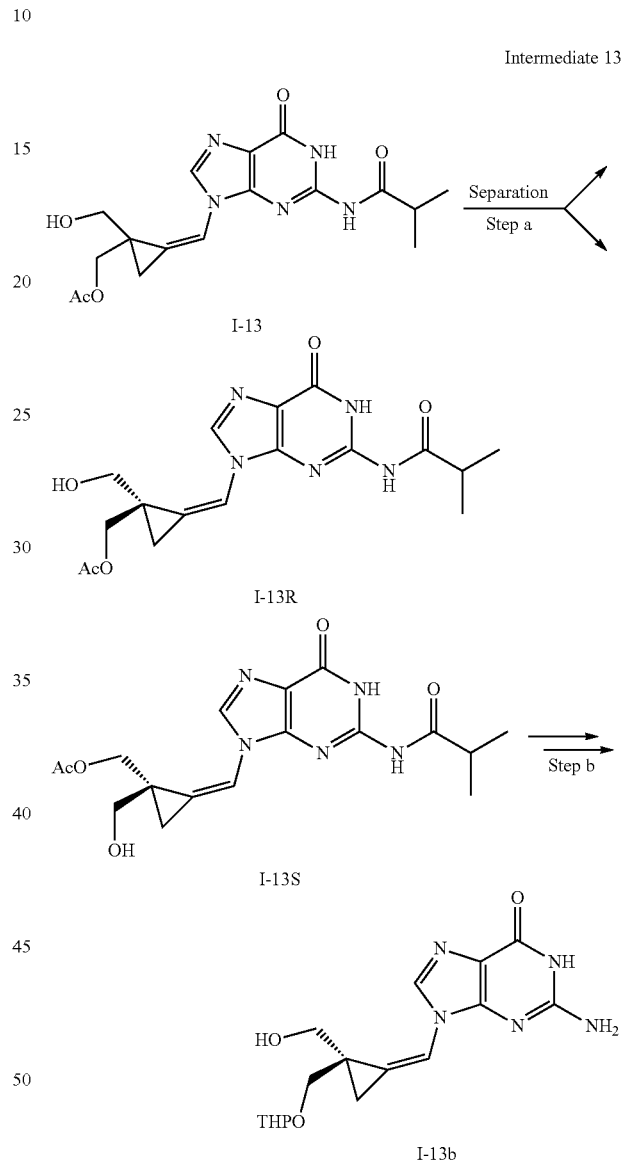

(Z)-(1-(Hydroxymethyl)-2-((2-isobutyramido-6-oxo-1H-purin-9(6H)-yl)methylene)cyclopropyl)methyl acetate (I-13)

The compound was prepared as a racemate as described By Li, Chengwei; Gentry, Brian G.; Drach, John C.; Zemlicka, Jiri in Nucleosides, Nucleotides & Nucleic Acids (2009), 28(9), 795-808. The two stereoisomers were separated by prep. NP HPLC.

Fraction-1 (200 mg, 14%) specific optical rotation (SOR)+21.10°,

Fraction-2, (230 mg, 16%), SOR −19.79°.

The chirality of the isomers was determined by comparison of SOR with the enzymatically prepared compound of Example 12 (+26.52°).

Preparative NP HPLC Conditions
  Column: Chiralpak IC (150×4.6) mm: 3μ
  Mobile phase: Acetonitrile 100% (isocratic)
  Flowrate: 1.0 ml/min
  Temperature: Ambient Step b) 2-Amino-9-((Z)-((2R)-2-(hydroxymethyl)-2-(((tetrahydro-2H-pyran-2-yl)oxy)methyl)cyclopropylidene)methyl)-1H-purin-6(9H)-one (I-13b)

Methanesulfonic acid (0.15 mL, 2.4 mmol) in DMF (10 mL) was added dropwise at rt to a stirred solution of compound I-13S (900 mg, 2.4 mmol) and 3,4-dihydro-2H-pyran (4.3 mL, 48 mmol) in DMF (40 mL). The reaction mixture was stirred at rt for 5 h, then triethyl amine (2.5 mL) was added and the mixture was concentrated. The afforded crude was dissolved in MeOH (80 mL) and 25% aq ammonia (65 mL, 420 mmol) was added at rt. The reaction mixture was stirred at 50° C. for 12 h, then concentrated. The crude compound was purified by column chromatography on silica gel eluted with 15% MeOH in DCM, which gave the title compound (700 mg, 69%) as a solid. LCMS (ES+) m/z 348.38 [M+H]$^+$.

Intermediate 14

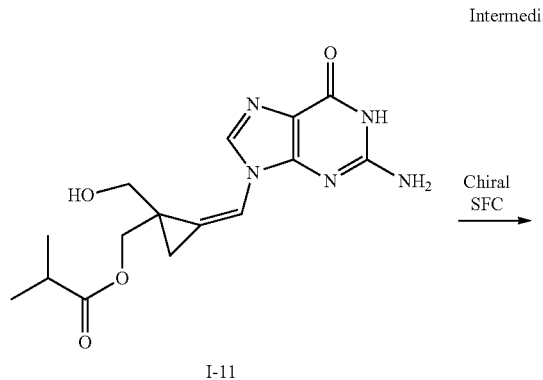

I-11

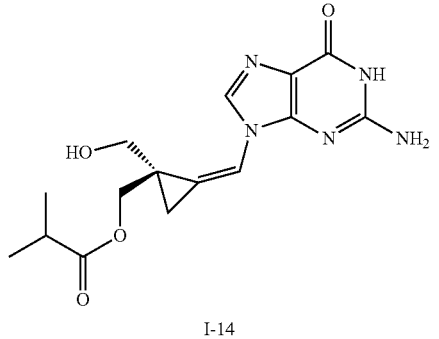

I-14

Step a) (R,Z)-(2-((2-amino-6-oxo-1,6-dihydro-9H-purin-9-yl)methylene)-1-(hydroxymethyl)cyclopropyl)methyl isobutyrate (I-14)

The racemate compound I-11 (450 mg) was purified by chiral SFC to obtain peak-1(150 mg, 23%) as a solid. The afforded compound was analysed by optical rotation (SOR). SOR of the afforded compound was found to be +10.7° (0.44%, DMSO) and was assumed as R-isomer.

Intermediate 15

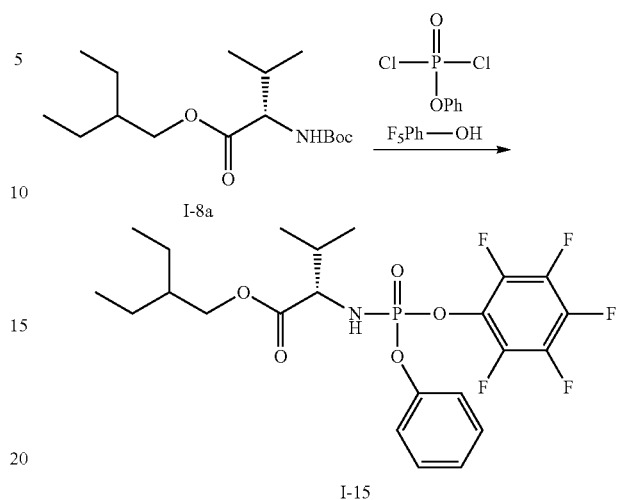

I-8a

I-15

(2S)-2-Ethylbutyl 3-methyl-2-(((perfluorophenoxy)(phenoxy)phosphoryl)amino)butanoate (I-15)

The title compound was prepared by reaction of I-8a according to the method described for I-4. Yield: 26%. LCMS (ES+) 524.29 [M+H]$^+$. Chiral HPLC showed 99.11% of the desired isomer.

Intermediate 16

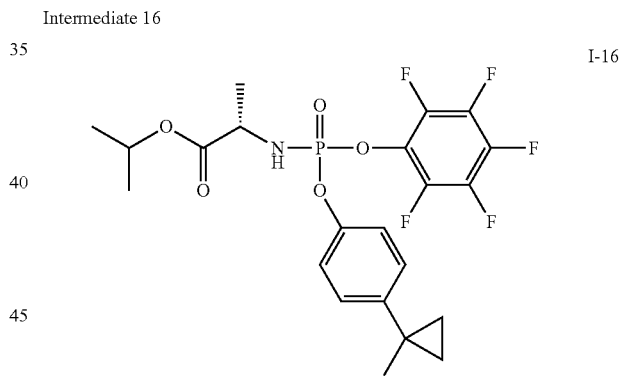

I-16

(2S)-Isopropyl 2-(((4-(1-methylcyclopropyl)phenoxy)(perfluorophenoxy)phosphoryl)amino)propanoate (I-16)

The title compound was prepared as described in WO2015/034420.

Intermediate 17

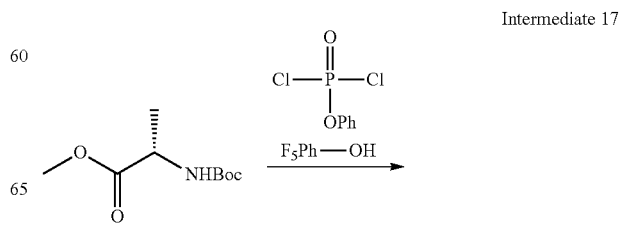

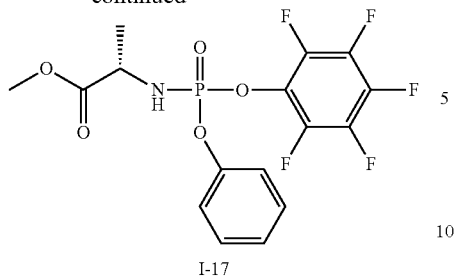

I-17

(2S)-methyl 2-(((Perfluorophenoxy)(phenoxy)phosphoryl)amino)propanoate (I-17)

The title compound was prepared by reaction of (S)-methyl 2-((tert-butoxycarbonyl)amino)propanoate according to the method described as described in I-3 step b. Yield: 25%. LCMS (ES+) m/z 426.13 [M+H]$^+$. The chiral purity of the title compound was 99.5% according to chiral HPLC.

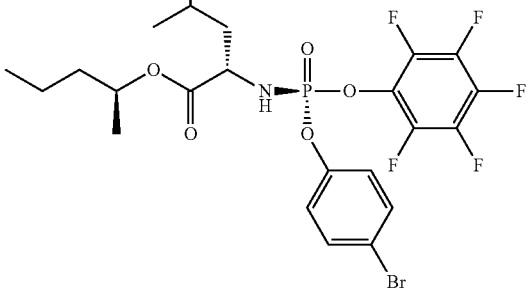

I-18

(S)-(S)-Pentan-2-yl 2-(((S)-(4-bromophenoxy)(perfluorophenoxy)phosphoryl)amino)-4-methylpentanoate (I-18)

The title compound was prepared by reaction of I-7a according to the method described in 1-7 step b. LCMS (ES+) m/z 602.10 & 604.10 [M+H]$^+$. The chiral purity of the title compound was 99% according to chiral HPLC.

Intermediate 18

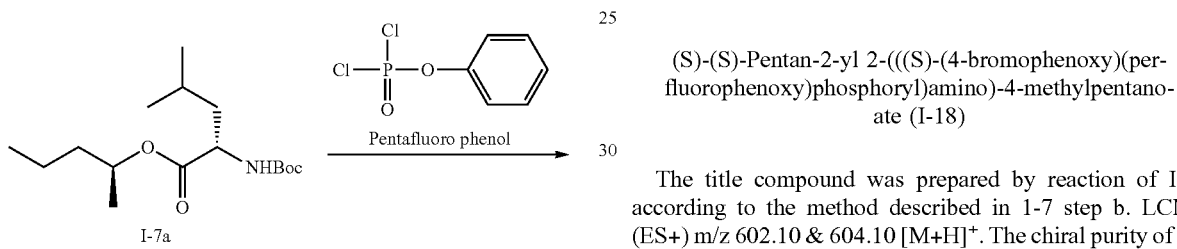

Intermediate 19

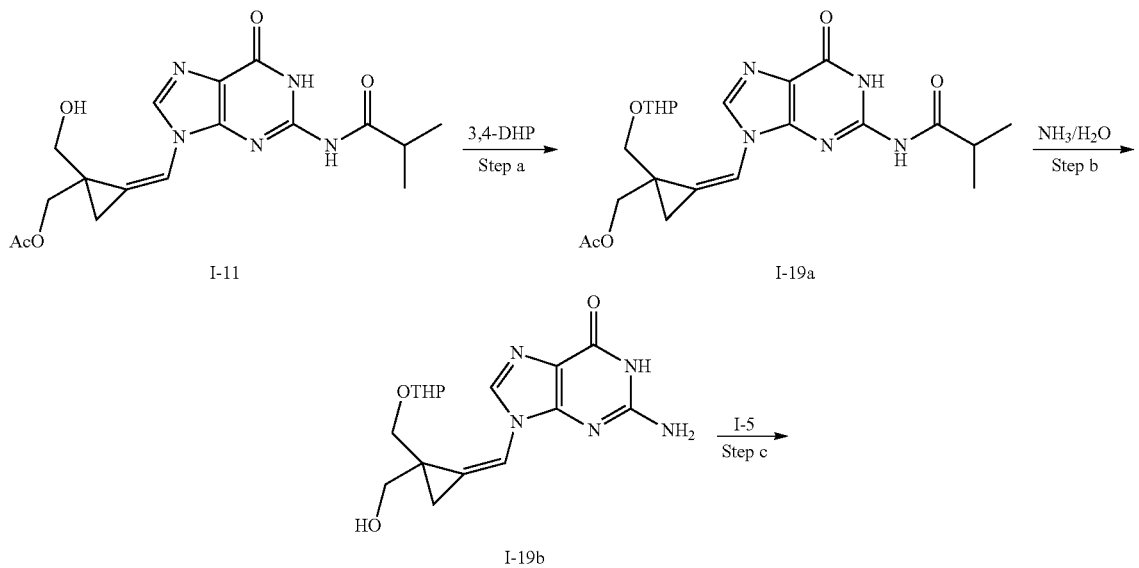

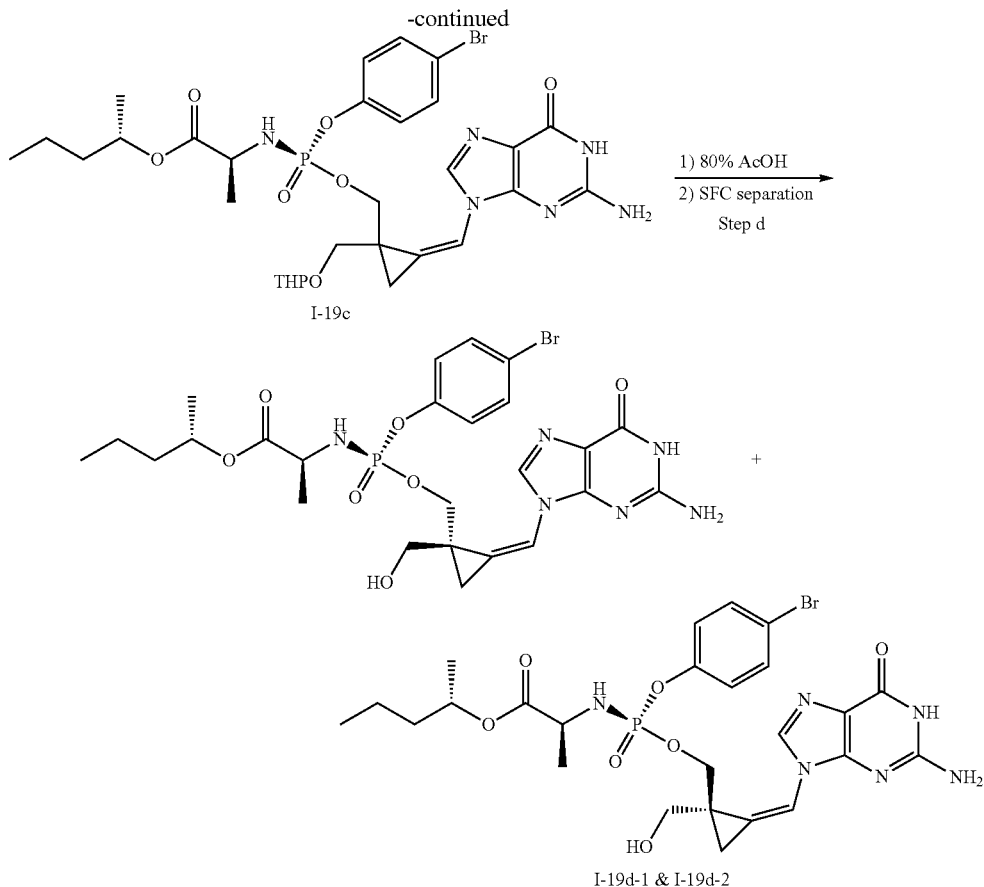

I-19c

I-19d-1 & I-19d-2

Step a) (Z)-(2-((2-Isobutyramido-6-oxo-1H-purin-9(6H)-yl)methylene)-1-(((tetrahydro-2H-pyran-2-yl)oxy)methyl)cyclopropyl)methyl acetate (I-19a)

3,4-Dihydro-2H-pyran (5 mL, 55.41 mmol) and CH$_3$SO$_3$H (0.2 mL, 3.5 mmol) were added at rt. to a stirred solution of compound I-11 (1.3 g, 3.5 mmol) in DMF (20 mL). The reaction mixture was stirred at rt for 5 h, then Et$_3$N (5 mL) was added and the mixture was concentrated under reduced pressure. The crude compound (1.4 g) was used in next step without further purification. MS (ES+) m/z 460.29 [M+H]$^+$.

Step b) (Z)-2-Amino-9-((2-(hydroxymethyl)-2-(((tetrahydro-2H-pyran-2-yl)oxy)methyl)cyclopropylidene)methyl)-1H-purin-6(9H)-one (I-19b)

To a stirred solution of compound I-19a (1.4 g) in MeOH (100 mL) was added 25% aq ammonia (150 mL, 975 mmol) at rt. The reaction mixture was stirred at 50° C. for 12 h, then allowed to attain rt and concentrated. The afforded crude compound was purified by column chromatography on silica gel eluted with 15% MeOH in DCM, which gave the title compound (850 mg, 71% over two steps) as a solid. MS (ES+) m/z 348.26 [M+H]$^+$.

Step c) (2S)—(S)-Pentan-2-yl 2-(((S)-(((Z)-2-((2-amino-6-oxo-1H-purin-9(6H)-yl)methylene)-1-(((tetrahydro-2H-pyran-2-yl)oxy)methyl)cyclopropyl)methoxy)(4-bromophenoxy)phosphoryl)amino)propanoate (I-19c)

tert-butylmagnesium chloride (1M in THF, 4.3 mL, 4.3 mmol) was added dropwise to a solution of compound I-19b (300 mg, 0.86 mmol) in DMF (30 mL). The reaction mixture was stirred at rt for 30 min, then compound I-5 (580 mg, 1.04 mmol) in dry THF (15 mL) was added dropwise. The reaction mixture was stirred at rt for 2 h, then concentrated and the afforded crude compound was purified by column chromatography on silica gel eluted with 10% MeOH in DCM, which gave the title compound (350 mg, 40%) as a solid. MS (ES+) m/z 723.21 & 725.22 [M+H]$^+$.

Step d) (S)-(S)-Pentan-2-yl 2-(((S)-(((S,Z)-2-((2-amino-6-oxo-1H-purin-9(6H)-yl)methylene)-1-(hydroxymethyl)cyclopropyl)methoxy)(4-bromophenoxy)phosphoryl)amino)propanoate (I-19d-1) & (S)-(S)-Pentan-2-yl 2-(((S)-(((R,Z)-2-((2-amino-6-oxo-1H-purin-9(6H)-yl)methylene)-1-(hydroxymethyl)cyclopropyl)methoxy)(4-bromophenoxy)phosphoryl)amino)propanoate (I-19d-2)

A solution of compound I-19c (400 mg, 0.553 mmol) in 80% acetic acid (40 mL, 558 mmol) was stirred at rt for 24 h, then concentrated under reduced pressure. The crude compound was purified by column chromatography on silica gel eluted with 12% MeOH in DCM, which gave a racemic mixture of the title compounds. The mixture was subjected to separation by prep. SFC, which gave isomer-1 (80 mg) as a solid and isomer-2 (100 mg).

Isomer 2 was further purified by prep HPLC using Method B, which gave the pure isomer (52 mg) as a solid.

Preparative SFC Conditions

Column/dimensions: Chiralpak AD-H (30×250 mm), 5µ

$CO_2$: 50.0%

Co solvent: 50.0% (100% IPA)

Total Flow: 90.0 g/min

Back Pressure: 90.0 bar

UV: 214 nm

Stack time: 8.5 min

Load/Inj.: 19.0 mg

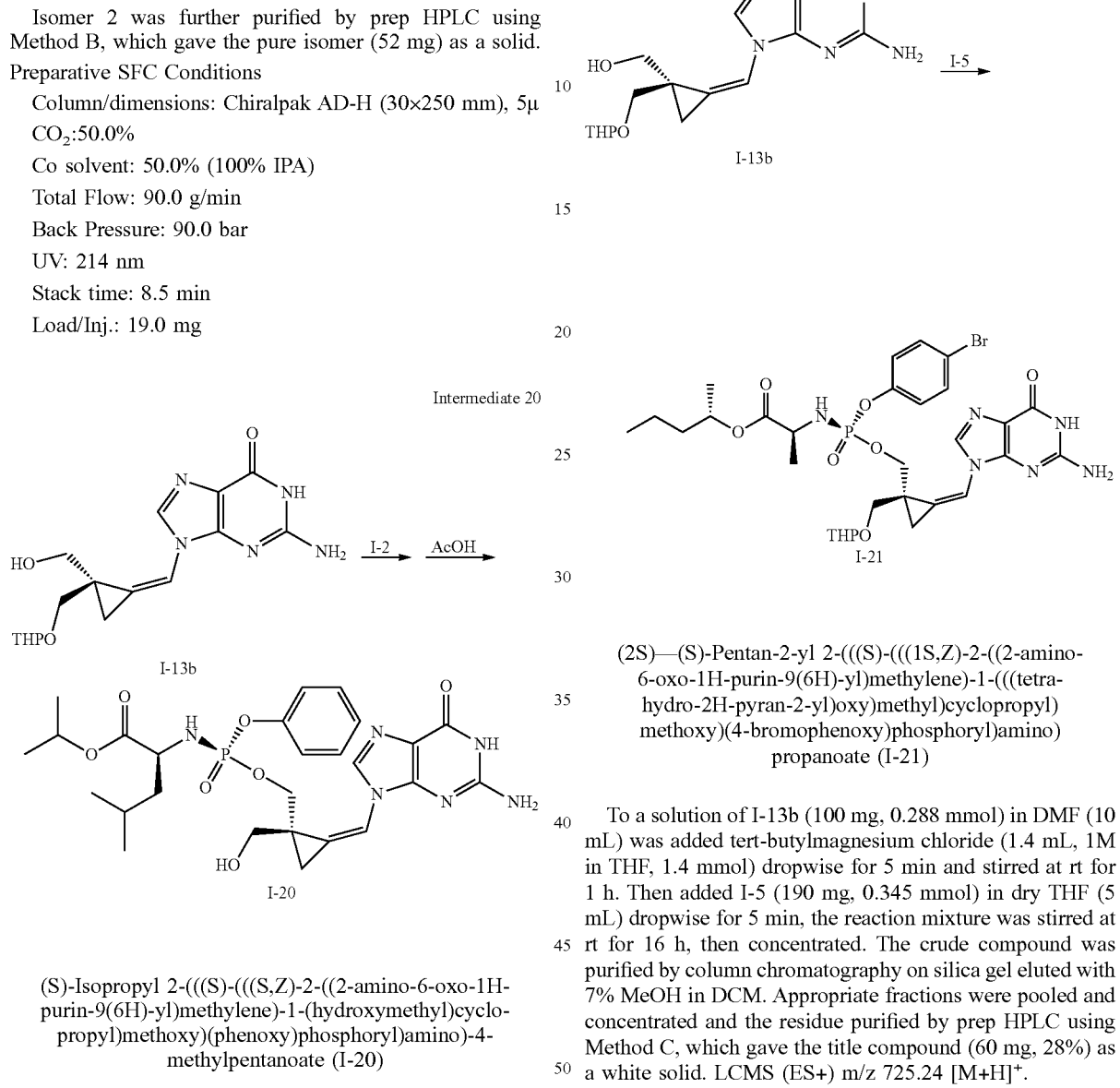

Intermediate 20

I-13b (S)-Isopropyl 2-(((S)-(((S,Z)-2-((2-amino-6-oxo-1H-purin-9(6H)-yl)methylene)-1-(hydroxymethyl)cyclopropyl)methoxy)(phenoxy)phosphoryl)amino)-4-methylpentanoate (I-20)

To a solution of I-13b (200 mg, 0.576 mmol) in DMF (12 mL) was added tert-butylmagnesium chloride (2.9 mL, 1M in THF, 2.9 mmol) dropwise. The mixture was stirred for 30 min at rt, then a solution of I-2 (343 mg, 0.691 mmol) in dry THF (8 mL) was added dropwise. The reaction mixture was stirred at rt for 24 h, then concentrated. The crude compound was purified by column chromatography on silica gel eluted with 4% MeOH. Appropriate fractions were pooled and concentrated and the residue dissolved in 80% acetic acid (37 mL, 509 mmol). The reaction mixture was stirred at rt for 24 h, then concentrated. The crude compound was purified by column chromatography on silica gel eluted with 8% MeOH in DCM. Pure fractions were pooled and concentrated and the residue was purified by prep HPLC using Method C, which gave the title compound (70 mg, 45%) as a solid. LCMS (ES+) m/z 575.31 [M+H]⁺.

Intermediate 21

I-13b

I-21

(2S)—(S)-Pentan-2-yl 2-(((S)-(((1S,Z)-2-((2-amino-6-oxo-1H-purin-9(6H)-yl)methylene)-1-(((tetrahydro-2H-pyran-2-yl)oxy)methyl)cyclopropyl)methoxy)(4-bromophenoxy)phosphoryl)amino)propanoate (I-21)

To a solution of I-13b (100 mg, 0.288 mmol) in DMF (10 mL) was added tert-butylmagnesium chloride (1.4 mL, 1M in THF, 1.4 mmol) dropwise for 5 min and stirred at rt for 1 h. Then added I-5 (190 mg, 0.345 mmol) in dry THF (5 mL) dropwise for 5 min, the reaction mixture was stirred at rt for 16 h, then concentrated. The crude compound was purified by column chromatography on silica gel eluted with 7% MeOH in DCM. Appropriate fractions were pooled and concentrated and the residue purified by prep HPLC using Method C, which gave the title compound (60 mg, 28%) as a white solid. LCMS (ES+) m/z 725.24 [M+H]⁺.

Intermediate 22

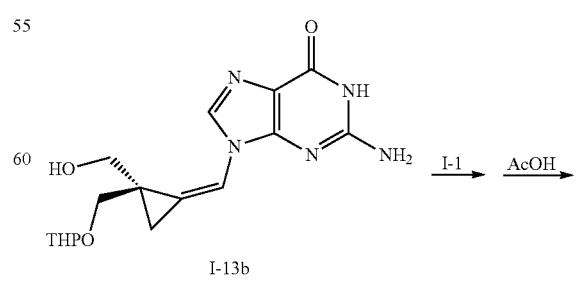

I-13b

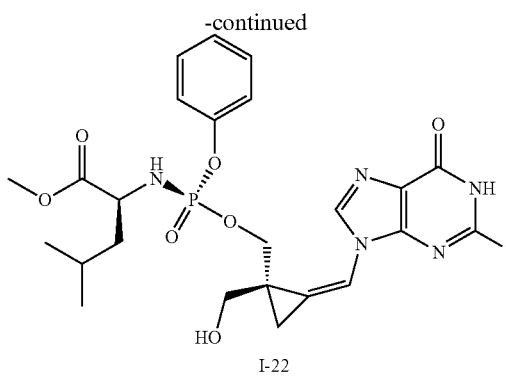

I-22

(S)-Methyl 2-(((S)-(((S,Z)-2-((2-amino-6-oxo-1H-purin-9(6H)-yl)methylene)-1-(hydroxymethyl)cyclopropyl)methoxy)(phenoxy)phosphoryl)amino)-4-methylpentanoate (I-22)

The title compound was prepared from I-13b and I-1 using the method described for Intermediate 20. Yield 21%. LCMS (ES+) m/z 631.44 [M+H]$^+$.

Intermediate 25

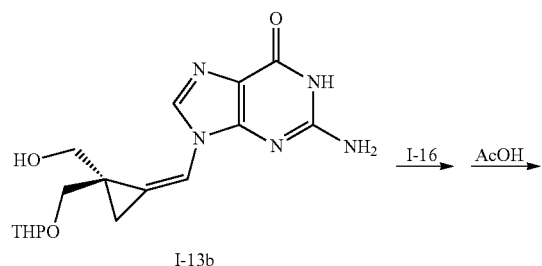

I-13b

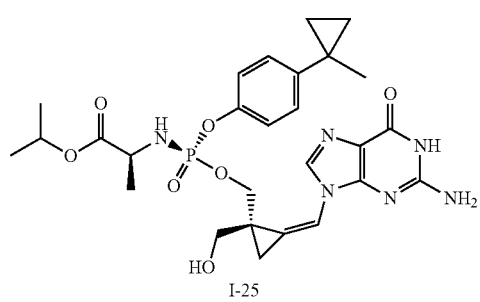

I-25

(S)-Isopropyl 2-(((S)-(((S,Z)-2-((2-amino-6-oxo-1H-purin-9(6H)-yl)methylene)-1-(hydroxymethyl)cyclopropyl)methoxy)(4-(1-methylcyclopropyl)phenoxy)phosphoryl)amino)propanoate (I-25)

The title compound was prepared from I-13b and I-4 using the method described for Intermediate 20. The final compound was purified by prep HPLC using method D. 26% yield. LCMS (ES+) m/z 587.26 [M+H]$^+$.

Intermediate 26

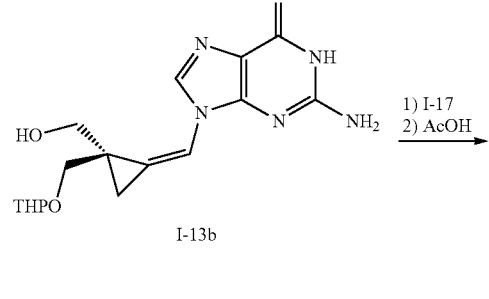

I-13b

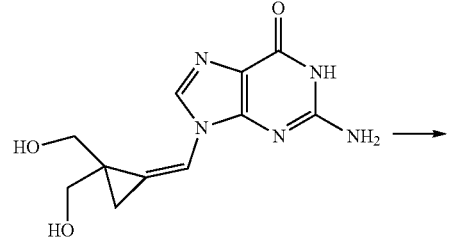

I-26

(S)-Methyl 2-(((S)-(((S,Z)-2-((2-amino-6-oxo-1H-purin-9(6H)-yl)methylene)-1-(hydroxymethyl)cyclopropyl)methoxy)(phenoxy)phosphoryl)amino)propanoate (I-26)

The title compound was prepared from I-13b and I-17 using the method described for Intermediate 20. The final compound was purified by prep SFC. 5.4% yield, LCMS (ES+) m/z 505.31 [M+H]$^+$.

Preparative SFC Conditions

Column/dimensions: Chiralpak AD-H (30×250 mm), 5μ

$CO_2$: 70.0%

Co solvent: 30.0% (100% MeOH)

Total Flow: 70.0 g/min

Back Pressure: 90.0 bar

UV: 214 nm

Stack time: 7.5 min

Load/inj.: 2.3 mg

Intermediate 27

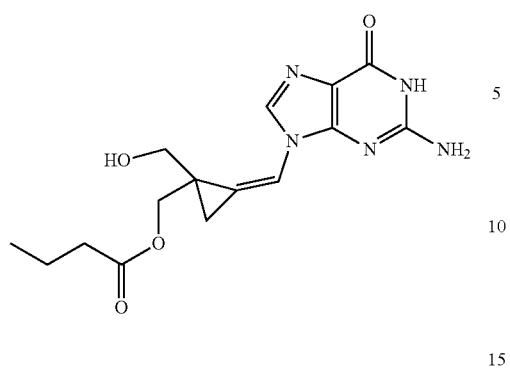

(Z)-(2-((2-Amino-6-oxo-1H-purin-9(6H)-yl)methylene)-1-(hydroxymethyl)cyclopropyl)methyl butyrate (I-27)

To a stirred solution of (Z)-2-amino-9-((2,2-bis(hydroxymethyl)cyclopropylidene)methyl)-1H-purin-6(9H)-one (500 mg, 1.9 mmol) in DMF (30 mL) were added trimethyl orthobutyrate (0.5 mL, 2.8 mmol) and pTSA (37 mg, 0.19 mmol) at rt. The reaction mixture was stirred at rt for 3 h, then triethyl amine (0.5 mL) was added and the mixture was concentrated. The residue was taken in 80% acetic acid in water (75 mL), stirred at rt for 2 h, then concentrated. The crude compound was purified by column chromatography on silica gel eluted with 8% MeOH in DCM, which gave the title compound (350 mg, 55%) as a solid. LCMS (ES+) m/z 34.23 [M+H]$^+$.

Intermediate 28

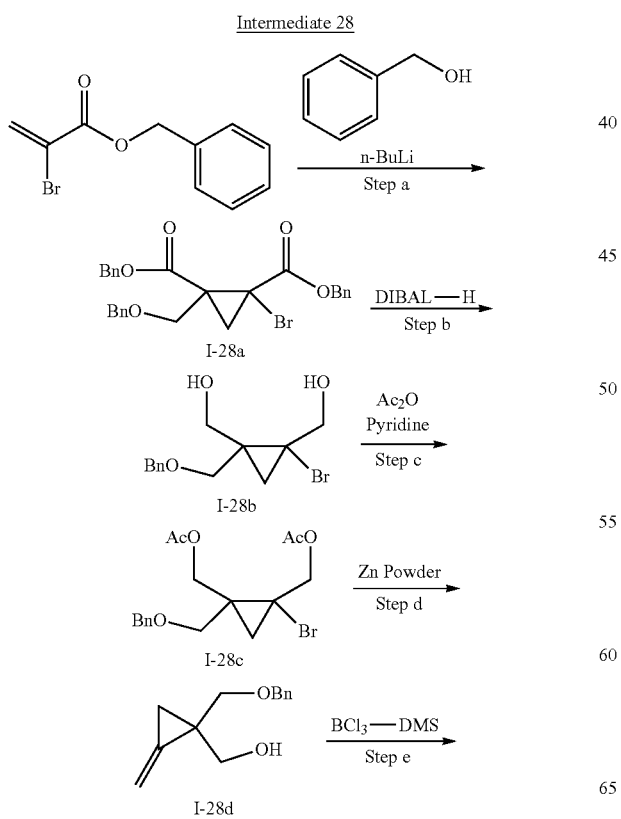

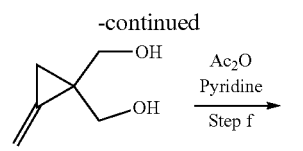

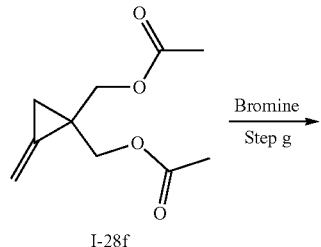

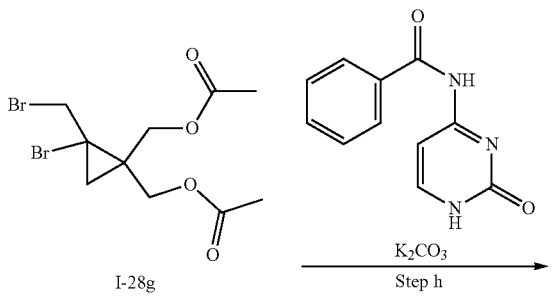

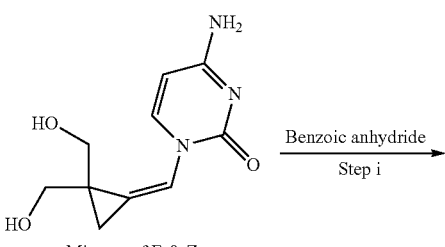

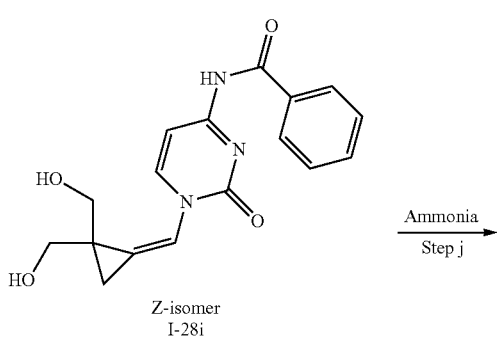

-continued

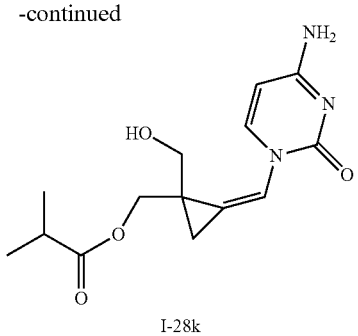

I-28k

Step a) dibenzyl 1-((benzyloxy)methyl)-2-bromocyclopropane-1,2-dicarboxylate (I-28a)

n-BuLi (1.6M in hexane) (520 mL, 829 mmol) was added dropwise at −78° C. under argon to a solution of benzyl alcohol (86 mL, 829 mmol) in dry THF (1000 mL) at −78° C. over a period of 1 h. The solution was stirred for 3 h at −78° C., then a solution of compound benzyl 2-bromoacrylate (400 g, 1659 mmol) in THF (500 mL) was added at −78° C. over a period of 1 h and stirred at that temperature for 4 h and 16 h at rt. To the reaction mixture, saturated ammonium chloride solution (700 mL) was added at 0° C. and the mixture was extracted with EtOAc (2×1500 mL). The combined organic layers were washed with water (1000 mL), brine (1000 mL), dried ($Na_2SO_4$), filtered and concentrated. The crude compound was purified by column chromatography on silica gel and eluted with 15% EtOAc in pet ether, which gave the title compound (270 g). MS (ES+) 511.09 [M+H]$^+$. The crude compound was used in next step without further purification.

Step b) (1-((benzyloxy)methyl)-2-bromocyclopropane-1,2-diyl)dimethanol (I-28b)

DIBAL-H (1M) (2120 mL, 2120 mmol) was added dropwise under argon to a solution of compound I-28a (270 g, 530.05 mmol) in dry THF (2300 mL) at 0° C. over a period of 2 h. The solution was stirred for 16 h at rt, then saturated ammonium chloride solution (700 mL) was added at 0° C. and precipitated solid was filtered and washed with EtOAc (2×1500 mL). The combined organic layers were washed with water (700 mL), brine (700 mL), dried ($Na_2SO_4$), filtered and concentrated. The crude compound was purified by column chromatography on silica gel and eluted with 50% EtOAc in pet ether, which gave the title compound (95 g, 54%). MS (ES+) 301.09 [M+H]$^+$.

Step c) (1-((benzyloxy)methyl)-2-bromocyclopropane-1,2-diyl)bis(methylene) diacetate (I-28c)

Pyridine (128 mL, 1577 mmol) and acetic anhydride (68.5 mL, 725.5 mmol) were added dropwise over a period of 30 min at 0° C. to a stirred solution of compound I-28b (95 g, 315.43 mmol) in DCM (450 mL). The reaction mixture was stirred for 16 h at rt, then quenched with 2N HCl (500 mL) at 0° C. and the mixture was extracted with DCM (2×400 mL). The combined organic layers were washed with water (500 mL), brine (500 mL), dried ($Na_2SO_4$), filtered and concentrated, which gave the title compound (120 g, 88%). MS (ES+) 404.15 [M+H]$^+$

Step d) (1-((benzyloxy)methyl)-2-methylenecyclopropyl)methanol (I-28d)

Zn powder (163 g, 2492 mmol) [activated by stirring commercial Zn powder (200 g) with 2M HCl (300 mL) for 1 h at rt, then Zn was filtered, washed with water (2×400 mL), acetone (2×400 mL) and dried under vacuum overnight] was added portionwise over a period of 15 min at rt to a stirred solution of compound I-28c (120 g, 311.5 mmol) in EtOH (800 mL). The reaction mixture was stirred at 80° C. for 16 h, then cooled to rt and filtered through the celite bed and washed with EtOAc (2×200 mL). The filtrate was concentrated to dryness under reduced pressure. The crude compound was purified by column chromatography on silica gel and eluted with 20% EtOAc in pet ether, which gave the title compound (34 g, 47%). MS (ES+) 205.25 [M+H]$^+$.

Step e) (2-methylenecyclopropane-1,1-diyl)dimethanol (I-28e)

$BCl_3$-DMS (2M in DCM) (100 mL, 200 mmol) was added dropwise over a period of 1H at 0° C. to a stirred solution of compound I-28d (34 g, 166.5 mmol) in DCM (400 mL). The reaction mixture was stirred for 5 h at rt, then filtered and washed with 10% MeOH in DCM (2×500 mL). The filtrate was concentrated to dryness under reduced pressure. The crude compound was purified by column chromatography on silica gel and eluted with 80% EtOAc in pet ether, which gave the title compound (18 g, 95%).

Step f) (2-methylenecyclopropane-1,1-diyl)bis(methylene) diacetate (I-28f)

Acetic anhydride (104.2 mL, 1104 mmol) were added dropwise over a period of 30 min at 0° C. to a stirred solution of compound I-28e (18 g, 157.7 mmol) in pyridine (45 mL, 552 mmol). The reaction mixture was stirred for 16 h at rt, then quenched with water (200 mL) at 0° C. and extracted with DCM (2×500 mL). The combined organic layers were washed 2N HCl (2×200 mL), water (200 mL), brine (200 mL), dried ($Na_2SO_4$), filtered and concentrated. The crude compound was purified by column chromatography on silica gel and eluted with 15% EtOAc in pet ether, which gave the title compound (27 g, 81%). MS (ES+) 216.27 [M+H]$^+$ as ammonium adduct.

Step a) (2-bromo-2-(bromomethyl)cyclopropane-1,1-diyl)bis(methylene) diacetate (I-28a)

Bromine (7 mL, 136.22 mmol) were added dropwise over a period of 30 min at 0° C. to a stirred solution of compound I-28f (27 g, 136.22 mmol) in carbon tetrachloride (250 mL). The reaction mixture was stirred for 1 h at 0° C., then diluted with DCM (300 mL) and washed with sodium thiosulphate solution (2×300 mL). The combined organic layers were washed saturated sodium bicarbonate solution (300 mL), water (300 mL), brine (300 mL), dried ($Na_2SO_4$), filtered and concentrated. The crude compound was purified by column chromatography on silica gel and eluted with 20% EtOAc in pet ether, which gave the title compound (40 g, 74%). MS (ES+) 376.02 [M+H]$^+$ as ammonium adduct.

Step h) (Z)-4-amino-1-((2,2-bis(hydroxymethyl)cyclopropylidene)methyl)pyrimidin-2(1H)-one (I-28h)

Dried $K_2CO_3$ (9.3 g, 67 mmol) and N4-Benzoylcytosine (2.4 g, 11.2 mmol) were added to a stirred solution of compound I-28g (4 g, 11.2 mmol) in DMF (400 mL). The reaction mixture was stirred at 100° C. for 12 h, then cooled to 50° C. and MeOH (40 mL) was added. The resulting reaction mixture was stirred for 2 h at 50° C., then cooled to rt and filtered. The filtrate was concentrated to dryness under reduced pressure. The crude compound was purified by column chromatography on silica gel and eluted with 10% MeOH in DCM, which gave the title compound (2.4 g) as a mixture of E and Z isomers. MS (ES+) 224.2 [M+H]+.

Step i) (Z)—N-(1-((2,2-bis(hydroxymethyl)cyclopropylidene)methyl)-2-oxo-1,2-dihydropyrimidin-4-yl)benzamide (I-28i)

Benzoic anhydride (7.3 g, 32.3 mmol) was added to a stirred solution of compound I-28h (2.4 g, 10.8 mmol) in EtOH (300 mL) and the reaction mixture at was stirred at 100° C. for 3 h, The reaction mixture was cooled to rt, filtered, the filtrate was concentrated to dryness under reduced pressure. The crude compound was purified by column chromatography on silica gel and eluted with 5% MeOH in DCM. The residue was further purified by column chromatography on silica gel and eluted with 5% MeOH in DCM, which gave the title compound (500 mg, 14%). MS (ES+) 328.29 [M+H]+.

Step i) (Z)-4-amino-1-((2,2-bis(hydroxymethyl) cyclopropylidene)methyl)pyrimidin-2(1H)-one (I-2j)

A stirred solution of compound I-28i (500 mg, 1.53) in 7M NH₃ in MeOH (50.2 mL) was stirred at rt for 16 h, then the precipitated solid was filtered and dried. The residue was further purified by prep. HPLC on an X-bridge C18 column (30×250) mm 5u using a gradient of 10 mM NH₄HCO₃ in H₂O:MeCN as mobile phase, which gave the title compound (80 mg) as a solid. The filtrate was concentrated under reduced pressure and the residue was purified by column chromatography on silica gel and eluted with 15% MeOH in DCM, which gave another lot of the title compound (80 mg). MS (ES+) 224.27 [M+H]+.

Step k) (Z)-(2-((4-amino-2-oxopyrimidin-1(2H)-yl) methylene)-1-(hydroxymethyl)cyclopropyl)methyl isobutyrate (I-28k)

To a stirred solution of compound I-28j (130 mg, 0.6 mmol) in DMF (10 mL) were added trimethyl orthoisobutyrate (0.14 mL, 0.9 mmol) and pTSA (11 mg, 0.1 mmol) at rt. The reaction mixture was stirred at rt for 3 h, then Et₃N (0.5 mL) was added and the mixture was concentrated. The residue was taken in 80% acetic acid in water (15 mL), stirred at rt for 2 h, then concentrated. The crude compound was purified by column chromatography on silica gel eluted with 7% MeOH in DCM, which gave the title compound (180 mg, 97%) as a solid. LCMS (ES+) m/z 294.26 [M+H]+.

Intermediate 29

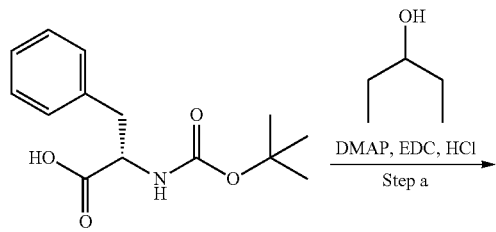

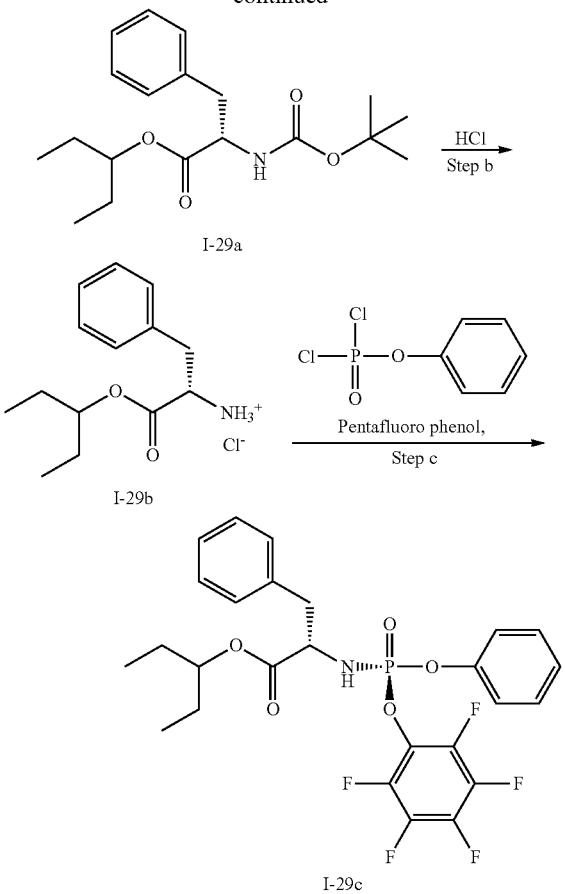

Step a) pentan-3-yl(tert-butoxycarbonyl)-L-phenylalaninate (I-29a)

To a stirred solution of (tert-butoxycarbonyl)-L-phenylalanine (7.2 g, 27.2 mmol) and pentan-3-ol (2.5 mL, 22.7 mmol) in DCM (150 mL) were added DMAP (416 mg, 3.4 mmol), EDCI (4.8 g, 25 mmol) at 0° C. The solution was stirred for 18 h, then diluted with DCM (100 mL), washed with water (2×50 mL) and brine (100 mL). The organic layer was dried over anhydrous sodium sulfate and concentrated under reduced pressure. The afforded crude compound was purified by column chromatography on silica gel, eluted with 10% ethyl acetate in hexane which gave the title compound (6.5 g, 85%).

Step b) (S)-1-oxo-1-(pentan-3-yloxy)-3-phenylpropan-2-aminium chloride (I-29b)

4M HCl in 1,4 dioxane (22 mL, 87.2 mmol) was added at 0° C. to a solution of compound I-29a (6.5 g, 19.4 mmol) in 1,4-dioxane (60 mL). The reaction mixture was stirred at room temperature for 2 h, then concentrated under reduced pressure, which gave the title compound (5 g, HCl salt) as a solid. The crude product was used in the next step without further purification.

Step bc pentan-3-yl((S)-(perfluorophenoxy)(phenoxy)phosphoryl)-L-phenylalaninate (I-29c)

Et₃N (5.4 mL, 38.6 mmol) was added dropwise over a period of 10 min at −78° C. to a stirred solution of compound I-29b (5 g, 18.4 mmol) in DCM (100 mL) followed by dropwise addition of a solution of phenyl phosphorodichloridate (2.8 mL, 18.4 mmol) in DCM (50 mL) over a period of 30 min. The reaction mixture was stirred at −78° C. for 30 min, then allowed to warm to 0° C. during 2 h and was then stirred for 1 h at 0° C. A solution of 2,3,4,5,6-pentafluorophenol (3 g, 16.6 mmol) and Et$_3$N (2.8 mL, 20.2 mmol) in DCM (50 mL) was added dropwise at 0° C. and the reaction mixture was then stirred for at rt 3 h, then concentrated to dryness under reduced pressure, The crude product was dissolved in MTBE (100 mL), insolubles were filtered off and the filtrate was concentrated to dryness under reduced pressure. The crude compound was purified by column chromatography on silica gel eluted with 10% EtOAc in hexane. Pure fractions were pooled and concentrated under reduced pressure. The afforded racemic compound was dissolved in 30% EtOAc in pet ether (250 mL) and kept at rt for 24 h, the crystals formed were filtered off and washed with pet ether (2×100 mL), and dried under vacuum which gave the title compound (2 g, 18%, chiral purity 99%). MS (ES+) m/z 558.30 [M+H]$^+$.

Intermediate 30

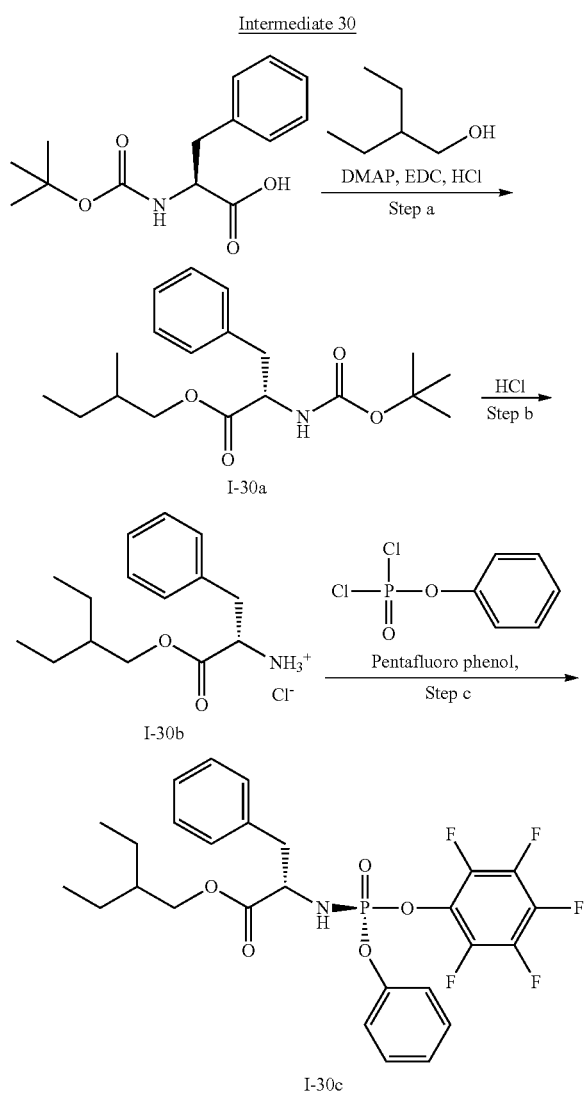

Step a) 2-ethylbutyl(tert-butoxycarbonyl)-L-phenyl-alaninate (I-30a)

To a stirred solution of (tert-butoxycarbonyl)-L-phenyl-alanine (7.8 g, 29.5 mmol) and 2-ethylbutan-1-ol (3.1 mL, 24.7 mmol) in DCM (80 mL) were added DMAP (450 mg, 3.7 mmol), EDCI (5.2 g, 27.1 mmol) at 0° C. The solution was stirred for 16 h at rt, then diluted with DCM (200 mL), washed with saturated sodium bicarbonate solution (100 mL) and brine (100 mL). The organic layer was dried over anhydrous sodium sulfate and concentrated under reduced pressure. The afforded crude compound was purified by column chromatography on silica gel, eluted with 20% ethyl acetate in hexane which gave the title compound (7.5 g, 87%). MS (ES+) m/z 350.47 [M+H]$^+$.

Step b) (S)-1-(2-ethylbutoxy)-1-oxo-3-phenylpropan-2-aminium chloride (I-30b)

4M HCl in 1,4 dioxane (32 mL, 128 mmol) was added at rt to a solution of compound I-30a (7.5 g, 21.5 mmol) in 1,4-dioxane (100 mL). The reaction mixture was stirred at room temperature for 4 h at rt, then concentrated under reduced pressure, which gave the title compound (5.5 g, 88%, HCl salt) as a solid.

Step c) 2-ethylbutyl((S)-(perfluorophenoxy)(phenoxy)phosphoryl)-L-phenylalaninate (I-30c)

Et$_3$N (5.6 mL, 40.1 mmol) was added dropwise over a period of 10 min at −78° C. to a stirred solution of compound I-30b (5.5 g, 19.2 mmol) in DCM (100 mL) followed by dropwise addition of a solution of phenyl phosphorodichloridate (2.9 mL, 19.4 mmol) in DCM (40 mL) over a period of 30 min. The reaction mixture was stirred at −78° C. for 30 min, then allowed to warm to 0° C. during 2 h and was then stirred for 1 h at 0° C. A solution of 2,3,4,5,6-pentafluorophenol (3.2 g, 17.4 mmol) and Et$_3$N (3.4 mL, 24.3 mmol) in DCM (50 mL) was added dropwise at 0° C. over a period of 15 min and the reaction mixture was then stirred for at rt 5 h, then concentrated to dryness under reduced pressure, The crude product was dissolved in MTBE (100 mL) and stirred for 10 min, insolubles were filtered off and the filtrate was concentrated to dryness under reduced pressure. The crude compound was purified by column chromatography on silica gel eluted with 20% EtOAc in hexane. Pure fractions were pooled and concentrated under reduced pressure. The afforded racemic compound was dissolved in 20% EtOAc in pet ether (100 mL) and kept in refrigerator for 4 h, the crystals formed were filtered off and washed with 20% EtOAc in pet ether (30 mL), and dried under vacuum which gave the title compound (1.5 g, 13%, chiral purity 99%). MS (ES+) m/z 572.30 [M+H]$^+$.

Intermediate 31

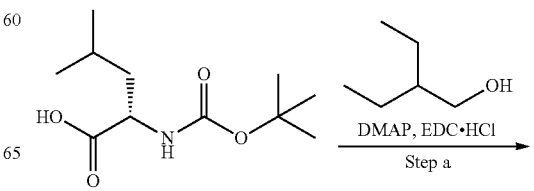

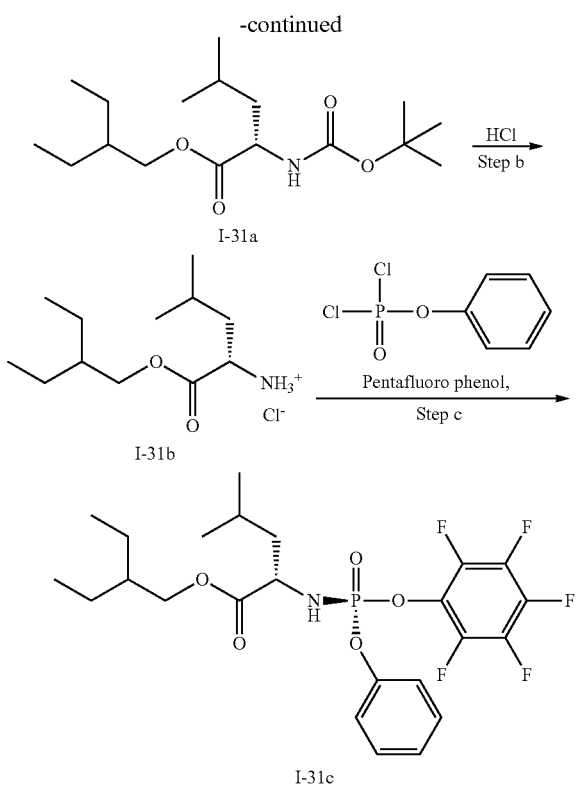

Step a)
2-ethylbutyl(tert-butoxycarbonyl)-L-leucinate (I-31a)

To a stirred solution of (tert-butoxycarbonyl)-L-leucine (6.8 g, 29.4 mmol) and 2-ethylbutan-1-ol (2.6 mL, 24.5 mmol) in DCM (100 mL) were added DMAP (449 mg, 3.7 mmol), EDCI (5.2 g, 26.9 mmol) at 0° C. The solution was stirred for 16 h at rt, then diluted with DCM (100 mL), washed with water (50 mL) and brine (50 mL). The organic layer was dried over anhydrous sodium sulfate and concentrated under reduced pressure. The afforded crude compound was purified by column chromatography on silica gel, eluted with 10% ethyl acetate in hexane, which gave the title compound (7.2 g, 93%). MS (ES+) m/z 316.43 [M+H]$^+$.

Step b) (S)-1-(2-ethylbutoxy)-4-methyl-1-oxopentan-2-aminium chloride (I-31b)

4M HCl in 1,4 dioxane (36 mL, 143.8 mmol) was added at rt to a solution of compound I-31a (7.2 g, 22.8 mmol) in 1,4-dioxane (50 mL). The reaction mixture was stirred at room temperature for 2 h at rt, then concentrated under reduced pressure, which gave the title compound (5.5 g, HCl salt) as a solid. MS (ES+) m/z 216.28 [M+H]$^+$. The crude product was used in the next step without further purification.

Step c) 2-ethylbutyl((S)-(perfluorophenoxy)(phenoxy)phosphoryl)-L-leucinate (I-31c)

Et$_3$N (6.4 mL, 46 mmol) was added dropwise over a period of 10 min at −78° C. to a stirred solution of compound I-31b (5.5 g, 22 mmol) in DCM (125 mL) followed by dropwise addition of a solution of phenyl phosphorodichloridate (3.3 mL, 22 mmol) in DCM (125 mL) over a period of 30 min. The reaction mixture was stirred at −78° C. for 30 min, then allowed to warm to 0° C. during 2 h and was then stirred for 1 h at 0° C. A solution of 2,3,4,5,6-pentafluorophenol (3.6 g, 20 mmol) and Et$_3$N (3.4 mL, 24 mmol) in DCM (50 mL) was added dropwise at 0° C. over a period of 15 min and the reaction mixture was then stirred for at rt 4 h, then concentrated to dryness under reduced pressure, The crude product was dissolved in MTBE (100 mL) and stirred for 10 min, insolubles were filtered off and the filtrate was concentrated to dryness under reduced pressure. The crude compound was purified by column chromatography on silica gel eluted with 20% EtOAc in hexane. Pure fractions were pooled and concentrated under reduced pressure. The afforded racemic compound was dissolved in 10% EtOAc in pet ether (100 mL) and kept in refrigerator for 12 h, the crystals formed were filtered off and washed with 5% EtOAc in pet ether (30 mL), and dried under vacuum. The obtained residue was further purified by chiral SFC, which gave the title compound (500 mg). MS (ES+) m/z 538.43 [M+H]$^+$.

Preparative SFC Conditions:
  Column/dimensions: Chiralpak IG (4.6×250 mm), 5μ
  CO$_2$:85.0%
  Co solvent: 15.0% (100% isopropanol)
  Total Flow: 3.0 g/min
  Back Pressure: 100.0 bar
  UV: 214 nm

Intermediate 32

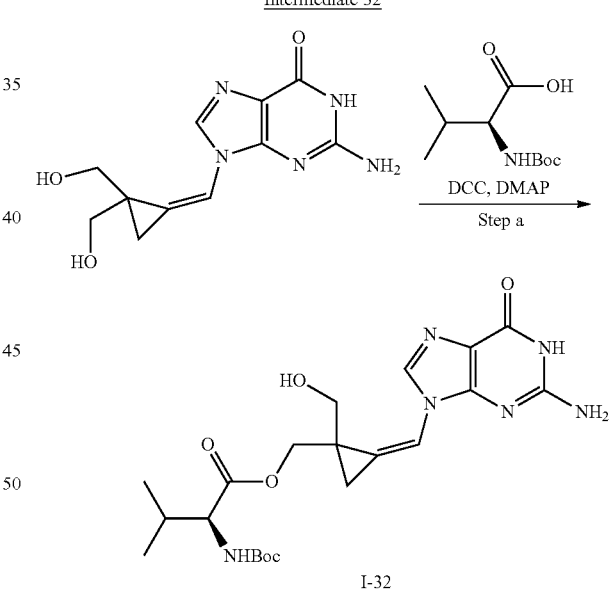

((Z)-2-((2-amino-6-oxo-1,6-dihydro-9H-purin-9-yl)methylene)-1-(hydroxymethyl)cyclopropyl)methyl (tert-butoxycarbonyl)-L-valinate (I-32a)

DCC (549 mg, 2.7 mmol) and DMAP (33 mg, 0.27 mmol) were added at rt to a stirred solution of (Z)-2-amino-9-((2,2-bis(hydroxymethyl)cyclopropylidene)methyl)-1H-purin-6 (9H)-one (350 mg, 1.3 mmol) and (tert-butoxycarbonyl)-L-valine (289 mg, 1.3 mmol) in DMF (20 mL). The resulting reaction mixture was stirred at rt for 16 h, then concentrated under reduced pressure. The crude compound was combined with another batch and purified by column chromatography on silica gel and eluted with 10% EtOAc in hexane. The pure compound was further purified by chiral SFC, which gave the title compound (65 mg, 10%) as a solid. MS (ES+) 463.43 [M+H]⁺.

Preparative SFC Conditions:
Column/dimensions: Chiralcel OX-H (250×30) mm, 5μ
CO₂:65.0%
Co solvent: 35.0% (MeOH)
Total Flow: 70 g/min
Back Pressure: 100.0 bar
UV: 214 nm
Load ability/inj.: 5.0 mg
Stack time: 14 min
Load/Inj.: 7 mg Intermediate 33

I-28j

I-33a

Step a) (Z)-(2-((4-amino-2-oxopyrimidin-1(2H)-yl)methylene)-1-(hydroxymethyl)cyclopropyl)methyl butyrate (I-33a)

To a stirred solution of compound I-28j (300 mg, 1.34 mmol) in DMF (20 mL) were added trimethyl orthobutyrate (0.32 mL, 2.02 mmol) and pTSA (26 mg, 0.13 mmol) at rt. The reaction mixture was stirred at rt for 3 h, then Et₃N (0.5 mL) was added and the mixture was concentrated. The residue was taken in 80% acetic acid in water (20 mL), stirred at rt for 2 h, then concentrated. The crude compound was purified by column chromatography on silica gel eluted with 8% MeOH in DCM, which gave the title compound (260 mg, 57%) as a solid. LCMS (ES+) m/z 294.34 [M+H]⁺.

Intermediate 34

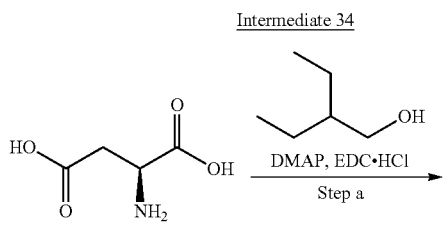

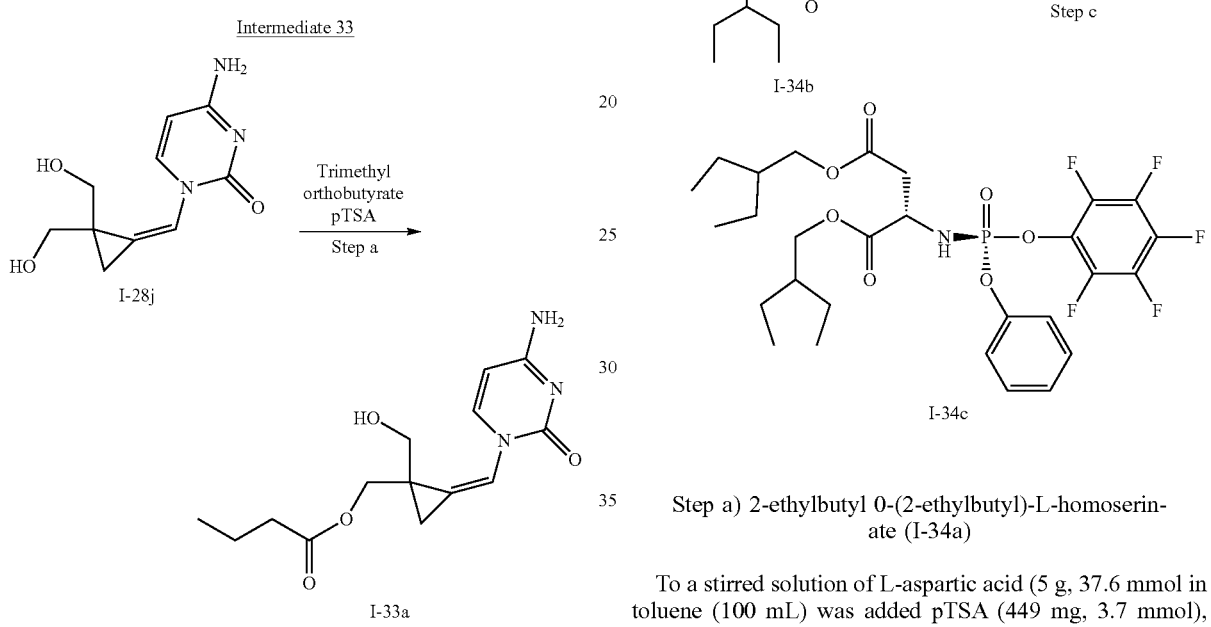

Step a) 2-ethylbutyl 0-(2-ethylbutyl)-L-homoserinate (I-34a)

To a stirred solution of L-aspartic acid (5 g, 37.6 mmol in toluene (100 mL) was added pTSA (449 mg, 3.7 mmol), followed by 2-ethylbutan-1-ol (7.7 g, 75.1 mmol) at 0° C. The solution was stirred for 16 h at 110° C., then concentrated under reduced pressure. The residue was dissolved in water and extracted with EtOAc. The combined organic extracts were washed with saturated sodium bicarbonate solution, brine, dried over sodium sulfate, filtered and concentrated under reduced pressure, which gave the title compound (7.15 g, 63%). MS (ES+) m/z 302.41 [M+H]⁺.

Step b) bis(2-ethylbutyl) L-aspartate hydrochloride (I-34b)

4M HCl in 1,4 dioxane (40 mL, 160 mmol) was added at rt to a solution of compound I-34a (7.15 g, 23.7 mmol) in 1,4-dioxane (35 mL). The reaction mixture was stirred at room temperature for 12 h, then concentrated under reduced pressure, which gave the title compound (8 g, HCl salt) as a solid. MS (ES+) m/z 302.28 [M+H]⁺.

Step c) bis(2-ethylbutyl) ((S)-(perfluorophenoxy)(phenoxy)phosphoryl)-L-aspartate (I-34c)

Et₃N (6.9 mL, 49.3 mmol) was added dropwise over a period of 5 min at −70° C. to a stirred solution of compound I-34b (8 g, 23.5 mmol) in DCM (40 mL) followed by dropwise addition of a solution of phenyl phosphorodichloridate (3.5 mL, 23.5 mmol) in DCM (20 mL) over a period of 10 min. The reaction mixture was stirred at −70° C. for 30 min, then allowed to warm to 0° C. during 2 h and was then stirred for 1 h at 0° C. A solution of 2,3,4,5,6-pentafluorophenol (3.9 g, 21.12 mmol) and Et$_3$N (3.6 mL, 25.8 mmol) in DCM (20 mL) was added dropwise at 0° C. and the reaction mixture was then stirred for at rt for 4 h, then concentrated to dryness under reduced pressure, The crude product was dissolved in MTBE (100 mL), insolubles were filtered off and the filtrate was concentrated to dryness under reduced pressure. The crude compound was purified by column chromatography on silica gel eluted with 10% EtOAc in hexane. Pure fractions were pooled and concentrated under reduced pressure. The afforded racemic compound was dissolved in 10% EtOAc in pet ether (90 mL) and kept at 0° C. for 12 h, the crystals formed were filtered off and dried under vacuum. The obtained compound was again dissolved in 10% EtOAc in pet ether (30 mL) and kept at 0° C. for 12 h, the crystals formed were filtered off and dried under vacuum. The obtained compound was again dissolved in 2% EtOAc in pet ether (50 mL) and kept at 0° C. for 4 h, the crystals formed were filtered off and dried under vacuum, which gave the title compound (2 g, 12%, chiral purity 98.6%). MS (ES+) m/z 624.60 [M+H]$^+$.

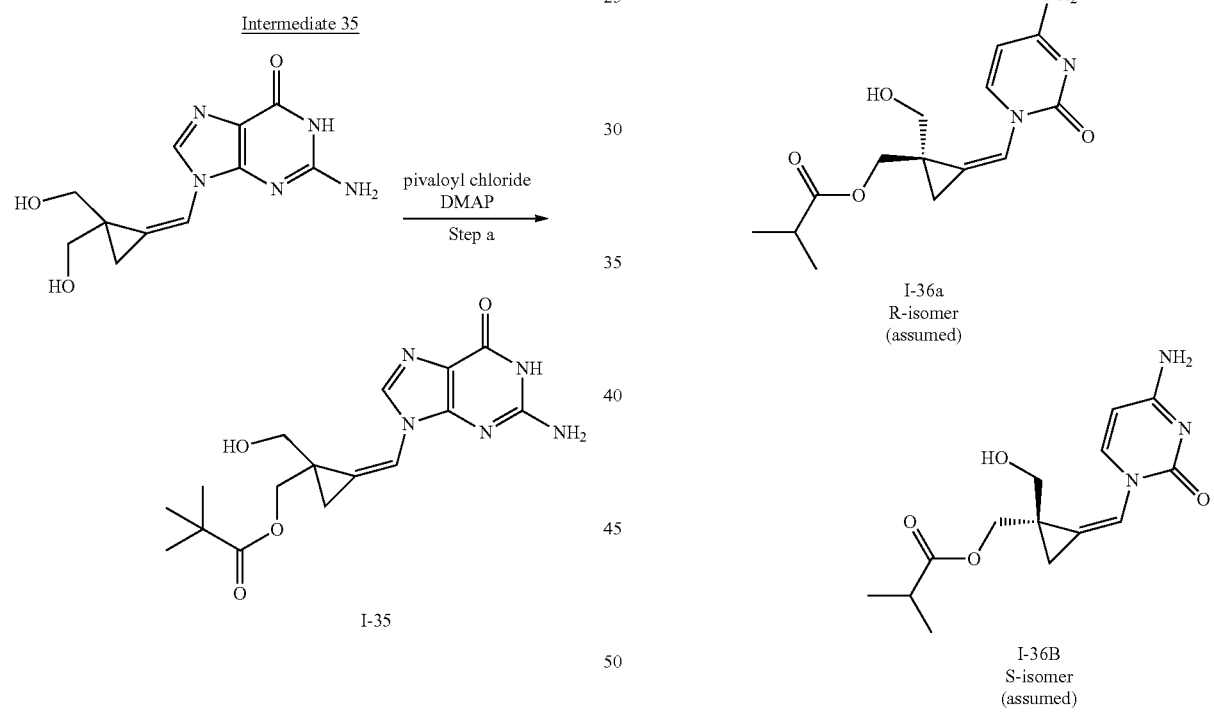

Step a) (Z)-(2-((2-amino-6-oxo-1,6-dihydro-9H-purin-9-yl)methylene)-1-(hydroxymethyl)cyclopropyl)methyl pivalate (I-35a)

DMAP (464 mg, 3.8 mmol) was added at rt to a stirred solution of (Z)-2-amino-9-((2,2-bis(hydroxymethyl)cyclopropylidene)methyl)-1H-purin-6(9H)-one (1 g, 3.8 mmol) in DMF (50 mL). The reaction mixture was cooled to 10° C., then pivaloyl chloride (920 mg, 7.6 mmol) was added. The resulting reaction mixture was stirred at rt for 1 h, then concentrated under reduced pressure. The crude compound was purified by column chromatography on silica gel and eluted with 8% MeOH in DCM. The pure compound was further purified by chiral SFC, which gave the title compound (100 mg) as a solid. MS (ES+) 348.41 [M+H]$^+$.

(R,Z)-(2-((4-amino-2-oxopyrimidin-1(2H)-yl)methylene)-1-(hydroxymethyl)cyclopropyl)methyl isobutyrate (I-36a) & (S,Z)-(2-((4-amino-2-oxopyrimidin-1(2H)-yl)methylene)-1-(hydroxymethyl)cyclopropyl)methyl isobutyrate (I-36b)

To a stirred solution of compound I-28j (300 mg, 1.34 mmol) in DMF (15 mL) were added trimethyl orthoisobutyrate (0.64 mL, 4.03 mmol) and pTSA (128 mg, 0.7 mmol) at rt. The reaction mixture was stirred at rt for 3 h, then Et$_3$N (1 mL) was added and the mixture was concentrated. The residue was taken in 80% acetic acid in water (20 mL), stirred at rt for 2 h, then concentrated. The crude compound was purified by column chromatography on silica gel eluted with 8% MeOH in DCM. The obtained compound was further purified by prep HPLC using Method G. The pure compound was further purified by chiral SFC, which gave the title compounds peak-1 (61 mg, 15%) and peak-2 (62 mg, 15%) as solids. MS (ES+) 294.30 [M+H]$^+$.

Peak-1:
SOR: +46.14° (based on the SOR value of the guanine coupled compound, the stereochemistry is assumed to be R-isomer).

Peak-2:
SOR: −46.18° (based on the SOR value of the guanine coupled compound, the stereochemistry is assumed to be S-isomer).

Preparative SFC Conditions
Column/dimensions: Chiralcel OX-H (30×250 mm), 5μ
$CO_2$:70.0%
Co solvent: 30.0% (EtOH)
Total flow: 70.0 g/min
Back pressure: 100.0 bar
UV: 214 nm
Stack time: 6.0 min
Load/inj.: 10.0 mg Intermediate 37

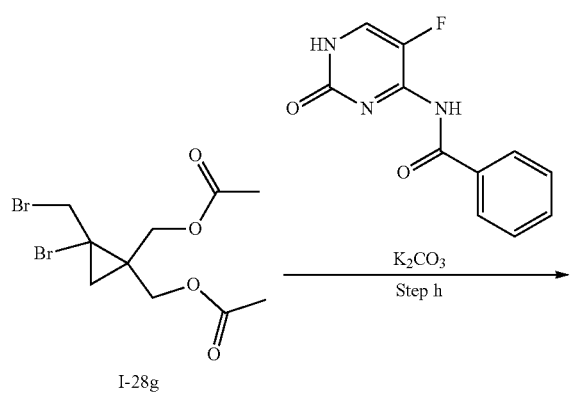

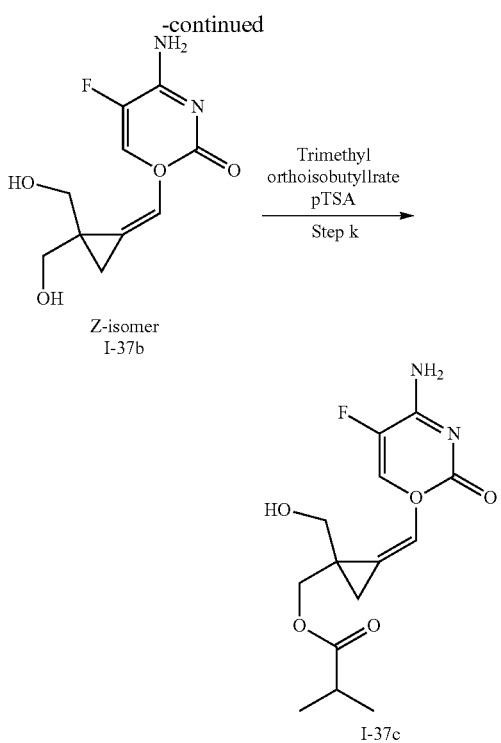

Step a) (Z)—N-(1-((2,2-bis(hydroxymethyl)cyclopropylidene)methyl)-5-fluoro-2-oxo-1,2-dihydropyrimidin-4-yl)benzamide (I-37a)

Dried $K_2CO_3$ (7.1 g, 51.5 mmol) and compound I-28g (3 g, 8.6 mmol) were added to a stirred solution of N-(5-fluoro-2-oxo-1,2-dihydropyrimidin-4-yl)benzamide (2.0 g, 8.6 mmol) in DMF (100 mL). The reaction mixture was stirred at 100° C. for 48 h, then cooled to 50° C. and MeOH (6 mL) was added. The resulting reaction mixture was stirred for 2 h at 50° C., then cooled to rt and filtered. The filtrate was concentrated to dryness under reduced pressure. The crude compound was purified by column chromatography on silica gel and eluted with 12% MeOH in DCM. The obtained residue was further purified by column chromatography on silica gel and eluted with 5% MeOH in DCM, which gave the title compound (500 g, 16%) as Z isomer. MS (ES+) 346.28 [M+H]$^+$.

Step b) (Z)-4-amino-1-((2,2-bis(hydroxymethyl) cyclopropylidene)methyl)-5-fluoropyrimidin-2(1H)-one (I-37b)

A stirred solution of compound I-37a (500 mg, 1.45 mmol) in 7M $NH_3$ in MeOH (20 mL, 14 mmol) was stirred at rt for 16 h, then concentrated. The residue was further purified by trituration with EtOAc (10 mL), filtered and dried, which gave the title compound (300 mg, 85%) as a solid. MS (ES+) 242.28 [M+H]$^+$.

Step c) (Z)-(2-((4-amino-5-fluoro-2-oxopyrimidin-1 (2H)-yl)methylene)-1-(hydroxymethyl)cyclopropyl) methyl isobutyrate (I-37c)

To a stirred solution of compound I-37b (250 mg, 1.04 mmol) in DMF (10 mL) were added trimethyl orthoisobutyrate (0.5 mL, 3.1 mmol) and pTSA (79 mg, 0.4 mmol) at rt. The reaction mixture was stirred at rt for 2 h, then Et$_3$N (2 mL) was added and the mixture was concentrated. The residue was taken in 80% acetic acid in water (30 mL), stirred at rt for 2 h, then concentrated. The crude compound was combined with another batch and purified by column chromatography on silica gel eluted with 8% MeOH in DCM, which gave the title compound (250 mg, 77%) as a solid. LCMS (ES+) m/z 312.39 [M+H]$^+$.

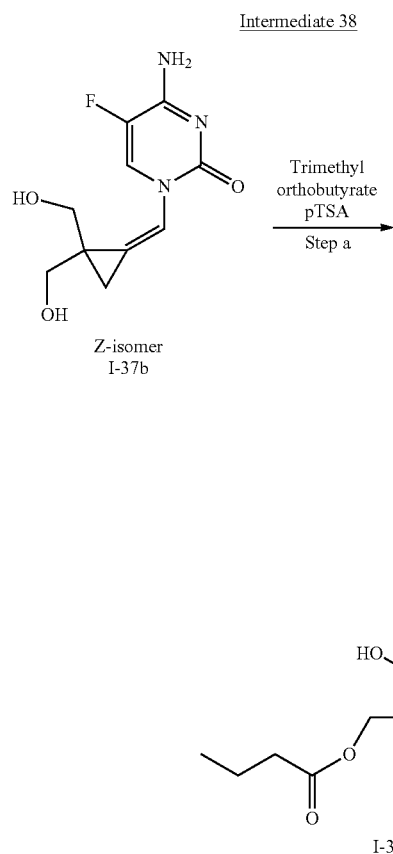

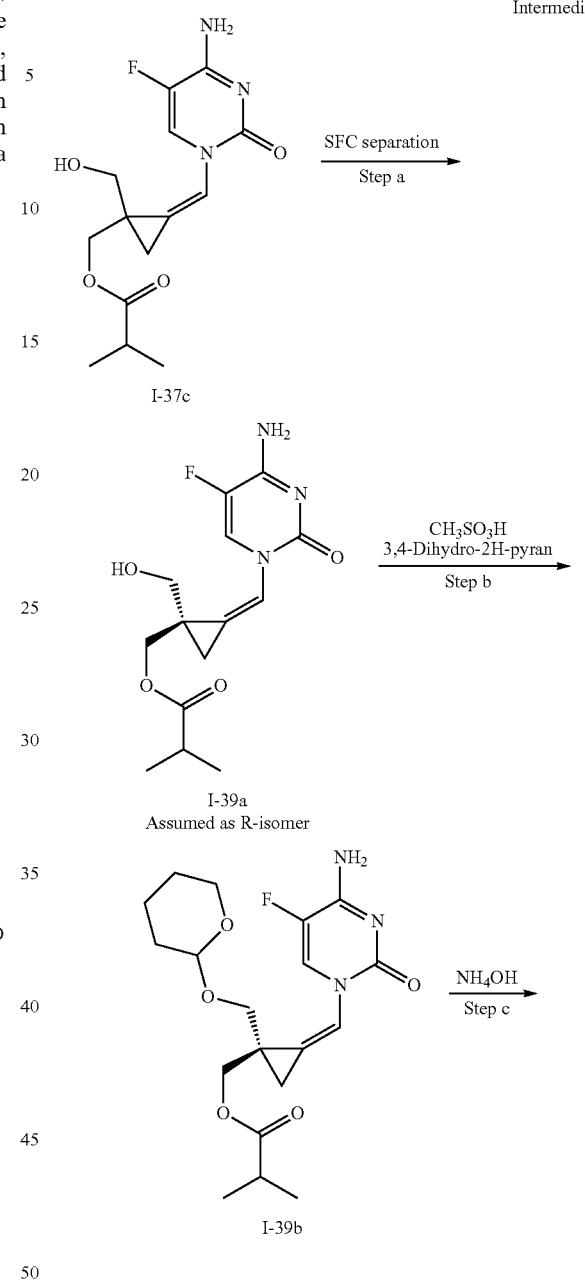

Step a) (Z)-(2-((4-amino-5-fluoro-2-oxopyrimidin-1 (2H)-yl)methylene)-1-(hydroxymethyl)cyclopropyl) methyl butyrate (I-38a)

To a stirred solution of compound I-37b (300 mg, 1.24 mmol) in DMF (30 mL) were added trimethyl orthobutyrate (0.6 mL, 3.7 mmol) and pTSA (119 mg, 0.6 mmol) at rt. The reaction mixture was stirred at rt for 3 h, then Et$_3$N (0.5 mL) was added and the mixture was concentrated. The residue was taken in 80% acetic acid in water (30 mL), stirred at rt for 2 h, then concentrated. The crude compound was purified by column chromatography on silica gel eluted with 7% MeOH in DCM, which gave the title compound (350 mg, 88%) as a solid. LCMS (ES+) m/z 312.31 [M+H]$^+$.

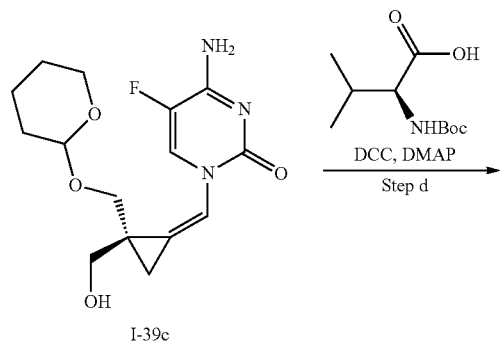

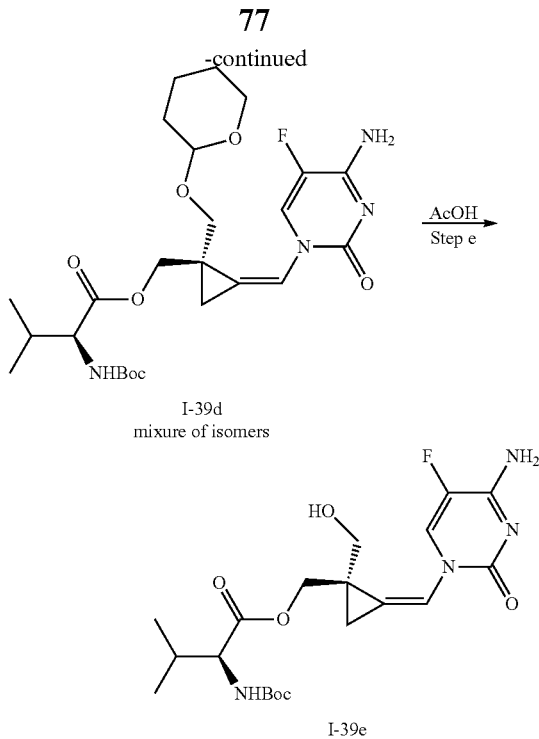

I-39d
mixure of isomers

I-39e

Step a) (R,Z)-(2-((4-amino-5-fluoro-2-oxopyrimidin-1(2H)-yl)methylene)-1-(hydroxymethyl)cyclopropyl)methyl isobutyrate (I-39a)

Compound I-37a (3.25 g) was further purified by chiral SFC, which gave the title compound (peak-2) (1.21 g, 31%) as a solid. MS (ES+) 312.35 [M+H]$^+$.
Peak-2:
SOR: +92.72° (based on the SOR value of the cytosine coupled compound, the stereochemistry is assumed to be R-isomer).
Preparative SFC Conditions:
Column/dimensions: Chiralpak IG (30×250 mm), 5μ
CO$_2$: 70.0%
Co solvent: 30.0% (100% MeOH)
Total Flow: 90.0 g/min
Back Pressure: 100.0 bar
UV: 214 nm
Stack time: 7.0 min
Load/inj.: 101.1 mg Step b) ((1R,Z)-2-((4-amino-5-fluoro-2-oxopyrimidin-1(2H)-yl)methylene)-1-(((tetrahydro-2H-pyran-2-yl)oxy)methyl)cyclopropyl)methyl isobutyrate (I-39b)

Methanesulfonic acid (0.53 mL, 8.1 mmol) in DMF (10 mL) was added dropwise at rt to a stirred solution of compound I-39a (1.1 g, 3.4 mmol) and 3,4-dihydro-2H-pyran (6.2 mL, 67.5 mmol) in DMF (30 mL). The reaction mixture was stirred at rt for 2 h, then Et$_3$N (10 mL) was added and concentrated at reduced pressure. The obtained crude compound (1.25 g) was used in next step without further purification. LCMS (ES+) m/z 396.37 [M+H]$^+$.

Step c) 4-amino-5-fluoro-1-((Z)-((2S)-2-(hydroxymethyl)-2-(((tetrahydro-2H-pyran-2-yl)oxy)methyl)cyclopropylidene)methyl)pyrimidin-2(1H)-one (I-39c)

To a stirred solution of compound I-39b (1.25 g, 3.2 mmol) in MeOH (60 mL) was added 25% aq ammonia (60 mL, 389.5 mmol) at rt. The reaction mixture was stirred at rt for 36 h, then concentrated under reduced pressure. The obtained crude compound was purified by column chromatography on silica gel and eluted with 7% MeOH in DCM, which gave the title compound (910 mg, 88%) as a solid. LCMS (ES+) m/z 326.34 [M+H]$^+$.

Step d) ((1R,Z)-2-((4-amino-5-fluoro-2-oxopyrimidin-1(2H)-yl)methylene)-1-(((tetrahydro-2H-pyran-2-yl)oxy)methyl)cyclopropyl)methyl(tert-butoxycarbonyl)-L-valinate (I-39d)

A mixture of (tert-butoxycarbonyl)-L-valine (1.52 mg, 7.0 mmol) and DCC (866 mg, 4.2 mmol) in DMF (60 mL) was stirred at rt for 3 h, then the insoluble solids were filtered and the filtrate was concentrated under reduced pressure. The obtained residue was dissolved in DMF (60 mL) and compound I-39c (910 mg, 2.8 mmol) was added followed by addition of DMAP (103 mg, 0.84 mmol). The resulting reaction mixture was stirred at rt for 16 h, then concentrated under reduced pressure. The crude compound was purified by column chromatography on silica gel and eluted with 4% MeOH in DCM, which gave the title compound as a mixture of isomers (930 mg, 63%) as a solid. MS (ES+) 525.46 [M+H]$^+$.

Step e)

((R,Z)-2-((4-amino-5-fluoro-2-oxopyrimidin-1(2H)-yl)methylene)-1-(hydroxymethyl)cyclopropyl)methyl(tert-butoxycarbonyl)-L-valinate (I-39e)

80% AcOH (100 mL, 1397.5 mmol) was added to compound I-39d (930 mg, 1.8 mmol) and the resulting reaction mixture was stirred for 36 h at rt, then concentrated under reduced pressure. The obtained crude compound was purified by column chromatography on silica gel eluted with 6% MeOH in DCM, which gave the title compound (520 mg, 64%) as a solid. LCMS (ES+) m/z 441.39 [M+H]$^+$.

Example 1

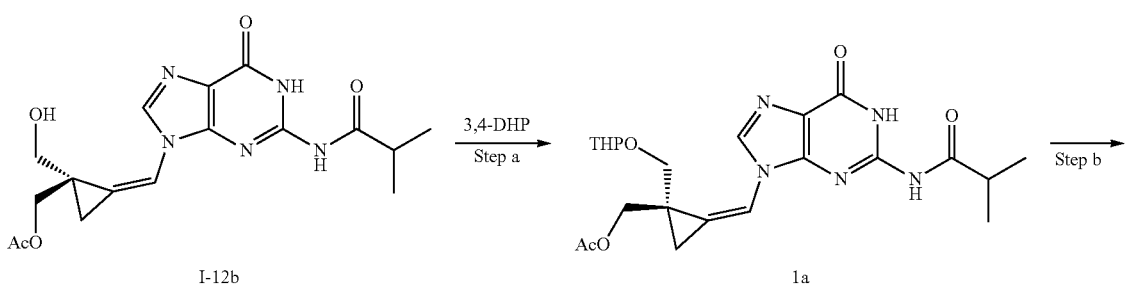

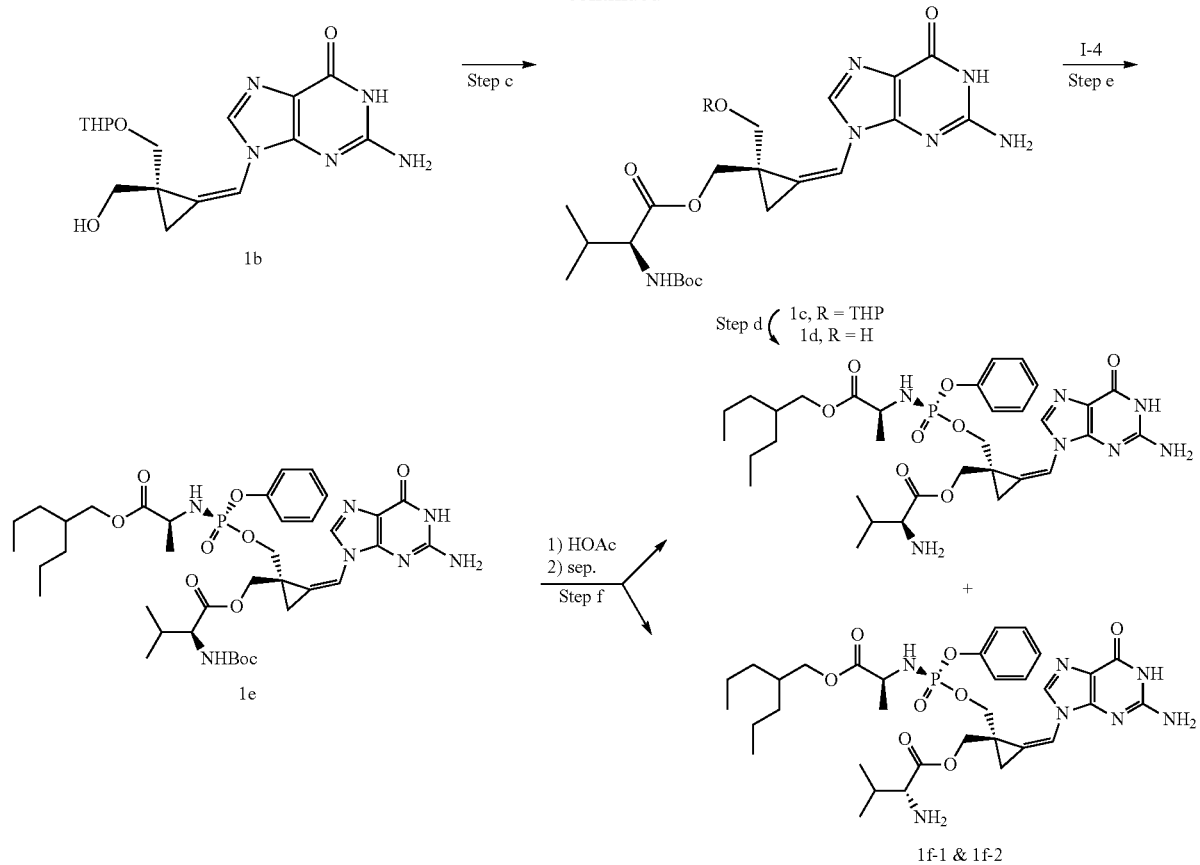

Step a) ((1R,Z)-2-((2-Isobutyramido-6-oxo-1H-purin-9(6H)-yl)methylene)-1-(((tetrahydro-2H-pyran-2-yl)oxy)methyl)cyclopropyl)methyl acetate (1a)

Methanesulfonic acid (0.3 mL, 4.3 mmol) in DMF (40 mL) was added dropwise at rt to a stirred solution of compound I-12b (800 mg, 2.13 mmol) in DMF (10 mL) and 3,4-dihydro-2H-pyran (3.9 mL, 43 mmol). The reaction mixture was stirred at rt for 4 h, then concentrated at reduced pressure. The obtained of crude compound (1.1 g) was used in next step without further purification. LCMS (ES+) m/z 460.26 [M+H]+.

Step b) 2-Amino-9-((Z)-((2S)-2-(hydroxymethyl)-2-(((tetrahydro-2H-pyran-2-yl)oxy)methyl)cyclopropylidene)methyl)-1H-purin-6(9H)-one (1b)

To a stirred solution of compound 1a (1.1 g, 2.4 mmol) in MeOH (50 mL) was added 25% aq ammonia (55 mL, 360 mmol) at rt. The reaction mixture was stirred at 50° C. for 12 h then concentrated at reduced pressure. The obtained crude compound was purified by column chromatography on silica gel and eluted with 15% MeOH, which gave the title compound (750 mg) as a solid. LCMS (ES+) m/z 348.20 [M+H]+.

Step c) (2S)-((1R,Z)-2-((2-Amino-6-oxo-1H-purin-9(6H)-yl)methylene)-1-(((tetrahydro-2H-pyran-2-yl)oxy)methyl)cyclopropyl)methyl 2-((tert-butoxycarbonyl)amino)-3-methylbutanoate (1c)

A mixture of N-Boc-L-valine (915 mg, 4.21 mmol) and dicyclohexylcarbodiimide (500 mg, 2.43 mmol) in DCM (40 mL) was stirred at rt for 3 h, then filtered and concentrated under reduced pressure. The obtained crude was dissolved in DMF (60 mL) and compound 1b (650 mg, 1.87 mmol) was added followed by addition of 4-dimethylaminopyridine (70 mg, 0.56 mmol). The reaction mixture was stirred at rt for 16 h, then concentrated under reduced pressure.

The afforded crude compound was purified by column chromatography on silica gel eluted with 7% MeOH in DCM, which gave the title compound (900 mg, 86%) as a solid. LCMS (ES+) m/z 547.37 [M+H]+.

Step d) (S)-((R,Z)-2-((2-Amino-6-oxo-1H-purin-9(6H)-yl)methylene)-1-(hydroxymethyl)cyclopropyl)methyl 2-((tert-butoxycarbonyl)amino)-3-methylbutanoate (1d)

A solution of compound 1c (900 mg, 1.6 mmol) in 80% acetic acid (90 mL, 1.3 mol) was stirred at rt for 16 h, then concentrated under reduced pressure. The crude compound was purified by column chromatography on silica gel eluted with 10-12% MeOH in DCM, which gave the title compound (600 mg, 67%) as a solid. LCMS (ES+) m/z 463.29 [M+H]+.

Step e) (S)-((S,Z)-2-((2-Amino-6-oxo-1H-purin-9(6H)-yl)methylene)-1-((((S)-(((S)-1-oxo-1-((2-propylpentyl)ox)propan-2-)amino)(phenoxy)phosphoryl)oxy)methyl)cyclopropyl)methyl 2-((tert-butoxycarbonyl)amino)-3-methylbutanoate (1e)

tert-Butylmagnesium chloride (1M in THF, 1.1 mL, 1.1 mmol) was added dropwise to a solution of compound 1d (100 mg, 0.22 mmol) in DMF (10 mL) the mixture was stirred at rt for 30 min, then a solution of 1-4 (140 mg, 0.26 mmol) in dry THF (5 mL) was added dropwise. The reaction mixture was stirred at rt for 12 h, then concentrated under reduced pressure. The crude compound was purified by column chromatography on silica gel and eluted with 10-12% MeOH in DCM, which gave the title compound (120 mg, 46%) as a solid. LCMS (ES+) m/z 802.42 [M+H]$^+$.

Step f) (S)-((S,Z)-2-((2-Amino-6-oxo-1H-purin-9 (6H)-yl)methylene)-1-(((((S)-(((S)-1-oxo-1-((2-propylpentyl)oxy)propan-2-yl)amino)(phenoxy)phosphoryl)oxy)methyl)cyclopropyl)methyl 2-amino-3-methylbutanoate (1f-1) & (R)-((S,Z)-2-((2-Amino-6-oxo-1H-purin-9(6H)-yl)methylene)-1-(((((S)-(((S)-1-oxo-1-((2-propylpentyl)oxy)propan-2-yl)amino) (phenoxy)phosphoryl)oxy)methyl)cyclopropyl) methyl 2-amino-3-methylbutanoate (1f-2)

A solution of compound 1e (120 mg, 0.14 mmol) in 60% acetic acid (12 mL, 126 mmol) was stirred for 5 h at 90° C.,

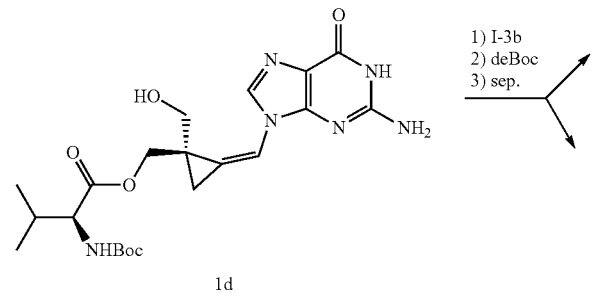

then allowed to attain rt and concentrated under reduced pressure. The obtained residue was purified by prep HPLC using HPLC Method A. The afforded residue was combined with another batch and purified by chiral NP HPLC.

which gave the two title compounds, 1f-1 (22 mg) & 1f-2 (8 mg).
Preparative NP-HPLC Conditions
  Column/dimensions: Chiralpak IC (250×30) mm, 5μ
  Mobile Phase: 0.2% DEA in n-hexane:EtOH (30:70)
  Flow: 38.0 ml/min
  Temperature: Ambient
  Wave length: 270 nm
  Run time: 17 min
  Solubility: EtOH+DCM
  Load ability/inj.: 5.0 mg
1f-1: LCMS (ES+) m/z 702.39 [M+H]$^+$.
$^1$H NMR (500 MHz, DMSO) δ 10.71 (s, 1H), 7.93 (s, 1H), 7.33 (m, J=4.0 Hz, 2H), 7.19 (m, J=8.1 Hz, 4H), 6.54 (s, 2H), 6.06 (q, J=7.7 Hz, 1H), 4.44 (d, J=11.6 Hz, 1H), 4.37 (q, J=5.8 Hz, 1H), 4.07 (q, J=5.5 Hz, 1H), 3.97 (m, J=3.8 Hz, 2H), 3.87 (m, J=4.9 Hz, 2H), 3.06 (d, J=5.4 Hz, 1H), 1.64 (t, J=6.1 Hz, 4H), 1.22 (m, J=3.2 Hz, 12H), 0.82 (q, J=4.3 Hz, 6H), 0.75 (d, J=6.8 Hz, 3H), 0.70 (d, J=6.8 Hz, 3H).

1f-2: LCMS (ES+) m/z 702.39 [M+H]$^+$.
$^1$H NMR (500 MHz, DMSO) δ 10.70 (s, 1H), 7.95 (s, 1H), 7.34 (t, J=7.9 Hz, 2H), 7.18 (m, J=6.0 Hz, 4H), 6.55 (s, 2H), 6.07 (q, J=7.8 Hz, 1H), 4.34 (d, J=11.6 Hz, 1H), 4.20 (m, J=5.4 Hz, 2H), 4.02 (d, J=11.6 Hz, 1H), 3.96 (q, J=5.6 Hz, 1H), 3.77 (m, J=3.8 Hz, 2H), 3.05 (d, J=5.2 Hz, 1H), 1.79 (m, J=4.7 Hz, 1H), 1.58 (m, J=4.9 Hz, 3H), 1.20 (m, J=5.7 Hz, 11H), 0.82 (m, J=3.5 Hz, 9H), 0.74 (d, J=6.8 Hz, 3H).

Example 2

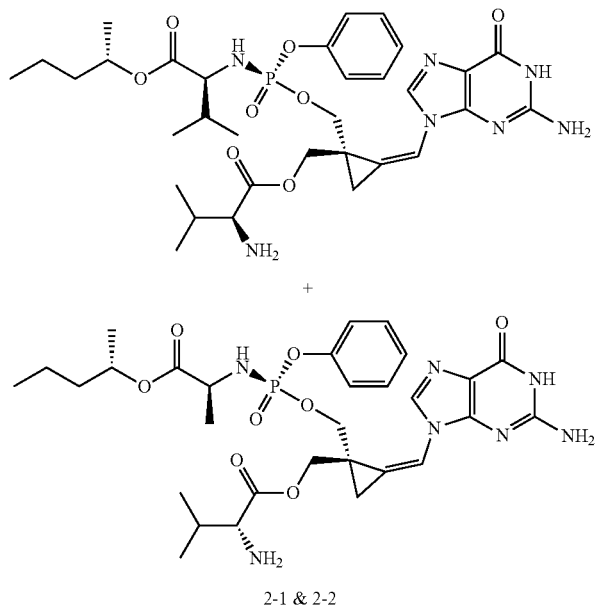

(S)-((S,Z)-2-((2-amino-6-oxo-1H-purin-9(6H)-yl) methylene)-1-(((((S)-(((S)-3-methyl-1-oxo-1-((S)-pentan-2-yloxy)butan-2-yl)amino)(phenoxy)phosphoryl)oxy)methyl)cyclopropyl)methyl 2-amino-3-methylbutanoate & (R)—((S,Z)-2-((2-amino-6-oxo-1H-purin-9(6H)-yl)methylene)-1-(((((S)-(((S)-3-methyl-1-oxo-1-((S)-pentan-2-yloxy)butan-2-yl) amino)(phenoxy)phosphoryl)oxy)methyl) cyclopropyl)methyl 2-amino-3-methylbutanoate (2-1 & 2-2)

The title compound was prepared from compound 1d and I-3b as Example 1 step e followed by removal of the Boc group by treatment of a solution of the Boc protected compound in dioxane with 4 M HCl in dioxane for 4h, then concentrate. The residue was purified by prep HPLC Method C followed by separation of the stereoisomers by chiral prep. NP HPLC.

Chiral Prep NP HPLC
  Column/dimensions: Chiralcel OX-H (250×30) mm, 5μ
  Mobile Phase: 0.2% DEA in n-hexane:EtOH (50:50)
  Flow: 44.0 ml/min
  Temperature: Ambient
  Wave length: 232 nm
  Run time: 22 min
  Solubility: EtOH:MeCN:IPA
  Load/inj.: 10.8 mg
  2-1: (60 mg, 27% yield) LCMS (MS+) 688.34 [M+H]$^+$, 99.4% chiral purity according to chiral NP HPLC.
  $^1$H NMR (500 MHz, DMSO) δ 10.70 (s, 1H), 7.92 (s, 1H), 7.30 (t, J=7.5 Hz, 2H), 7.22 (s, 1H), 7.13 (d, J=7.7 Hz, 3H), 6.54 (s, 2H), 5.90 (t, J=11.3 Hz, 1H), 4.77 (d, J=6.1 Hz, 1H), 4.42 (m, J=10.7 Hz, 2H), 4.08 (q, J=5.3 Hz, 1H), 3.98 (d, J=11.6 Hz, 1H), 3.51 (q, J=9.1 Hz, 2H), 3.04 (d, J=4.9 Hz, 1H), 1.91 (t, J=6.3 Hz, 1H), 1.64 (s, 3H), 1.48 (s, 1H), 1.39 (d, J=13.6 Hz, 1H), 1.26 (m, J=10.0 Hz, 3H), 1.11 (d, J=6.0 Hz, 3H), 0.82 (t, J=6.8 Hz, 9H), 0.71 (q, J=11.4 Hz, 6H).
  2-2. (12 mg, 5.2% yield) LCMS (MS+) 688.38 [M+H]$^+$, 97.8% chiral purity according to chiral NP HPLC.
  $^1$H NMR (500 MHz, DMSO) δ 10.73 (s, 1H), 7.93 (s, 1H), 7.31 (t, J=7.8 Hz, 2H), 7.17 (m, J=9.9 Hz, 5H), 6.56 (s, 1H), 5.89 (t, J=11.6 Hz, 1H), 4.75 (q, J=6.1 Hz, 1H), 4.36 (d, J=11.6 Hz, 1H), 4.21 (m, J=5.7 Hz, 2H), 4.00 (q, J=6.0 Hz, 2H), 3.47 (m, J=6.9 Hz, 1H), 3.04 (d, J=5.1 Hz, 1H), 1.91 (q, J=6.5 Hz, 2H), 1.77 (t, J=6.2 Hz, 1H), 1.61 (q, J=8.5 Hz, 2H), 1.42 (m, J=10.1 Hz, 3H), 1.23 (m, J=7.6 Hz, 5H), 1.08 (d, J=6.2 Hz, 3H), 0.78 (m, J=12.6 Hz, 17H).

Example 3

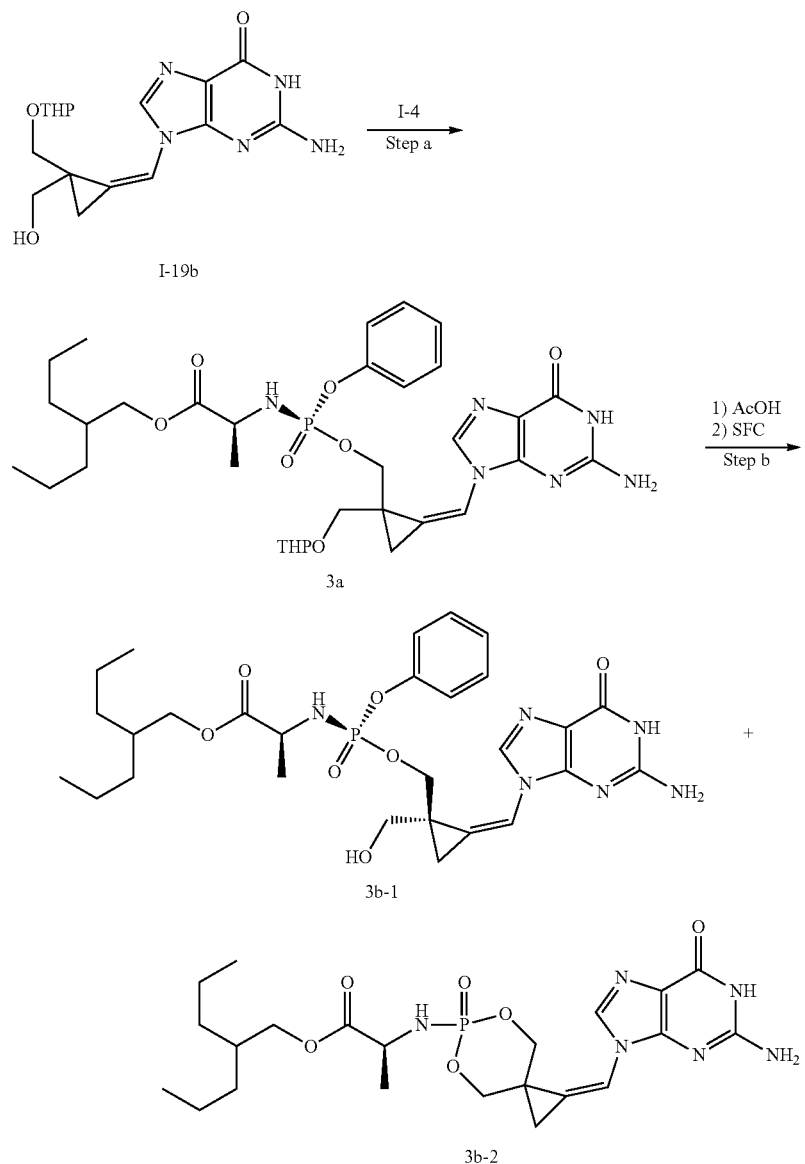

Step a) (2S)-2-propylpentyl 2-(((S)-(((Z)-2-((2-amino-6-oxo-1H-purin-9(6H)-yl)methylene)-1-(((tetrahydro-2H-pyran-2-yl)oxy)methyl)cyclopropyl)methoxy)(phenoxy)phosphoryl)amino)-propanoate (3a)

tert-Butylmagnesium chloride (0.7 mL, 1M in THF, 0.72 mmol) was added dropwise at rt to a solution of compound I-19b (50 mg, 0.14 mmol) in DMF (5 mL). The reaction mixture was stirred at rt for 30 min. Then a solution of compound I-4 (90 mg, 0.17 mmol) in dry THF (2.5 mL) was added dropwise. The reaction mixture was stirred at rt for 2 h, then concentrated. The crude compound was purified by column chromatography on silica gel eluted with 10% MeOH in DCM, which gave the title compound (55 mg, 53%) as a solid. LCMS (ES+) m/z 687.39 [M+H]+.

Step b) (S)-2-Propylpentyl 2-(((S)-(((R,Z)-2-((2-amino-6-oxo-1H-purin-9(6H)-yl)methylene)-1-(hydroxymethyl)cyclopropyl)methoxy)(phenoxy)phosphoryl)amino)propanoate (S,Z)-2-Propylpentyl 2-((1-((2-amino-6-oxo-1H-purin-9(6H)-yl)methylene)-6-oxido-5,7-dioxa-6-phosphaspiro[2.5]octan-6-yl)amino)propanoate (3b-1 & 3b-2)

A solution of compound 3a (400 mg, 0.582 mmol) in 80% acetic acid (40 mL, 559 mmol) was stirred at rt for 24 h, then concentrated. The obtained crude compound was purified by column chromatography on silica gel eluted with 12% MeOH in DCM. The afforded residue was subjected to chiral prep SFC purification which gave two fractions, 3b-1 and 3b-2.

3b-1 was purified by prep HPLC using Method B with gradient 0/35, 9/67, 9.1/99, 10/99, 10.1/35, 12/35, which gave the title compound (35 mg). Purity according to LCMS: 96.6% & chiral HPLC 99.9%. LCMS (ES+) m/z 607.31 [M+H]+.

3b-2 was purified by chiral prep NP HPLC, followed by chiral prep SFC using the "IPA method", which gave the cyclized compound 3b-2. LCMS (ES+) m/z 509.19 [M+H]+.

Preparative SFC Conditions "IPA Method"

Column/dimensions: Chiralpak AD-H (21×250 mm), 5μ

$CO_2$: 75.0%

Co solvent: 25.0% (100% IPA)

Total Flow: 60.0 g/min

Back Pressure: 80.0 bar

UV: 229 nm

Stack time: 10.0 min

Load/inj.: 5.0 mg

Example 4

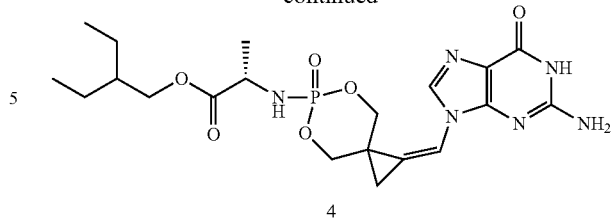

4

(S,Z)-2-Ethylbutyl 2-((1-((2-amino-6-oxo-1H-purin-9(6H)-yl)methylene)-6-oxido-5,7-dioxa-6-phosphaspiro[2.5]octan-6-yl)amino)propanoate (4)

A solution of 1,8-diazabicyclo[5.4.0]undec-7-ene (0.2 mL, 1.14 mmol) in DMF (2 mL) was added at rt dropwise over a period of 30 min to a stirred suspension of (Z)-2-amino-9-((2,2-bis(hydroxymethyl)cyclopropylidene)methyl)-1H-purin-6(9H)-one (150 mg, 0.57 mmol) and I-6 (0.31 g, 0.62 mmol) in DMF (3 mL). The mixture was stirred at rt for 3 h, then diluted with $NaHCO_3$ aq. (10 mL) and extracted with DCM (25 mL). The organic layer was dried over $Na_2SO_4$, filtered and concentrated under reduced pressure. The crude compound was purified by column chromatography on silica gel eluted 5% MeOH in DCM. Appropriate fractions were pooled, concentrated and purified by prep HPLC using Method C, which gave the title compound (18 mg, 6.6%) as a mixture of P-isomers. LCMS (ES+) m/z 481.25 [M+H]+.

Example 5

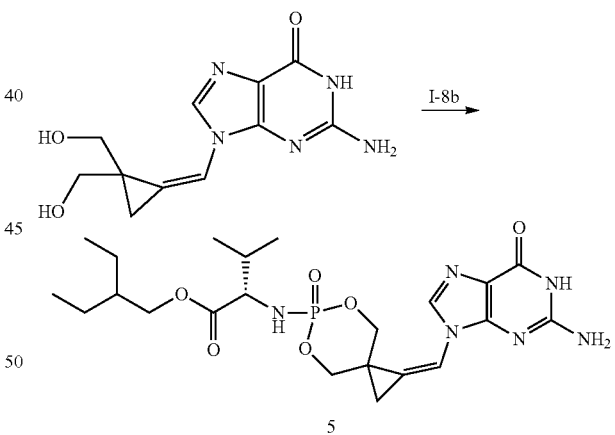

5

(S,Z)-2-Ethylbutyl 2-((1-((2-amino-6-oxo-1H-purin-9(6H)-yl)methylene)-6-oxido-5,7-dioxa-6-phosphaspiro[2.5]octan-6-yl)amino)-3-methylbutanoate (5)

To a stirred suspension of (Z)-2-amino-9-((2,2-bis(hydroxymethyl)cyclopropylidene)methyl)-1H-purin-6(9H)-one (0.1 g, 0.38 mmol) and I-8b (0.2 g, 0.38 mmol) in DMF (10 mL) was added a solution of 1,8-diazabicyclo[5.4.0]undec-7-ene (0.12 mL, 0.760 mmol) in DMF (5 mL) dropwise over a period of 30 min at rt. The mixture was stirred 3 h, then diluted with $NaHCO_3$ aq (5 mL) and extracted with DCM (3×20 mL). The organic layer was dried (Na$_2$SO$_4$), filtered and concentrated under reduced pressure. The crude compound was purified by column chromatography on silica gel eluted with 5% MeOH in DCM. The afforded residue was purified by prep HPLC using Method A, which gave the title compound (12 mg) as a mixture of P-stereoisomers. LCMS (ES+) 509.32 [M+H]$^+$.

dry THF (20 mL) was added dropwise. The mixture was stirred at rt for 2 h, then concentrated. The residue was combined with another batch and purified by column chromatography using a Combi flash instrument eluted with 7% DCM in MeOH. Appropriate fractions were pooled and concentrated and the residue was purified by prep HPLC using Method B. Appropriate fractions were pooled and concentrated. Chiral HPLC showed two enantiomers which were separated by prep. SFC.

Example 6

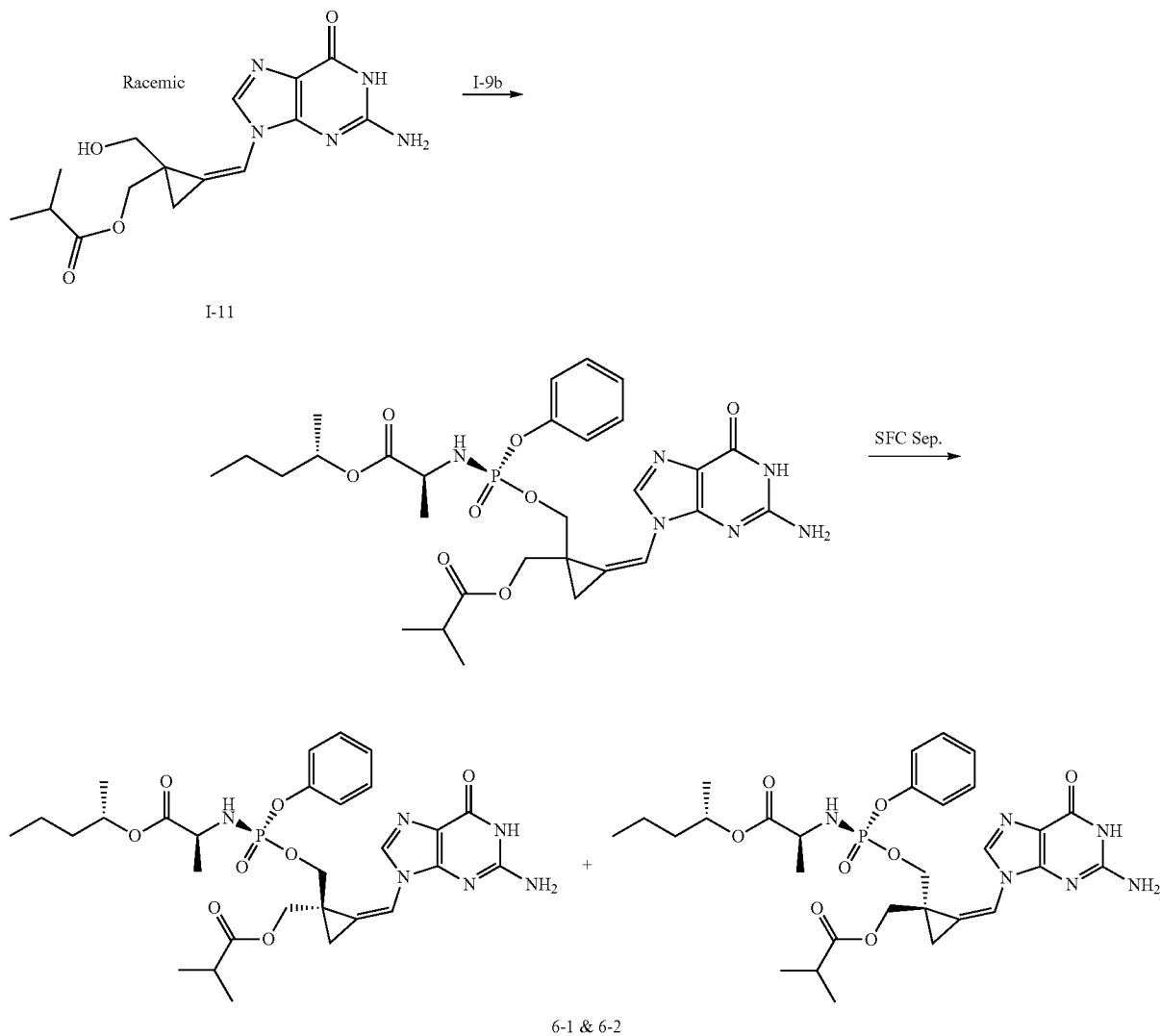

6-1 & 6-2

((R,Z)-2-((2-amino-6-oxo-1H-purin-9(6H)-yl)methylene)-1-(((((S)-(((S)-1-oxo-1-((S)-pentan-2-yloxy)propan-2-yl)amino)(phenoxy)phosphoryl)oxy)methyl)cyclopropyl)methyl isobutyrate & ((S,Z)-2-((2-amino-6-oxo-1H-purin-9(6H)-yl)methylene)-1-(((((S)-(((S)-1-oxo-1-((S)-pentan-2-yloxy)propan-2-yl)amino)(phenoxy)phosphoryl)oxy)methyl)cyclopropyl)methyl isobutyrate (6-1 & 6-2)

tert-Butylmagnesium chloride (2.7 mL, 1M in THF, 2.700 mmol) was added dropwise to a solution of I-11 (180 mg, 0.540 mmol) in DMF (20 mL). The mixture was stirred at rt for 20 min, then a solution of I-9b (312 mg, 0.648 mmol) in 6-1: LCMS (ES+) m/z 631.30 [M+H]$^+$. Chiral HPLC showed 99.9% purity.
6-2: LCMS (ES+) m/z 631.30 [M+H]$^+$. Chiral HPLC showed 99.8% purity.
Preparative SFC Conditions
Column/dimensions: Chiralcel OX-H (30×250 mm), 5μ
CO$_2$:50.0%
Co solvent: 50.0% (100% IPA)
Total flow: 90.0 g/min
Back pressure: 100.0 bar
UV: 214 nm
Stack time: 12.6 min
Load/inj.: 13.0 mg

Example 7

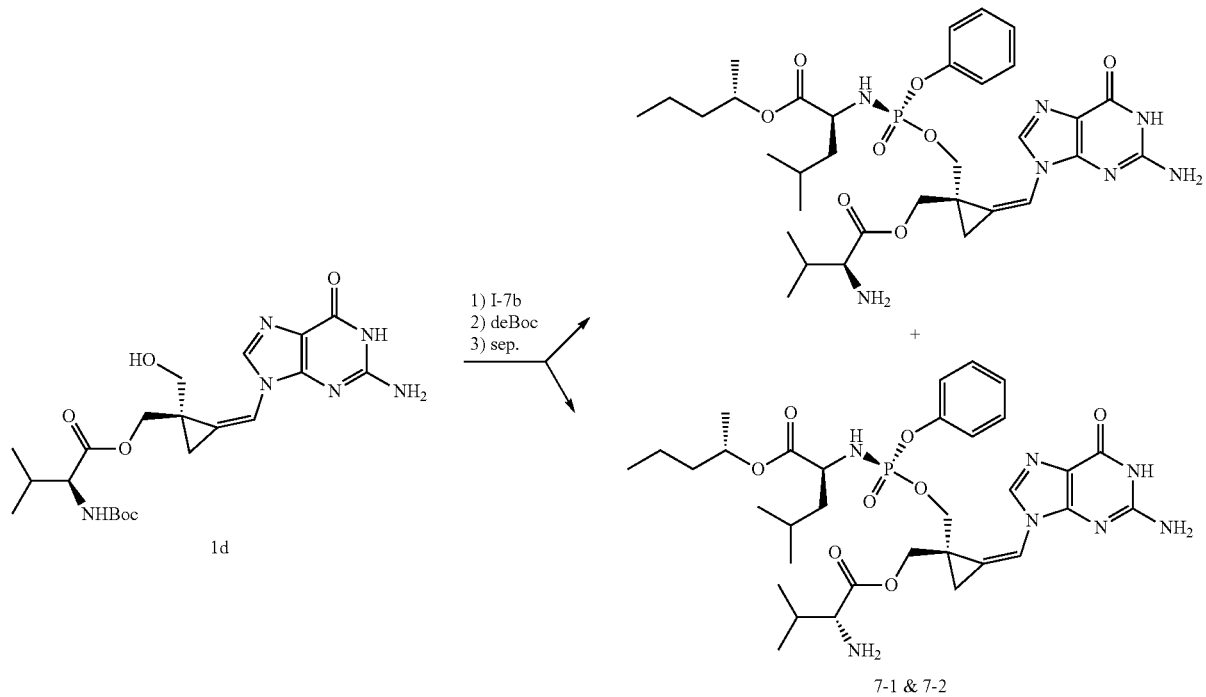 [SMILES: CC(C)[C@H](NC(=O)OC(C)(C)C)C(=O)OC[C@]1(CO)C/C1=C/n1cnc2c(=O)[nH]c(N)nc21 ; CCC[C@H](C)OC(=O)[C@H](CC(C)C)N[P@](=O)(OC[C@@]1(COC(=O)[C@H](N)C(C)C)C/C1=C/n1cnc2c(=O)[nH]c(N)nc21)Oc1ccccc1 ; CCC[C@H](C)OC(=O)[C@H](CC(C)C)N[P@](=O)(OC[C@@]1(COC(=O)[C@@H](N)C(C)C)C/C1=C/n1cnc2c(=O)[nH]c(N)nc21)Oc1ccccc1]

(S)-(S)-pentan-2-yl 2-(((S)-(((S,Z)-1-((((S)-2-amino-3-methylbutanoyl)oxy)methyl)-2-((2-amino-6-oxo-1H-purin-9(6H)-yl)methylene)cyclopropyl)methoxy)(phenoxy)phosphoryl)amino)-4-methylpentanoate & (S)-(S)-pentan-2-yl 2-(((S)-(((S,Z)-1-((((R)-2-amino-3-methylbutanoyl)oxy)methyl)-2-((2-amino-6-oxo-1H-purin-9(6H)-yl)methylene)cyclopropyl)methoxy)(phenoxy)phosphoryl)amino)-4-methylpentanoate (7-1 & 7-2)

The title compound was prepared from compound 1d and I-7b as Example 1 steps e and f with the difference that the purification/separation of the final compound was performed by
1) Prep. HPLC Method C
2) Separation of isomers by prep. chiral NP HPLC]
3) Fraction 2 was purified by prep HPLC Method C
Prep Chiral NP HPLC
  Column/dimensions: Chiralcel OX-H (250×30) mm, 5μ
  Mobile Phase: 0.2% DEA in n-hexane:EtOH (55:45)
  Flow: 42.0 ml/min
  Temperature: Ambient
  Wave length: 232 nm
  Run time: 22 min
  Solubility: EtOH
  Load/inj.: 8.1 mg 7-1: LCMS (ES+) m/z 702.35 [M+H]$^+$, 99.96% chiral purity according to chiral NP HPLC.

$^1$H NMR (500 MHz, DMSO) δ 10.83 (s, 1H), 7.90 (s, 1H), 7.32 (m, J=4.0 Hz, 2H), 7.22 (t, J=1.8 Hz, 1H), 7.14 (t, J=7.3 Hz, 3H), 6.60 (s, 2H), 6.01 (q, J=7.7 Hz, 1H), 4.77 (m, J=4.8 Hz, 1H), 4.42 (m, J=7.6 Hz, 2H), 4.04 (q, J=5.5 Hz, 1H), 3.96 (d, J=11.5 Hz, 1H), 3.71 (m, J=4.7 Hz, 1H), 3.03 (d, J=5.5 Hz, 1H), 1.63 (q, J=4.1 Hz, 4H), 1.43 (m, J=3.0 Hz, 4H), 1.24 (m, J=2.9 Hz, 2H), 1.11 (d, J=6.3 Hz, 3H), 0.83 (q, J=3.1 Hz, 5H), 0.79 (t, J=5.6 Hz, 4H), 0.74 (d, J=6.8 Hz, 3H), 0.69 (d, J=6.8 Hz, 3H).

7-2: LCMS (ES+) m/z 702.35 [M+H]$^+$, 97.97% chiral purity according to chiral NP HPLC.

$^1$H NMR (500 MHz, DMSO) δ 10.93 (s, 1H), 7.90 (s, 1H), 7.32 (q, J=5.3 Hz, 2H), 7.22 (t, J=1.8 Hz, 1H), 7.15 (m, J=6.7 Hz, 3H), 6.72 (s, 2H), 6.01 (q, J=7.8 Hz, 1H), 4.75 (q, J=6.4 Hz, 1H), 4.34 (d, J=11.5 Hz, 1H), 4.20 (m, J=6.1 Hz, 2H), 4.00 (d, J=11.5 Hz, 1H), 3.66 (m, J=8.7 Hz, 1H), 3.03 (d, J=5.2 Hz, 1H), 1.78 (m, J=5.4 Hz, 1H), 1.59 (m, J=4.4 Hz, 4H), 1.42 (m, J=4.1 Hz, 5H), 1.23 (m, J=3.8 Hz, 3H), 1.07 (t, J=5.6 Hz, 3H), 1.05 (s, 1H), 0.81 (m, J=4.1 Hz, 13H), 0.74 (d, J=6.8 Hz, 3H).

Example 8

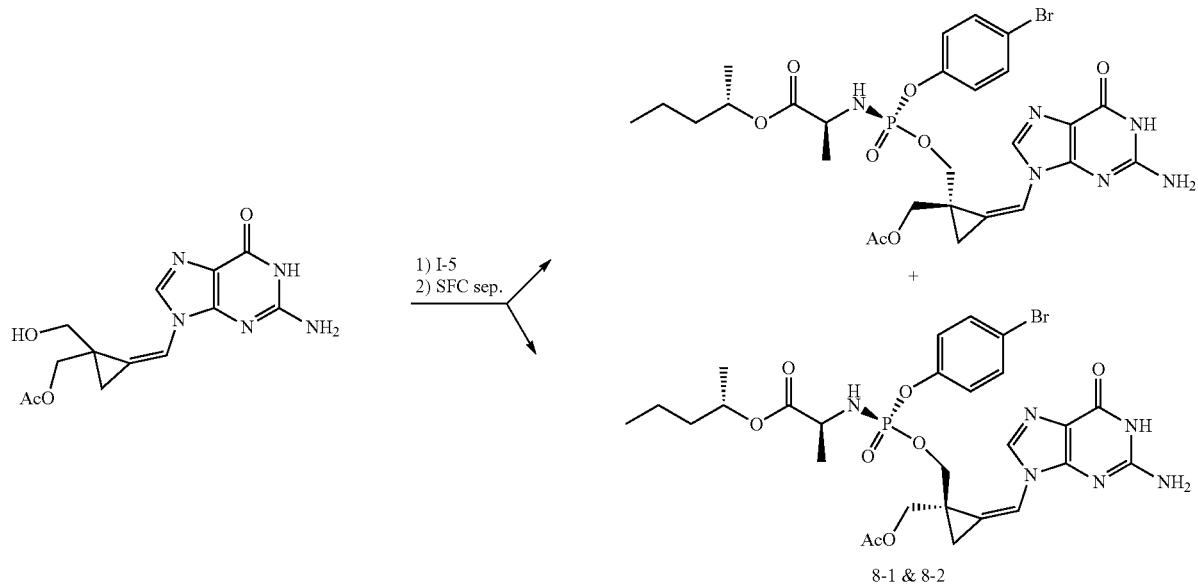 [SMILES: CC(=O)OCC1(CO)C/C1=C/n1cnc2c(=O)[nH]c(N)nc21 ; CCC[C@H](C)OC(=O)[C@H](C)N[P@](=O)(OC[C@]1(COC(C)=O)C/C1=C/n1cnc2c(=O)[nH]c(N)nc21)Oc1ccc(Br)cc1 ; CCC[C@H](C)OC(=O)[C@H](C)N[P@](=O)(OC[C@@]1(COC(C)=O)C/C1=C/n1cnc2c(=O)[nH]c(N)nc21)Oc1ccc(Br)cc1]

(S)-(S)-Pentan-2-yl 2-(((S)-(((S,Z)-1-(acetoxymethyl)-2-((2-amino-6-oxo-1H-purin-9(6H)-yl)methylene)cyclopropyl)methoxy)(4-bromophenoxy)phosphoryl)amino) & (S)-(S)-Pentan-2-yl 2-(((S)-(((R,Z)-1-(acetoxymethyl)-2-((2-amino-6-oxo-1H-purin-9(6H)-yl)methylene)cyclopropyl)methoxy)(4-bromophenoxy)phosphoryl)amino)propanoate propanoate (8-1 & 8-2)

(Z)-(2-((2-Amino-6-oxo-1H-purin-9(6H)-yl)methylene)-1-(hydroxymethyl)cyclopropyl)methyl acetate and I-5 were reacted according to the method described in Example 1 step e. The afforded compound was purified by prep HPLC using Method A. The racemic mixture was separated by SFC, which gave the two isomers as separate compounds.

8-1: 2.7% yield, 98.82% chiral purity according to chiral HPLC, LCMS (ES+) m/z 681.16[M+H]$^+$.

8-2: 3.2% yield, 99.7% chiral purity according to chiral HPLC, LCMS (ES+) m/z 681.16 [M+H]$^+$.

Preparative SFC Conditions

Column/dimensions: Chiralpak AD-H (30×250 mm), 5μ
$CO_2$:50.0%
Co solvent: 50.0% (0.5% diethylamine in EtOH)
Total Flow: 90.0 g/min
Back Pressure: 90.0 bar
UV: 214 nm
Stack time: 9.4 min
Load/inj.: 11.0 mg

Example 9

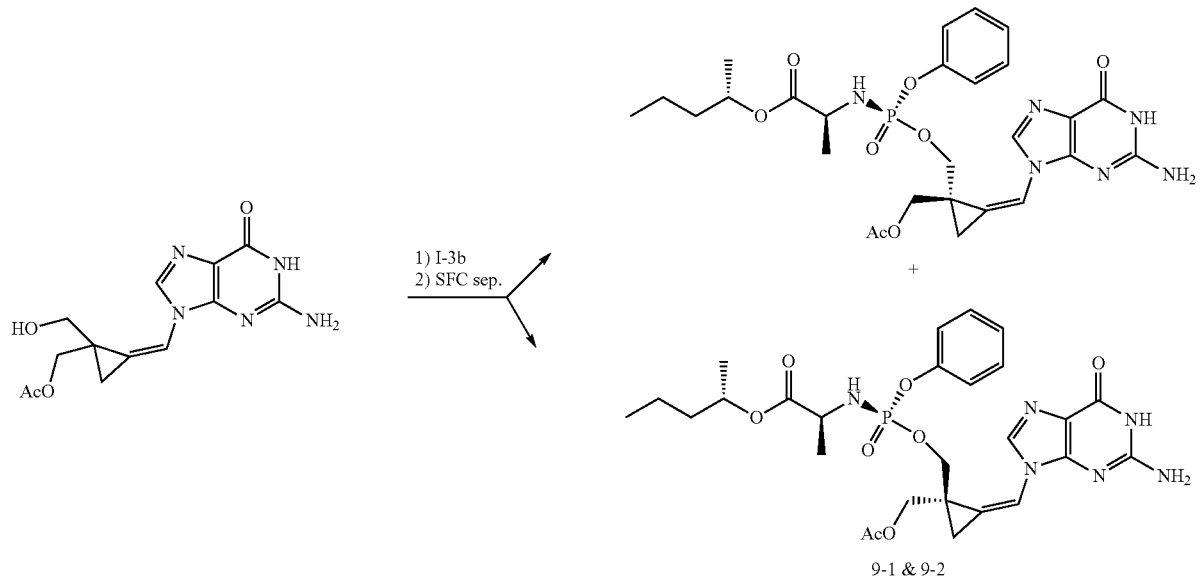 [SMILES: CC(=O)OCC1(CO)C/C1=C/n1cnc2c(=O)[nH]c(N)nc21 ; CCC[C@H](C)OC(=O)[C@H](C)N[P@](=O)(OC[C@]1(COC(C)=O)C/C1=C/n1cnc2c(=O)[nH]c(N)nc21)Oc1ccccc1 ; CCC[C@H](C)OC(=O)[C@H](C)N[P@](=O)(OC[C@@]1(COC(C)=O)C/C1=C/n1cnc2c(=O)[nH]c(N)nc21)Oc1ccccc1]

(S)-(S)-Pentan-2-yl 2-(((S)-(((S,Z)-1-(acetoxymethyl)-2-((2-amino-6-oxo-1H-purin-9(6H)-yl)methylene)cyclopropyl)methoxy)(phenoxy)phosphoryl)amino)propanoate & (S)-(S)-Pentan-2-yl 2-(((S)-(((R,Z)-1-(acetoxymethyl)-2-((2-amino-6-oxo-1H-purin-9(6H)-yl)methylene)cyclopropyl)methoxy)(phenoxy)phosphoryl)amino)propanoate (9-1 & 9-2)

(Z)-(2-((2-Amino-6-oxo-1H-purin-9(6H)-yl)methylene)-1-(hydroxymethyl)cyclopropyl)methyl acetate and I-3b were reacted according to the method described in Example 1 step e. The afforded compound was purified by prep HPLC using Method D. The racemic mixture was separated by prep SFC, which gave the two isomers as separate compounds.

9-1: 6.0% yield, 98.07% chiral purity according to chiral HPLC, LCMS (ES+) m/z 631.30 [M+H]+.

9-2: 6.0% yield, 98.9% chiral purity according to chiral HPLC, LCMS (ES+) m/z 631.30 [M+H]+.

Preparative SFC Conditions
 Column/dimensions: Chiralcel OX-H (30×250 mm), 5μ
 $CO_2$: 60.0%
 Co solvent: 40.0% (100% MeOH)
 Total Flow: 90.0 g/min
 Back Pressure: 100.0 bar
 UV: 214 nm
 Stack time: 5.5 min
 Load/inj.: 3.0 mg

Example 10

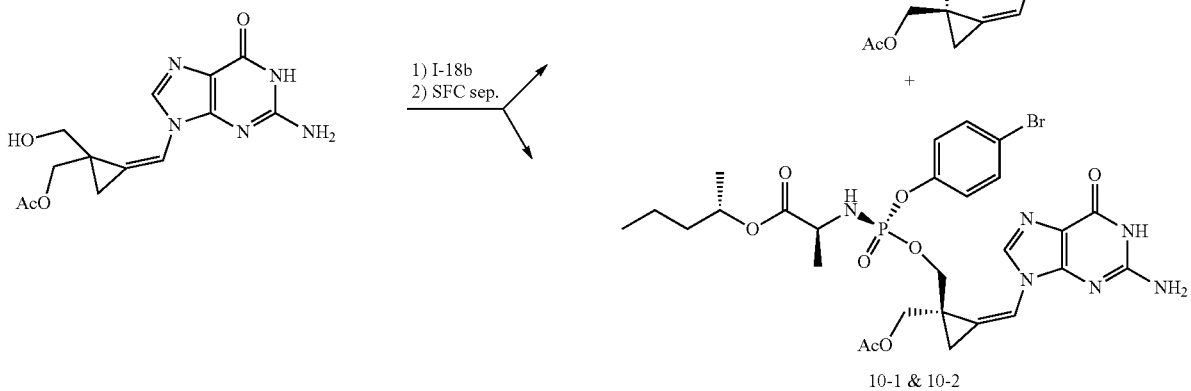

(S)-(S)-Pentan-2-yl 2-(((S)-(((S,Z)-1-(acetoxymethyl)-2-((2-amino-6-oxo-1H-purin-9(6H)-yl)methylene)cyclopropyl)methoxy)(4-bromophenoxy)phosphoryl)amino)propanoate & (S)-(S)-Pentan-2-yl 2-(((S)-(((R,Z)-1-(acetoxymethyl)-2-((2-amino-6-oxo-1H-purin-9(6H)-yl)methylene)cyclopropyl)methoxy)(4-bromophenoxy)phosphoryl)amino)propanoate (10-1 & 10-2)

(Z)-(2-((2-Amino-6-oxo-1H-purin-9(6H)-yl)methylene)-1-(hydroxymethyl)cyclopropyl)methyl acetate and I-18b were reacted according to the method described in Example 1 step e. The afforded compound was purified by prep HPLC using Method D. The racemic mixture was separated by prep SFC, which gave the two isomers as separate compounds.

10-1: Yield 5.1%, 99.9% chiral purity according to analytical SFC, LCMS (ES+) m/z 723.22 & 725.20 [M+H]$^+$.

10-2: Yield 8.0%, 99.34% chiral purity according to analytical SFC, LCMS (ES+) m/z 723.19 & 725.20 [M+H]$^+$.

Preparative SFC Conditions
Column/dimensions: Chiralcel OX-H (30×250 mm), 5μ
$CO_2$:60.0%
Co solvent: 40.0% (100% EtOH)
Total Flow: 90.0 g/min
Back Pressure: 100.0 bar
UV: 214 nm
Stack time: 6.2 min
Load/inj.: 9.1 mg Example 11

((S,Z)-2-((2-Amino-6-oxo-1H-purin-9(6H)-yl)methylene)-1-(((((S)-(((S)-1-oxo-1-((2-propylpentyl)oxy)propan-2-yl)amino)(phenoxy)phosphoryl)oxy)methyl) cyclopropyl)methyl butyrate &A ((R,Z)-2-((2-Amino-6-oxo-1H-purin-9(6H)-yl)methylene)-1-(((((S)-(((S)-1-oxo-1-((2-propylpentyl)oxy)propan-2-yl)amino)(phenoxy)phosphoryl)oxy)methyl) cyclopropyl)methyl butyrate (11-1 & 11-2)

I-27 and I-4 were reacted according to the method described in Example 1 step e. The afforded compound was purified by prep HPLC using Method A. The racemic mixture was separated by prep SFC, which gave the two isomers as separate compounds.

11-1 Yield 4.2%, chiral purity 99.95% according to SFC, LCMS (ES+) m/z 673.33 [M+H]$^+$. $^1$H NMR (500 MHz, DMSO) δ 10.79 (s, 1H), 7.93 (s, 1H), 7.33 (t, J=7.8 Hz, 2H), 7.22 (s, 1H), 7.15 (t, J=7.3 Hz, 3H), 6.58 (s, 2H), 6.05 (q, J=7.7 Hz, 1H), 4.35 (m, J=7.0 Hz, 2H), 4.04 (q, J=6.6 Hz, 2H), 3.97 (q, J=5.5 Hz, 1H), 3.88 (m, J=5.6 Hz, 2H), 2.18 (m, J=7.4 Hz, 2H), 1.60 (d, J=9.4 Hz, 3H), 1.45 (q, J=7.1 Hz, 2H), 1.24 (d, J=6.9 Hz, 11H), 0.81 (m, J=4.9 Hz, 9H).

11-2: Yield 4.0%, chiral purity 99.14% according to SFC, LCMS (ES+) m/z 673.29 [M+H]$^+$. $^1$H NMR (500 MHz, DMSO) δ 10.74 (s, 1H), 7.94 (s, 1H), 7.34 (t, J=7.8 Hz, 2H), 7.20 (d, J=7.1 Hz, 3H), 7.16 (t, J=7.4 Hz, 1H), 6.57 (s, 2H), 6.05 (q, J=7.8 Hz, 1H), 4.27 (d, J=11.6 Hz, 1H), 4.18 (m, J=6.0 Hz, 2H), 4.02 (d, J=11.6 Hz, 1H), 3.96 (q, J=5.6 Hz, 1H), 3.79 (m, J=5.0 Hz, 2H), 2.17 (m, J=7.7 Hz, 2H), 1.56 (q, J=10.5 Hz, 3H), 1.45 (q, J=7.3 Hz, 2H), 1.20 (m, J=7.1 Hz, 11H), 0.81 (q, J=7.8 Hz, 9H).

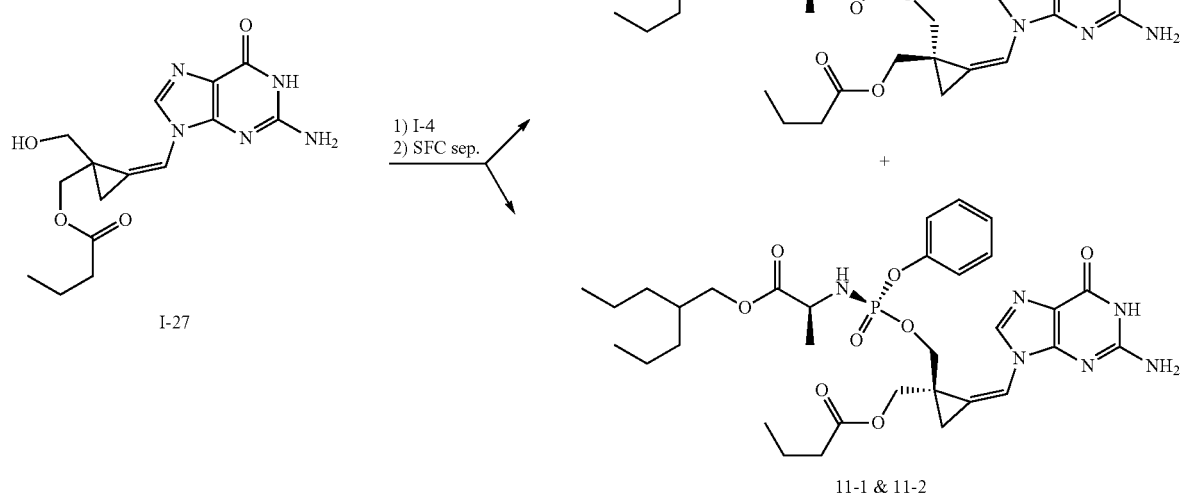

11-1 & 11-2

Preparative SFC Conditions
  Column/dimensions: Chiralcel OX-H (30×250 mm), 5μ
  $CO_2$: 50.0%
  Co solvent: 50.0% (100% IPA)
  Total Flow: 90.0 g/min
  Back Pressure: 100.0 bar
  UV: 214 nm
  Stack time: 23.0 min
  Load/inj.: 28.0 mg Example 12

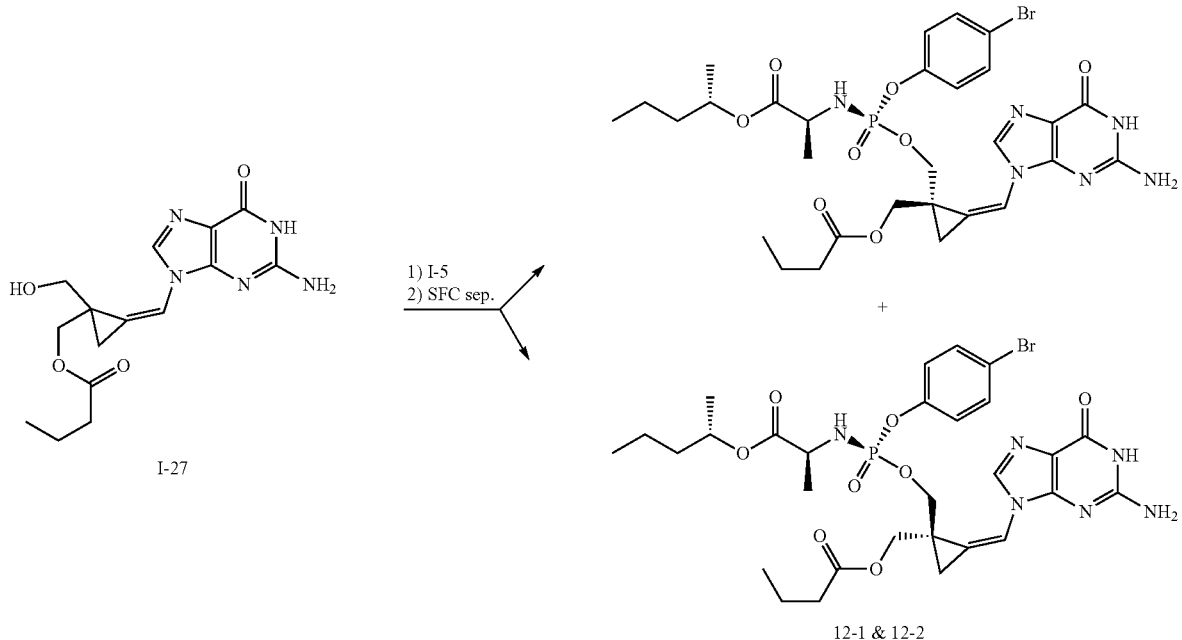

((S,Z)-2-((2-Amino-6-oxo-1H-purin-9(6H)-yl)methylene)-1-((((S)-(4-bromophenoxy)(((S)-1-oxo-1-((S)-pentan-2-yloxy)propan-2-yl)amino)phosphoryl)oxy)methyl)cyclopropyl)methyl butyrate & ((R,Z)-2-((2-Amino-6-oxo-1H-purin-9(6H)-yl)methylene)-1-((((S)-(4-bromophenoxy)(((S)-1-oxo-1-((S)-pentan-2-yloxy)propan-2-yl)amino)phosphoryl)oxy)methyl)cyclopropyl)methyl butyrate (12-1 & 12-2)

I-27 and I-5 were reacted according to the method described in Example 1 step e. The afforded compound was purified by prep HPLC using Method D. The racemic mixture was separated by prep SFC, which gave the two isomers as separate compounds.

12-1: Yield 3.5%, 99.48% chiral purity according to analytical SFC, LCMS (ES+) m/z 709.41 & 711.35 [M+H]$^+$.

$^1$H nmr (500 MHz, DMSO) δ 10.74 (s, 1H), 7.91 (s, 1H), 7.51 (d, J=8.5 Hz, 2H), 7.22 (s, 1H), 7.13 (d, J=8.5 Hz, 2H), 6.56 (s, 2H), 6.09 (t, J=11.5 Hz, 1H), 4.78 (m, J=6.2 Hz, 1H), 4.36 (m, J=7.0 Hz, 2H), 4.04 (t, J=9.9 Hz, 2H), 3.81 (q, J=8.9 Hz, 1H), 2.18 (m, J=7.4 Hz, 2H), 1.63 (s, 2H), 1.44 (m, J=7.0 Hz, 4H), 1.23 (d, J=6.9 Hz, 5H), 1.12 (d, J=6.2 Hz, 3H), 0.81 (m, J=7.3 Hz, 6H).

12-2: Yield 4.0%, 98.93% chiral purity according to analytical SFC, LCMS (ES+) m/z 709.41 & 711.39 [M+H]$^+$.

$^1$H nmr (500 MHz, DMSO) δ 10.72 (s, 1H), 7.92 (s, 1H), 7.51 (d, J=8.5 Hz, 2H), 7.21 (s, 1H), 7.16 (d, J=8.4 Hz, 2H), 6.55 (s, 2H), 6.09 (t, J=11.6 Hz, 1H), 4.75 (q, J=6.1 Hz, 1H), 4.29 (d, J=11.6 Hz, 1H), 4.20 (d, J=5.8 Hz, 2H), 4.04 (d, J=11.5 Hz, 1H), 3.73 (q, J=9.0 Hz, 1H), 2.16 (m, J=7.8 Hz, 2H), 1.61 (s, 2H), 1.42 (m, J=6.7 Hz, 4H), 1.22 (t, J=7.1 Hz, 5H), 1.09 (d, J=6.3 Hz, 3H), 0.81 (m, J=6.8 Hz, 6H).

Preparative SFC Conditions
  Column/dimensions: Chiralpak AD-H (30×250 mm), 5μ
  $CO_2$: 60.0%
  Co solvent: 40.0% (100% EtOH)
  Total Flow: 70.0 g/min
  Back Pressure: 90.0 bar
  UV: 219 nm
  Stack time: 10.5 min
  Load/inj.: 5.1 mg

Example 13

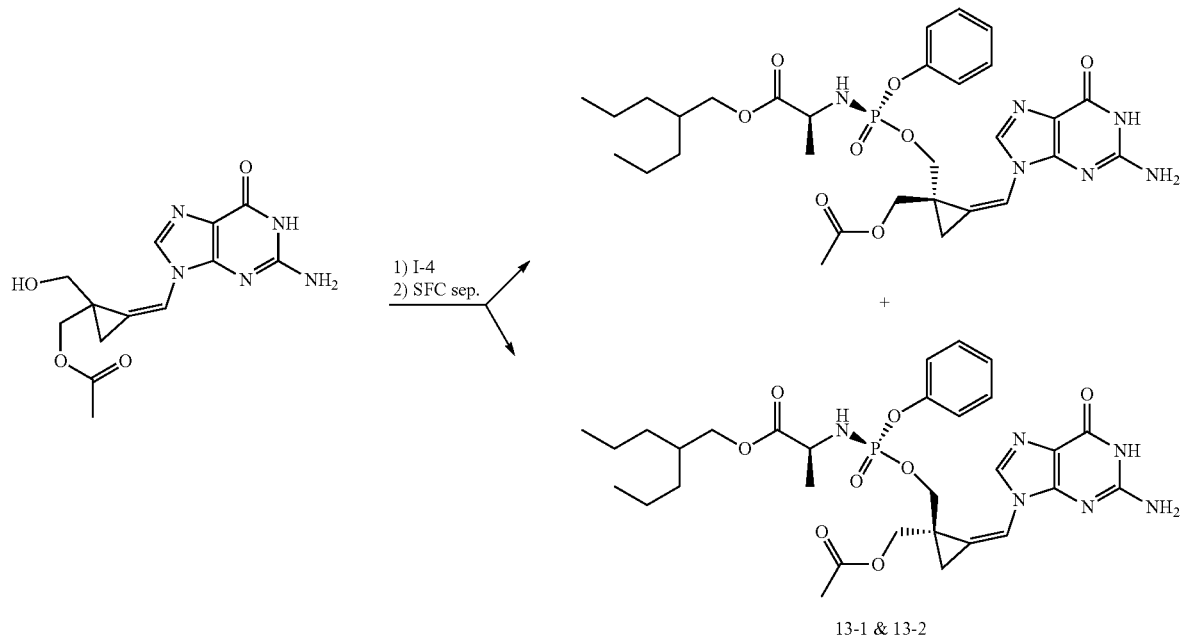 [SMILES: CC(=O)OCC1(CO)C/C1=C/n1cnc2c(=O)[nH]c(N)nc21 ; CCCC(CCC)COC(=O)[C@H](C)N[P@](=O)(OC[C@@]1(COC(C)=O)C/C1=C/n1cnc2c(=O)[nH]c(N)nc21)Oc1ccccc1 ; CCCC(CCC)COC(=O)[C@H](C)N[P@](=O)(OC[C@]1(COC(C)=O)C/C1=C/n1cnc2c(=O)[nH]c(N)nc21)Oc1ccccc1]

13-1 & 13-2

(S)-2-propylpentyl 2-(((S)-(((S,Z)-1-(acetoxymethyl)-2-((2-amino-6-oxo-1H-purin-9(6H)-yl)methylene)cyclopropyl)methoxy)(phenoxy)phosphoryl)amino)propanoate & (S)-2-propylpentyl 2-(((S)-(((R,Z)-1-(acetoxymethyl)-2-((2-amino-6-oxo-1H-purin-9(6H)-yl)methylene)cyclopropyl)methoxy)(phenoxy)phosphoryl)amino)propanoate (13-1 & 13-2)

(Z)-(2-((2-Amino-6-oxo-1H-purin-9(6H)-yl)methylene)-1-(hydroxymethyl)cyclopropyl)methyl acetate and I-4 were reacted according to the method described in Example 1 step e. The afforded compound was purified by prep HPLC. The racemic mixture was separated by prep SFC, which gave the two isomers as separate compounds.

13-1: Yield 14%, 96.88% chiral purity according to analytical SFC, LCMS (ES+) m/z 645.35 $[M+H]^+$.

$^1$H NMR (500 MHz, DMSO)_10.81 (s, 1H), 7.93 (s, 1H), 7.33 (t, J=7.7 Hz, 2H), 7.22 (s, 1H), 7.15 (t, J=7.9 Hz, 3H), 6.60 (s, 2H), 6.05 (t, J=11.5 Hz, 1H), 4.32 (m, J=6.7 Hz, 2H), 4.06 (t, J=9.7 Hz, 2H), 3.96 (q, J=5.5 Hz, 1H), 3.87 (m, J=7.1 Hz, 2H), 1.93 (s, 3H), 1.61 (s, 3H), 1.24 (d, J=6.8 Hz, 11H), 0.82 (t, J=6.2 Hz, 6H). 13-2: Yield 18%, 98.23% chiral purity according to analytical SFC LCMS (ES+) m/z 645.39 $[M+H]^+$.

$^1$H NMR (500 MHz, DMSO)_11.22 (s, 1H), 7.92 (s, 1H), 7.34 (t, J=7.6 Hz, 2H), 7.21 (d, J=7.0 Hz, 3H), 7.16 (t, J=7.4 Hz, 1H), 6.74 (s, 2H), 6.05 (t, J=11.7 Hz, 1H), 4.20 (t, J=10.9 Hz, 3H), 4.05 (d, J=11.6 Hz, 1H), 3.96 (q, J=5.5 Hz, 1H), 3.80 (q, J=5.3 Hz, 2H), 1.92 (s, 3H), 1.57 (d, J=21.6 Hz, 3H), 1.20 (m, J=7.3 Hz, 11H), 0.82 (t, J=6.7 Hz, 6H).

Preparative SFC Conditions
  Column/dimensions: Chiralpak IC (21×250 mm), 5μ
  $CO_2$: 75.0%
  Co solvent: 25% (100% IPA)
  Total Flow: 70.0 g/min
  Back Pressure: 100.0 bar
  UV: 227 nm
  Stack time: 7.0 min
  Load/inj.: 3.0 mg

Example 14

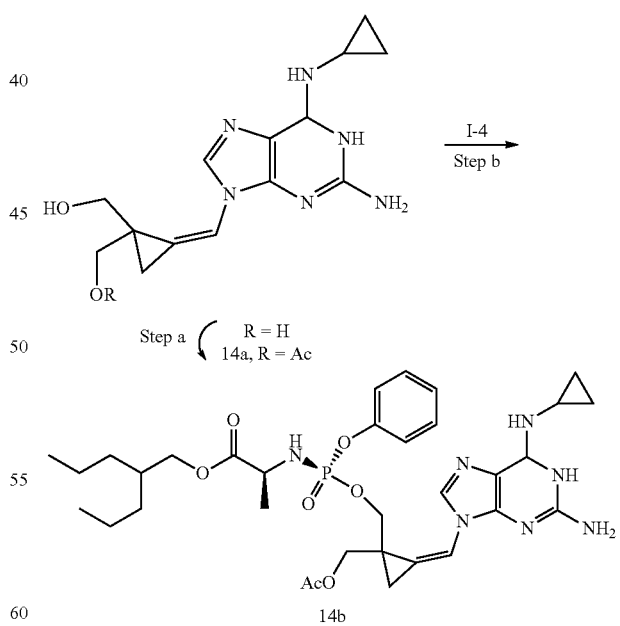

Step a) (Z)-(2-((2-amino-6-(cyclopropylamino)-1H-purin-9(6H)-yl)methylene)-1-(hydroxymethyl)cyclopropyl)methyl acetate (14a)

To a stirred solution of (Z)-(2-((2-amino-6-(cyclopropylamino)-1H-purin-9(6H)-yl)methylene)cyclopropane-1,1- diyl)dimethanol (700 mg, 2.22 mmol) in DMF (70 mL) were added Trimethyl orthoacetate (1.15 ml, 8.90 mmol) and pTSA (425 mg, 2.23 mmol) at rt. The reaction mixture was stirred at rt for 3 h, then concentrated. The residue was taken in 80% acetic acid (aq., 100 mL), the mixture was stirred at rt for 3 h, then concentrated. The crude compound was purified by column chromatography on silica gel eluted with 4.5% MeOH in DCM. the afforded compound was purified by prep HPLC using Method C, which gave the title compound (180 mg, 24%) of as a solid. LCMS (ES+) m/z 345.31 [M+H]$^+$.

Step b) (2S)-2-propylpentyl 2-(((S)-(((Z)-1-(acetoxymethyl)-2-((2-amino-6-cyclopropylamino-1H-purin-9(6H)-yl)methylene)cyclopropyl)methoxy)(phenoxy)phosphoryl)amino)propanoate (14b)

To a solution of 14a (50 mg, 0.14 mmol) in dry THF (4 mL) was added tert-butylmagnesium chloride (0.8 mL, 1M in THF, 0.8 mmol) dropwise for 5 min. The mixture was stirred for 30 min at rt, then 1-4 (92 mg, 0.18 mmol) in dry THF (2 mL) was added dropwise. The reaction mixture was stirred at rt for 2 h, then concentrated. The crude product was purified by column chromatography on silica gel eluted with 8% MeOH in DCM. Appropriate fractions were pooled and concentrated. The afforded residue was purified by prep HPLC using Method D, which gave the title compound (10 mg, 10%) as a solid. LCMS (ES+) m/z 684.45 [M+H]$^+$.
$^1$H NMR (500 MHz, DMSO) δ 7.98 (d, J=4.6 Hz, 1H), 7.44 (s, 1H), 7.31 (m, J=7.3 Hz, 3H), 7.16 (q, J=9.5 Hz, 3H), 6.02 (m, J=6.9 Hz, 3H), 4.36 (m, J=13.5 Hz, 1H), 4.18 (m, J=9.5 Hz, 2H), 3.97 (m, J=5.2 Hz, 1H), 3.83 (m, J=7.3 Hz, 2H), 3.03 (s, 1H), 1.92 (d, J=3.0 Hz, 3H), 1.59 (d, J=7.0 Hz, 3H), 1.20 (m, J=7.6 Hz, 12H), 0.81 (d, J=6.9 Hz, 6H), 0.66 (d, J=6.6 Hz, 2H), 0.60 (s, 2H).

Example 15

(S)-((S,Z)-2-((2-amino-6-oxo-1H-purin-9(6H)-yl)methylene)-1-((((S)-(((S)-1-oxo-1-((S)-pentan-2-yloxy)propan-2-yl)amino)(phenoxy)phosphoryl)oxy)methyl)cyclopropyl)methyl 2-amino-3-methylbutanoate & (R)—((S,Z)-2-((2-amino-6-oxo-1H-purin-9(6H)-yl)methylene)-1-((((S)-(((S)-1-oxo-1-((S)-pentan-2-yloxy)propan-2-yl)amino)(phenoxy)phosphoryl)oxy)methyl)cyclopropyl)methyl 2-amino-3-methylbutanoate (15-1 & (15-2)

The title compound was prepared from compounds 1d and I-9b as Example 1 steps e and f with the difference that the purification/separation of the final compounds was performed by
1) Prep. chiral NP HPLC which gave a first (15-1) and second fraction (15-2).
2-1) First fraction was combined with another batch of the same compound and purified by prep HPLC, Method C.
2-2) Second fraction was combined with another batch of the same compound and purified by prep HPLC, Method A.
3) The second fraction was purified by prep chiral NP HPLC.
Prep NP HPLC
Column/dimensions: Chiralcel OX-H (250×30) mm, 5μ
Mobile Phase: 0.2% DEA in n-hexane:EtOH (45:55)
Flow: 38.0 ml/min
Temperature: Ambient
Wave length: 270 nm
Run time: 24 min
Solubility: EtOH
Load/inj.: 9.7 mg
15-1: LCMS (ES+) m/z 660.33 [M+H]$^+$, 99.2% chiral purity according to chiral NP HPLC.
$^1$H NMR (500 MHz, DMSO) δ 10.60 (s, 1H), 7.93 (s, 1H), 7.33 (m, J=3.2 Hz, 2H), 7.23 (t, J=1.8 Hz, 1H), 7.16 (d, J=7.9 Hz, 3H), 6.54 (s, 2H), 6.02 (q, J=7.7 Hz, 1H), 4.79 (m, J=3.8 Hz, 1H), 4.46 (d, J=11.6 Hz, 1H), 4.38 (q, J=5.8 Hz, 1H), 4.06 (q, J=5.5 Hz, 1H), 3.96 (d, J=11.5 Hz, 1H), 3.80 (m,

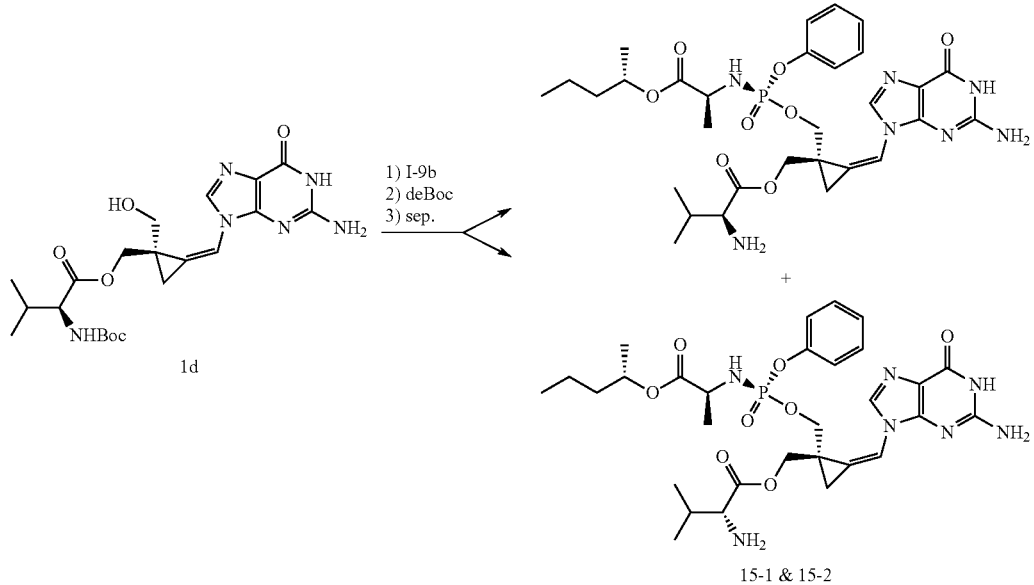 [SMILES: CC(C)[C@H](NC(=O)OC(C)(C)C)C(=O)OC[C@]1(CO)C/C1=C/n1cnc2c(=O)[nH]c(N)nc21 ; CCC[C@H](C)OC(=O)[C@H](C)N[P@](=O)(OC[C@@]1(COC(=O)[C@@H](N)C(C)C)C/C1=C/n1cnc2c(=O)[nH]c(N)nc21)Oc1ccccc1 ; CCC[C@H](C)OC(=O)[C@H](C)N[P@](=O)(OC[C@@]1(COC(=O)[C@H](N)C(C)C)C/C1=C/n1cnc2c(=O)[nH]c(N)nc21)Oc1ccccc1]

15-1 & 15-2

J=5.1 Hz, 1H), 3.03 (d, J=5.5 Hz, 1H), 1.63 (q, J=4.0 Hz, 4H), 1.45 (m, J=3.5 Hz, 2H), 1.22 (d, J=7.1 Hz, 5H), 1.13 (d, J=6.3 Hz, 3H), 0.83 (t, J=7.4 Hz, 3H), 0.74 (d, J=6.8 Hz, 3H), 0.69 (d, J=6.8 Hz, 3H).

15-2: LCMS (ES+) m/z 660.33 [M+H]$^+$, 99.0% chiral purity according to chiral NP HPLC.

$^1$H NMR (500 MHz, DMSO) δ 11.01 (s, 1H), 7.93 (s, 1H), 7.33 (q, J=5.3 Hz, 2H), 7.18 (m, J=5.2 Hz, 4H), 6.70 (s, 2H), 6.03 (q, J=7.8 Hz, 1H), 4.76 (q, J=6.4 Hz, 1H), 4.35 (d, J=11.6 Hz, 1H), 4.20 (m, J=3.3 Hz, 2H), 4.03 (d, J=11.5 Hz, 1H), 3.73 (m, J=5.1 Hz, 1H), 3.04 (d, J=5.2 Hz, 1H), 1.78 (m, J=3.8 Hz, 1H), 1.61 (m, J=4.0 Hz, 3H), 1.42 (m, J=3.2 Hz, 3H), 1.28 (q, J=4.4 Hz, 1H), 1.22 (m, J=5.7 Hz, 5H), 1.09 (d, J=6.3 Hz, 3H), 0.82 (t, J=7.3 Hz, 6H), 0.74 (d, J=6.8 Hz, 3H).

Example 16 was added dropwise over a period of 10 min. The reaction mixture was stirred at rt for 4 h, then concentrated and the afforded crude compound was combined with another batch and purified by column chromatography on silica gel eluted with 8-10% MeOH in DCM. The afforded product was further purified by prep HPLC using Method C. The pure compound was further purified by chiral SFC, which gave the title compound (peak-1)(9 mg) as a solid. LCMS (ES+) m/z 633.53 [M+H]$^+$.

$^1$H NMR (500 MHz, DMSO): δ 7.74 (t, J=5.5 Hz, 1H), 7.43 (t, J=1.7 Hz, 2H), 7.35 (t, J=8.0 Hz, 3H), 7.16 (q, J=3.7 Hz, 3H), 6.05 (q, J=7.7 Hz, 1H), 5.80 (d, J=7.4 Hz, 1H), 4.37 (d, J=11.5 Hz, 1H), 4.22 (q, J=5.6 Hz, 1H), 3.99 (m, J=5.4 Hz, 2H), 3.88 (m, J=5.7 Hz, 3H), 2.46 (t, J=3.5 Hz, 1H), 1.60 (t, J=5.7 Hz, 1H), 1.47 (d, J=1.8 Hz, 2H), 1.23 (m, J=6.3 Hz, 12H), 1.06 (t, J=3.5 Hz, 3H), 1.03 (q, J=3.1 Hz, 3H), 0.84 (m, J=2.5 Hz, 6H).

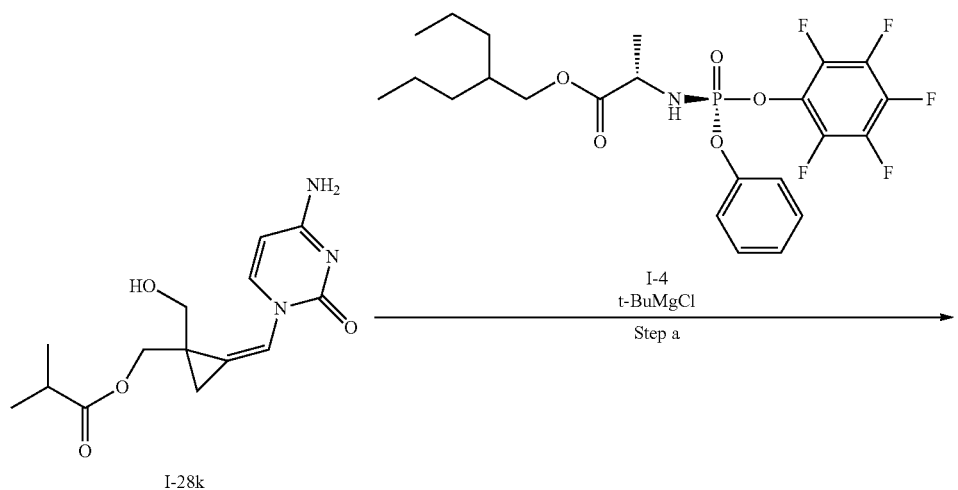

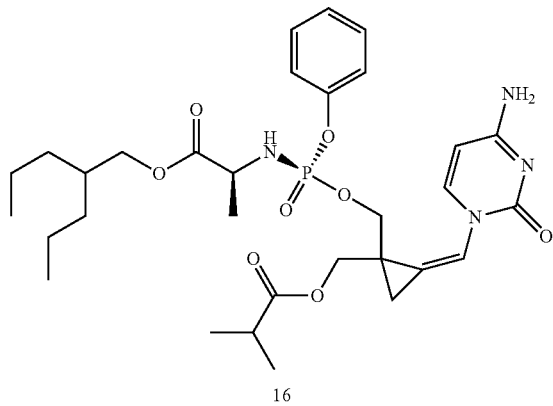

((Z)-2-((4-amino-2-oxopyrimidin-1(2H)-yl)methylene)-1-((((((S)-1-oxo-1-((2-propylpentyl)oxy)propan-2-yl)amino)(phenoxy)phosphoryl)oxy)methyl)cyclopropyl)methyl isobutyrate tert-Butylmagnesium chloride (1M in THF, 2.6 mL, 2.6 mmol) was added dropwise over a period of 10 min to a solution of compound I-28k (150 mg, 0.51 mmol) in DMF (15 mL). The reaction mixture was stirred at rt for 30 min, then compound I-4 (322 mg, 0.6 mmol) in dry THF (10 mL)

Preparative SFC Conditions:
Column/dimensions: Chiralpak IC (30×250 mm), 5μ
$CO_2$:50.0%
Co solvent: 50.0% (100% isopropanol)
Total Flow: 90.0 g/min
Back Pressure: 100.0 bar
UV: 214 nm
Stack time: 14.0 min
Load/inj.: 7.0 mg

Example 17

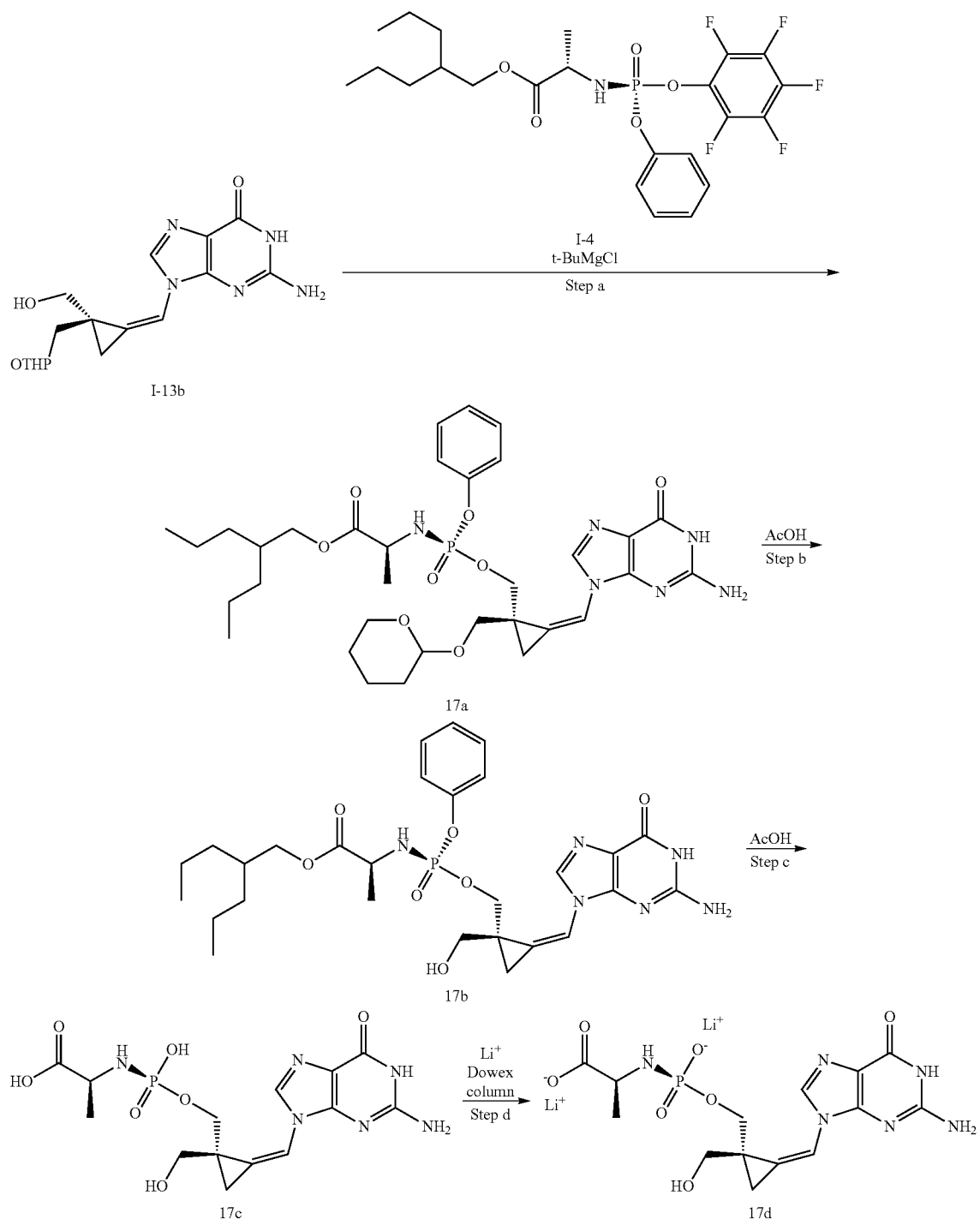

Step a) 2-propylpentyl((S)-(((1S,Z)-2-((2-amino-6-oxo-1,6-dihydro-9H-purin-9-yl)methylene)-1-(((tetrahydro-2H-pyran-2-yl)oxy)methyl)cyclopropyl)methoxy)(phenoxy)phosphoryl)-L-alaninate (17a)

tert-Butylmagnesium chloride (1M in THF, 5 mL, 5.0 mmol) was added dropwise over a period of 5 min to a solution of compound I-13b (350 mg, 1 mmol) in DMF (35 mL). The reaction mixture was stirred at rt for 30 min, then compound I-4 (633 mg, 1.2 mmol) in dry THF (17 mL) was added dropwise over a period of 5 min. The reaction mixture was stirred at rt for 16 h, then concentrated and the afforded crude compound was combined with was purified by column chromatography on silica gel eluted with 10% MeOH in DCM, which gave the title compound (250 mg) as a solid. LCMS (ES+) m/z 687.29 [M+H]+.

Step b) 2-propylpentyl((S)-(((S,Z)-2-((2-amino-6-oxo-1,6-dihydro-9H-purin-9-yl)methylene)-1-(hydroxymethyl)cyclopropyl)methoxy)(phenoxy)phosphoryl)-L-alaninate (17b)

80% AcOH (104.2 mL, 1455.7 mmol) was added to compound 17a (250 mg, 0.4 mmol) and the resulting reaction mixture was stirred for 48 h at rt, then concentrated. The obtained crude compound was purified by column chromatography on silica gel eluted with 12% MeOH in DCM. The afforded product was further purified by prep HPLC using Method A, which gave the title compound (110 mg, 42%) as a solid. LCMS (ES+) m/z 603.48 [M+H]+.

Step c) (((((S,Z)-2-((2-amino-6-oxo-1,6-dihydro-9H-purin-9-yl)methylene)-1-(hydroxymethyl)cyclopropyl)methoxy)(hydroxy)phosphoryl)-L-alanine (17c)

A solution of compound 17b (40 mg, 0.07 mmol) in Et$_3$N (1 mL) and water (0.25 mL) was stirred at 50° C. for 46 h. The reaction mixture was lyophilised and purified by prep HPLC using Method G, which gave the title compound (15 mg) as a solid. LCMS (ES+) m/z 603.48 [M+H]+.

Step d) lithium ((((S,Z)-2-((2-amino-6-oxo-1,6-dihydro-9H-purin-9-yl)methylene)-1-(hydroxymethyl)cyclopropyl)methoxy)oxidophosphoryl)-L-alaninate (17d)

Dowex 50 WX4-200, ion exchange resin was taken in a column (2×10 cm), washed with water: MeOH (1:1, 100 mL) until colorless eluent was obtained, then washed with Milli Q water (100 mL) to wash off MeOH. The ion exchange resin was again eluted with 0.5M sulphuric acid (50 mL) until acidic pH was attained and washed with water (200 mL) until neutral pH. The ion exchange resin was again eluted with 1M lithium hydroxide (50 mL) until basic pH was attained and washed with water (200 mL) until neutral pH. A solution of compound 17c (13 mg, 0.031 mmol) in Milli Q water (2 mL) was passed through the above freshly prepared Dowex Li+ column. The appropriate fractions were lypholyised, which gave the title compound (8 mg) as a solid. LCMS (ES+) m/z 415.30 [M+H]+.

$^1$H NMR (500 MHz, D2O) δ 8.31 (d, J=11.3 Hz, 1H), 7.23 (m, J=2.2 Hz, 1H), 4.01 (m, J=5.3 Hz, 1H), 3.77 (m, J=5.2 Hz, 3H), 3.49 (m, J=5.7 Hz, 1H), 1.54 (m, J=3.1 Hz, 2H), 1.19 (d, J=7.0 Hz, 3H).

Example 18

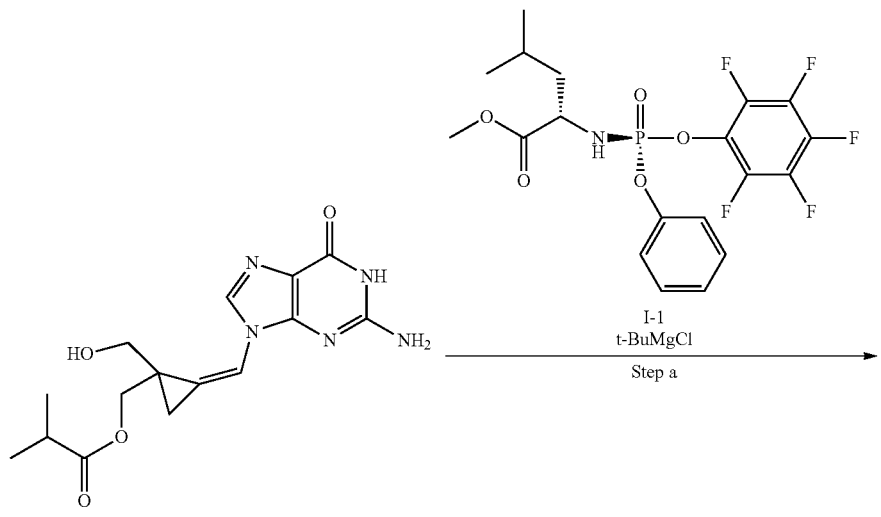

I-11

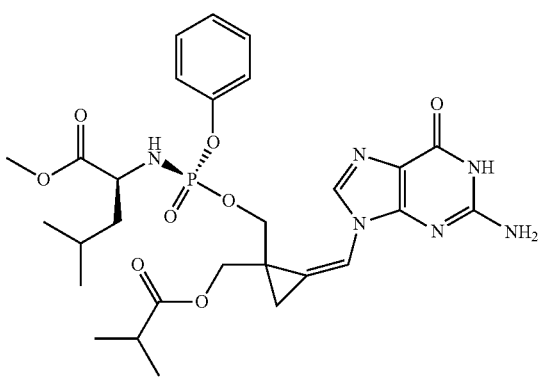

18 methyl((S)-(((Z)-2-((2-amino-6-oxo-1,6-dihydro-9H-purin-9-yl)methylene)-1-((isobutyryloxy)methyl)cyclopropyl)methoxy)(phenoxy)phosphoryl)-L-leucinate (18)

tert-Butylmagnesium chloride (1M in THF, 1.5 mL, 1.5 mmol) was added dropwise over a period of 15 min to a solution of compound I-11a (210 mg, 0.63 mmol) in DMF (25 mL). The reaction mixture was stirred at rt for 20 min, then compound I-1 (308 mg, 0.66 mmol) in dry THE (10 mL) was added dropwise over a period of 5 min. The reaction mixture was stirred at rt for 2 h, then concentrated under reduced pressure and the afforded crude compound was combined with another batch and purified by column chromatography on silica gel eluted with 7% MeOH in DCM. The afforded product was further purified by prep HPLC using Method D. The pure compound was further purified by chiral SFC, which gave the title compound (peak-2)(67 mg, 17%) as a solid. LCMS (ES+) m/z 617.46 [M+H]⁺.

¹H NMR (500 MHz, DMSO): δ 10.69 (s, 1H), 7.92 (s, 1H), 7.32 (t, J=7.9 Hz, 2H), 7.22 (s, 1H), 7.14 (q, J=6.7 Hz, 3H), 6.55 (s, 2H), 6.05 (q, J=7.8 Hz, 1H), 4.38 (m, J=6.9 Hz, 2H), 4.01 (m, J=7.3 Hz, 2H), 3.75 (q, J=5.2 Hz, 1H), 3.57 (s, 3H), 2.44 (m, J=7.0 Hz, 1H), 1.61 (d, J=1.4 Hz, 3H), 1.43 (m, J=4.7 Hz, 2H), 1.04 (d, J=7.0 Hz, 3H), 0.99 (d, J=7.0 Hz, 3H), 0.82 (d, J=6.7 Hz, 3H), 0.78 (d, J=6.6 Hz, 3H).

Preparative SFC Conditions:
Column/dimensions: Chiralpak IE (30×250 mm), 5µ
CO₂:65.0%
Co solvent: 35.0% (0.5% DEA in EtOH)
Total Flow: 90.0 g/min
Back Pressure: 100.0 bar
UV: 214 nm
Stack time: 8.0 min
Solubility: 30 mL of acetonitrile+5 mL of MeOH
Load/inj.: 10.0 mg Example 19

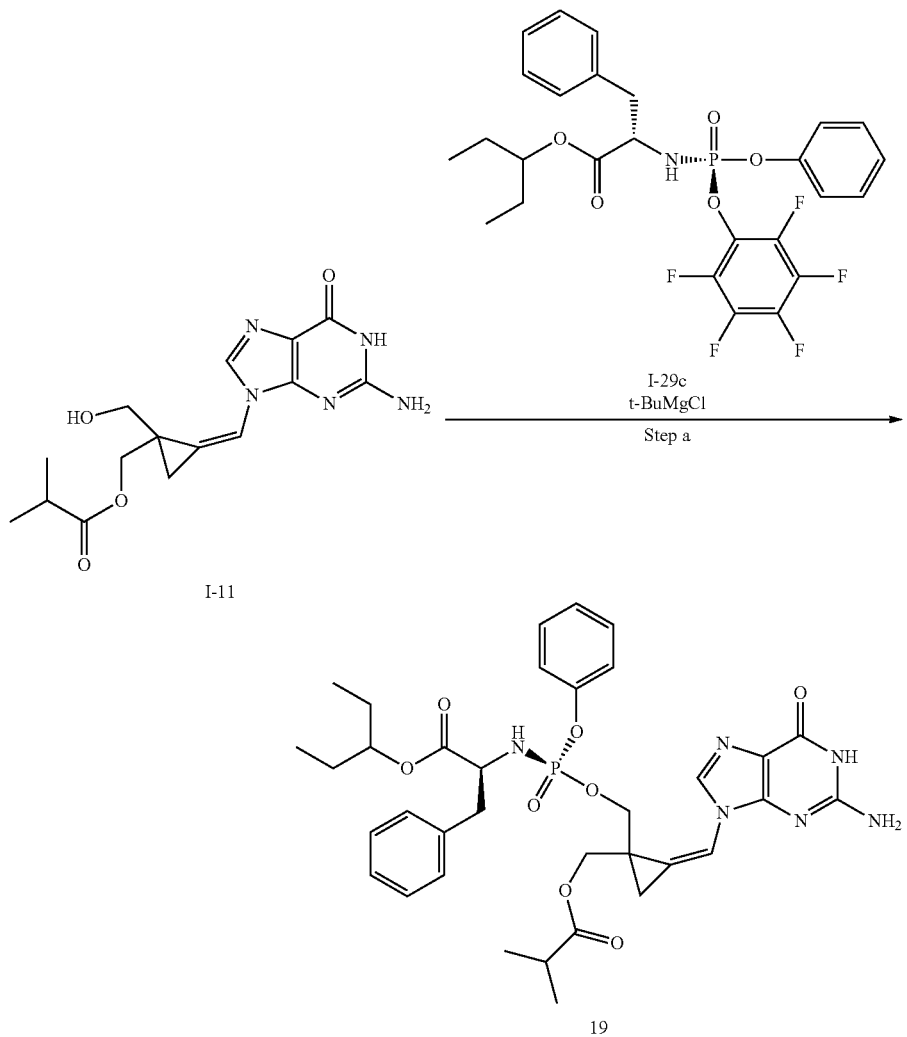

Pentan-3-yl((S)-(((Z)-2-((2-amino-6-oxo-1,6-dihydro-9H-purin-9-yl)methylene)-1-((isobutyryloxy)methyl)cyclopropyl)methoxy)(phenoxy)phosphoryl)-L-phenylalaninate tert-Butylmagnesium chloride (1M in THF, 2.3 mL, 2.3 mmol) was added dropwise over a period of 10 min at rt to a solution of compound I-11 (300 mg, 0.9 mmol) in DMF (15 mL). The reaction mixture was stirred at rt for 30 min, then compound I-29c (552 mg, 1.0 mmol) in dry THE (10 mL) was added dropwise over a period of 10 min. The reaction mixture was stirred at rt for 4 h, then concentrated under reduced pressure and the afforded crude compound was combined with another batch and purified by column chromatography on silica gel eluted with 8% MeOH in DCM. The afforded product was further purified by prep HPLC using Method D. The pure compound was further purified by chiral SFC, which gave the title compound (peak-2)(90 mg) as a solid. LCMS (ES+) m/z 707.70 [M+H]+.

$^1$H NMR (500 MHz, DMSO): δ 10.82 (s, 1H), 7.88 (s, 1H), 7.28 (t, J=7.9 Hz, 2H), 7.20 (t, J=2.8 Hz, 5H), 7.11 (m, J=4.3 Hz, 2H), 7.06 (d, J=8.4 Hz, 2H), 6.62 (s, 2H), 6.13 (q, J=7.8 Hz, 1H), 4.58 (m, J=3.5 Hz, 1H), 4.25 (d, J=11.6 Hz, 1H), 3.96 (q, J=5.4 Hz, 1H), 3.87 (m, J=6.1 Hz, 2H), 3.69 (q, J=5.8 Hz, 1H), 3.25 (t, J=7.6 Hz, 1H), 2.98 (m, J=3.2 Hz, 1H), 2.77 (q, J=7.5 Hz, 1H), 2.41 (q, J=7.0 Hz, 1H), 1.53 (t, J=5.0 Hz, 1H), 1.41 (m, J=5.3 Hz, 5H), 1.02 (d, J=7.0 Hz, 3H), 0.97 (d, J=7.0 Hz, 3H), 0.75 (t, J=7.4 Hz, 3H), 0.64 (t, J=7.4 Hz, 3H).

Preparative SFC Conditions:
Column/dimensions: Lux Cellulose-2 (250×30) mm, 5μ
CO$_2$:60.0%
Co solvent: 40.0% (MeOH)
Total Flow: 90.0 g/min
Back Pressure: 100.0 bar
UV: 214 nm
Stack time: 13.0 min
Load/inj.: 15.62 mg Example 20

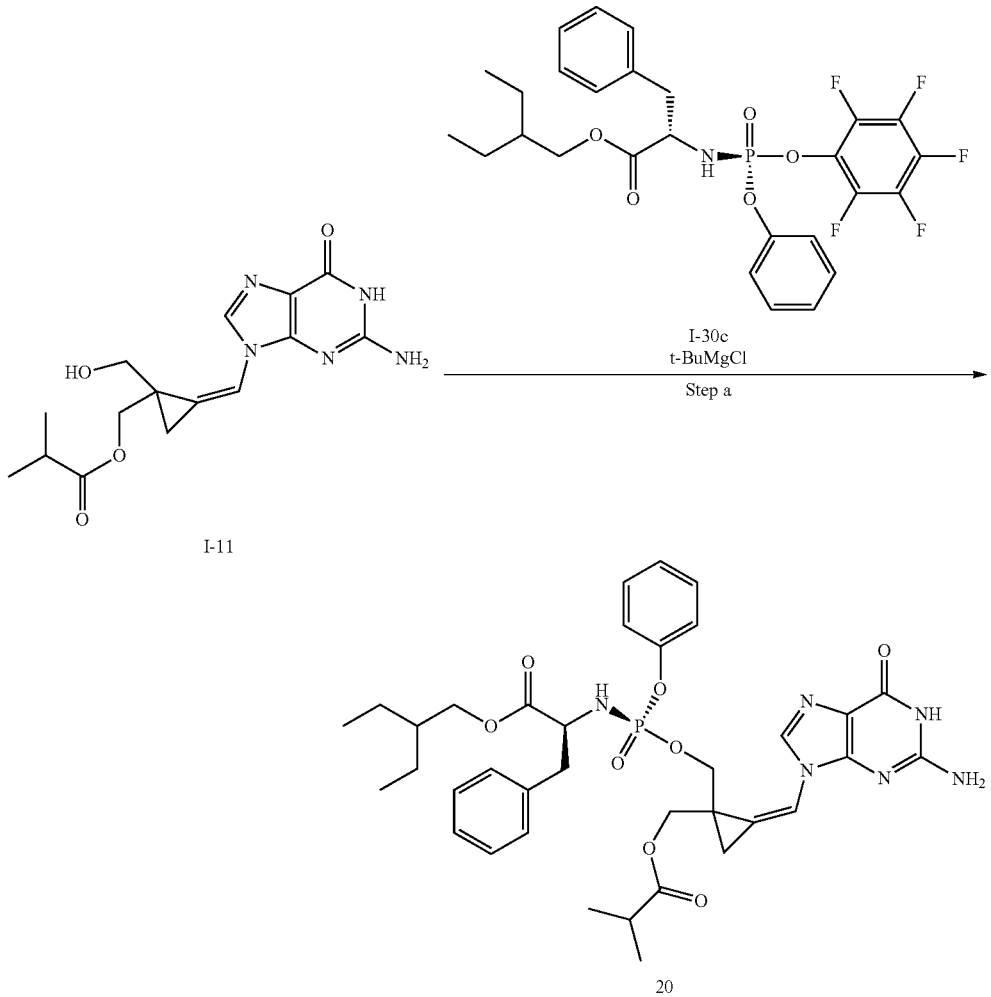

2-ethylbutyl((S)-(((Z)-2-((2-amino-6-oxo-1,6-dihydro-9H-purin-9-yl)methylene)-1-((isobutyryloxy)methyl)cyclopropyl)methoxy)(phenoxy)phosphoryl)-L-phenylalaninate (20)

tert-Butylmagnesium chloride (1M in THF, 2.1 mL, 2.1 mmol) was added dropwise over a period of 15 min at rt to a solution of compound I-11 (300 mg, 0.9 mmol) in DMF (25 mL). The reaction mixture was stirred at rt for 20 min, then compound I-30c (566 mg, 1.0 mmol) in dry THE (10 mL) was added dropwise over a period of 5 min. The reaction mixture was stirred at rt for 2 h, then concentrated under reduced pressure and the afforded crude compound was combined with another batch and purified by column chromatography on silica gel eluted with 8% MeOH in DCM. The afforded product was further purified by prep HPLC using Method D.

The pure compound was further purified by chiral SFC. The impure compound was again purified by chiral SFC, which gave the title compound (peak-2)(75 mg, 11%) as a solid. LCMS (ES+) m/z 721.64 [M+H]+.

$^1$H NMR (500 MHz, DMSO): δ 10.73 (s, 1H), 7.86 (s, 1H), 7.27 (q, J=5.3 Hz, 2H), 7.20 (d, J=4.4 Hz, 5H), 7.10 (m, J=5.1 Hz, 2H), 7.00 (d, J=8.6 Hz, 2H), 6.56 (s, 2H), 6.13 (q, J=7.7 Hz, 1H), 4.35 (d, J=11.6 Hz, 1H), 4.07 (q, J=5.8 Hz, 1H), 4.00 (q, J=5.5 Hz, 1H), 3.87 (m, J=5.3 Hz, 3H), 3.58 (q, J=5.4 Hz, 1H), 2.97 (m, J=3.3 Hz, 1H), 2.78 (q, J=7.5 Hz, 1H), 2.43 (m, J=7.0 Hz, 1H), 1.55 (t, J=5.1 Hz, 1H), 1.50 (q, J=3.6 Hz, 1H), 1.36 (t, J=6.2 Hz, 1H), 1.20 (m, J=4.5 Hz, 4H), 1.03 (d, J=7.0 Hz, 3H), 0.98 (d, J=7.0 Hz, 3H), 0.77 (m, J=3.5 Hz, 6H).

Preparative SFC Conditions-1:
  Column/dimensions: Chiralpak IE (30×250 mm), 5μ
  Total Flow: 40.0 mL/min
  Stack time: 11.0 min
  Solubility: 30 mL of acetonitrile+5 mL of MeOH
  Load/inj.: 17.3 mg
Preparative SFC Conditions-2:
  Column/dimensions: Chiralpak IA (30×250 mm), 5μ
  $CO_2$:70.0%
  Co solvent: 30.0% (100% EtOH)
  Total Flow: 90.0 g/min
  Back Pressure: 100.0 bar
  UV: 214 nm
  Stack time: 6.5 min
  Load/inj.: 20 mg Example 21

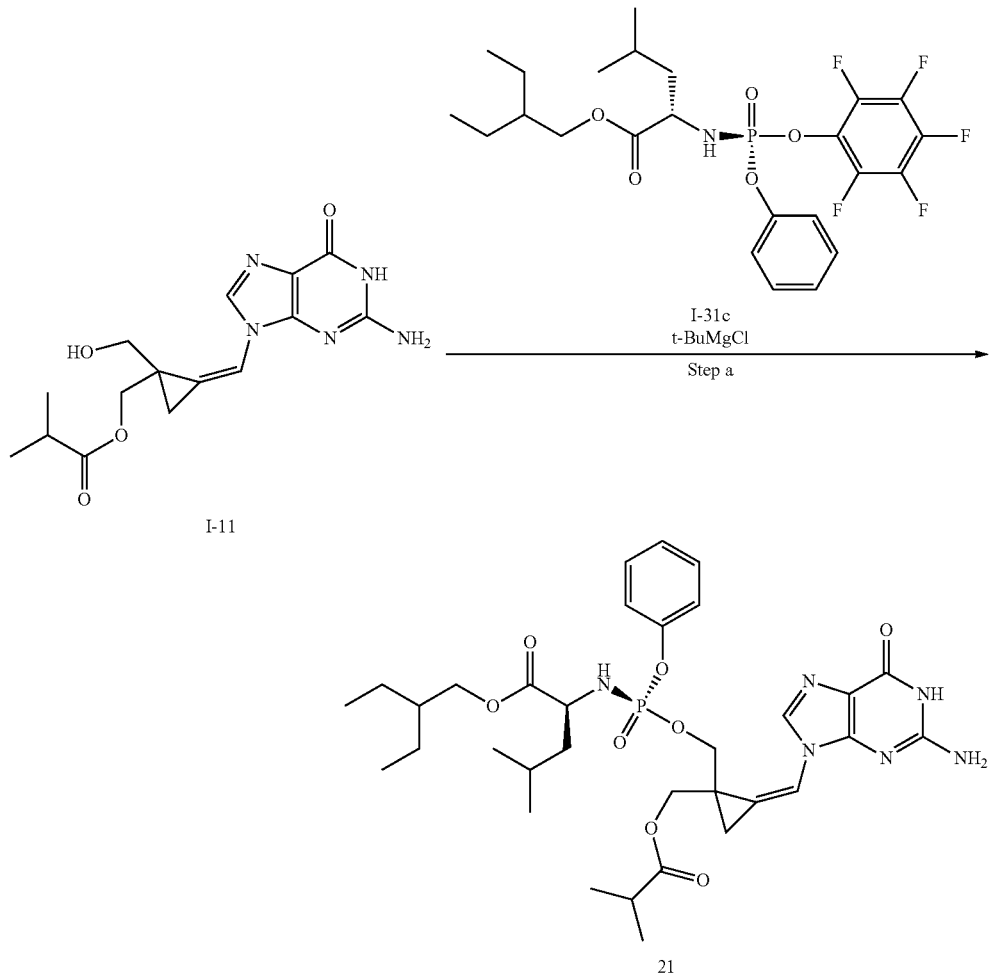

2-ethylbutyl((S)-(((Z)-2-((2-amino-6-oxo-1,6-di-hydro-9H-purin-9-yl)methylene)-1-((isobutyryloxy) methyl)cyclopropyl)methoxy)(phenoxy)phosphoryl)-L-leucinate (21)

tert-Butylmagnesium chloride (1M in THF, 1.4 mL, 2.1 mmol) was added dropwise over a period of 3 min at rt to a solution of compound I-11 (200 mg, 0.6 mmol) in DMF (15 mL). The reaction mixture was stirred at rt for 20 min, then compound I-31c (360 mg, 0.7 mmol) in dry THF (8 mL) was added dropwise over a period of 5 min. The reaction mixture was stirred at rt for 2 h, then concentrated under reduced pressure and the afforded crude compound was combined with another batch and purified by column chromatography on silica gel eluted with 8% MeOH in DCM. The afforded product was further purified by prep HPLC using Method F. The pure compound was further purified by chiral SFC. The impure isomer was again purified by chiral SFC, which gave the title compound (peak-2) (7.5 mg) as a solid. LCMS (ES+) m/z 687.71 [M+H]⁺.

¹H NMR (500 MHz, DMSO): δ 7.89 (s, 1H), 7.32 (t, J=7.9 Hz, 2H), 7.22 (s, 1H), 7.14 (t, J=8.6 Hz, 3H), 6.69 (s, 2H), 6.02 (t, J=11.6 Hz, 2H), 4.38 (t, J=10.1 Hz, 2H), 4.00 (q, J=5.2 Hz, 2H), 3.92 (t, J=5.8 Hz, 2H), 3.76 (q, J=8.3 Hz, 1H), 2.44 (q, J=7.0 Hz, 1H), 1.60 (d, J=9.6 Hz, 3H), 1.43 (t, J=5.9 Hz, 3H), 1.27 (m, J=7.2 Hz, 4H), 1.04 (d, J=7.0 Hz, 3H), 0.99 (d, J=7.0 Hz, 3H), 0.81 (m, J=6.8 Hz, 12H).

Preparative SFC Conditions-1
   Column/dimensions: Chiralpak AD-H (30×250 mm), 5μ
   $CO_2$:80.0%
   Co solvent: 20.0% (100% EtOH)
   Total Flow: 60.0 g/min
   Back Pressure: 100.0 bar
   UV: 214 nm
   Stack time: 13 min
   Load/Inj. 4.1 mg Preparative SFC Conditions-2
   Column/dimensions: Chiralpak AD-H (30×250 mm), 5μ
   $CO_2$:75.0%
   Co solvent: 25.0% (100% EtOH)
   Total Flow: 70.0 g/min
   Back Pressure: 90.0 bar
   UV: 230 nm
   Stack time: 6.5 min
   Load/Inj.: 2 mg Example 22

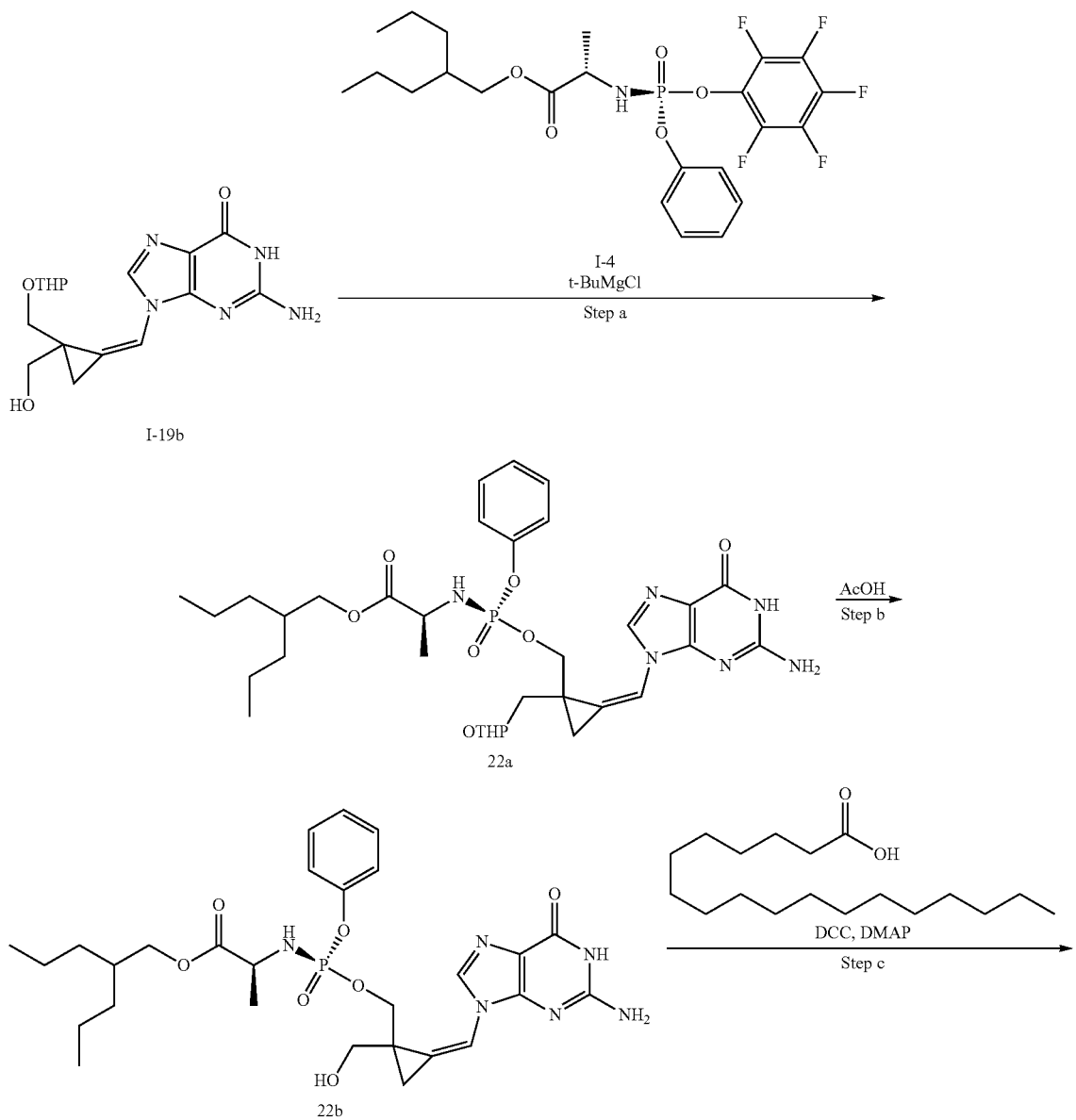

-continued

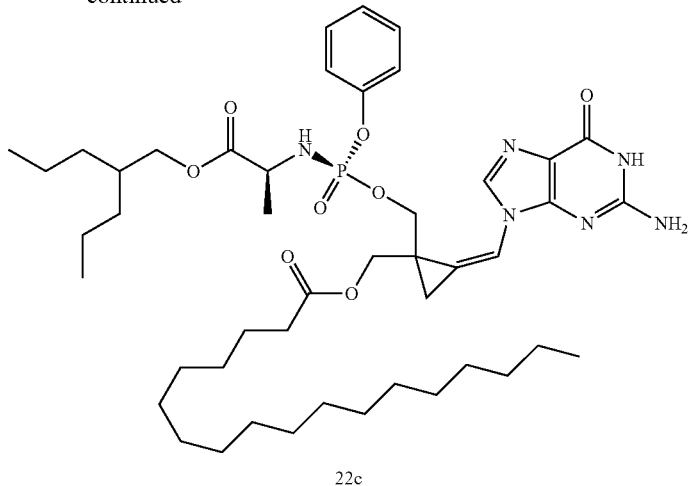

22c

Step a) 2-propylpentyl((S)-(((Z)-2-((2-amino-6-oxo-1,6-dihydro-9H-purin-9-yl)methylene)-1-(((tetrahydro-2H-pyran-2-yl)oxy)methyl)cyclopropyl)methoxy)(phenoxy)phosphoryl)-L-alaninate (22a)

tert-Butylmagnesium chloride (1M in THF, 4.3 mL, 4.3 mmol) was added dropwise over a period of 5 min at rt to a solution of compound I-19b (300 mg, 0.9 mmol) in DMF (33 mL). The reaction mixture was stirred at rt for 45 min, then compound I-4 (545 mg, 1.01 mmol) in dry THF (17 mL) was added dropwise over a period of 10 min. The reaction mixture was stirred at rt for 16 h, then concentrated under reduced pressure and the afforded crude compound was combined with another batch and purified by column chromatography on silica gel eluted with 7% MeOH in DCM, which gave the title compound (250 mg) as a solid. LCMS (ES+) m/z 687.71 [M+H]$^+$. The crude product was used in the next step without further purification.

Step b) 2-propylpentyl((S)-(((Z)-2-((2-amino-6-oxo-1,6-dihydro-9H-purin-9-yl)methylene)-1-(hydroxymethyl)cyclopropyl)methoxy)(phenoxy)phosphoryl)-L-alaninate (22b)

80% AcOH (105 mL, 1455.7 mmol) was added to 22a (250 mg, 0.4 mmol) and the resulting reaction mixture was stirred for 24 h at rt, then concentrated. The obtained crude compound was purified by column chromatography on silica gel eluted with 12% MeOH in DCM. The crude product was used in the next step without further purification.

Step c) ((Z)-2-((2-amino-6-oxo-1,6-dihydro-9H-purin-9-yl)methylene)-1-((((S)-(((S)-1-oxo-1-((2-propylpentyl)oxy)propan-2yl)amino)(phenoxy)phosphoryl)oxy)methyl)cyclopropyl)methyl stearate (22c)

DCC (154 mg, 0.75 mmol) and DMAP (6 mg, 0.1 mmol) were added at rt to a stirred solution of compound 22b (100 mg, 0.17 mmol) and stearic acid (142 mg, 0.5 mmol) in DMF (10 mL). The resulting reaction mixture was stirred at rt for 20 h, then concentrated under reduced pressure. The crude compound was purified by column chromatography on silica gel and eluted with 5% MeOH in DCM. The obtained compound was further purified by prep HPLC using Method D. The pure compound was further purified by chiral SFC, which gave the title compound (peak-1) (7 mg, 5%) as a solid. MS (ES+) 869.77 [M+H]$^+$.

$^1$H NMR (500 MHz, DMSO): δ 10.68 (s, 1H), 7.94 (s, 1H), 7.32 (m, J=3.2 Hz, 2H), 7.22 (d, J=1.7 Hz, 1H), 7.16 (d, J=7.8 Hz, 3H), 6.53 (s, 2H), 6.05 (q, J=7.7 Hz, 1H), 4.34 (m, J=7.1 Hz, 2H), 4.04 (m, J=6.5 Hz, 2H), 3.97 (q, J=5.6 Hz, 1H), 3.87 (m, J=4.2 Hz, 2H), 2.19 (m, J=7.3 Hz, 2H), 1.61 (s, 3H), 1.42 (d, J=3.9 Hz, 2H), 1.21 (t, J=20.3 Hz, 40H), 0.84 (m, J=4.1 Hz, 9H).

Note: (S) Stereochemistry of the amino acid side chain was based on the chirality defined by starting material used for the synthesis of 1-4.

(S) Stereochemistry of the phosphorous centre was defined based on the literature report No loss of chiral purity is assumed although not verified (or) proven.

Preparative SFC Conditions

Column/dimensions: Chiralpak AD-H(30×2 50 mm), 5μ

$CO_2$:75.0%

Co solvent: 25.0% (IPA)

Total Flow: 60.0 g/min

Back Pressure: 100.0 bar

UV: 214 nm

Stack time: 10 min

Load/Inj.: 3.5 mg

Example 23
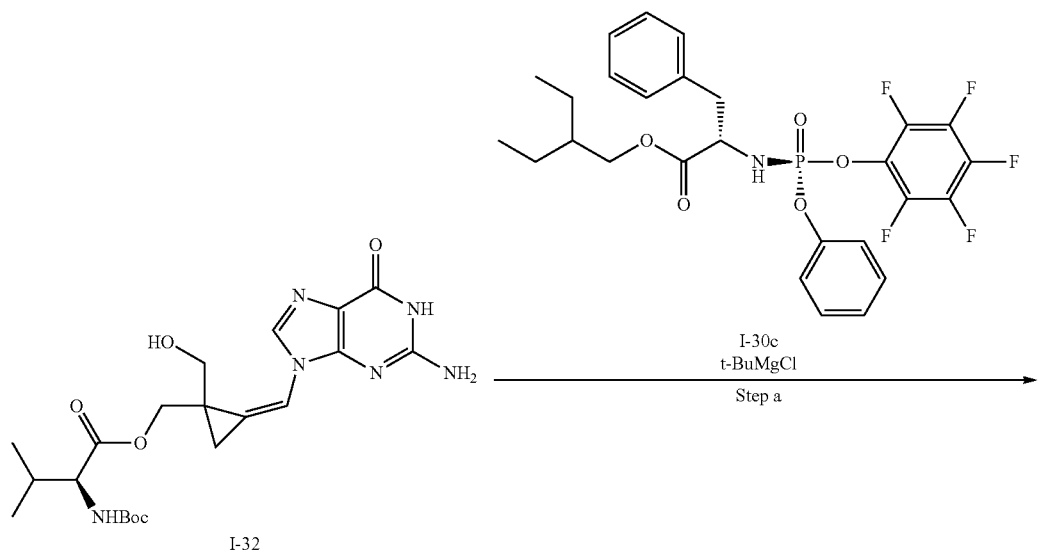
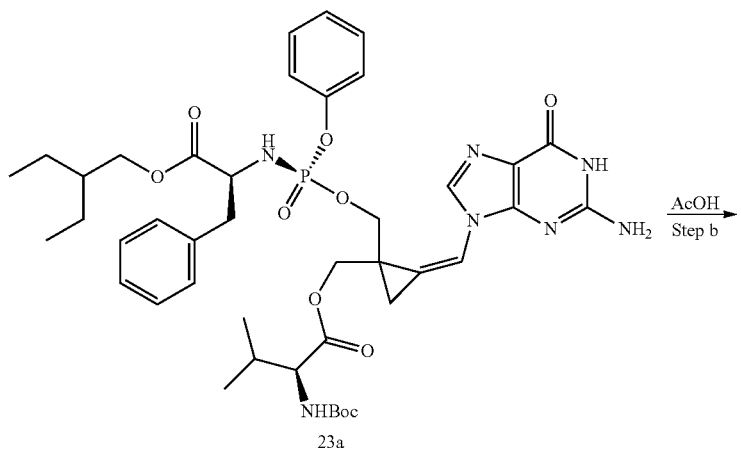
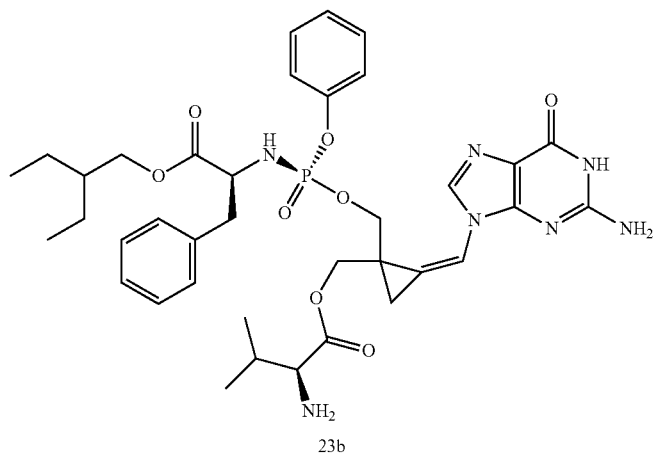

Step a) ((Z)-2-((2-amino-6-oxo-1,6-dihydro-9H-purin-9-yl)methylene)-1-((((S)-(((S)-1-(2-ethylbutoxy)-1-oxo-3-phenylpropan-2-yl)amino)(phenoxy)phosphoryl)oxy)methyl)cyclopropyl)methyl (tert-butoxycarbonyl)-L-valinate (23a)

tert-Butylmagnesium chloride (1M in THF, 0.7 mL, 0.7 mmol) was added dropwise over a period of 15 min at rt to a solution of compound I-32 (65 mg, 0.14 mmol) in DMF (10 mL). The reaction mixture was stirred at rt for 40 min, then compound I-30c (97 mg, 0.17 mmol) in dry THF (5 mL) was added dropwise over a period of 15 min. The reaction mixture was stirred at rt for 16 h, then concentrated under reduced pressure and the afforded crude compound was purified by column chromatography on silica gel eluted with 5% MeOH in DCM, which gave the title compound (65 mg) as a solid. LCMS (ES+) m/z 850.85 [M+H]$^+$. The crude product was used in the next step without further purification.

Step b) ((Z)-2-((2-amino-6-oxo-1,6-dihydro-9H-purin-9-yl)methylene)-1-((((S)-(((S)-1-(2-ethylbutoxy)-1-oxo-3-phenylpropan-2-yl)amino)(phenoxy)phosphoryl)oxy)methyl)cyclopropyl)methyl L-valinate (23b)

60% AcOH (13 mL, 129 mmol) was added to compound 23a (130 mg, 0.15 mmol) and the resulting reaction mixture was stirred for 5 h at 90° C., then concentrated under reduced pressure. The obtained crude compound was purified by prep HPLC using Method D. The pure compound was further purified by chiral SFC, which gave the title compound (18 mg) as a solid. MS (ES+) 750.71 [M+H]$^+$.

$^1$H NMR (500 MHz, DMSO): δ 10.72 (s, 1H), 7.84 (s, 1H), 7.27 (t, J=7.9 Hz, 2H), 7.20 (t, J=2.4 Hz, 5H), 7.11 (m, J=5.8 Hz, 2H), 6.99 (d, J=8.6 Hz, 2H), 6.54 (s, 2H), 6.14 (q, J=7.7 Hz, 1H), 4.40 (d, J=11.6 Hz, 1H), 4.09 (q, J=5.6 Hz, 1H), 4.00 (t, J=8.3 Hz, 1H), 3.85 (q, J=5.5 Hz, 3H), 3.63 (q, J=5.4 Hz, 1H), 3.03 (d, J=5.5 Hz, 1H), 2.95 (t, J=3.2 Hz, 1H), 2.78 (q, J=7.5 Hz, 1H), 1.57 (m, J=7.6 Hz, 4H), 1.35 (q, J=6.2 Hz, 1H), 1.20 (m, J=5.4 Hz, 5H), 0.77 (m, J=3.5 Hz, 6H), 0.71 (q, J=10.0 Hz, 6H).

Preparative SFC Conditions:
Column/dimensions: Chiralcel OX-H (250×30) mm, 5µ
Mobile Phase A: 0.2% DEA in n-hexane
Mobile Phase B: EtOH
Flow: 42.0 ml/min
% Of Mobile phase A:Mobile phase B: 55:45
Temperature: Ambient
Wave length: 230 nm
Stack time: 16 min
No of Injections: 5
Load ability/inj.: 10.0 mg Example 24

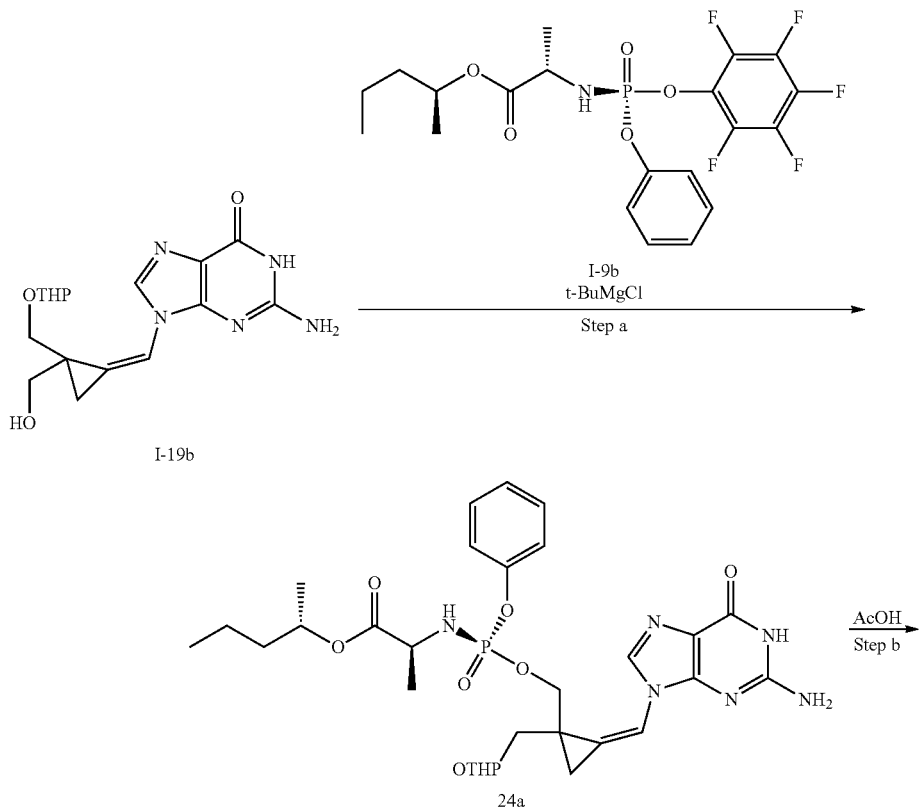

-continued

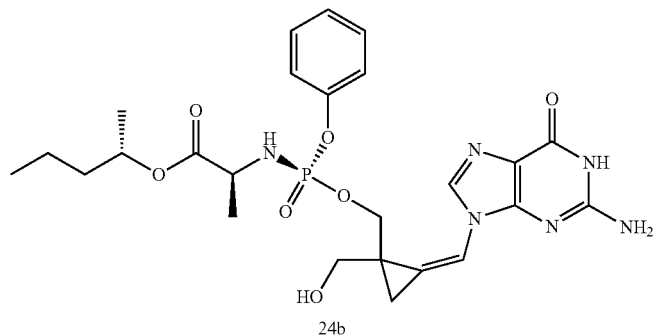

24b

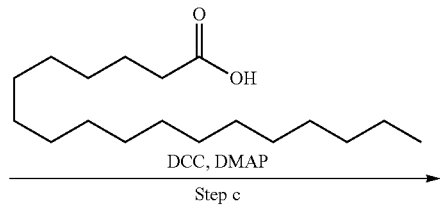

DCC, DMAP
Step c

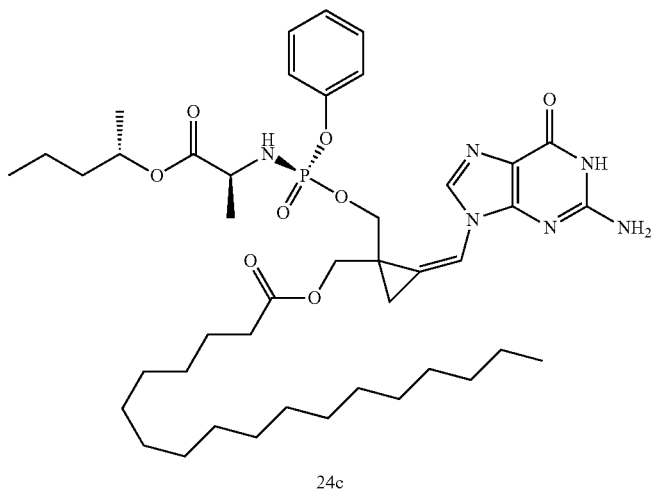

24c

Step a) (S)-pentan-2-yl((S)-(((Z)-2-((2-amino-6-oxo-1,6-dihydro-9H-purin-9-yl)methylene)-1-(((tetrahydro-2H-pyran-2-yl)oxy)methyl)cyclopropyl)methoxy)(phenoxy)phosphoryl)-L-alaninate (24a)

tert-Butylmagnesium chloride (1M in THF, 2.9 mL, 2.9 mmol) was added dropwise over a period of 5 min at rt to a solution of compound I-19b (200 mg, 0.6 mmol) in DMF (30 mL). The reaction mixture was stirred at rt for 45 min, then compound I-9b (333 mg, 0.7 mmol) in dry THF (15 mL) was added dropwise over a period of 10 min. The reaction mixture was stirred at rt for 16 h, then concentrated under reduced pressure and the afforded crude compound was purified by column chromatography on silica gel eluted with 5% MeOH in DCM, which gave the title compound (200 mg) as a solid. LCMS (ES+) m/z 645.64 [M+H]$^+$. The crude product was used in the next step without further purification.

Step b) (S)-pentan-2-yl((S)-(((Z)-2-((2-amino-6-oxo-1,6-dihydro-9H-purin-9-yl)methylene)-1-(hydroxymethyl)cyclopropyl)methoxy)(phenoxy)phosphoryl)-L-alaninate (24b)

80% AcOH (88.8 mL, 1240.6 mmol) was added to compound 25a (200 mg, 0.3 mmol) and the resulting reaction mixture was stirred for 24 h at rt, then concentrated under reduced pressure. The obtained crude compound was purified by column chromatography on silica gel eluted with 12% MeOH in DCM, which gave the title compound (85 mg, 46%) as a solid. MS (ES−) 559.58 [M−H]$^-$.

Step c) ((Z)-2-((2-amino-6-oxo-1,6-dihydro-9H-purin-9-yl)methylene)-1-((((S)-(((S)-1-oxo-1-(((S)-pentan-2-yl)oxy)propan-2-yl)amino)(phenoxy)phosphoryl)oxy)methyl)cyclopropyl)methyl stearate (24c)

DCC (141 mg, 0.7 mmol) and DMAP (6 mg, 0.05 mmol) were added at rt to a stirred solution of compound 24b (85 mg, 0.15 mmol) and stearic acid (130 mg, 0.5 mmol) in DMF (3 mL). The resulting reaction mixture was stirred at rt for 16 h, then concentrated under reduced pressure. The crude compound was purified by column chromatography on silica gel and eluted with 5% MeOH in DCM. The pure compound was further purified by chiral SFC, which gave the title compound (8 mg) as a solid. MS (ES+) 827.71 [M+H]$^+$.

$^1$H NMR (500 MHz, DMSO): δ 10.73 (s, 1H), 7.93 (s, 1H), 7.32 (q, J=5.3 Hz, 2H), 7.18 (m, J=7.2 Hz, 4H), 6.56 (s, 2H), 5.99 (m, J=7.2 Hz, 1H), 4.79 (m, J=6.4 Hz, 1H), 4.36 (m, J=6.6 Hz, 2H), 4.04 (q, J=5.8 Hz, 2H), 3.81 (m, J=3.4 Hz, 1H), 2.19 (m, J=7.4 Hz, 2H), 1.62 (s, 2H), 1.44 (m, J=4.5 Hz, 4H), 1.18 (m, J=13.4 Hz, 37H), 0.84 (m, J=4.7 Hz, 6H).

Preparative SFC Conditions:
Column/dimensions: Lux Cellulose-2 (250×30) mm, 5µ
CO$_2$: 55.0%
Co solvent: 45.0% (MeOH)
Total Flow 70.0 g/min
Back Pressure 90.0 bar
UV 227 nm
Stack time 13.1 min
Load/inj. 7.1 mg

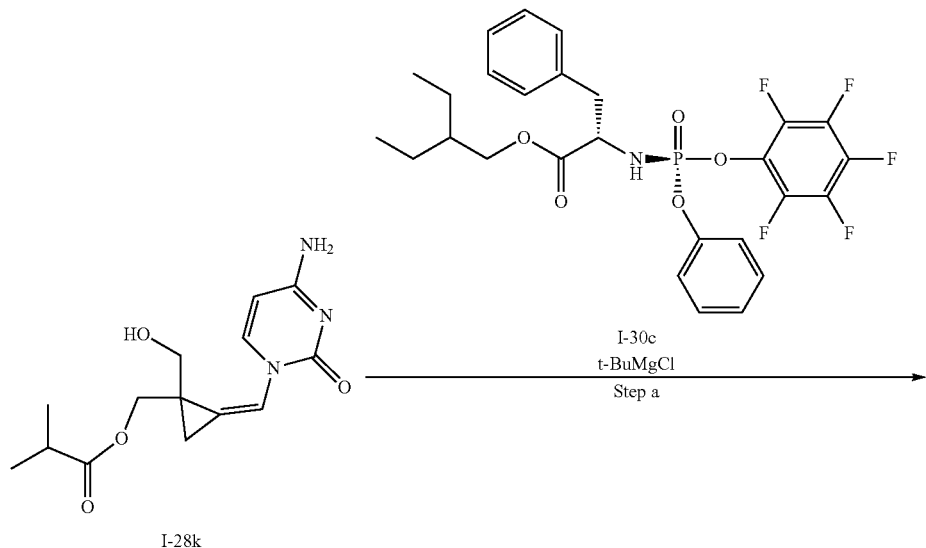

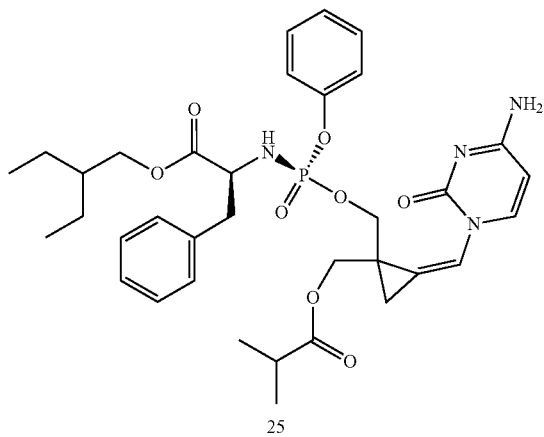

Step a) 2-ethylbutyl((S)-(((Z)-2-((4-amino-2-oxopyrimidin-1 (2H)-yl) methylene)-1-((isobutyryloxy) methyl)cyclopropyl)methoxy)(phenoxy)phosphoryl)-L-phenylalaninate (25)

tert-Butylmagnesium chloride (1M in THF, 1.4 mL, 1.4 mmol) was added dropwise over a period of 10 min at rt to a solution of compound I-28k (80 mg, 0.27 mmol) in DMF (10 mL). The reaction mixture was stirred at rt for 30 min, then compound I-30c (187 mg, 0.33 mmol) in dry THF (5 mL) was added dropwise over a period of 10 min. The reaction mixture was stirred at rt for 4 h, then concentrated under reduced pressure and the afforded crude compound was purified by column chromatography on silica gel eluted with 6% MeOH in DCM. The obtained compound was combined with another batch and further purified by prep HPLC using Method D. The pure compound was further purified by chiral SFC (twice), which gave the title compound (peak-2) (26 mg, 14%) as a solid. MS (ES+) 681.66 [M+H]$^+$.

$^1$H NMR (500 MHz, DMSO): δ 7.67 (d, J=7.5 Hz, 1H), 7.42 (q, J=5.1 Hz, 2H), 7.36 (s, 1H), 7.27 (m, J=6.1 Hz, 4H), 7.17 (m, J=7.0 Hz, 4H), 7.00 (d, J=8.6 Hz, 2H), 6.15 (q, J=7.8 Hz, 1H), 5.79 (d, J=7.4 Hz, 1H), 4.20 (d, J=11.5 Hz, 1H), 3.95 (m, J=4.1 Hz, 1H), 3.89 (q, J=5.6 Hz, 1H), 3.79 (m, J=5.1 Hz, 4H), 2.96 (m, J=3.3 Hz, 1H), 2.77 (q, J=7.5 Hz, 1H), 2.46 (m, J=7.0 Hz, 1H), 1.36 (m, J=5.3 Hz, 4H), 1.21 (m, J=3.7 Hz, 4H), 1.03 (q, J=7.5 Hz, 6H), 0.77 (q, J=4.8 Hz, 6H).

Preparative SFC Conditions-1
  Column/dimensions Chiralpak AS-H (30×250 mm), 5μ
  $CO_2$ 70.0%
  Co solvent 30.0% (EtOH)
  Total Flow 60.0 g/min
  Back Pressure 90.0 bar
  UV 214 nm
  Stack time 8.8 min
  Load/Inj. 10.9 mg Preparative SFC Conditions-2:
  Column/dimensions: Lux Cellulose-2 (250×30) mm, 5μ
  $CO_2$:75.0%
  Co solvent: 25.0% (MeOH)
  Total Flow: 70.0 g/min
  Back Pressure: 90.0 bar
  UV: 214 nm
  Stack time: 5.0 min
  Load/inj.: 1.5 mg

Example 26

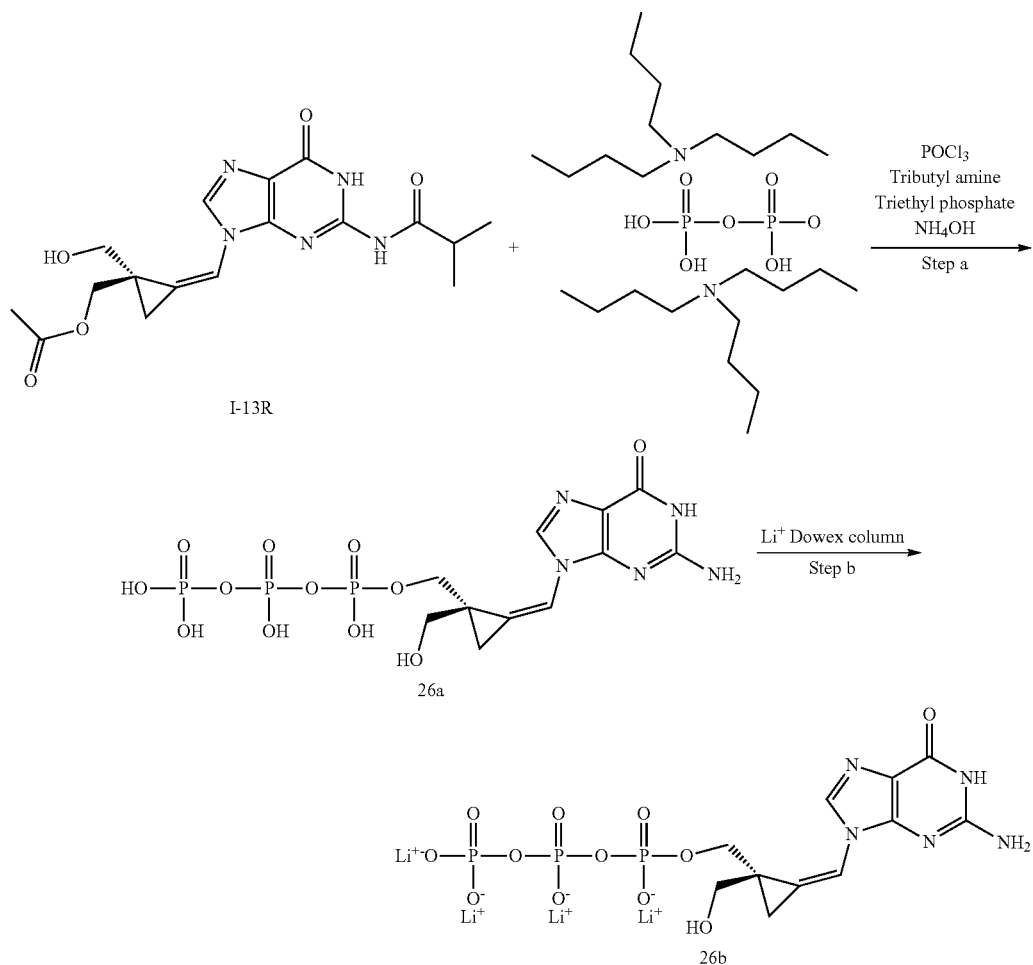

Step a) ((S,Z)-2-((2-amino-6-oxo-1,6-dihydro-9H-purin-9-yl)methylene)-1-(hydroxymethyl)cyclopropyl)methyl tetrahydrogen triphosphate (26a)

POCl$_3$ (0.5 mL, 0.53 mmol) was added to a suspension of I-13R (100 mg, 0.27 mmol) in triethyl phosphate (0.07 mL, 3.8 mmol) at 0° C. and stirred at 0° C. for 4 h. To the above reaction mixture, tributylamine (0.07 mL, 0.3 mmol) was added followed by addition of a solution of tributyl ammonium pyrophosphate (731 mg, 1.33 mmol) in DMF (2 mL) and stirred at 0° C. for 30 min and 1 h at rt. Ammonium hydroxide solution (10 mL, 65 mmol) was added and continued stirring for 16 h at rt. The reaction mixture was concentrated under reduced pressure, then lyophilised. The crude compound was purified by prep HPLC using method H. The residue contained di and tri phosphate compounds and was purified again by prep HPLC using method I. The impure compound was further purified by prep HPLC using method I. The obtained impure title compound was further purified by prep HPLC using method I, which gave the title compound (25 mg) as a solid. MS (ES+) 504.31 [M+H]$^+$.

Step b) lithium(S,Z)-(2-((2-amino-6-oxo-1,6-dihydro-9H-purin-9-yl)methylene)-1-(hydroxymethyl)cyclopropyl)methyl triphosphate (26b)

Dowex 50 WX8 hydrogen form, ion exchange resin was taken in a column (2×10 cm), washed with water:MeOH (1:1, 100 mL) until colorless eluent was obtained, then washed with Milli Q water (100 mL) to wash off MeOH. The ion exchange resin was again eluted with 0.5M sulphuric acid (50 mL) until acidic pH was attained and washed with water (200 mL) until neutral pH was observed. The ion exchange resin was again eluted with 1M lithium hydroxide (50 mL) until basic pH was attained and washed with water (200 mL) until neutral pH. A solution of compound 26a (25 mg, 0.05 mmol) in Milli Q water (3 mL) was passed through the above freshly prepared Dowex Li$^+$ column. The appropriate fractions were lypholyised, which gave the title compound (15 mg) as a solid. LCMS (ES+) m/z 504.27 [M+H]$^+$.

$^1$H NMR (500 MHz, D2O): δ 8.23 (s, 1H), 7.18 (s, 1H), 4.14 (q, J=5.3 Hz, 1H), 4.02 (q, J=5.3 Hz, 1H), 3.70 (d, J=4.2 Hz, 2H), 3.27 (d, J=1.0 Hz, 1H), 1.58 (d, J=9.4 Hz, 1H), 1.49 (d, J=9.3 Hz, 1H).

Example 27

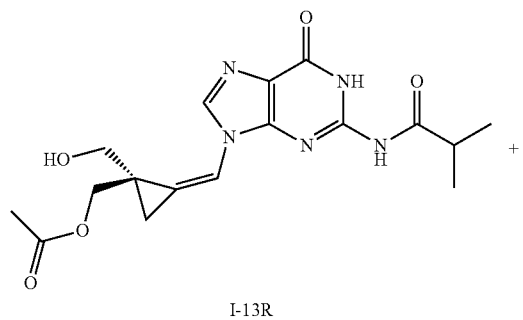

I-13R

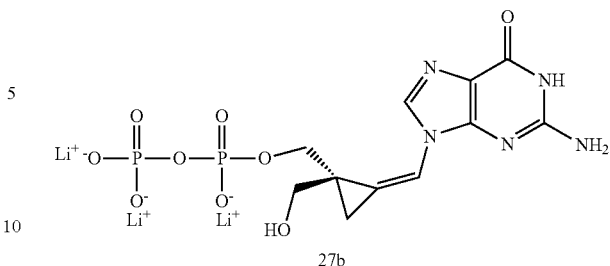

27b

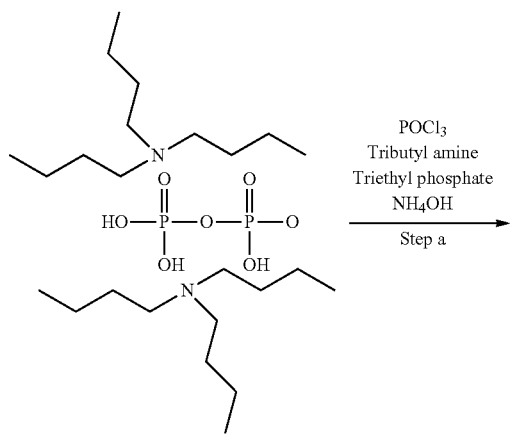

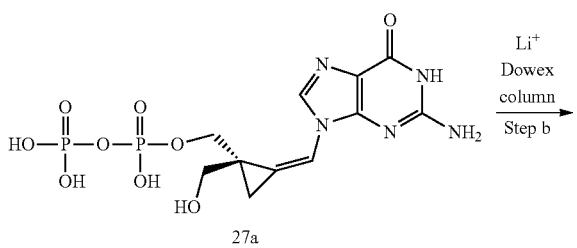

27a

Step a) ((S,Z)-2-((2-amino-6-oxo-1,6-dihydro-9H-purin-9-yl)methylene)-1-(hydroxymethyl)cyclopropyl)methyl trihydrogen diphosphate (27a)

POCl₃ (0.5 mL, 0.53 mmol) was added to a suspension of I-13R (100 mg, 0.27 mmol) in triethyl phosphate (0.07 mL, 3.8 mmol) at 0° C. and stirred at 0° C. for 4 h. To the above reaction mixture, tributylamine (0.07 mL, 0.3 mmol) was added followed by addition of a solution of tributyl ammonium pyrophosphate (731 mg, 1.33 mmol) in DMF (2 mL) and stirred at 0° C. for 30 min and 1 h at rt. Ammonium hydroxide solution (10 mL, 65 mmol) was added and continued stirring for 16 h at rt. The reaction mixture was concentrated under reduced pressure, then lyophilised. The crude compound was purified by prep HPLC using method H. The residue contained di and tri phosphate compounds and was purified again by prep HPLC using method I. The impure compound was further purified by prep HPLC using method I. The obtained impure title compound was further purified by prep HPLC using method I, which gave the title compound (15 mg) as a solid. MS (ES+) 424.30 [M+H]⁺.

Step b) lithium(S,Z)-(2-((2-amino-6-oxo-1,6-dihydro-9H-purin-9-yl)methylene)-1-(hydroxymethyl)cyclopropyl)methyl diphosphate (27b)

Dowex 50 WX8 hydrogen form (50-100 mesh), ion exchange resin was taken in a column (2×10 cm), washed with water:MeOH (1:1, 100 mL) until colorless eluent was obtained, then washed with Milli Q water (100 mL) to wash off MeOH. The ion exchange resin was again eluted with 0.5M sulphuric acid (50 mL) until acidic pH was attained and washed with water (200 mL) until neutral pH was observed. The ion exchange resin was again eluted with 1M lithium hydroxide (50 mL) until basic pH was attained and washed with water (200 mL) until neutral pH. A solution of compound 27a (15 mg, 0.04 mmol) in Milli Q water (3 mL) was passed through the above freshly prepared Dowex Li⁺ column. The appropriate fractions were lypholyised, which gave the title compound (13 mg) as a solid. LCMS (ES+) m/z 424.34 [M+H]⁺. ¹H NMR (500 MHz, D2O): δ 8.36 (s, 1H), 7.26 (s, 1H), 4.21 (q, J=5.2 Hz, 1H), 4.05 (q, J=5.3 Hz, 1H), 3.83 (d, J=12.2 Hz, 1H), 3.69 (m, J=9.4 Hz, 2H), 1.64 (q, J=3.5 Hz, 1H), 1.57 (d, J=9.0 Hz, 1H).

Example 28

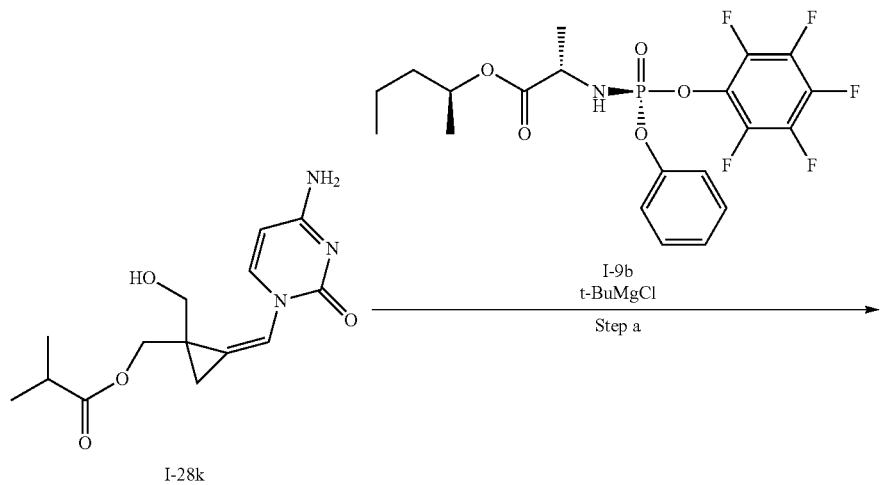

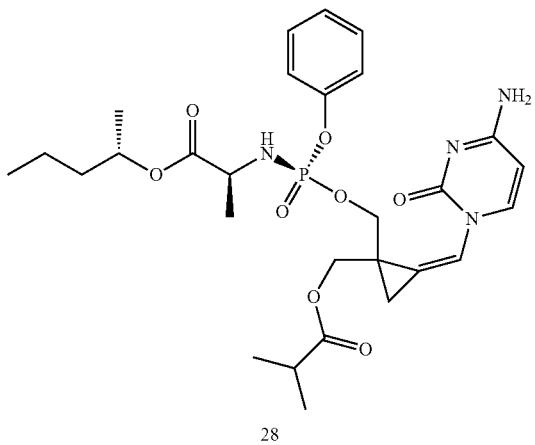

Step a) ((Z)-2-((4-amino-2-oxopyrimidin-1(2H)-yl)methylene)-1-((((S)-(((S)-1-oxo-1-(((S)-pentan-2-yl)oxy)propan-2-yl)amino)(phenoxy)phosphoryl)oxy)methyl)cyclopropyl)methyl isobutyrate (28)

tert-Butylmagnesium chloride (1M in THF, 3.4 mL, 3.4 mmol) was added dropwise over a period of 10 min at rt to a solution of compound I-28k (200 mg, 0.7 mmol) in DMF (15 mL). The reaction mixture was stirred at rt for 30 min, then compound I-9b (394 mg, 0.82 mmol) in dry THF (10 mL) was added dropwise over a period of 10 min. The reaction mixture was stirred at rt for 4 h, then concentrated under reduced pressure and the afforded crude compound was purified by column chromatography on silica gel eluted with 4% MeOH in DCM. The obtained compound was further purified by prep HPLC using Method G. The pure compound was further purified by chiral SFC, which gave the title compound (peak-2) (36 mg, 9%) as a solid. MS (ES+) 591.60 [M+H]$^+$.

$^1$H NMR (500 MHz, DMSO): δ 7.73 (d, J=7.5 Hz, 1H), 7.43 (s, 1H), 7.35 (q, J=5.3 Hz, 1H), 7.16 (q, J=4.7 Hz, 1H), 6.00 (q, J=7.7 Hz, 1H), 5.80 (d, J=7.5 Hz, 1H), 4.80 (m, J=4.8 Hz, 1H), 4.38 (d, J=11.5 Hz, 1H), 4.23 (q, J=5.7 Hz, 1H), 3.99 (q, J=5.3 Hz, 1H), 3.88 (d, J=11.5 Hz, 1H), 3.79 (m, J=3.5 Hz, 1H), 2.47 (d, J=7.0 Hz, 1H), 1.47 (t, J=6.6 Hz, 1H), 1.23 (t, J=6.0 Hz, 1H), 1.13 (d, J=6.3 Hz, 1H), 1.04 (q, J=7.9 Hz, 1H), 0.84 (t, J=7.4 Hz, 1H).

Preparative SFC Conditions
  Column/dimensions: Chiralpak AD-H (30×250 mm), 5μ
  $CO_2$:80.0%
  Co solvent: 20.0% (IPA)
  Total Flow: 70.0 g/min
  Back Pressure: 90.0 bar
  UV: 214 nm
  Stack time: 9.7 min
  Load/Inj.: 7.0 mg

Example 29

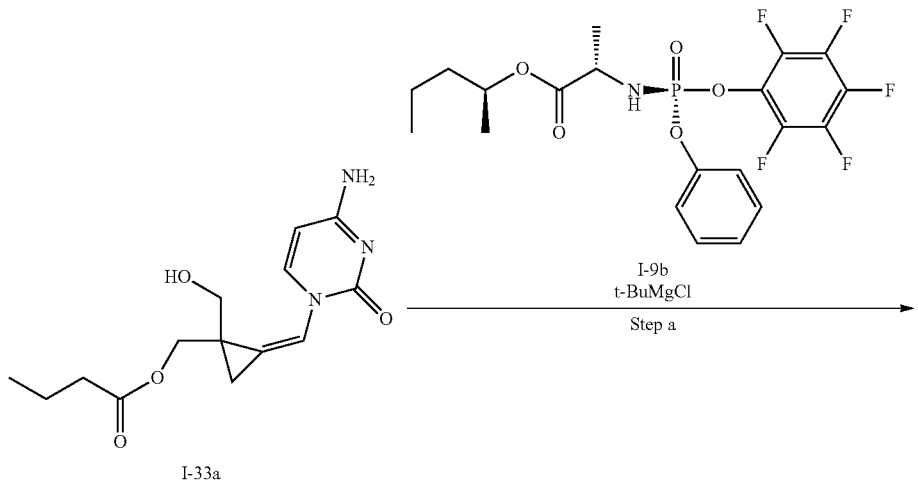

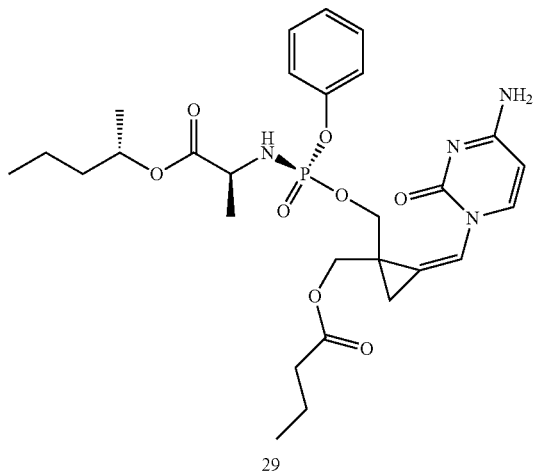

Step a) ((Z)-2-((4-amino-2-oxopyrimidin-1(2H)-yl)methylene)-1-((((S)-(((S)-1-oxo-1-(((S)-pentan-2-yl)oxy)propan-2-yl)amino)(phenoxy)phosphoryl)oxy)methyl)cyclopropyl)methyl butyrate (29)

tert-Butylmagnesium chloride (1M in THF, 4.3 mL, 4.3 mmol) was added dropwise over a period of 10 min at rt to a solution of compound I-33a (250 mg, 0.9 mmol) in DMF (20 mL). The reaction mixture was stirred at rt for 30 min, then compound I-9b (492 mg, 1.02 mmol) in dry THF (10 mL) was added dropwise over a period of 10 min. The reaction mixture was stirred at rt for 4 h, then concentrated under reduced pressure and the afforded crude compound was purified by column chromatography on silica gel eluted with 4% MeOH in DCM. The obtained compound was further purified by prep HPLC using Method G. The pure compound was further purified by chiral SFC, which gave the title compound (peak-1) (45 mg, 9%) as a solid. MS (ES+) 591.57 [M+H]$^+$.

$^1$H NMR (500 MHz, DMSO): δ 7.73 (d, J=7.5 Hz, 1H), 7.53 (s, 1H), 7.41 (t, J=1.8 Hz, 1H), 7.36 (m, J=4.6 Hz, 3H), 7.17 (d, J=7.4 Hz, 3H), 6.01 (q, J=7.7 Hz, 1H), 5.82 (d, J=7.4 Hz, 1H), 4.79 (m, J=4.2 Hz, 1H), 4.35 (d, J=11.5 Hz, 1H), 4.23 (q, J=5.7 Hz, 1H), 3.99 (q, J=5.4 Hz, 1H), 3.91 (d, J=11.5 Hz, 1H), 3.80 (m, J=3.5 Hz, 1H), 2.22 (m, J=5.7 Hz, 2H), 1.48 (m, J=3.7 Hz, 6H), 1.22 (t, J=3.6 Hz, 6H), 1.13 (d, J=6.3 Hz, 3H), 0.84 (m, J=3.1 Hz, 6H).

Preparative SFC Conditions

Column/dimensions: Chiralpak AD-H (30×250 mm), 5µ
$CO_2$:90.0%
Co solvent: 10.0% (MeOH)
Total Flow: 70.0 g/min
Back Pressure: 90.0 bar
UV: 214 nm
Stack time: 10.5 min
Load/Inj.: 6.9 mg

Example 30

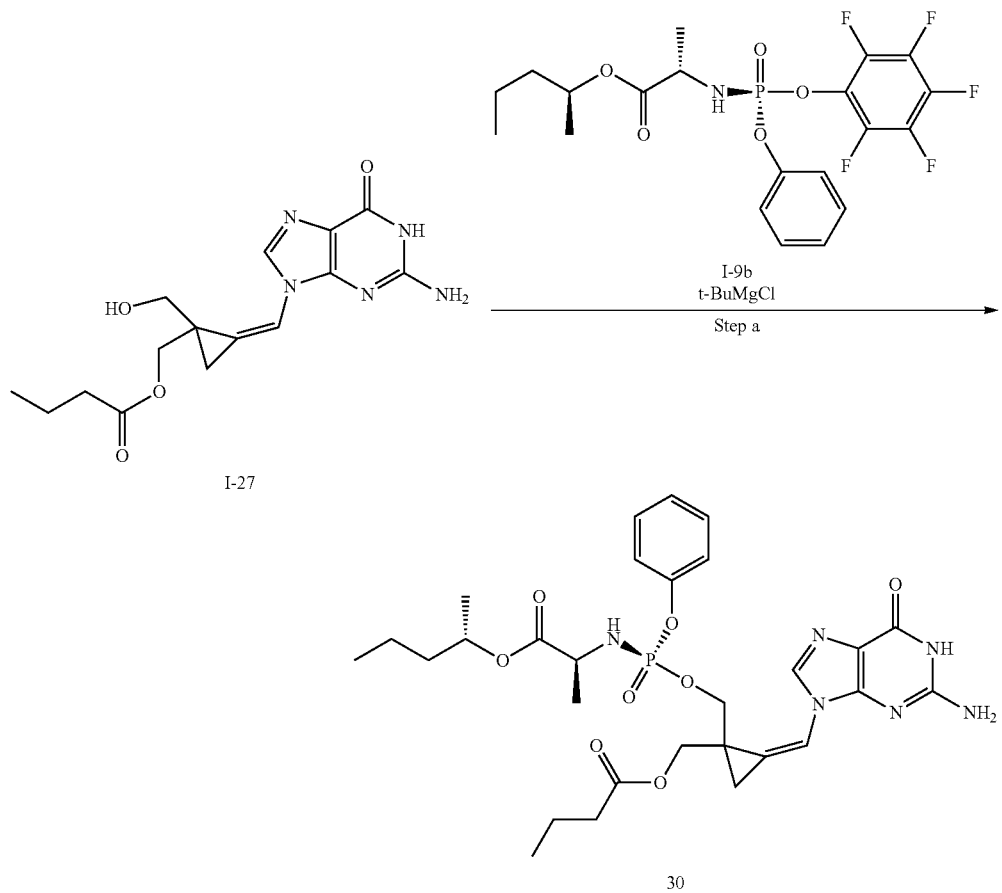

Step a) ((Z)-2-((2-amino-6-oxo-1,6-dihydro-9H-purin-9-yl)methylene)-1-(((((S)-(((S)-1-oxo-1-(((S)-pentan-2-yl)oxy)propan-2-yl)amino)(phenoxy)phosphoryl)oxy)methyl)cyclopropyl)methyl butyrate (30)

tert-Butylmagnesium chloride (1M in THF, 3.8 mL, 3.8 mmol) was added dropwise over a period of 10 min at rt to a solution of compound I-27 (250 mg, 0.8 mmol) in DMF (20 mL). The reaction mixture was stirred at rt for 40 min, then compound I-9b (433 mg, 0.9 mmol) in dry THF (10 mL) was added dropwise over a period of 15 min. The reaction mixture was stirred at rt for 16 h, then concentrated under reduced pressure and the afforded crude compound was purified by column chromatography on silica gel eluted with 5% MeOH in DCM. The obtained compound was further purified by prep HPLC using Method G. The pure compound was further purified by chiral SFC, which gave the title compound (peak-1)(28 mg) as a solid. MS (ES+) 631.62 [M+H]$^+$. $^1$H NMR (500 MHz, DMSO): δ 10.71 (s, 1H), 7.93 (s, 1H), 7.33 (m, J=3.2 Hz, 2H), 7.22 (t, J=1.9 Hz, 1H), 7.16 (d, J=7.9 Hz, 3H), 6.55 (s, 2H), 6.02 (q, J=7.7 Hz, 1H), 4.79 (m, J=3.2 Hz, 1H), 4.37 (m, J=7.5 Hz, 2H), 4.03 (q, J=5.4 Hz, 2H), 3.84 (s, 1H), 2.18 (m, J=6.1 Hz, 2H), 1.62 (d, J=1.2 Hz, 2H), 1.45 (m, J=3.0 Hz, 4H), 1.22 (t, J=7.0 Hz, 5H), 1.13 (d, J=6.3 Hz, 3H), 0.81 (m, J=7.6 Hz, 6H).

Preparative SFC Conditions:
Column/dimensions: Chiralcel-OX-H (250×30) mm, 5µ
CO$_2$: 65.0%
Co solvent: 35.0% (EtOH)
Total Flow: 70.0 g/min
Back Pressure: 90.0 bar
UV: 214 nm
Stack time: 9.2 min
Load/inj.: 6.3 mg

Example 31

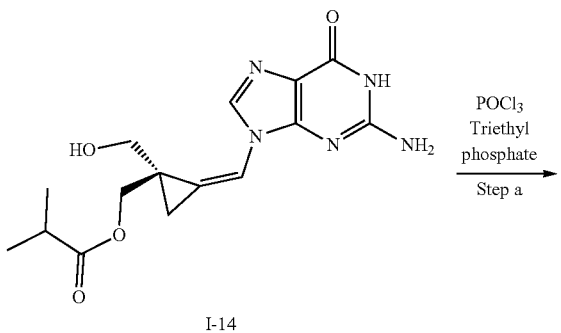

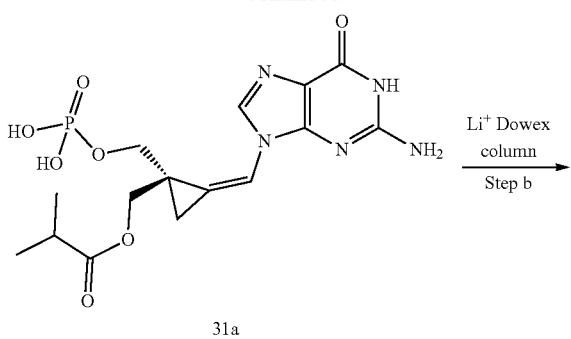

31a

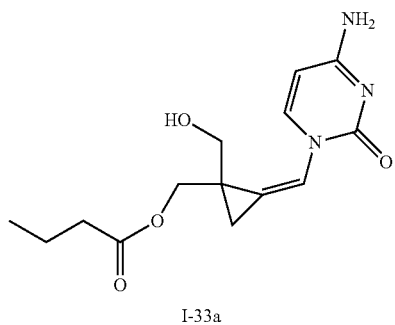

31b

Step a) (S,Z)-(2-((2-amino-6-oxo-1,6-dihydro-9H-purin-9-yl)methylene)-1-((phosphonooxy)methyl)cyclopropyl)methyl isobutyrate (31a)

POCl₃ (0.1 mL, 0.84 mmol) was added to a suspension of 1-14 (140 mg, 0.42 mmol) in triethyl phosphate (1.6 mL, 9.3 mmol) at 0° C. and stirred at 0° C. for 2 h. The excess POCl₃ was quenched by adding triethyl ammonium bicarbonate buffer (1 M, pH=8) (8 mL) at 0° C. The reaction mixture was concentrated under reduced pressure. The crude compound was purified by prep HPLC using method A, which gave the title compound (65 mg, 37%) as a solid. MS (ES+) 414.44 [M+H]⁺.

Step b) lithium (S,Z)-(2-((2-amino-6-oxo-1,6-dihydro-9H-purin-9-yl)methylene)-1-((isobutyryloxy)methyl)cyclopropyl)methyl phosphate (31b)

Dowex 50 WX8 hydrogen form (50-100 mesh), ion exchange resin was taken in a column (2×10 cm), washed with water:MeOH (1:1, 100 mL) until colorless eluent was obtained, then washed with Milli Q water (100 mL) to wash off MeOH. The ion exchange resin was again eluted with 0.5M sulphuric acid (50 mL) until acidic pH was attained and washed with water (200 mL) until neutral pH was observed. The ion exchange resin was again eluted with 1M lithium hydroxide (50 mL) until basic pH was attained and washed with water (200 mL) until neutral pH. A solution of compound 31a (55 mg, 0.13 mmol) in Milli Q water (10 mL) was passed through the above freshly prepared Dowex Li⁺ column. The appropriate fractions were lypholyised, which gave the title compound (55 mg, 93%) as a solid. LCMS (ES+) m/z 414.37 [M+H]⁺.

¹H NMR (500 MHz, D2O): δ 8.07 (s, 1H), 7.22 (s, 1H), 4.63 (d, J=11.5 Hz, 1H), 4.20 (q, J=5.4 Hz, 1H), 3.92 (m, J=6.4 Hz, 2H), 2.31 (m, J=4.7 Hz, 1H), 1.80 (d, J=9.6 Hz, 1H), 1.67 (d, J=9.6 Hz, 1H), 0.97 (q, J=2.6 Hz, 3H), 0.88 (q, J=2.6 Hz, 3H).

Example 32

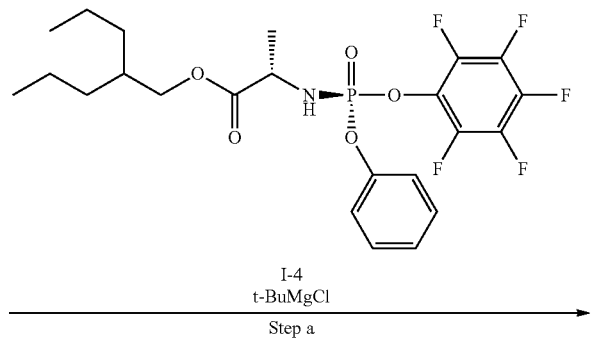

-continued

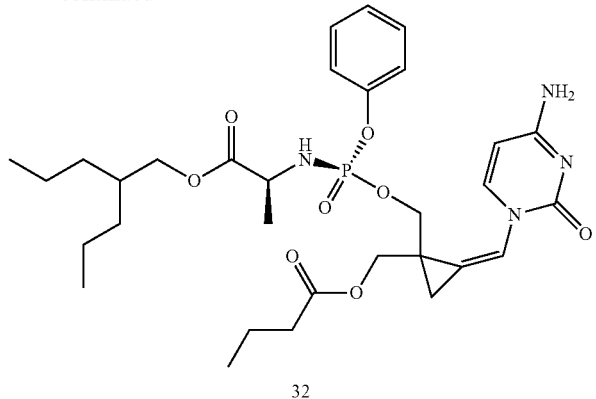

32

Step a) ((Z)-2-((4-amino-2-oxopyrimidin-1(2H)-yl) methylene)-1-((((S)-(((S)-1-oxo-1-((2-propylpentyl) oxy)propan-2-yl)amino)(phenoxy)phosphoryl)oxy) methyl)cyclopropyl)methyl butyrate (32)

tert-Butylmagnesium chloride (1M in THF, 1.7 mL, 1.7 mmol) was added dropwise over a period of 10 min at rt to a solution of compound I-33a (100 mg, 0.34 mmol) in DMF (20 mL). The reaction mixture was stirred at rt for 30 min, then compound I-4 (214 mg, 0.4 mmol) in dry THF (10 mL) was added dropwise over a period of 10 min. The reaction mixture was stirred at rt for 4 h, then concentrated under reduced pressure and the afforded crude compound was combined with another batch and purified by column chromatography on silica gel eluted with 5% MeOH in DCM. The obtained compound was further purified by prep HPLC using Method G. The pure compound was further purified by chiral SFC, which gave the title compound (peak-1) (20 mg) as a solid. MS (ES+) 633.72 [M+H]+.

$^1$H NMR (500 MHz, DMSO): δ 7.72 (d, J=7.5 Hz, 1H), 7.42 (s, 2H), 7.35 (q, J=5.3 Hz, 3H), 7.17 (t, J=6.8 Hz, 3H), 6.04 (q, J=7.7 Hz, 1H), 5.81 (d, J=7.4 Hz, 1H), 4.34 (d, J=11.5 Hz, 1H), 4.21 (q, J=5.6 Hz, 1H), 3.98 (m, J=3.6 Hz, 2H), 3.87 (m, J=8.1 Hz, 3H), 2.21 (m, J=7.9 Hz, 2H), 1.60 (s, 1H), 1.49 (m, J=5.0 Hz, 4H), 1.25 (q, J=5.7 Hz, 11H), 0.84 (m, J=3.0 Hz, 9H).

Preparative SFC Conditions:
  Column/dimensions: Chiralpak IC (30×250 mm), 5μ
  $CO_2$: 50.0%
  Co solvent: 50.0% (isopropanol)
  Total Flow: 70.0 g/min
  Back Pressure: 100.0 bar
  UV: 214 nm
  Stack time: 9.3 min
  Load/inj.: 4.95 mg Example 33

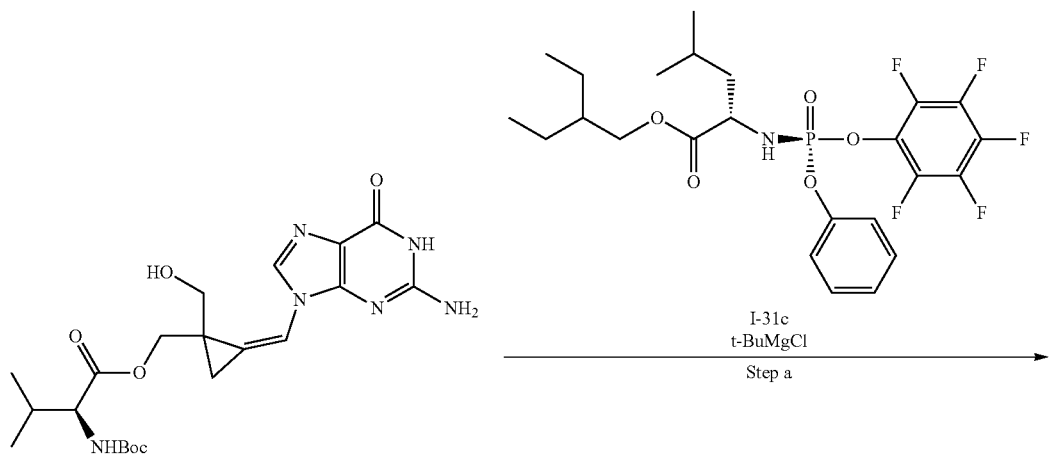

-continued

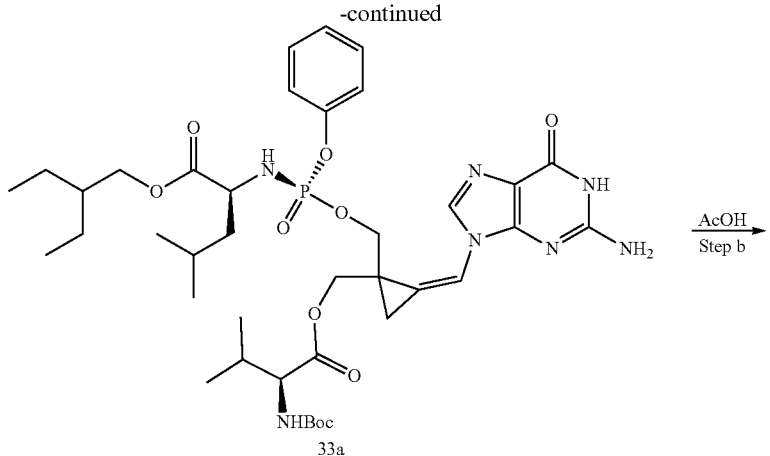

33a

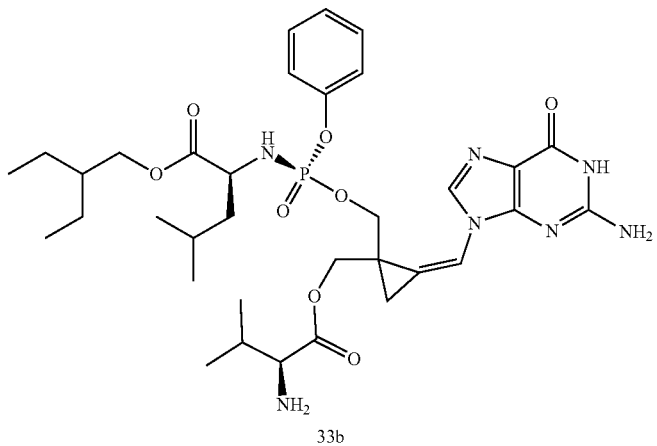

33b

Step a) 2-ethylbutyl((S)-(((Z)-2-((2-amino-6-oxo-1,6-dihydro-9H-purin-9-yl)methylene)-1-((((tert-butoxycarbonyl)-L-valyl)oxy)methyl)cyclopropyl)methoxy)(phenoxy)phosphoryl)-L- leucinate (33a)

tert-Butylmagnesium chloride (1M in THF, 1 mL, 1 mmol) was added dropwise over a period of 15 min at rt to a solution of compound I-32 (90 mg, 0.2 mmol) in DMF (20 mL). The reaction mixture was stirred at rt for 40 min, then compound I-4 (126 mg, 0.23 mmol) in dry THE (10 mL) was added dropwise over a period of 15 min. The reaction mixture was stirred at rt for 16 h, then concentrated under reduced pressure and the afforded crude compound was purified by column chromatography on silica gel eluted with 5% MeOH in DCM, which gave the title compound (70 mg, 37%) as a solid. MS (ES+) 816.89 [M+H]$^+$.

Step b) 2-ethylbutyl((S)-(((Z)-1-((((L-valyl)oxy)methyl)-2-((2-amino-6-oxo-1,6-dihydro-9H-purin-9-yl)methylene)cyclopropyl)methoxy)(phenoxy)phosphoryl)-L-leucinate (33b)

60% AcOH (9 mL, 92.7 mmol) was added to compound 33a (90 mg, 0.11 mmol) and the resulting reaction mixture was stirred for 5 h at 90° C., then concentrated under reduced pressure. The obtained compound was further purified by prep HPLC using Method G. The pure compound was further purified by chiral SFC, which gave the title compound (peak-1)(10 mg, 12%) as a solid. MS (ES+) 716.51 [M+H]$^+$.

$^1$H NMR (500 MHz, DMSO): δ 10.69 (s, 1H), 7.91 (s, 1H), 7.33 (t, J=7.9 Hz, 2H), 7.23 (t, J=1.8 Hz, 1H), 7.15 (m, J=4.6 Hz, 3H), 6.55 (s, 2H), 6.05 (q, J=7.8 Hz, 1H), 4.42 (m, J=7.9 Hz, 2H), 4.06 (q, J=5.5 Hz, 1H), 3.94 (m, J=5.4 Hz, 3H), 3.75 (m, J=8.8 Hz, 1H), 1.62 (m, J=6.2 Hz, 5H), 1.43 (q, J=5.9 Hz, 4H), 1.27 (m, J=7.3 Hz, 6H), 0.77 (m, J=9.4 Hz, 20H).

Preparative SFC Conditions:
Column/dimensions: Chiralpak IG (30×250 mm), 5μ
$CO_2$: 70.0%
Co solvent: 30.0% (0.5% DEA in EtOH)
Total Flow: 70.0 g/min
Back Pressure: 100.0 bar
UV: 214 nm
Stack time: 15 min
Load/inj.: 3.5 mg

Example 34

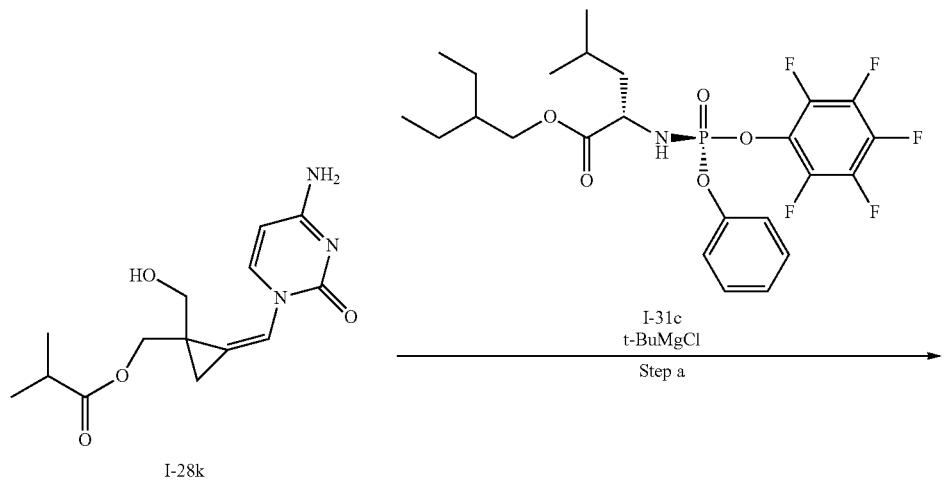

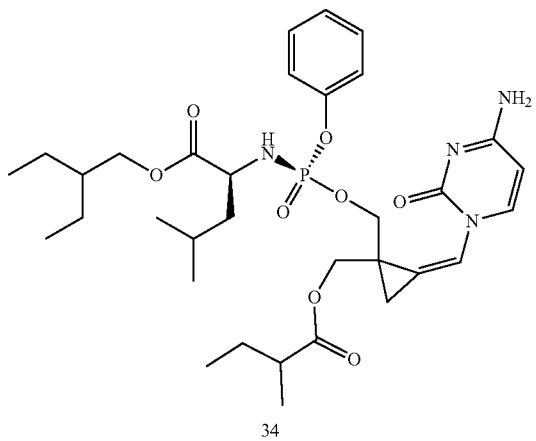

Step a) 2-ethylbutyl((S)-(((Z)-2-((4-amino-2-oxopyrimidin-1(2H)-yl)methylene)-1-((isobutyryloxy)methyl)cyclopropyl)methoxy)(phenoxy)phosphoryl)-L-leucinate (34)

tert-Butylmagnesium chloride (1M in THF, 3.4 mL, 3.4 mmol) was added dropwise over a period of 10 min at rt to a solution of compound I-28k (200 mg, 0.7 mmol) in DMF (15 mL). The reaction mixture was stirred at rt for 30 min, then compound I-4 (403 mg, 0.8 mmol) in dry THF (8 mL) was added dropwise over a period of 10 min. The reaction mixture was stirred at rt for 4 h, then concentrated under reduced pressure and the afforded crude compound was purified by column chromatography on silica gel eluted with 8% MeOH in DCM. The obtained compound was further purified by prep HPLC using Method G. The pure compound was further purified by chiral SFC, which gave the title compound (peak-2)(56 mg, 12%) as a solid. MS (ES+) 647.69 [M+H]$^+$.

$^1$H NMR (500 MHz, DMSO): δ 7.72 (d, J=7.4 Hz, 1H), 7.43 (t, J=1.7 Hz, 2H), 7.34 (m, J=4.0 Hz, 3H), 7.15 (m, J=4.1 Hz, 3H), 6.03 (q, J=7.8 Hz, 1H), 5.80 (d, J=7.4 Hz, 1H), 4.36 (d, J=11.5 Hz, 1H), 4.23 (q, J=5.6 Hz, 1H), 3.92 (m, J=5.7 Hz, 4H), 3.73 (m, J=5.0 Hz, 1H), 2.46 (t, J=7.0 Hz, 1H), 1.59 (m, J=6.7 Hz, 1H), 1.44 (m, J=3.8 Hz, 5H), 1.28 (m, J=3.3 Hz, 4H), 1.04 (q, J=8.0 Hz, 6H), 0.81 (m, J=4.7 Hz, 12H).

Preparative SFC Conditions:
  Column/dimensions: Chiralpak-IA (250×30) mm, 5μ
  Mobile Phase A: n-hexane
  Mobile Phase B: isopropanol
  Flow: 42.0 ml/min
  % Of Mobile phase A: Mobile phase B: 50:50
  Temperature: Ambient
  Wave length: 298 nm
  Stack time: 10 min
  No of Injections: 6
  Load ability/inj.: 24.16 mg

Example 35

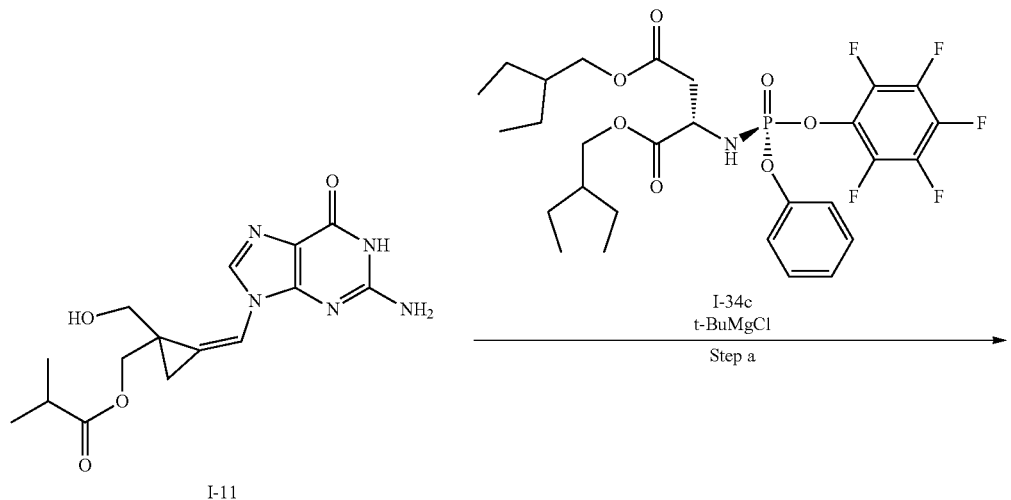

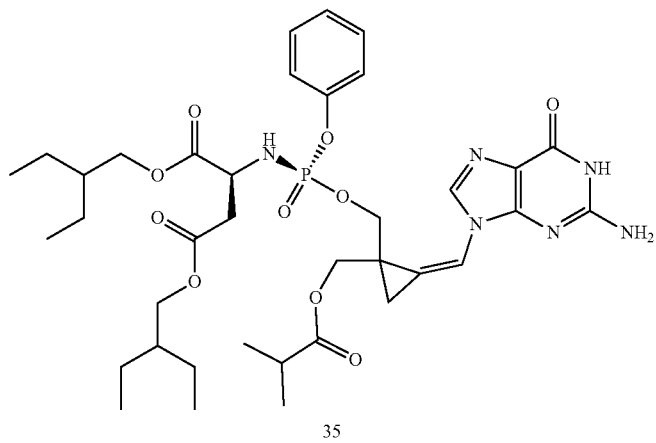

Step a) bis(2-ethylbutyl) ((S)-(((Z)-2-((2-amino-6-oxo-1,6-dihydro-9H-purin-9-yl)methylene)-1-((isobutyryloxy)methyl)cyclopropyl)methoxy)(phenoxy)phosphoryl)-L-aspartate (35)

tert-Butylmagnesium chloride (1M in THF, 1.9 mL, 1.9 mmol) was added dropwise over a period of 5 min at rt to a solution of compound I-11 (125 mg, 0.4 mmol) in DMF (8 mL). The reaction mixture was stirred at rt for 20 min, then compound I-34c (257 mg, 0.4 mmol) in dry THF (4 mL) was added dropwise over a period of 5 min. The reaction mixture was stirred at rt for 3 h, then concentrated under reduced pressure and the afforded crude compound was combined with another batch and purified by column chromatography on silica gel eluted with 5% MeOH in DCM. The obtained compound was further purified by prep HPLC using Method H. The pure compound was further purified by chiral SFC, which gave the title compound (peak-1) (51 mg) as a solid. MS (ES+) 773.80 [M+H]$^+$.

$^1$H NMR (500 MHz, DMSO): δ 10.72 (s, 1H), 7.93 (s, 1H), 7.33 (q, J=5.3 Hz, 2H), 7.22 (t, J=1.8 Hz, 1H), 7.15 (m, J=4.3 Hz, 3H), 6.56 (s, 2H), 6.11 (q, J=7.6 Hz, 1H), 4.40 (m, J=7.7 Hz, 2H), 4.16 (m, J=3.5 Hz, 1H), 3.94 (m, J=4.1 Hz, 6H), 2.75 (q, J=8.0 Hz, 1H), 2.62 (m, J=5.6 Hz, 1H), 2.45 (m, J=7.0 Hz, 1H), 1.61 (d, J=1.6 Hz, 2H), 1.42 (m, J=4.2 Hz, 2H), 1.25 (m, J=3.2 Hz, 8H), 1.01 (q, J=11.4 Hz, 6H), 0.80 (q, J=7.0 Hz, 12H).

Preparative SFC Conditions:
  Column/dimensions: Chiralcel OX-H (250×30) mm, 5μ
  CO$_2$: 65.0%
  Co solvent: 35.0% (EtOH)
  Total Flow: 70 g/min
  Back Pressure: 90.0 bar
  UV: 214 nm
  Stack time: 13.7 min
  Load/Inj.: 5.6 mg

Example 36

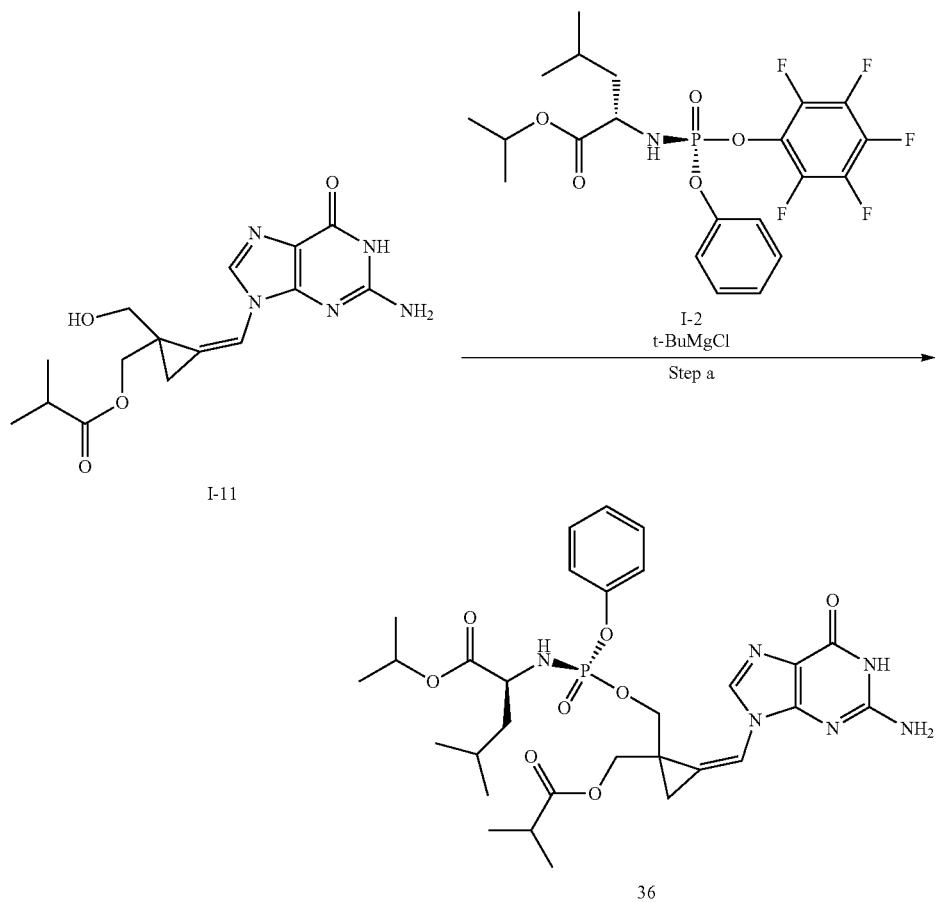

Step a) isopropyl((S)-(((Z)-2-((2-amino-6-oxo-1,6-dihydro-9H-purin-9-yl)methylene)-1-((isobutyryloxy)methyl)cyclopropyl)methoxy)(phenoxy)phosphoryl)-L-leucinate (36)

tert-Butylmagnesium chloride (1M in THF, 4.5 mL, 4.5 mmol) was added dropwise over a period of 5 min at rt to a solution of compound I-11 (300 mg, 0.9 mmol) in DMF (18 mL). The reaction mixture was stirred at rt for 20 min, then compound I-2 (490 mg, 1.0 mmol) in dry THF (9 mL) was added dropwise over a period of 5 min. The reaction mixture was stirred at rt for 3 h, then concentrated under reduced pressure and the afforded crude compound was combined with another batch and purified by column chromatography on silica gel eluted with 7% MeOH in DCM. The obtained compound was further purified by prep HPLC using Method D. The pure compound was further purified by chiral SFC, which gave the title compound (Peak-2) (62 mg) as a solid. MS (ES+) 645.64 [M+H]+.

$^1$H NMR (500 MHz, DMSO): δ 10.70 (s, 1H), 7.92 (s, 1H), 7.32 (t, J=7.9 Hz, 2H), 7.22 (t, J=1.8 Hz, 1H), 7.14 (t, J=7.8 Hz, 3H), 6.55 (s, 2H), 5.99 (q, J=7.8 Hz, 1H), 4.84 (m, J=6.3 Hz, 1H), 4.39 (m, J=7.5 Hz, 2H), 4.01 (m, J=7.1 Hz, 2H), 3.69 (m, J=5.0 Hz, 1H), 2.44 (m, J=7.0 Hz, 1H), 1.61 (d, J=1.3 Hz, 3H), 1.41 (m, J=4.3 Hz, 2H), 1.14 (t, J=6.2 Hz, 6H), 1.01 (q, J=11.1 Hz, 6H), 0.81 (q, J=10.0 Hz, 6H).

Preparative SFC Conditions
  Column/dimensions: Chiralpak AD-H (30×250 mm), 5µ
  $CO_2$: 70.0%
  Co solvent: 30.0% (EtOH)
  Total Flow: 70.0 g/min
  Back Pressure: 90.0 bar
  UV: 214 nm
  Stack time: 11.8 min
  Load/inj.: 12 mg

Example 37

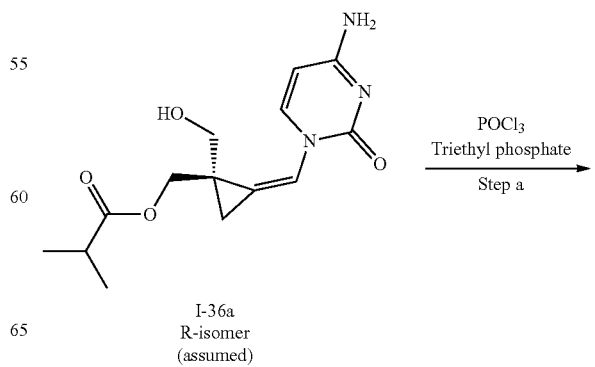

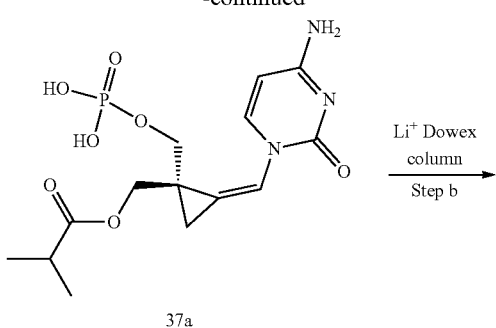

37a

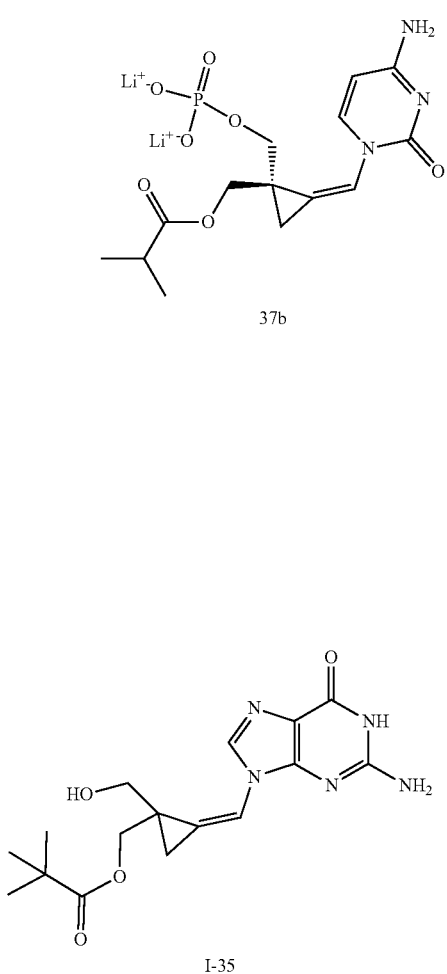

37b

Step a) (S,Z)-(2-((4-amino-2-oxopyrimidin-1(2H)-yl)methylene)-1-((phosphonooxy)methyl)cyclopropyl)methyl isobutyrate (37a)

POCl$_3$ (0.03 mL, 0.34 mmol) was added to a suspension of 1-36a (50 mg, 0.17 mmol) in triethyl phosphate (0.64 mL, 3.8 mmol) at 0° C. and stirred at 0° C. for 2 h. To the above reaction mixture, triethyl ammonium bicarbonate buffer (1 M, pH=8) (2 mL) was added at 0° C. and lyophilised. The crude compound was purified by prep HPLC using method C, which gave the title compound (15 mg, 23%) as a solid. MS (ES+) 374.27 [M+H]$^+$.

Step b) Lithium(S,Z)-(2-((4-amino-2-oxopyrimidin-1(2H)-yl)methylene)-1-((isobutyryloxy)methyl)cyclopropyl)methyl phosphate (37b)

Dowex 50 WX8 hydrogen form (50-100 mesh), ion exchange resin was taken in a column (2×10 cm), washed with water:MeOH (1:1, 100 mL) until colorless eluent was obtained, then washed with Milli Q water (100 mL) to wash off MeOH. The ion exchange resin was again eluted with 0.5M sulphuric acid (25 mL) until acidic pH was attained and washed with water (100 mL) until neutral pH was observed. The ion exchange resin was again eluted with 1M lithium hydroxide (25 mL) until basic pH was attained and washed with water (100 mL) until neutral pH. A solution of compound 37a (15 mg, 0.04 mmol) in Milli Q water (1 mL) was passed through the above freshly prepared Dowex LI$^+$ column. The appropriate fractions were lypholyised, which gave the title compound (15 mg, 96%) as a solid. LCMS (ES+) m/z 374.42 [M+H]$^+$.

$^1$H NMR (500 MHz, D2O): δ 7.86 (q, J=2.8 Hz, 1H), 7.25 (s, 1H), 6.14 (d, J=7.5 Hz, 1H), 4.61 (d, J=11.5 Hz, 1H), 4.08 (q, J=5.3 Hz, 1H), 3.96 (q, J=5.0 Hz, 1H), 3.88 (d, J=11.5 Hz, 1H), 2.47 (m, J=5.6 Hz, 1H), 1.68 (q, J=3.8 Hz, 1H), 1.59 (d, J=9.4 Hz, 1H), 1.05 (m, J=4.2 Hz, 6H).

Example 38

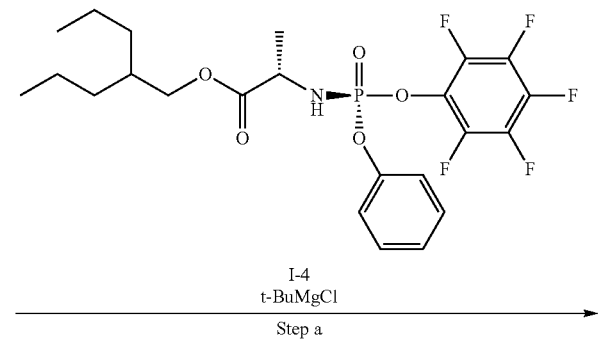

I-35

I-4
t-BuMgCl
Step a

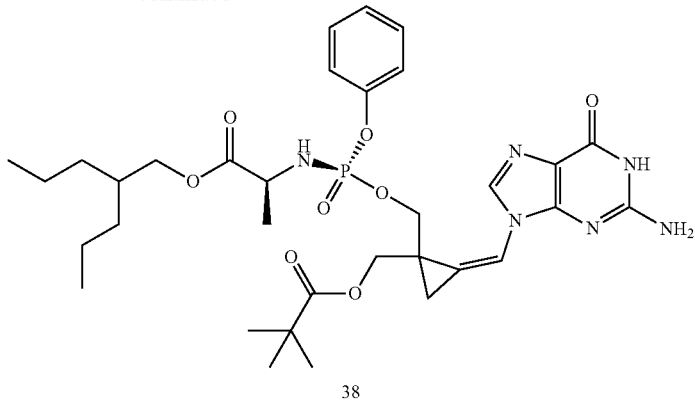

38

Step a) ((Z)-2-((2-amino-6-oxo-1,6-dihydro-9H-purin-9-yl)methylene)-1-(((((S)-(((S)-1-oxo-1-((2-propylpentyl)oxy)propan-2-yl)amino)(phenoxy)phosphoryl)ox)methyl)cyclopropyl)methyl pivalate (38)

tert-Butylmagnesium chloride (1M in THF, 1.44 mL, 1.44 mmol) was added dropwise over a period of 2 min at rt to a solution of compound I-35 (100 mg, 0.3 mmol) in DMF (10 mL). The reaction mixture was stirred at rt for 30 min, then compound I-4 (181 mg, 0.35 mmol) in dry THF (5 mL) was added dropwise over a period of 5 min. The reaction mixture was stirred at rt for 16 h, then concentrated under reduced pressure and the afforded crude compound was combined with another batch and purified by column chromatography on silica gel eluted with 10% MeOH in DCM. The obtained compound was further purified by prep HPLC using Method A, which gave the title compound (15 mg) as a solid. MS (ES+) 687.75 [M+H]$^+$.

$^1$H NMR (500 MHz, DMSO): δ 10.68 (s, 1H), 7.93 (s, 1H), 7.33 (m, J=3.9 Hz, 2H), 7.18 (m, J=4.5 Hz, 4H), 6.54 (s, 2H), 6.06 (m, J=4.4 Hz, 1H), 4.29 (m, J=10.1 Hz, 3H), 3.99 (m, J=6.5 Hz, 2H), 3.86 (m, J=4.1 Hz, 1H), 3.77 (m, J=3.9 Hz, 1H), 1.57 (m, J=4.6 Hz, 3H), 1.19 (m, J=5.3 Hz, 12H), 1.08 (d, J=1.1 Hz, 9H), 0.82 (m, J=2.6 Hz, 6H).

Example 39

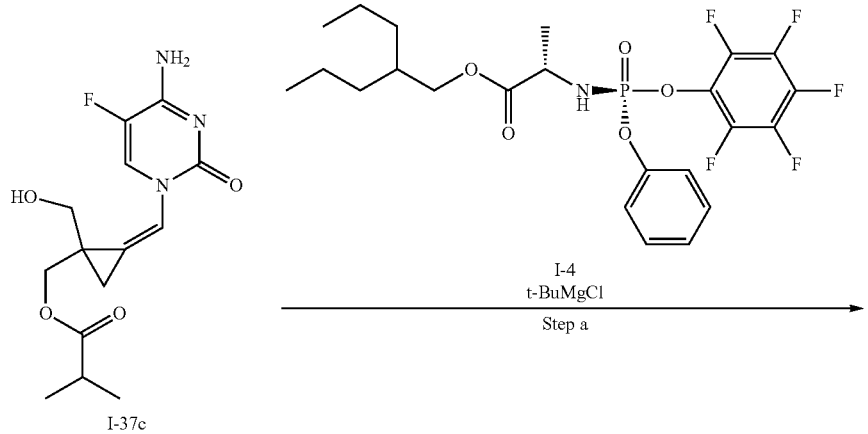

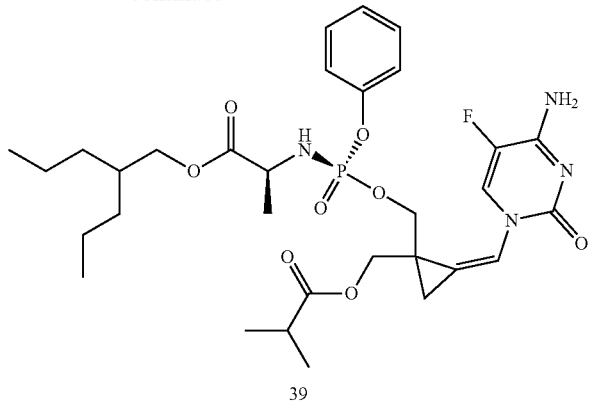

39

Step a) ((Z)-2-((4-amino-5-fluoro-2-oxopyrimidin-1 (2H)-yl)methylene)-1-(((((S)-(((S)-1-oxo-1-((2-propylpentyl)oxy)propan-2-yl)amino)(phenoxy)phosphoryl)oxy)methyl)cyclopropyl)methyl isobutyrate (39)

tert-Butylmagnesium chloride (1M in THF, 4 mL, 4.0 mmol) was added dropwise over a period of 5 min at rt to a solution of compound I-37c (250 mg, 0.8 mmol) in DMF (12 mL). The reaction mixture was stirred at rt for 20 min, then compound I-4 (462 mg, 0.9 mmol) in dry THF (6 mL) was added dropwise over a period of 5 min. The reaction mixture was stirred at rt for 3 h, then concentrated under reduced pressure and the afforded crude compound was combined with another batch and purified by column chromatography on silica gel eluted with 4% MeOH in DCM. The obtained compound was further purified by prep HPLC using Method B. The pure compound was further purified by chiral SFC, which gave the title compound (Peak-2) (70 mg) as a solid. MS (ES+) 651.69 [M+H]$^+$.

$^1$H NMR (500 MHz, DMSO): δ 8.02 (s, 1H), 7.97 (d, J=6.8 Hz, 1H), 7.79 (s, 1H), 7.39 (d, J=2.0 Hz, 1H), 7.34 (t, J=8.0 Hz, 2H), 7.16 (q, J=3.9 Hz, 3H), 6.05 (q, J=7.8 Hz, 1H), 4.46 (d, J=11.6 Hz, 1H), 4.17 (q, J=5.5 Hz, 1H), 4.05 (q, J=5.2 Hz, 1H), 3.97 (q, J=5.5 Hz, 1H), 3.89 (q, J=5.5 Hz, 1H), 3.82 (m, J=5.0 Hz, 2H), 2.47 (d, J=7.0 Hz, 1H), 1.60 (t, J=5.9 Hz, 1H), 1.49 (d, J=1.6 Hz, 2H), 1.24 (m, J=5.6 Hz, 12H), 1.06 (q, J=8.8 Hz, 6H), 0.84 (q, J=4.4 Hz, 6H).

Preparative SFC Conditions
Column/dimensions (R,R) WHELK-01 (250×30)mm, 5μ
CO$_2$: 75.0%
Co solvent: 25.0% (EtOH)
Total Flow: 100.0 g/min
Back Pressure 100.0 bar
UV: 214 nm
Stack time: 8.5 min
Load/inj.: 22 mg Example 40

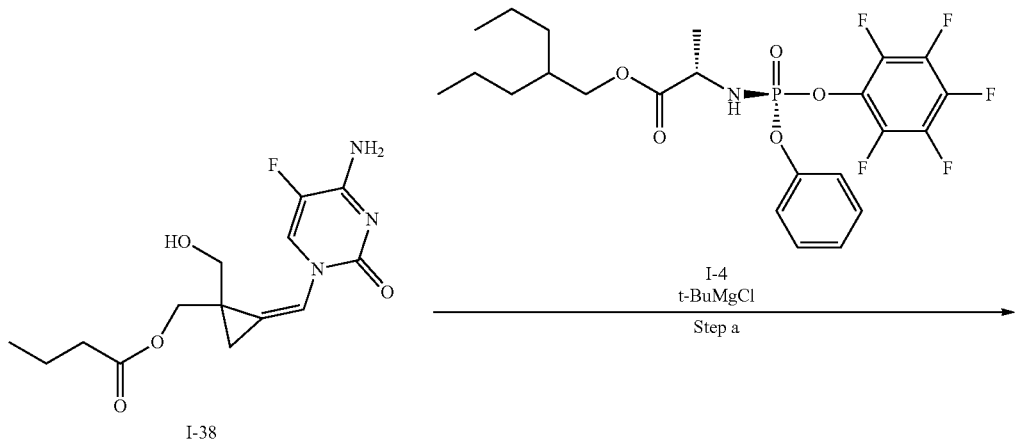

I-38 → I-4, t-BuMgCl, Step a

-continued

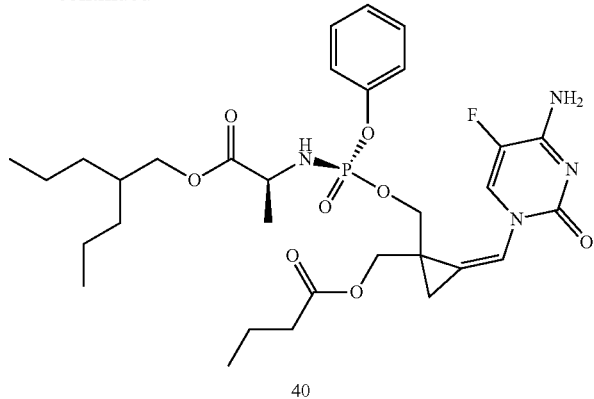

40

Step a) ((Z)-2-((4-amino-5-fluoro-2-oxopyrimidin-1 (2H)-yl)methylene)-1-(((((S)-(((S)-1-oxo-1-((2-propylpentyl)oxy)propan-2-yl)amino)(phenoxy)phosphoryl)oxy)methyl)cyclopropyl)methyl butyrate (40)

tert-Butylmagnesium chloride (1M in THF, 3.2 mL, 3.2 mmol) was added dropwise over a period of 10 min at rt to a solution of compound I-38 (200 mg, 0.64 mmol) in DMF (20 mL). The reaction mixture was stirred at rt for 30 min, then compound I-4 (403 mg, 0.8 mmol) in dry THF (10 mL) was added dropwise over a period of 10 min. The reaction mixture was stirred at rt for 4 h, then concentrated under reduced pressure and the afforded crude compound was combined with another batch and purified by column chromatography on silica gel eluted with 4% MeOH in DCM. The obtained compound was further purified by prep HPLC using Method A. The pure compound was further purified by chiral SFC, which gave the title compound (36 mg) as a solid. MS (ES+) 651.73 [M+H]+.

$^1$H NMR (500 MHz, DMSO): δ 8.02 (d, J=7.0 Hz, 2H), 7.80 (s, 1H), 7.35 (m, J=4.1 Hz, 3H), 7.17 (t, J=4.3 Hz, 3H), 6.06 (q, J=7.8 Hz, 1H), 4.40 (d, J=11.6 Hz, 1H), 4.20 (q, J=5.5 Hz, 1H), 4.01 (q, J=5.5 Hz, 1H), 3.95 (q, J=5.6 Hz, 1H), 3.82 (m, J=5.2 Hz, 3H), 2.22 (q, J=7.1 Hz, 2H), 1.58 (t, J=6.0 Hz, 1H), 1.49 (m, J=5.1 Hz, 4H), 1.22 (m, J=4.5 Hz, 12H), 0.83 (m, J=3.7 Hz, 9H).

Preparative SFC Conditions
Column/dimensions Chiralpak AD-H (30×250 mm), 5μ
CO$_2$ 85.0%
Co solvent 15.0% (100% IPA)
Total Flow 70.0 g/min
Back Pressure 90.0 bar
UV 214 nm
Stack time 6.0 min
Load/Inj. 8.9 mg.

Example 41

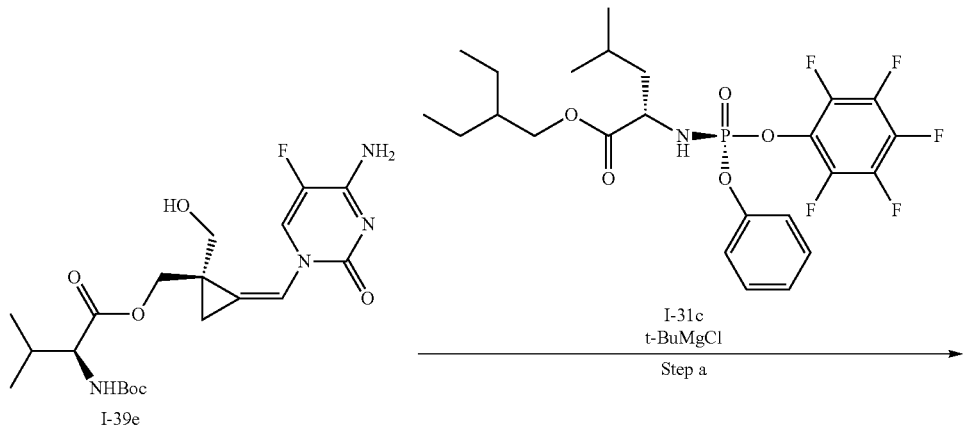

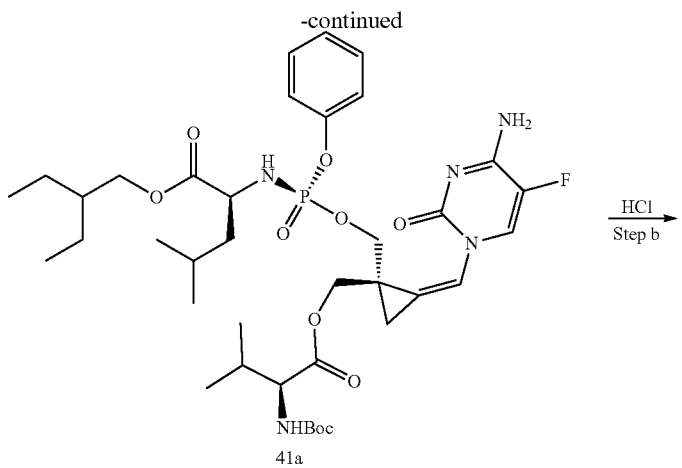

41a

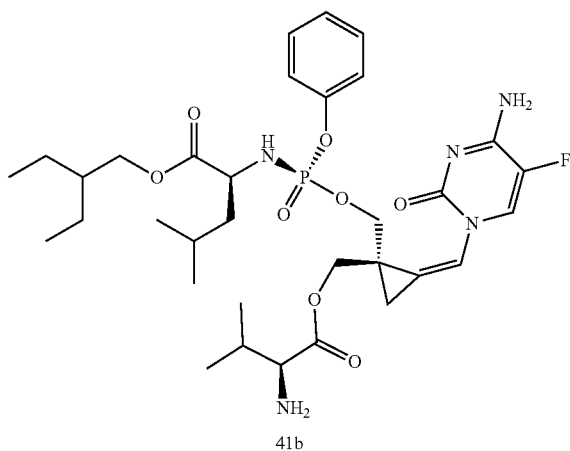

41b

Step a) 2-ethylbutyl((S)-(((S,Z)-2-((4-amino-5-fluoro-2-oxopyrimidin-1(2H)-yl)methylene)-1-((((tert-butoxycarbonyl)-L-valyl)oxy)methyl) cyclopropyl)methoxy)(phenoxy)phosphoryl)-L-leucinate (41a)

tert-Butylmagnesium chloride (1M in THF, 1.8 mL, 1.8 mmol) was added dropwise over a period of 5 min at rt to a solution of compound I-39e (150 mg, 0.34 mmol) in DMF (10 mL). The reaction mixture was stirred at rt for 20 min, then compound I-31c (201 mg, 0.4 mmol) in dry THF (5 mL) was added dropwise over a period of 5 min. The reaction mixture was stirred at rt for 3 h, then concentrated under reduced pressure and the afforded crude compound was combined with another batch and purified by column chromatography on silica gel eluted with 4% MeOH in DCM, which gave the title compound (170 mg) as a semi-solid. MS (ES+) 794.92[M+H]$^+$.

Step b) 2-ethylbutyl((S)-(((S,Z)-1-(((L-valyl)oxy)methyl)-2-((4-amino-5-fluoro-2-oxopyrimidin-1(2H)-yl)methylene)cyclopropyl)methoxy)(phenoxy)phosphoryl)-L-leucinate (41b)

4M HCl in 1,4 dioxane (1 mL, 4 mmol) was added at 0° C. to a solution of compound 41a (150 mg, 0.2 mmol) in 1,4-dioxane (20 mL). The reaction mixture was stirred at room temperature for 1 h, then concentrated under reduced pressure. The obtained compound was purified twice by prep HPLC using Method A. The pure compound was further purified by chiral SFC and lyophilised, which gave the title compound (26 mg) as a solid. MS (ES+) 694.78 [M+H]$^+$.

$^1$H NMR (500 MHz, DMSO): δ 8.02 (s, 1H), 7.89 (d, J=6.7 Hz, 1H), 7.81 (s, 1H), 7.39 (d, J=2.0 Hz, 1H), 7.33 (m, J=4.0 Hz, 1H), 7.14 (q, J=5.8 Hz, 1H), 6.04 (q, J=7.8 Hz, 1H), 4.52 (d, J=11.6 Hz, 1H), 4.22 (q, J=5.6 Hz, 1H), 4.04 (q, J=5.3 Hz, 1H), 3.92 (m, J=5.1 Hz, 1H), 3.75 (m, J=7.6 Hz, 1H), 3.08 (d, J=5.2 Hz, 1H), 1.74 (q, J=6.4 Hz, 1H), 1.59 (m, J=6.7 Hz, 1H), 1.50 (s, 1H), 1.43 (q, J=6.1 Hz, 1H), 1.27 (m, J=3.9 Hz, 1H), 0.79 (m, J=5.1 Hz, 1H).

Preparative SFC Conditions:
Column/dimensions Chiralcel OX-H (250×30) mm, 5μ
$CO_2$:80.0%
Co solvent: 20.0% (MeOH)
Total Flow: 70 g/min
Back Pressure: 90.0 bar
UV: 214 nm
Stack time: 10.5 min
Load/Inj. 8.0 mg

Example 42

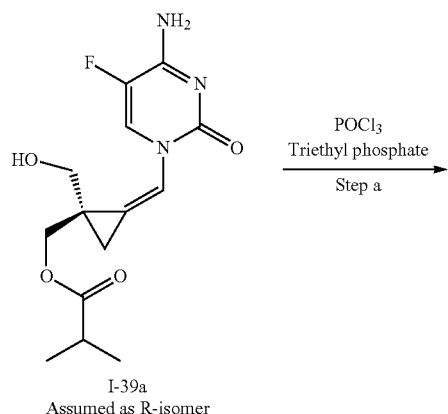

I-39a
Assumed as R-isomer

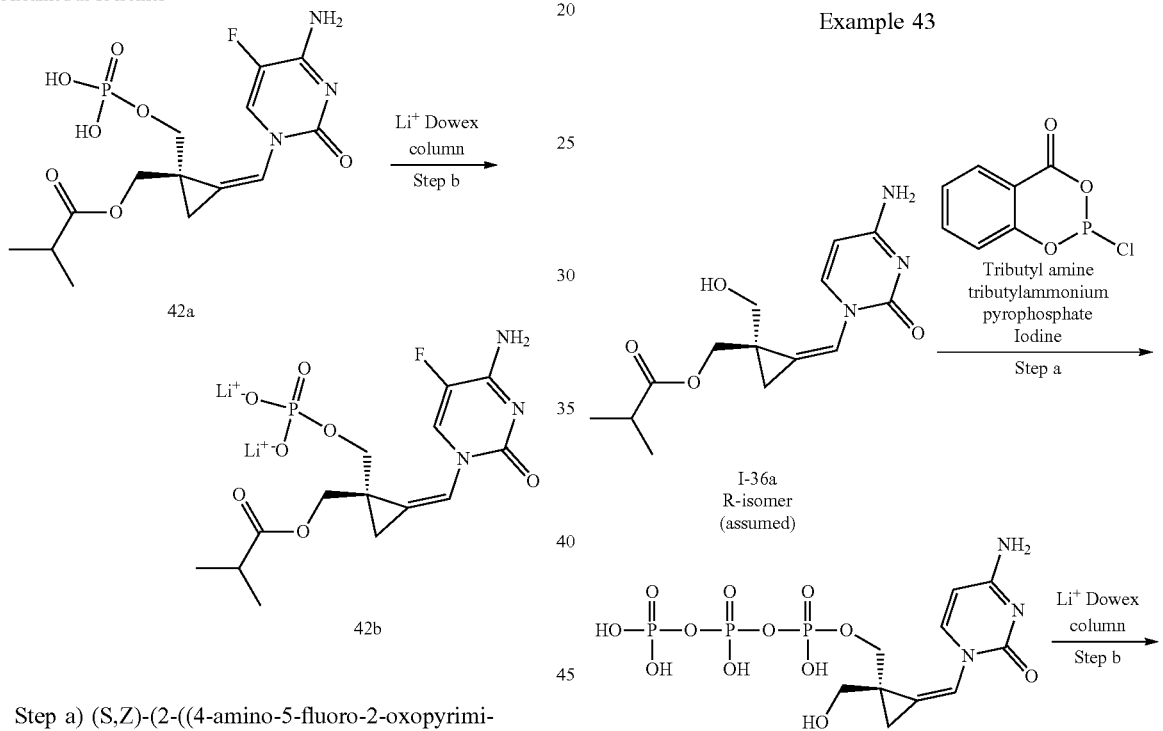

42a

42b

Step a) (S,Z)-(2-((4-amino-5-fluoro-2-oxopyrimidin-1(2H)-yl)methylene)-1-((phosphonooxy)methyl)cyclopropyl)methyl isobutyrate (42a)

Distilled $POCl_3$ (0.1 mL, 1.0 mmol) was added to a suspension of I-39a (150 mg, 0.5 mmol) in triethyl phosphate (1.9 mL, 11.2 mmol) at 0° C. and stirred at 0° C. for 3 h. To the above reaction mixture, triethyl ammonium bicarbonate buffer (1 M, pH=8) (7 mL) was added at 0° C. and concentrated under reduced pressure. The crude compound was purified twice by prep HPLC using method A and lyophilised, which gave the title compound (40 mg, 19%) as a solid. MS (ES+) 392.36 $[M+H]^+$.

Step b) lithium (S,Z)-(2-((4-amino-5-fluoro-2-oxopyrimidin-1(2H)-yl)methylene)-1-((isobutyryloxy)methyl)cyclopropyl)methyl phosphate (42b)

Dowex 50 WX8 hydrogen form (50-100 mesh), ion exchange resin was taken in a column (2×10 cm), washed with water:MeOH (1:1, 100 mL) until colourless eluent was obtained, then washed with Milli Q water (100 mL) to wash off MeOH. The ion exchange resin was again eluted with 0.5M sulphuric acid (50 mL) until acidic pH was attained and washed with water (200 mL) until neutral pH was observed. The ion exchange resin was again eluted with 1M lithium hydroxide (50 mL) until basic pH was attained and washed with water (200 mL) until neutral pH. A solution of compound 41a (40 mg, 0.1 mmol) in Milli Q water (5 mL) was passed through the above freshly prepared Dowex $LI^+$ column. The appropriate fractions were lyophilised, which gave the title compound (40 mg, 92%) as a solid. LCMS (ES+) m/z 392.36 $[M+H]^+$.

$^1$H NMR (500 MHz, D2O): δ 8.14 (d, J=6.1 Hz, 1H), 7.26 (d, J=1.6 Hz, 1H), 4.67 (d, J=11.5 Hz, 1H), 4.04 (q, J=5.2 Hz, 1H), 3.96 (q, J=5.0 Hz, 1H), 3.92 (d, J=11.4 Hz, 1H), 2.51 (m, J=7.0 Hz, 1H), 1.66 (q, J=3.7 Hz, 1H), 1.56 (d, J=9.2 Hz, 1H), 1.08 (d, J=7.0 Hz, 3H), 1.03 (d, J=7.0 Hz, 3H).

Example 43

I-36a
R-isomer
(assumed)

43a

43b

Step a) ((S,Z)-2-((4-amino-2-oxopyrimidin-1(2H)-yl)methylene)-1-(hydroxymethyl)cyclopropyl)methyl tetrahydrogen triphosphate (43a)

A solution of 2-chloro-4H-benzo[d][1,3,2]dioxaphosphinin-4-one (54 mg, 0.3 mmol) was added at rt to a solution of compound I-36a (75 mg, 0.3 mmol) in dry DMF (2 mL)

and dry pyridine (0.6 mL) and stirred at rt for 30 min. A solution of tributylammonium pyrophosphate (130 mg, 0.23 mmol) and dry tributylamine (0.15 mL, 0.64 mmol) in dry DMF (1.2 mL) was added and stirred at RT for 45 min. A solution of iodine (84 mg, 0.33 mmol) in pyridine/water: 98:2 (5.25 mL/0.15 mL) was added and the reaction stirred for 15 min at rt. 5% NaHSO$_3$ (1.5 mL) was added and concentrated under reduced pressure. Ammonium hydroxide (1.5 mL) was added to the residue and stirred at rt for 16 h, then concentrated under reduced pressure. The obtained crude was combined with another batch and purified twice by prep HPLC using method F and lyophilised, which gave the title compound (23 mg, 18%) as a solid. MS (ES+) 464.32[M+H]$^+$.

Step b) lithium (S,Z)-(2-((4-amino-2-oxopyrimidin-1(2H)-yl)methylene)-1-(hydroxymethyl)cyclopropyl)methyl triphosphate (43b)

Dowex 50 WX8 hydrogen form (50-100 mesh), ion exchange resin was taken in a column (2×10 cm), washed with water:MeOH (1:1, 50 mL) until colourless eluent was obtained, then washed with Milli Q water (50 mL) to wash off MeOH. The ion exchange resin was again eluted with 0.5M sulphuric acid (25 mL) until acidic pH was attained and washed with water (100 mL) until neutral pH was observed. The ion exchange resin was again eluted with 1M lithium hydroxide (25 mL) until basic pH was attained and washed with water (100 mL) until neutral pH. A solution of compound 43a (23 mg, 0.05 mmol) in Milli Q water (1 mL) was passed through the above freshly prepared Dowex Li$^+$ column. The appropriate fractions were lyophilised. The obtained residue was purified by prep HPLC using method F and lyophilised, which gave the title compound (7 mg, 23%) as a solid. LCMS (ES+) m/z 464.29 [M+H]$^+$.

$^1$H NMR (500 MHz, D2O): δ 8.11 (d, J=7.5 Hz, 1H), 7.33 (s, 1H), 6.16 (d, J=7.5 Hz, 1H), 4.32 (q, J=5.2 Hz, 1H), 3.94 (q, J=5.3 Hz, 1H), 3.82 (d, J=12.1 Hz, 1H), 3.61 (d, J=12.1 Hz, 1H), 1.51 (m, J=7.0 Hz, 2H).

Example 44-1 & 44-2

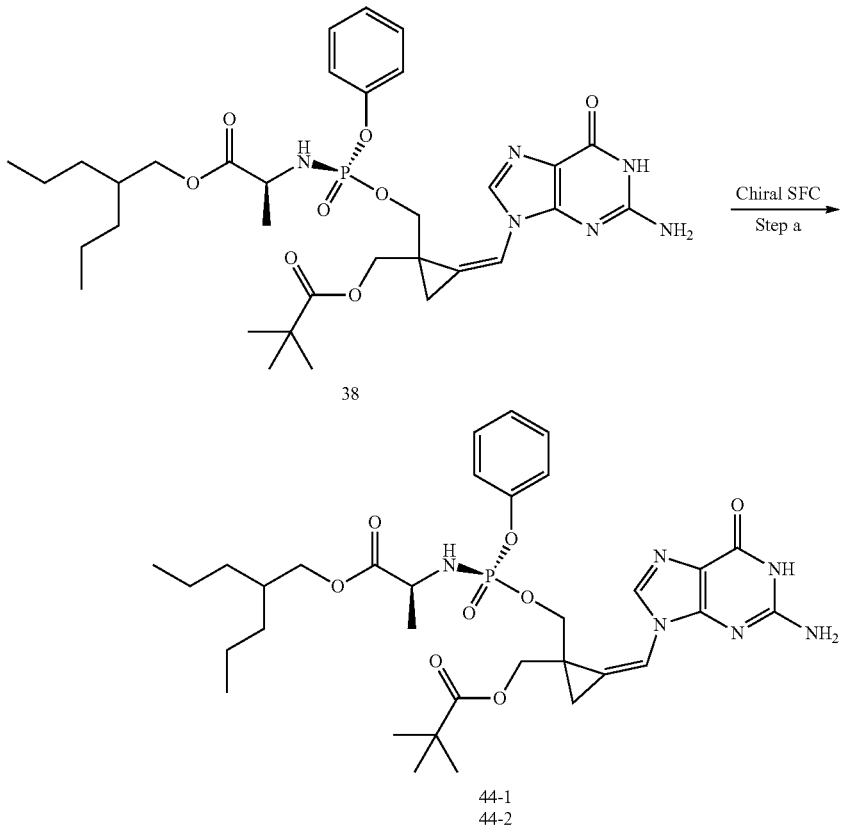

Step a) ((Z)-2-((2-amino-6-oxo-1,6-dihydro-9H-purin-9-yl)methylene)-1-((((S)-(((S)-1-oxo-1-((2-propylpentyl)oxy)propan-2-yl)amino)(phenoxy)phosphoryl)oxy)methyl)cyclopropyl)methyl pivalate (44-1 & 44-2)

Compound 38 (55 mg) was further purified by normal phase HPLC.
44-1:
Peak-1 was concentrated and lyophilised, which gave the title compound (13.6 mg, 35) as a solid.
MS (ES+) m/z 687.75 [M+H]$^+$.
$^1$H NMR (500 MHz, DMSO): δ 10.69 (s, 1H), 7.93 (s, 1H), 7.33 (m, J=4.0 Hz, 2H), 7.18 (m, J=4.8 Hz, 4H), 6.54 (s, 25H), 6.06 (q, J=7.8 Hz, 1H), 4.28 (d, J=11.5 Hz, 1H), 4.18 (m, J=6.1 Hz, 2H), 3.95 (q, J=5.6 Hz, 2H), 3.77 (m, J=3.9 Hz, 2H), 1.57 (m, J=4.3 Hz, 3H), 1.20 (m, J=4.4 Hz, 11H), 1.08 (s, 9H), 0.81 (t, J=7.0 Hz, 6H).
44-2:
Peak-2 was concentrated and lyophilised, which gave the title compound (11.6 mg, 3%) as a solid. MS (ES+) m/z 687.75 [M+H]$^+$.

¹H NMR (500 MHz, DMSO): δ 10.70 (s, 1H), 7.93 (s, 1H), 7.32 (t, J=8.0 Hz, 2H), 7.22 (t, J=1.8 Hz, 1H), 7.15 (m, J=3.2 Hz, 3H), 6.55 (s, 2H), 6.06 (q, J=7.7 Hz, 1H), 4.43 (d, J=11.6 Hz, 1H), 4.35 (q, J=5.7 Hz, 1H), 4.02 (q, J=5.4 Hz, 1H), 3.96 (m, J=5.7 Hz, 2H), 3.86 (m, J=4.1 Hz, 2H), 1.60 (s, 3H), 1.22 (m, J=5.0 Hz, 11H), 1.08 (s, 9H), 0.82 (m, J=3.1 Hz, 6H).

Normal Phase HPLC Conditions:
 Column/dimensions: Chiralpak IA (30×250 mm), 5μ
 Mobile Phase: n-hexane:EtOH (30:70)
 Flow: 40.0 ml/min
 Temperature: Ambient
 Wave length: 236 nm
 Run time: 13 min
 Load ability/inj.: 9.2 mg Example 45-1 & 45-2

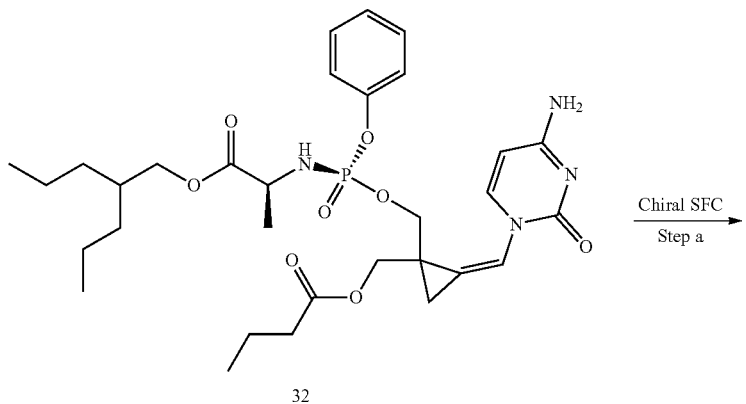

32

Chiral SFC
Step a
→

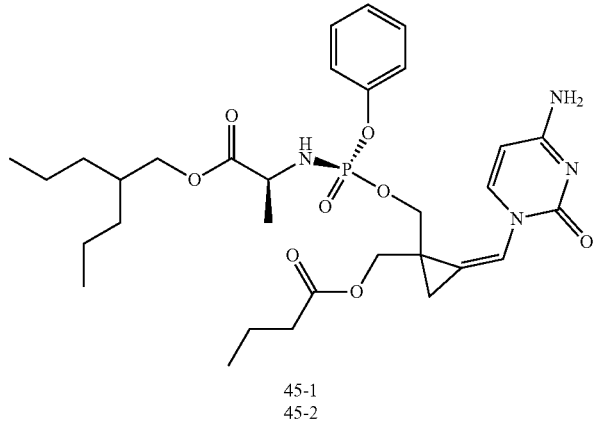

45-1
45-2

Step a) ((Z)-2-((4-amino-2-oxopyrimidin-1(2H)-yl)methylene)-1-((((S)-(((S)-1-oxo-1-((2-propylpentyl)oxy)propan-2-yl)amino)(phenoxy)phosphoryl)oxy)methyl)cyclopropyl)methyl butyrate (45-1 & 45-2)

Compound 32 (1.5 g) was further purified by chiral SFC.
45-1:
 The residue obtained from Peak-1 was further purified by prep HPLC using method A. The impure compound was further purified by chiral SFC and lyophilised, which gave the title compound (215 mg) as a solid. LCMS (ES+) m/z 633.72 [M+H]⁺
 ¹H NMR (500 MHz, DMSO): δ 7.72 (d, J=7.5 Hz, 1H), 7.42 (t, J=1.8 Hz, 2H), 7.35 (m, J=4.0 Hz, 3H), 7.17 (m, J=3.5 Hz, 3H), 6.04 (q, J=7.7 Hz, 1H), 5.80 (d, J=7.4 Hz, 1H), 4.34 (d, J=11.5 Hz, 1H), 4.21 (q, J=5.6 Hz, 1H), 3.98 (m, J=3.6 Hz, 2H), 3.87 (m, J=8.1 Hz, 3H), 2.22 (m, J=6.7 Hz, 2H), 1.61 (q, J=5.8 Hz, 1H), 1.49 (m, J=4.4 Hz, 4H), 1.25 (m, J=4.3 Hz, 11H), 0.84 (m, J=2.2 Hz, 9H).

45-2:
 The residue obtained from Peak-2 was further purified by prep HPLC using method A and lyophilised, which gave the title compound (280 mg) as a solid. LCMS (ES+) m/z 633.72 [M+H]⁺ ¹H NMR (500 MHz, DMSO): δ 7.74 (d, J=7.4 Hz, 1H), 7.42 (d, J=1.8 Hz, 2H), 7.35 (m, J=3.2 Hz, 3H), 7.17 (t, J=7.8 Hz, 3H), 6.06 (q, J=7.8 Hz, 1H), 5.80 (d, J=7.4 Hz, 1H), 4.24 (d, J=11.5 Hz, 1H), 4.17 (q, J=5.5 Hz, 1H), 4.06 (q, J=5.5 Hz, 1H), 3.97 (m, J=3.8 Hz, 2H), 3.86 (q, J=5.5 Hz, 1H), 3.80 (m, J=3.4 Hz, 1H), 2.22 (q, J=7.1 Hz, 2H), 1.60 (q, J=6.0 Hz, 1H), 1.48 (m, J=6.1 Hz, 4H), 1.23 (m, J=5.1 Hz, 11H), 0.84 (m, J=3.3 Hz, 9H).

Preparative SFC Conditions:
 Column/dimensions: Chiralpak IC (30×250 mm), 5μ
 CO₂: 50.0%
 Co solvent: 50.0% (isopropanol)
 Total Flow: 110.0 g/min
 Back Pressure: 100.0 bar
 UV: 214 nm
 Stack time: 13 min
 Load/inj.: 50 mg
Preparative SFC Conditions (example 45-1):
 Column/dimensions: Chiralpak IG (30×250 mm), 5μ
 CO₂: 70.0%
 Co solvent: 30.0% (100% isopropanol)
 Total Flow: 100 mg/min Back Pressure: 100 bar
UV: 214 nm
Stack time: 12.2 min
Load/inj.: 24.5 mg Comparative Example 1

Instability of Triester Phosphoroalaninates

Intermediate compounds I-19 d2 and I-25 synthesised above are triesterphosphoro-alaninates resembling the prior art compound described in Yan et al, J Med Chem 2005 48 91-99:

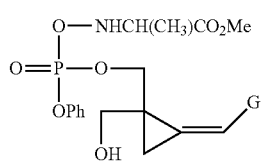

7a

The structural integrity of these model compounds was assessed by LC MS over a 22-29 day period, as follows:

| Day | LCMS purity, Intermediate I-19 d2 | LCMS purity, Intermediate I-25 |
|---|---|---|
| 0 | 96.86% | 95.56% |
| 5 | 94.32% | 88.14% |
| 14 | 88.76% | 82.67% |
| 22 | 73.76% | 77.76% |
| 29 | na | 72.84% |

It is thus concluded that about a quarter of the respective triesterphosphoralinate has decomposed in a little over three weeks.

Biology Example 1

Compounds of the invention were evaluated for activity against the leukemia cell lines THP-1, EOL-1 and MV4-11, using the following assay:

Materials

Cells and Cell Culture:

THP-1 (human acute monocytic leukemia) from ATCC Cat. no TIB-202 was grown in complete cell medium: RPMI-1640 medium Gibco Cat. no. 11835-063 (Fisher Scientific), 10% Fetal Bovine serum (FBS), HyClone Cat. no. SV30160.03, lot no RAB35924 (GE Healthcare Life Sciences), Penicillin 50 u/ml/Streptomycin 0.05 mg/ml PAA Cat. no. P11-010 from Fisher Scientific.

MV4-11 cells, human B-myelomonocytic leukemia, from ATCC Cat no. CRL-9591 was grown in complete cell medium: IMDM (w. GLUTAMAX-1) Cat no. 31980022 (Fisher Scientific), 10% Fetal Bovine serum (FBS) HyClone Cat. no. SV30160.03, lot no RAB35924 (GE Healthcare Life Sciences), Penicillin 50 u/ml/Streptomycin 0.05 mg/ml PAA Cat. no. P11-010 from Fisher Scientific.

EOL-1 (human acute monocytic leukemia) from DSMZ Cat. no ACC 386 was grown in complete cell medium: RPMI-1640 medium Gibco Cat. no. 11835-063 (Fisher Scientific), 10% Fetal Bovine serum (FBS), HyClone Cat. no. A15102, lot no 10211-2117 (GE Healthcare Life Sciences), Penicillin 50 u/ml/Streptomycin 0.05 mg/ml PAA Cat. no. P11-010 from Fisher Scientific.

Cell culture flask 75 $cm^2$, Cat. no. 83.1813 from Sarstedt AB.

Compound dilution plate, 96-well, V-bottom PP plate, Nunc Cat. no. 249944 from Thermo Scientific.

Cell assay plate, 96-well, Cat. no. 128009296 from Fisher Scientific

Cell Counting Kit-8 CK04 from Dojindo.

Test compounds were made up to 10 mM stock solution in DMSO

Method

Leukemia cells (THP-1, EOL-1 and MV4-11) were grown in a cell culture flask 75 $cm^2$ with approximately 100 ml complete cell medium. The cells were counted using a Scepter-hand held automated cell counter, using 60 μm sensors (Millipore) and suspended in complete cell medium to $2 \times 10^5$ cells. 100 μl of the cell suspension were seeded to all wells ($2 \times 10^4$ cells/well).

Test Compound Dilutions:

The compounds were tested in twelve concentrations, 10-fold serial dilutions, 50 μM-$5 \times 10^{-10}$ μM.

100 μl from a compound dilution plate were transferred to the cell assay plate=200 μl/well total volume and incubated for 5 days, at 37° C., 5% $CO_2$ incubator.

After 5 days, 10l of KIT-8 was added and the culture was incubated for 3-4 hours, at 37° C., 5% $CO_2$ incubator.

Plate were read in the spectrophotometer at wavelength 450 nm with a reference filter of 620 nm.

Data Analysis $CC_{50}$ values are calculated by plotting the degree of inhibition (compared to the vehicle ctrl) against the logarithm of the compound concentration. Result values in the dilution series are fitted to a 4-parameter sigmoidal dose-response curve described by the expression:

$$F(x)=D+(A-D)/(1+(x/C)^B)$$

where:
A=Minimum
B=Slope.
C=Inflection point. The inflection point is defined as the point on the curve where the curvature changes direction or signs.
D=Maximum
F=fraction inhibition The $CC_{50}$ value is the x-value giving F=0.5, as tabulated in Table 4 below: Table 4

TABLE 4

| Example | THP-1 $CC_{50}$ (μM) | MV4-11 $CC_{50}$ (μM) | EOL.1 $CC_{50}$ (μM) | Example | THP-1 $CC_{50}$ (μM) | MV4-11 $CC_{50}$ (μM) | EOL.1 $CC_{50}$ (μM) |
|---|---|---|---|---|---|---|---|
| 1f-1 | 0.67 | 0.46 | 0.12 | 6-2 | 0.74 | 0.43 | 0.19 |
| 8-1 | 0.26 | na | 0.34 | 11-1 | 0.19 | 0.071 | 0.14 |
| 12-1 | 0.29 | na | 0.17 | 13-1 | 0.87 | 1.1 | |
| 15-1 | 1 | na | | 16-1 | 0.35 | 0.19 | |

TABLE 4-continued

| Example | THP-1 CC$_{50}$ (μM) | MV4-11 CC$_{50}$ (μM) | EOL.1 CC$_{50}$ (μM) | Example | THP-1 CC$_{50}$ (μM) | MV4-11 CC$_{50}$ (μM) | EOL.1 CC$_{50}$ (μM) |
|---|---|---|---|---|---|---|---|
| 18-2 | 1.8 | 0.80 | | 20-2 | 0.90 | 0.38 | 3.6 |
| 21-2 | 0.39 | 0.51 | | 23 | 2.4 | 0.85 | |
| 24 | 3.8 | 2.1 | | 25-2 | 0.41 | 0.086 | 0.1 |
| 28-2 | 0.88 | 1 | | 29-1 | 0.71 | 1.2 | |
| 30-1 | 0.46 | 0.43 | 0.94 | 32-1 | 0.19 | 0.18 | 0.059 |
| 34-2 | 0.34 | 0.44 | 0.17 | 35-1 | 0.29 | 0.18 | |
| 38 | 0.19 | 0.31 | 0.21 | 39-2 | 0.6 | 2.6 | |
| 40 | | 3.1 | | | | | |
| 45-1 | 0.19 | 0.18 | 0.059 | 45-2 | 2 | 2.2 | |
| Cyclo-propavir | 5.1 | 11 | 11 | | | | |

It will be apparent that the compounds of the invention are substantially more active in this leukemia cell line models than the cyclopropavir nucleoside of the prior art.

The invention claimed is:

1. A compound represented by formula I:

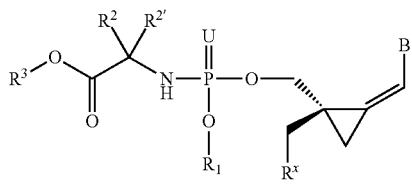

(I)

wherein:

B is a nucleobase selected from the groups (a) to (d):

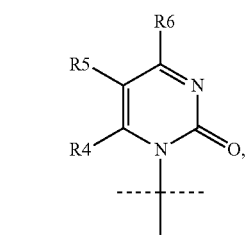

(a)

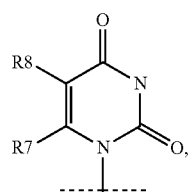

(b)

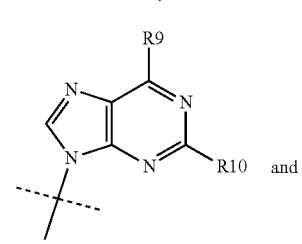

(c)

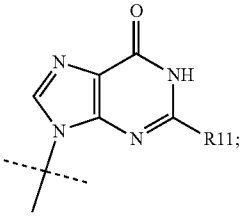

(d)

U is O or S;

$R^x$ is —OC(=O)$R^y$, —OC(=O)CH($R^y$)NH$_2$, or —OCH$_2$OC(=O)$R^y$;

$R^y$ is C$_1$-C$_{20}$alkyl or C$_2$-C$_{20}$alkenyl any of which is optionally substituted with one, two or three substituents each independently selected from fluoro, hydroxy and amino; or $R^y$ is the side chain of a natural amino acid, which may be in the D or L configuration;

$R^1$ is H, or a cyclic group selected from phenyl, benzyl, naphthyl, pyridyl or indolyl, each of which cyclic groups is optionally substituted with one, two or three $R^{22}$;

each $R^{22}$ is independently selected from halo, hydroxy, C$_1$-C$_6$alkyl, C$_3$-C$_6$cycloalkyl, haloC$_1$-C$_6$alkyl, hydroxyC$_1$-C$_6$alkyl, C$_1$-C$_6$alkoxy, haloC$_1$-C$_6$alkoxy, C$_1$-C$_6$alkylcarbonyl, C$_3$-C$_6$cycloalkylcarbonyl, azido, cyano, amino, or any two $R^{22}$ groups attached to adjacent ring carbon atoms can combine to form —O—(CH$_2$)$_{1-2}$—O—, wherein C$_3$-C$_6$cycloalkyl is optionally substituted with C$_1$-C$_3$alkyl; or $R^1$ and $R^x$ together define a bond, thus forming a cyclic phosphate;

$R^2$ and $R^{2'}$ are each independently selected from H, C$_1$-C$_6$alkyl, C$_3$-C$_7$cycloalkyl, C$_3$-C$_7$cycloalkylC$_1$-C$_3$alkyl, phenyl, benzyl and indolyl; or $R^2$ and $R^{2'}$ together with the carbon atom to which they are attached form a C$_3$-C$_7$cycloalkylene group;

wherein each C$_1$-C$_6$alkyl is optionally substituted with halo or OR$^{12}$, and each C$_3$-C$_7$cycloalkyl, C$_3$-C$_7$cycloalkylene, phenyl and benzyl is optionally substituted with one or two groups independently selected from C$_1$-C$_3$alkyl, halo and OR$^{12}$; or one of $R^2$ and $R^{2'}$ is H, and the other is the side chain of a natural amino acid, wherein the carboxy terminus of an Asp or Glu is optionally esterified with C$_1$-C$_6$ alkyl;

$R^3$ is C$_1$-C$_{10}$alkyl, C$_3$-C$_7$cycloalkyl, C$_1$-C$_3$alkylC$_3$-C$_7$cycloalkyl, phenyl or benzyl; any of which is optionally substituted with 1, 2 or 3 substituents each independently selected from halo, hydroxy, C$_1$-C$_6$alkoxy, $C_1$-$C_6$haloalkoxy and $N(R^{12})_2$; $R^4$, $R^5$, $R^7$ and $R^8$ are each independently H, $C_1$-$C_6$alkyl, $C_1$-$C_6$haloalkyl, $C_1$-$C_6$hydroxyalkyl, halo, —$OR^{12}$ or —$N(R^{12})_2$;

$R^6$, $R^9$, $R^{10}$ and $R^{11}$ are each independently H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, $OR^{12}$, —$N(R^{12})_2$, —NHC(O)$OR^{12}$, cyano, —C(O)$OR^{12}$, —C(O)$N(R^{12})_2$ or —NHC(O)$R^{13}$, wherein $C_2$-$C_6$alkenyl and $C_2$-$C_6$alkynyl is optionally substituted with halo or $C_3$-$C_5$cycloalkyl;

each $R^{12}$ is independently H, $C_1$-$C_6$alkyl, halo$C_1$-$C_6$alkyl, $C_3$-$C_7$cycloalkyl or $C_1$-$C_6$alkyl$C_3$-$C_7$cycloalkyl;

$R^{13}$ is $R^{12}$ or $CH_2CH(NH_2)C(=O)OH$;

or a pharmaceutically acceptable salt thereof.

2. The compound according to claim 1, wherein B is the group (d):

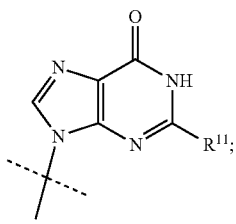

(d)

wherein
$R^{11}$ is $NH_2$ or $NHCOC_1$-$C_6$alkyl.

3. The compound according to claim 1, wherein B is the group (c):

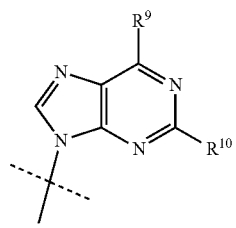

(c)

wherein $R^9$ is $C_1$-$C_6$alkoxy, $C_3$-$C_6$cycloalkoxy, $C_1$-$C_6$alkylamine or $C_3$-$C_6$cycloalkylamine, and $R^{10}$ is $NH_2$ or $NHCOC_1$-$C_6$alkyl.

4. The compound according to claim 1, wherein B is the group (a):

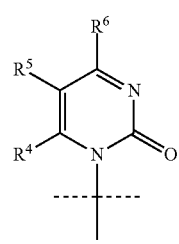

(a)

wherein: $R^4$ is H,
$R^5$ is F or H, and
$R^6$ is $NH_2$.

5. The compound according to claim 1, wherein $R^1$ is H, or phenyl which is optionally substituted with one or two $R^{22}$, and each $R^{22}$ is independently selected from halo, $C_1$-$C_3$alkyl, $C_3$-$C_4$cycloalkyl, halo$C_1$-$C_3$alkyl, $C_1$-$C_3$alkoxy, halo$C_1$-$C_3$alkoxy, $C_1$-$C_3$alkylcarbonyl, $C_3$-$C_4$cycloalkylcarbonyl, wherein $C_3$-$C_4$cycloalkyl is optionally substituted with methyl.

6. The compound according to claim 5, wherein phenyl is substituted in the 4-position with Br.

7. The compound according to claim 5, wherein the phenyl is unsubstituted.

8. The compound according to claim 1, wherein $R^{2t}$ is H and $R^2$ is $C_1$-$C_6$alkyl or halo$C_1$-$C_6$alkyl.

9. The compound according to claim 8, wherein the stereochemistry is as indicated in the partial formula:

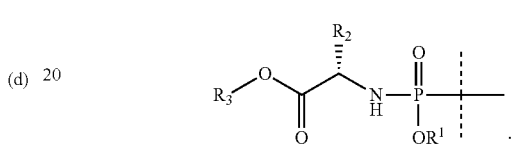

10. The compound according to claim 8, wherein $R^2$ is methyl.

11. The compound according to claim 1, wherein $R^3$ is $C_4$-$C_{10}$alkyl.

12. The compound according to claim 1, wherein $R^3$ is benzyl or $C_3$-$C_7$cycloalkyl.

13. The compound according to claim 1, wherein $R^x$ is —OC(=O)$C_1$-$C_6$alkyl.

14. The compound according to claim 1, wherein $R^x$ is —OC(=O)$C_{16}$-$C_{20}$alkyl.

15. The compound according to claim 1, wherein $R^x$ is —OC(=O)CH($R^y$)$NH_2$ and $R^y$ is the side chain of a natural amino acid and the configuration at the chiral center to which $R^y$ is attached is that of an L-amino acid.

16. The compound of claim 1, wherein $R^x$ is —$OCH_2OC(=O)CH_3$ or —$OCH_2OC(=O)C(CH_3)_3$.

17. The compound of claim 1, wherein U is O.

18. The compound of claim 1, selected from

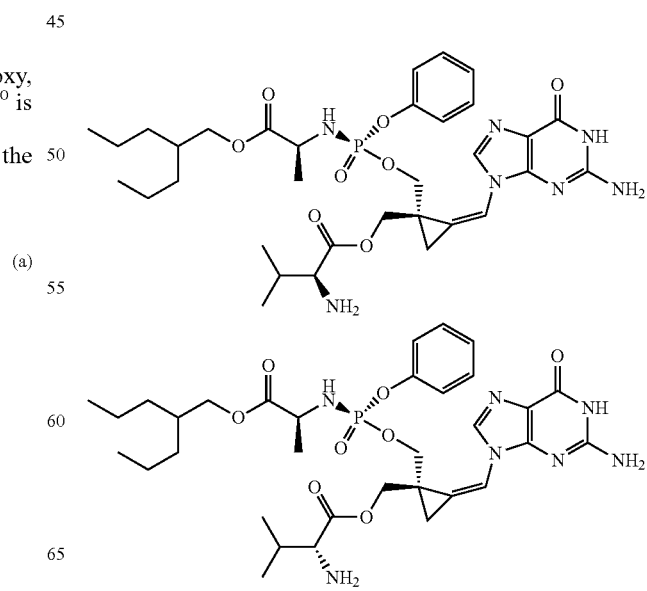

171
-continued
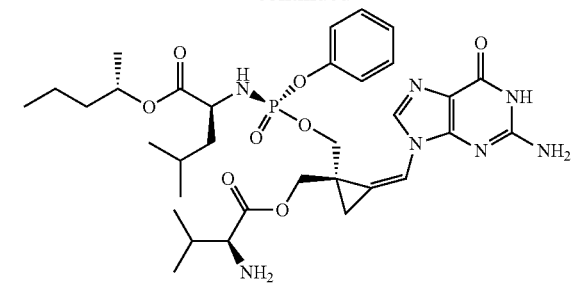
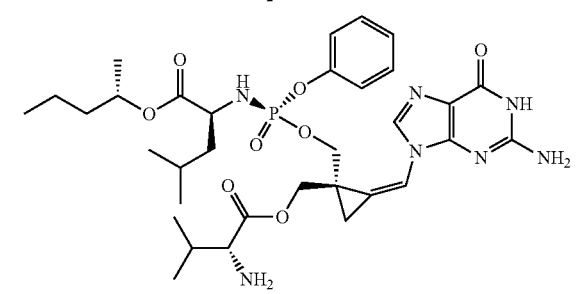
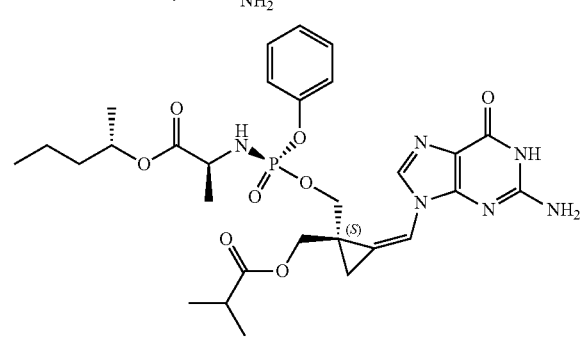
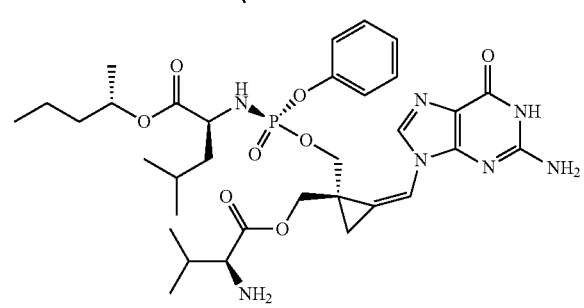
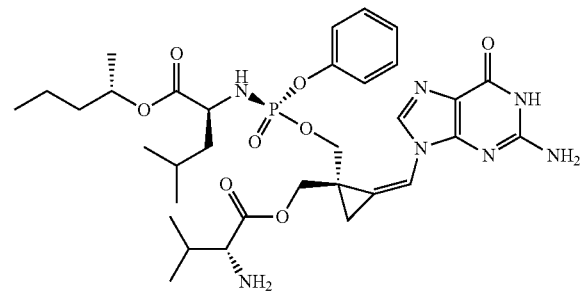
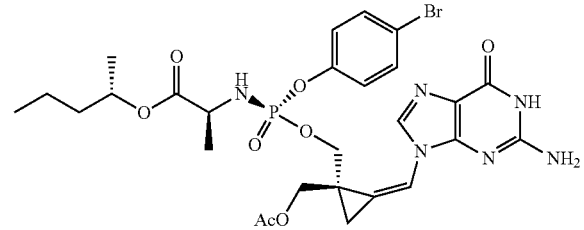
172
-continued
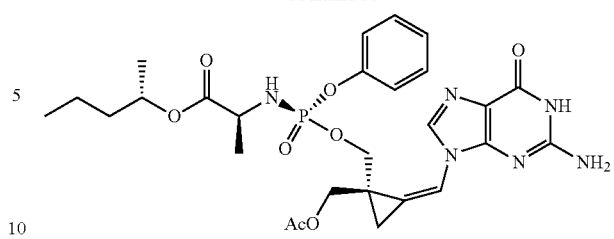
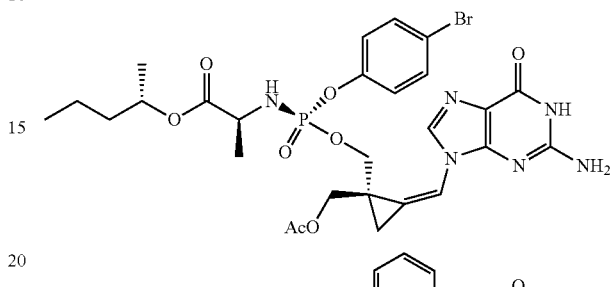
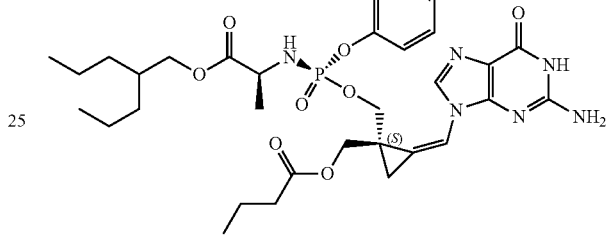
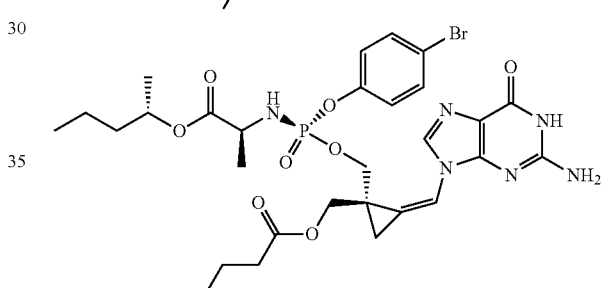
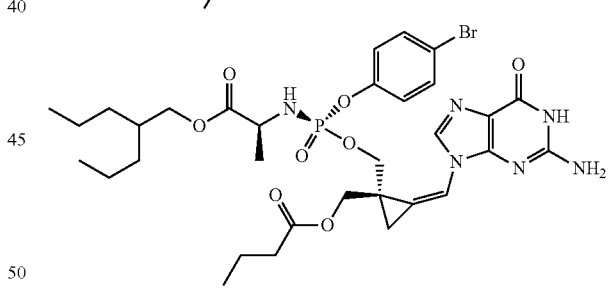
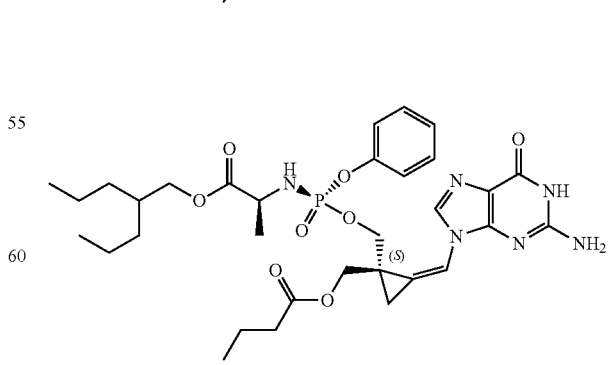

-continued

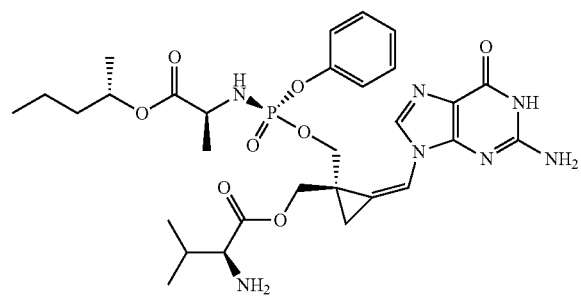

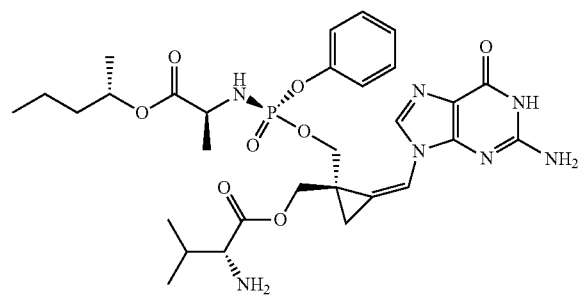

or

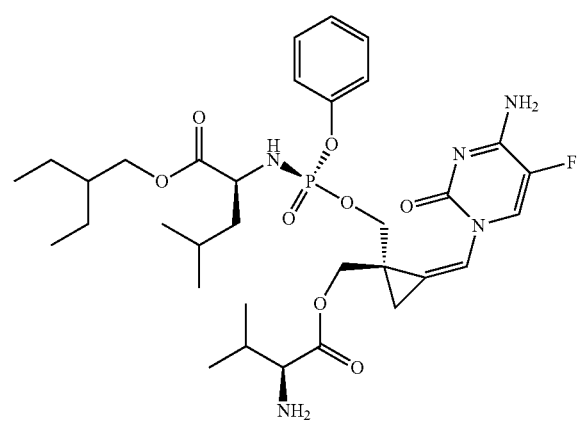

or a pharmaceutically acceptable salt thereof.

19. A compound according to claim 1, selected from

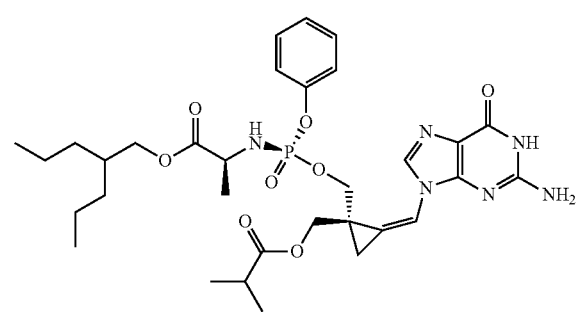

-continued

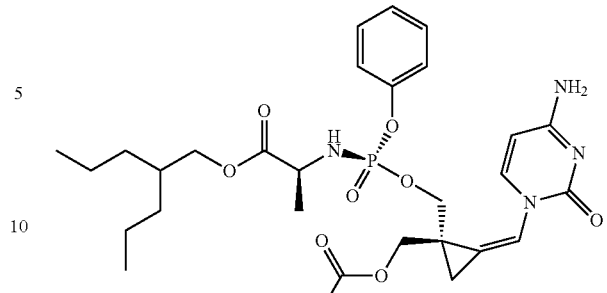

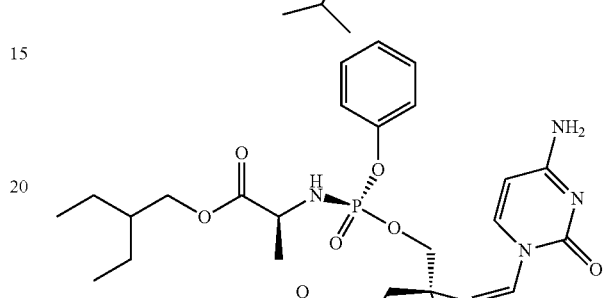

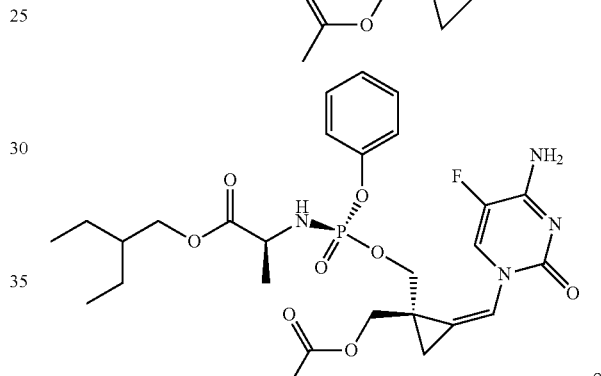

or

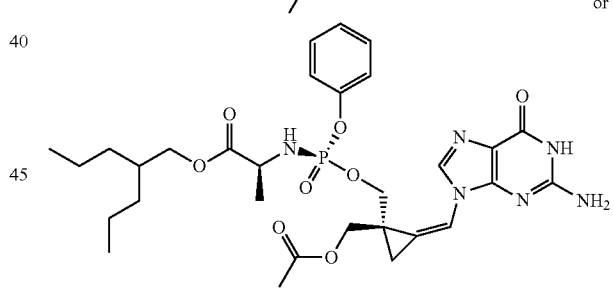

or a pharmaceutically acceptable salt thereof.

20. A pharmaceutical composition comprising a compound according to claim 1, in association with a pharmaceutically acceptable adjuvant, diluent or carrier.

21. A method for the treatment of cancer comprising the administration to a subject in need thereof an effective amount of a compound according to claim 1, wherein the cancer is leukemia.

22. The compound according to claim 11, wherein $R^3$ is 2-propylpentyl or 2-ethlybutyl.

23. The compound according to claim 13, wherein the $C_1$-$C_6$alkyl moiety is methyl, isopropyl, isobutyl or t-butyl.

24. The compound according to claim 14, wherein $R^x$ is —OC(=O)$C_{17}$alkyl.

25. The compound according to claim 15, wherein the natural amino acid is alanine.

26. The compound according to claim 16, wherein $R^x$ is —$OCH_2OC(=O)C(CH_3)_3$.

* * * * *